(12) United States Patent
Kiuchi et al.

(10) Patent No.: US 7,195,851 B2
(45) Date of Patent: Mar. 27, 2007

(54) CHARGE-TRANSFER MATERIAL AND PROCESS FOR PRODUCING THE SAME, ELECTRON-TRANSFER AGENT, PHOTORECEPTOR FOR ELECTROPHOTOGRAPHY AND ORGANIC ELECTROLUMINESCENCE ELEMENT USING SAID CHARGE-TRANSFER MATERIAL

(75) Inventors: Yasuyuki Kiuchi, Yokohama (JP); Toyozoh Satoh, Yokohama (JP); Hitoshi Takahashi, Yokohama (JP); Hiroki Suzuki, Kofu (JP); Mitsuyo Momose, Kofu (JP)

(73) Assignees: Yamanashi Electronics Co., Ltd., Kofu (JP); Permachem Asia, Ltd., Tokyo (JP)

( * ) Notice: Subject to any disclaimer, the term of this patent is extended or adjusted under 35 U.S.C. 154(b) by 27 days.

(21) Appl. No.: 11/289,507

(22) Filed: Nov. 30, 2005

(65) Prior Publication Data

US 2006/0134539 A1   Jun. 22, 2006

Related U.S. Application Data

(60) Division of application No. 10/673,405, filed on Sep. 30, 2003, now abandoned, which is a continuation of application No. PCT/JP02/02965, filed on Mar. 27, 2002.

(30) Foreign Application Priority Data

Sep. 11, 2001 (JP) .............................. 2001-274861
Mar. 30, 2003 (JP) .............................. 2001-98301

(51) Int. Cl.
*G03G 15/02* (2006.01)

(52) U.S. Cl. ................................................ 430/58.55

(58) Field of Classification Search .............. 430/58.55
See application file for complete search history.

(56) References Cited

FOREIGN PATENT DOCUMENTS

| EP | 0 115 136 A2 | 8/1984 |
|---|---|---|
| JP | A 55-53335 | 4/1980 |

(Continued)

OTHER PUBLICATIONS

Hlavka et al., "The Partial Structure of LL-AV290†—A New Antibiotic," Tetrahedron Letters No.2, pp. 175-178, 1974.

(Continued)

*Primary Examiner*—Mark A. Chapman
(74) *Attorney, Agent, or Firm*—Armstrong, Kratz, Quintos, Hanson & Brooks, LLP

(57) ABSTRACT

A photosensitive layer contains an electron-transfer agent that makes use of a compound represented by the following general formula (1):

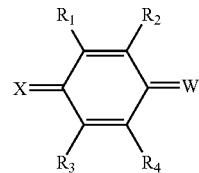

General formula (1)

wherein $R_1$ through $R_4$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and W is a 4- to 8-membered ring.

3 Claims, 83 Drawing Sheets

FOREIGN PATENT DOCUMENTS

| | | |
|---|---|---|
| JP | A 7-168377 | 7/1995 |
| JP | A 9-136858 | 5/1997 |
| JP | A 2000-226354 | 8/2000 |
| JP | A 2001-342182 | 12/2001 |
| WO | WO99/01798 | 1/1999 |

OTHER PUBLICATIONS

Isomura et al., Studies on the Synthesis and Anti-inflammatory Activity of 2,6-Di-*tert*-butylphenols with a heterocyclic Group at the 4-Position. IV.[1]) Photo-Induced and Base-Catalyzed Oxygenation of 4-(3,5-Di-*tert*-buyl-4-hydroxyphenyl)-2-oxo-4-imidazolines, Journal of the Pharmaceutical Society of Japan, 104(8), pp. 909-914, 1984.

Wilson et al., "The Condensation of Dicarbonyl Compounds with *N*-Phenyltriazolinedione-Dienone Ylides Derived from Phenols: The Facile Preparation of Novel Quinone Methides," J. Am Chem. Soc., 113, pp. 2301-2302, 1991.

Said et al., "Chemistry of Phosphorus Ylides 17. Reactions with Phosphacumulenes X. The Behaviour of Phosphacumulenes Towards *o*- and *p*-Quinones. Facile Synthesis of Cyclobunetadione Derivatives," Phosphorus, Sulfur, and Silicon, 108, pp. 41-49, 1996.

Itoh et al., "Synthesis and Polymerization of 7-Alkoxycarbonyl-7,8,8-tricyanoquinodimethanes and 7,7-Bis(alkoxycarbonyl)-8,8-dicyanoquinodimethanes," Tetrahedron 53(45), pp. 15247-15261, 1997.

Sergediene et al., "Prooxidant toxicity of polyphenolic antioxidants to HL-60 cells: description of quantitative structure- activity relationships," FEBS Lett., 462, pp. 392-396, 1999.

Dangles et al., "One-electron oxidation of quercetin and quercetin derivatives in protic and non protic media," J. Chem. Soc., Perkin Trans. 2, (7), pp. 1387-1395, 1999.

Pavlickova et al. "Solvatochromic Study of Internal Charge Transfer in 7,7-Disubstituted Quinone Methides," Collect., Czech Chem. Commun., 48, pp. 2376-2385, 1983.

Yokelson et al., "Oxidative Ring Opening and Rearrangement of an Anthroquinocyclopropene., Molecular Structure of a Novel Spiro-3-Furanone" Tetrahedron Lett., 34(35), pp. 5559-5562, 1993.

Lycka et al., C-NMR Study of 7,7-Disubstituted Quinone Methides, Collect. Czech. Chem. Commun., 46, pp. 2083-2090, 1981.

Khodorkovsky et al., "Sysnthesis and Properties of a Novel Electronic Acceptor Derived from *p*-Benzoquinone," Tetrahedron Lett., 40(26), pp. 4851-4854, 1999.

Zhou et al., "Electron transfer reactions of extended *0-*, *p*-quinonesvoltammetric and EPR/ENDOR spectroscopic investigations," J. Chem. Soc., Perkins Trans. 2, pp. 343-348, 1998.

Schulz et al., "Free Radical Reactions of N-Heterocyclic Compounds. XI. Reaction of 3-Methyl-pyrazolin-5-ones with Phenoxy Radicals," J. parkt. Chem., 335, pp. 607-615, 1993.

CHARGE-TRANSFER MATERIAL AND PROCESS FOR PRODUCING THE SAME, ELECTRON-TRANSFER AGENT, PHOTORECEPTOR FOR ELECTROPHOTOGRAPHY AND ORGANIC ELECTROLUMINESCENCE ELEMENT USING SAID CHARGE-TRANSFER MATERIAL

CROSS REFERENCE TO RELATED APPLICATION

This is a divisional of U.S. Ser. No. 10/673,405 filed Sep. 30, 2003 now abandoned, which is a continuation of International Application No. PCT/JP02/02965 filed Mar. 27, 2002. The entire disclosure of the prior application is herein incorporated by reference in its entirety.

BACKGROUND OF THE INVENTION

1. Field of Invention

The present invention relates to a technical field involving the use of electron-transfer materials, and more particularly, to a novel electron-transfer compound as well as to a process for producing such a compound. The present invention further relates to an electron-transfer agent containing such a compound, and also, to an electrophotographic photoreceptor and an organic electroluminescence element containing such an agent.

2. Description of Related Art

Photocopiers, laser printers and other electrophotographic apparatuses are equipped with an electrophotographic photoreceptor. In the early days of development of photocopiers and laser printers, inorganic film was used in the photosensitive layer of the electrophotographic photoreceptors. Such inorganic film was formed of inorganic materials such as selenium, selenium-tellurium, selenium-arsenic and amorphous silicon.

As demand increases for inexpensive, environmentally less harmful electrophotographic photoreceptors, the photoreceptors incorporating organic film have become widely used and have replaced those with conventional photosensitive layers formed of inorganic film. The photosensitive layers formed of organic film are generally divided into two structurally different types: single-layered and multi-layered.

The single-layered photosensitive layer comprises a single layer of charge-transfer medium in which a charge-generation material has been dispersed. The single layer serves both to generate electrical charge and to transport charge. In comparison, the multi-layered photosensitive layer is formed as a multi-layered film comprising a charge-generation layer (CGL) and a charge-transfer layer (CTL) that are laminated on top of one another. The two layers have different functions with the charge-generation layer generating electrical charge and the charge-transfer layer transferring the generated charge.

While both types of the photosensitive layers are in use today, each requires a charge-transfer material with a high mobility in order to increase sensitivity.

The organic photosensitive layers are also divided into two different types, namely, positive charge photosensitive layers and negative charge photosensitive layers, based on the polarity they can be charged as well. Most of the known charge-transfer materials that have high mobility and are in practical use today are hole-drift type charge-transfer materials. Accordingly, the photoreceptors used in commercial electrophotographic products employ a negative charge photosensitive layer.

When these photosensitive layers are negatively charged by means of corona discharge phenomena, significant amounts of ozone are produced, causing many problems such as pollution of indoor environments and accelerated deterioration of the electrophotographic photoreceptor.

In order to avoid these problems occurring during the negative charging process, conventional electrophotographic apparatuses employ ozone filters or a special ozone-free charging technique. These approaches, however, bring about new problems, such as resulting in an undesirably large construction of the apparatus or complex electrophotography process. Further, none of these approaches has ever provided a practical solution.

As a result, the positive charge photoreceptors, which produce little ozone, are demanded in the marketplace as an effective countermeasure to the above-described problems, and to this end, a highly mobile electron-transfer material must be developed that can be used in the positive charge photosensitive layer.

Negative charge photoreceptors are better suited for use in color printers because of available toners. Also, by constructing the photosensitive layer as a single layer in a negative charge photoreceptor, the time required for the coating process, and thus the production cost, can be reduced. Constructing such a photosensitive layer, however, requires an electron-transfer material with even higher mobility, and no material has ever been found to have a sufficiently high electron mobility to provide such characteristics.

Therefore, a highly mobile electron-transfer material is as important in the negative charge photoreceptor as it is in the positive charge photoreceptor. Much effort has been made to find such material. The electron-transfer materials for use in the positive charge photoreceptor that are known to date include trinitrofluorenon (TNF), tetracyanoethylene, tetracyanoquinodimethane (TCNQ), quinone, diphenoquinone, naphthoquinone, anthraquinone, and derivatives thereof. Most of these electron-transfer materials, however, have a poor compatibility with binder resins so that it is difficult to uniformly disperse these materials in a photosensitive layer at a high concentration. Thus, the amount of the electron-transfer material contained in the photosensitive layer tends to be too small to provide sufficient electrical characteristics.

Unlike other electron-transfer materials, diphenoquinone compounds are known to have an exceptionally high compatibility with resins as well as a high electron mobility. On the other hand, diphenoquinone compounds tend to exhibit a strong color due to the long conjugated system within the molecule, and when used to form a photosensitive layer, diphenoquinone compounds absorb light that would otherwise reach the charge-generation material. As a result, the sensitivity of the photosensitive layer is decreased. Further, these compounds generate electrically stable radicals due to the symmetrical structure of their molecule skeletons. The radicals form electrical traps to hinder movement of electrons in a low electric field. Not only does this result in a reduced luminescence efficiency, and thus a reduced brightness of organic electroluminescence elements, but it also results in a high residual potential in the photosensitive layer of the photoreceptor.

One example of the electron-transfer material that has overcome the problem of reduced electron mobility in low electric fields is a compound described in Japanese Patent Laid-Open Publication No. Hei 9-34141, which has the structure shown by the following chemical formula 24:

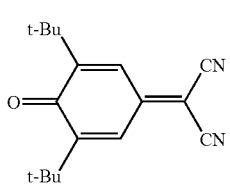

Chemical formula (24)

The compound has a conjugated system involving three double bonds between an oxygen atom and a dicyanomethylene group within its molecular skeleton. Because of this relatively short conjugated system, the compound is capable of coloring only faintly and is thus less likely to absorb light.

Also, the dicyanomethylene group attached to one end of the quinone structure serves to keep the lives of the radicals produced during the movement of electrons short. As a result, the radicals are less likely to form traps even in a low electric field. However, movement of electrons is more restricted in this compound than in diphenoquinone compounds since its short conjugated system permits electrons to move within the molecule only over relatively short distances.

In practice, electrophotographic photoreceptors using the above compound are less than satisfactory when compared to the commercially available negative charge electrophotographic photoreceptors in terms of sensitivity and residual potential.

It is thus necessary for a practically useful electron-transfer material to meet two contradictory requirements: it must have a reduced ability to color and it must ensure a large degree of electron movement within the molecule. The former requirement is met by a short conjugated system in the chemical structure, whereas the latter is met by a long conjugated system provided by a larger molecular skeleton. A strong demand exists for a molecular structure that, aside from meeting these requirements, does not produce stable radicals.

SUMMARY OF THE INVENTION

The present invention has been devised to address the above-identified problems associated with the conventional art. It is thus an objective of the present invention to provide a novel useful electron-transfer material that can be dispersed in a photosensitive layer at a high concentration and has a high electron mobility. It is also an objective of the present invention to provide an electrophotographic photoreceptor with an improved sensitivity and residual potential, as well as to provide an organic electroluminescence element with a high luminescence efficiency.

In the search for a way to solve the above-described problems, the present inventors have found that a compound can be provided that has a novel molecular skeleton in which a quinone ring is connected via a double bond to a ring structure having an active methylene, as well as a production process of such a compound, a novel electron-transfer material, and an electrophotographic photoreceptor and an organic electroluminescence element containing such an electron-transfer material. The discovery ultimately led the present inventors to bring the present invention to completion.

Having been devised based on the above-described findings, the present invention provides a compound represented by the following general formula (1):

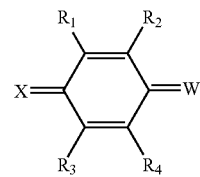

General formula (1)

wherein $R_1$ through $R_4$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and W is a 4- to 8-membered ring and has the structure shown in the following general formula (1') that replaces the general formula (1) above:

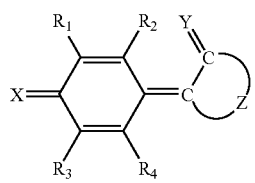

General formula (1')

wherein Y is oxygen or sulfur, and Z is a structure that has 2 or more atoms and forms a part of the ring.

Figure 1:
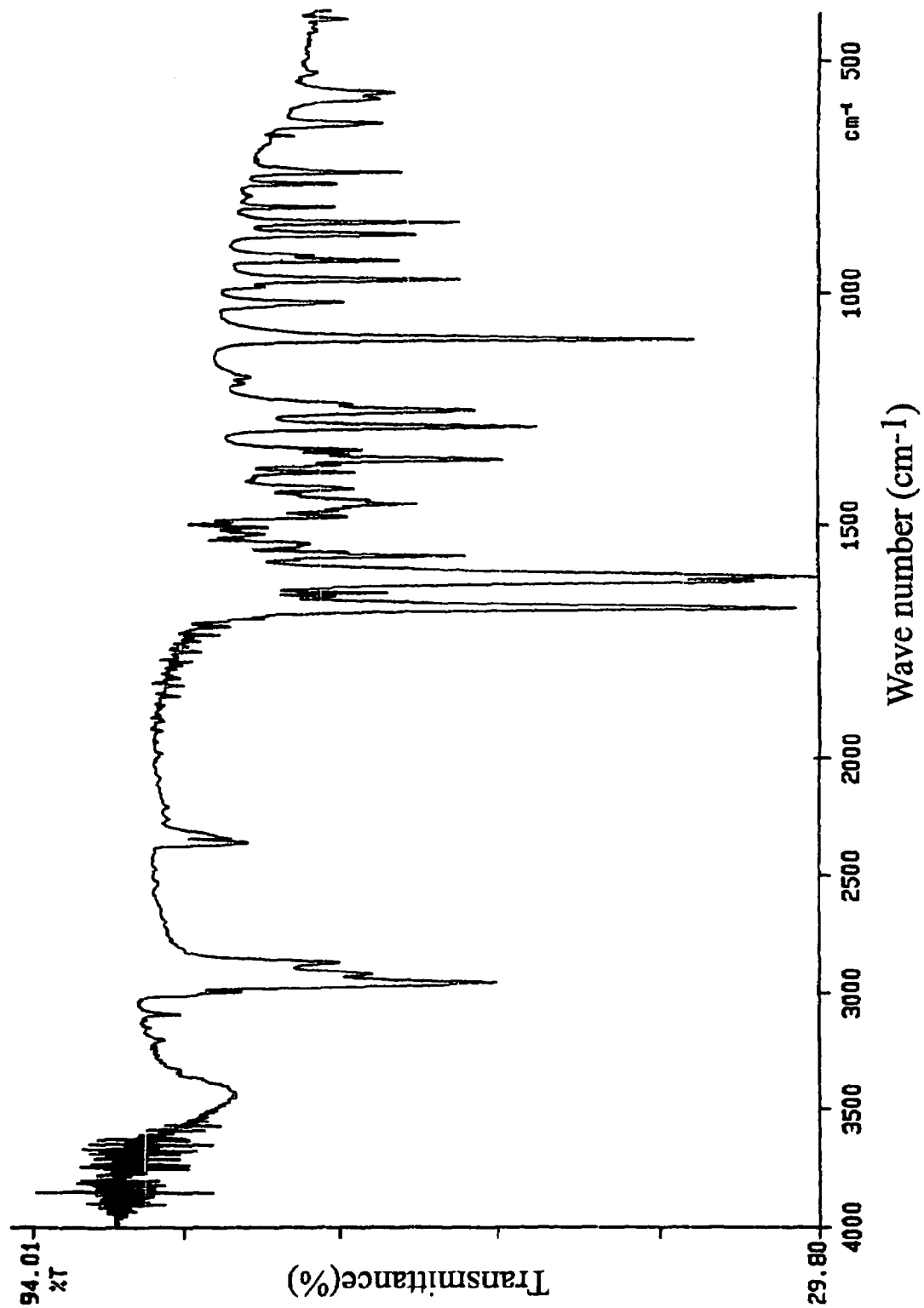
FIG. 1 is an IR spectrum of a compound represented by the chemical formula (7).
Figure 2:
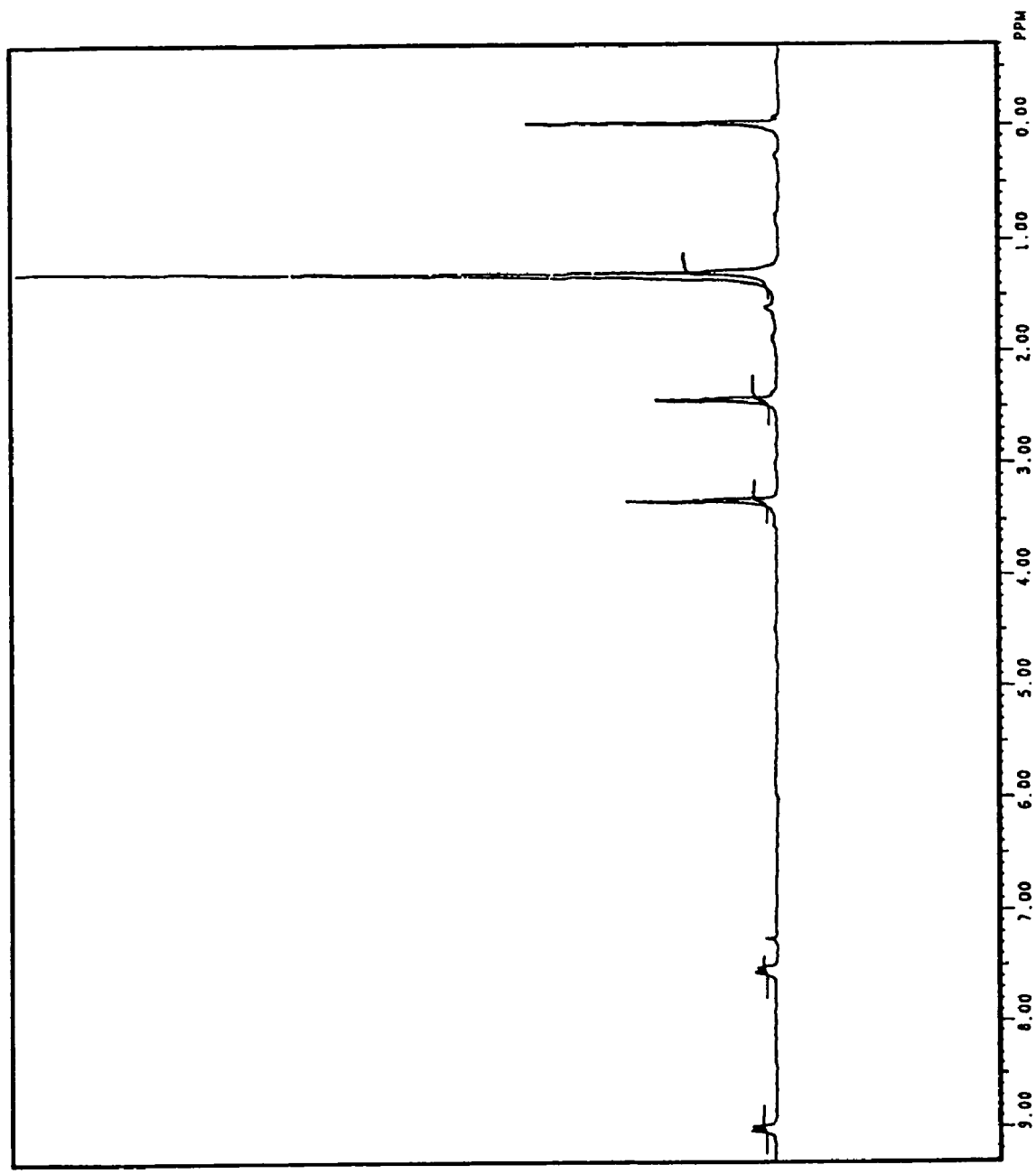
FIG. 2 is a $^1$H-NMR spectrum of the compound represented by the chemical formula (7).
Figure 3:
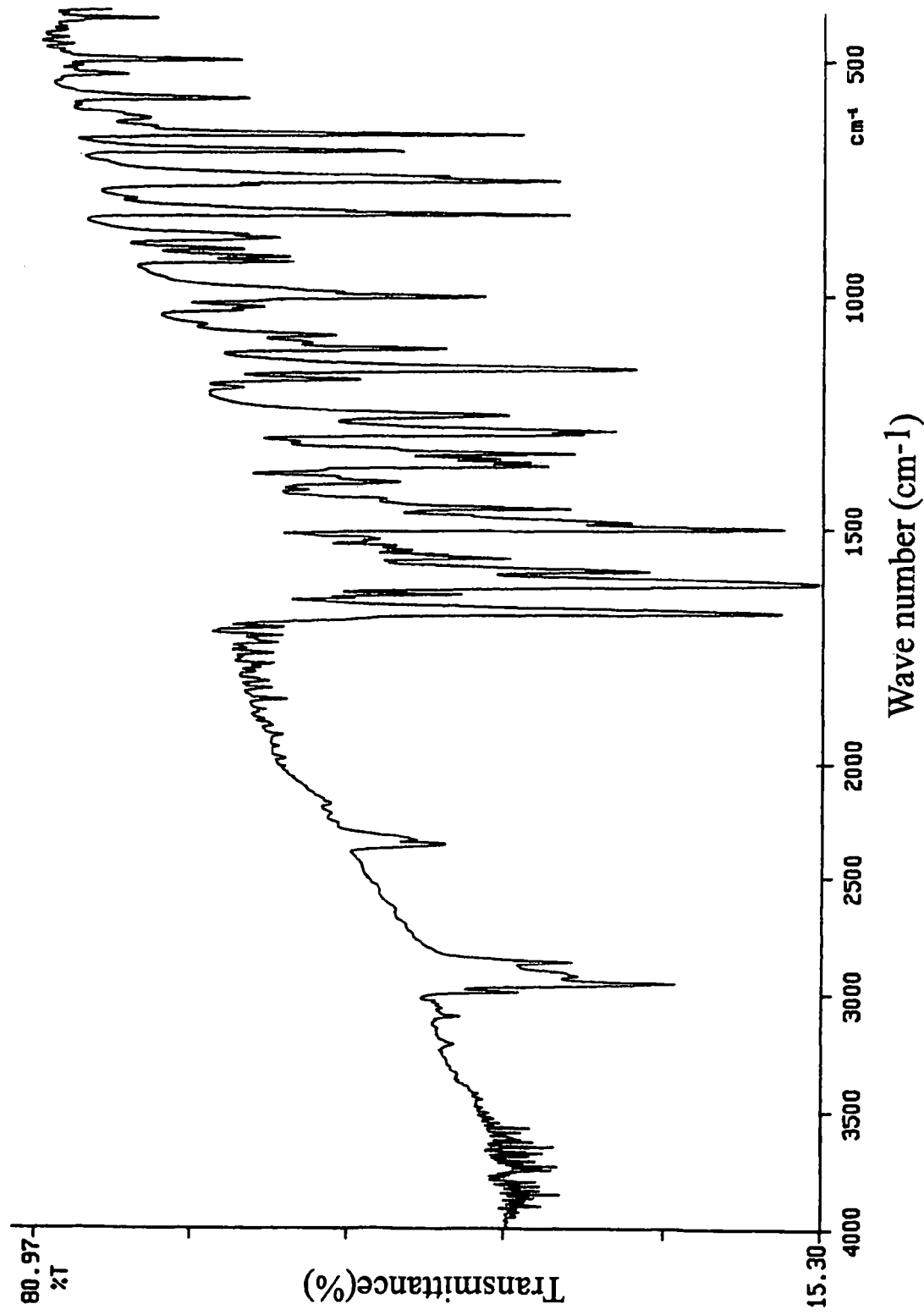
FIG. 3 is an IR spectrum of a compound represented by the chemical formula (8).
Figure 4:
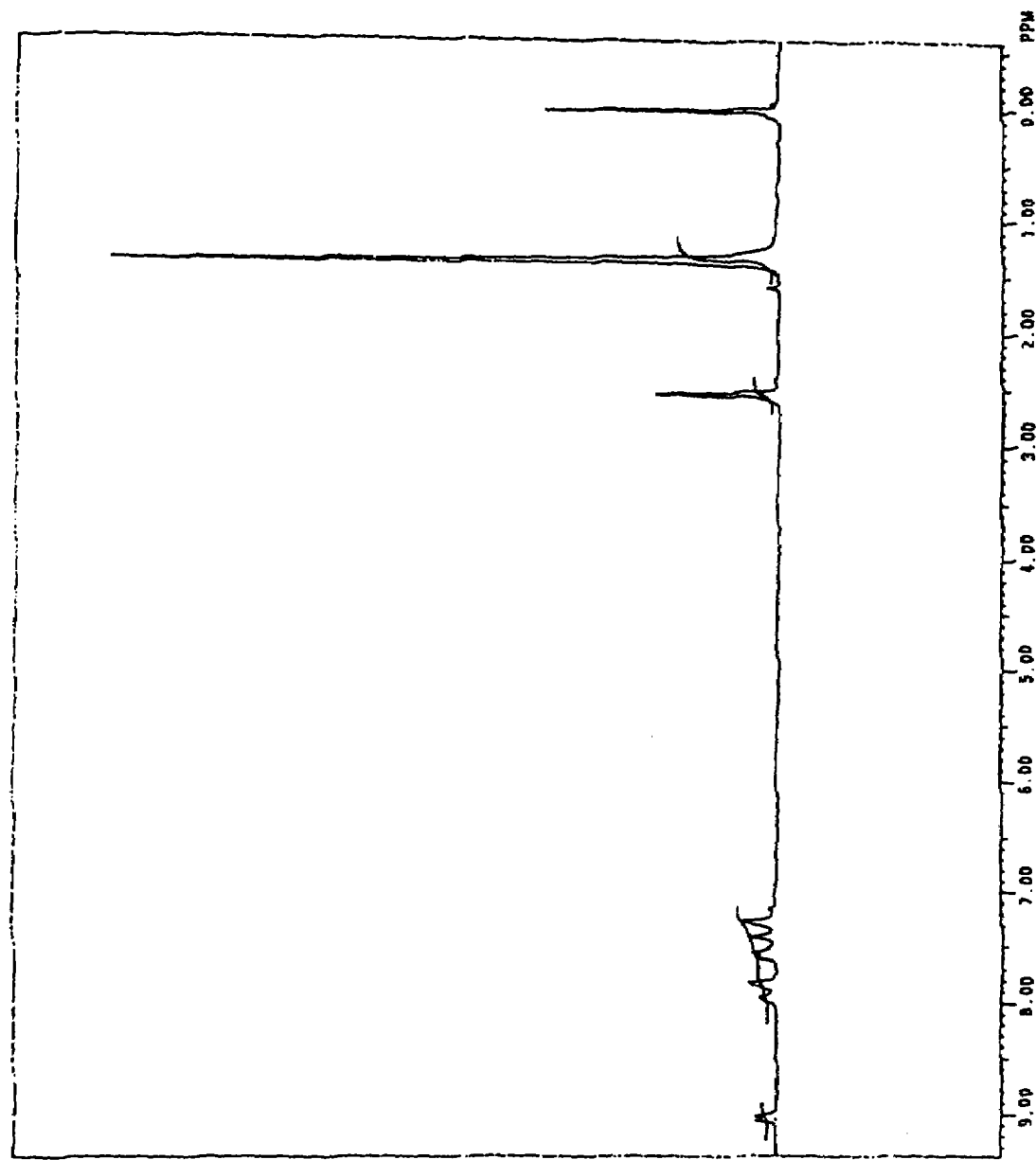
FIG. 4 is a $^1$H-NMR spectrum of the compound represented by the chemical formula (8).
Figure 5:
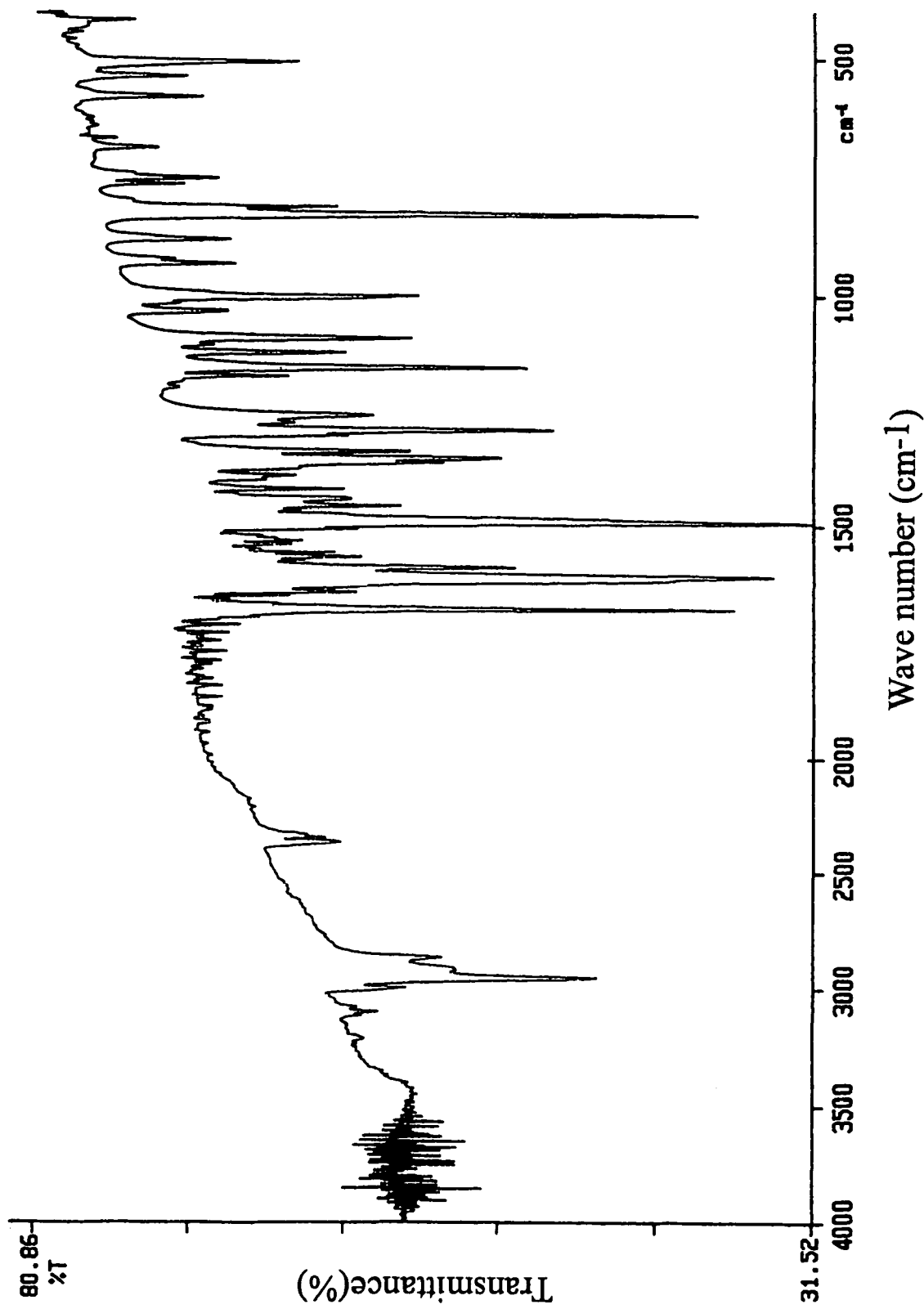
FIG. 5 is an IR spectrum of a compound represented by the chemical formula (9).
Figure 6:
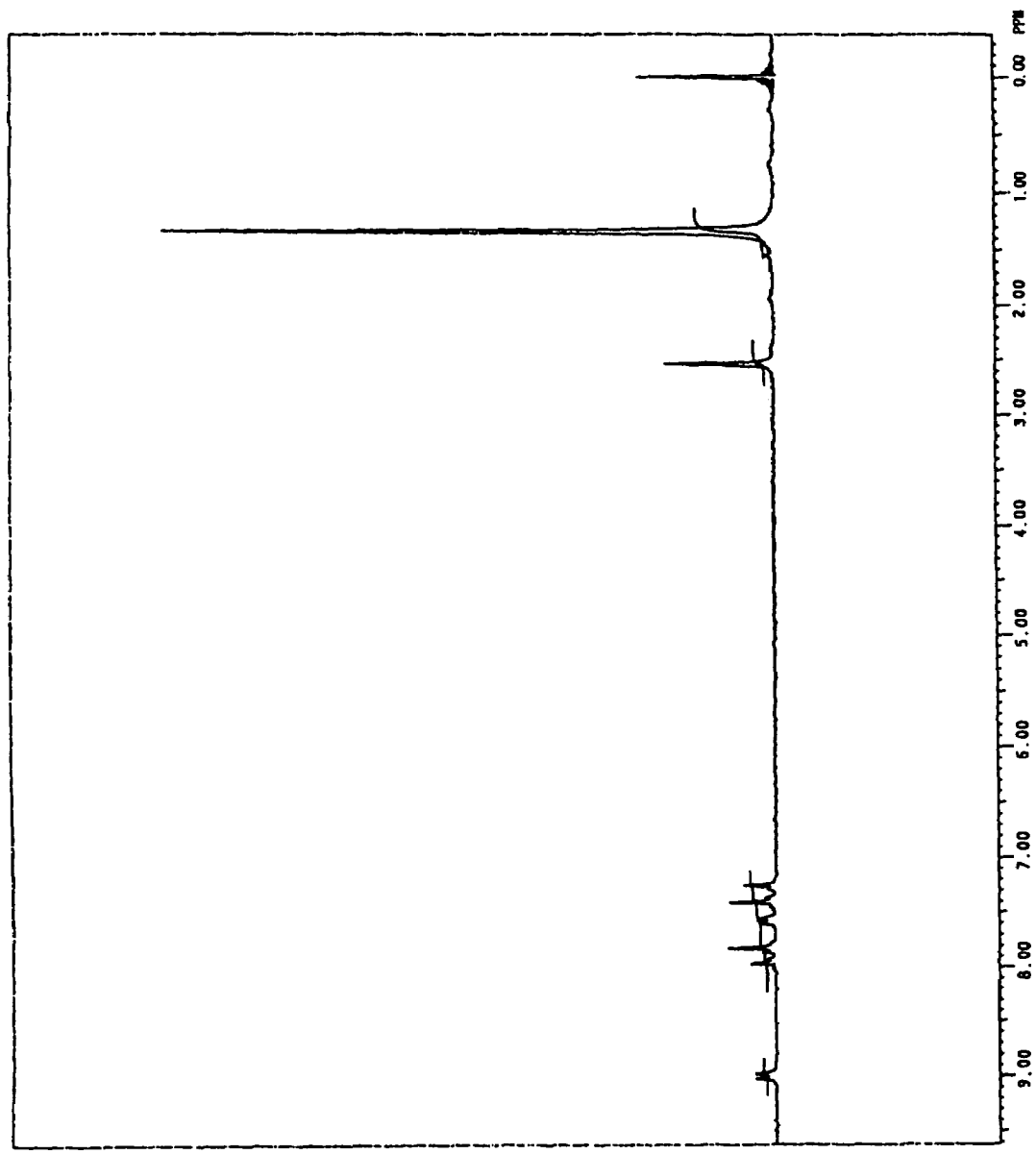
FIG. 6 is a $^1$H-NMR spectrum of the compound represented by the chemical formula (9).
Figure 7:
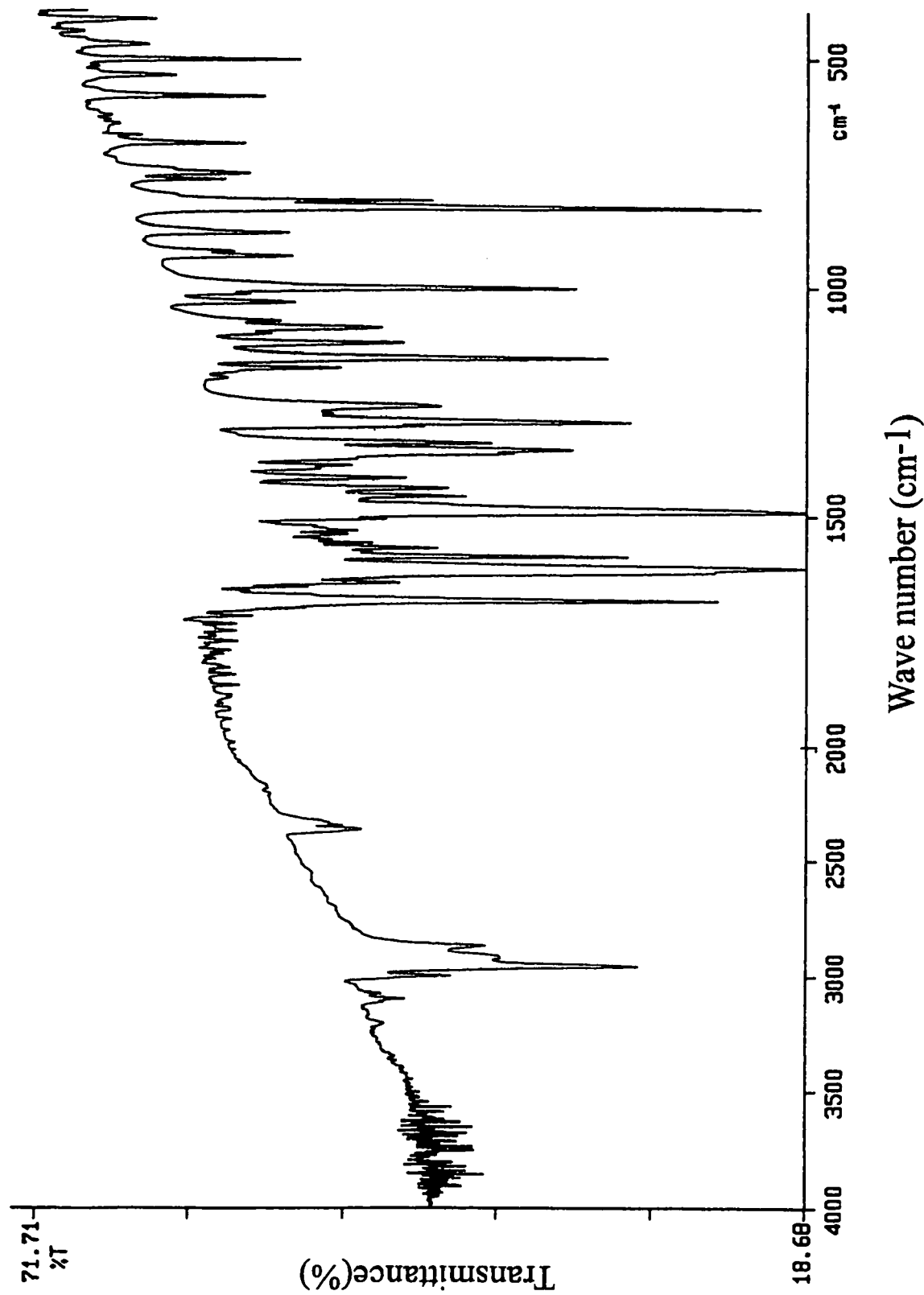
FIG. 7 is an IR spectrum of a compound represented by the chemical formula (10).
Figure 8:
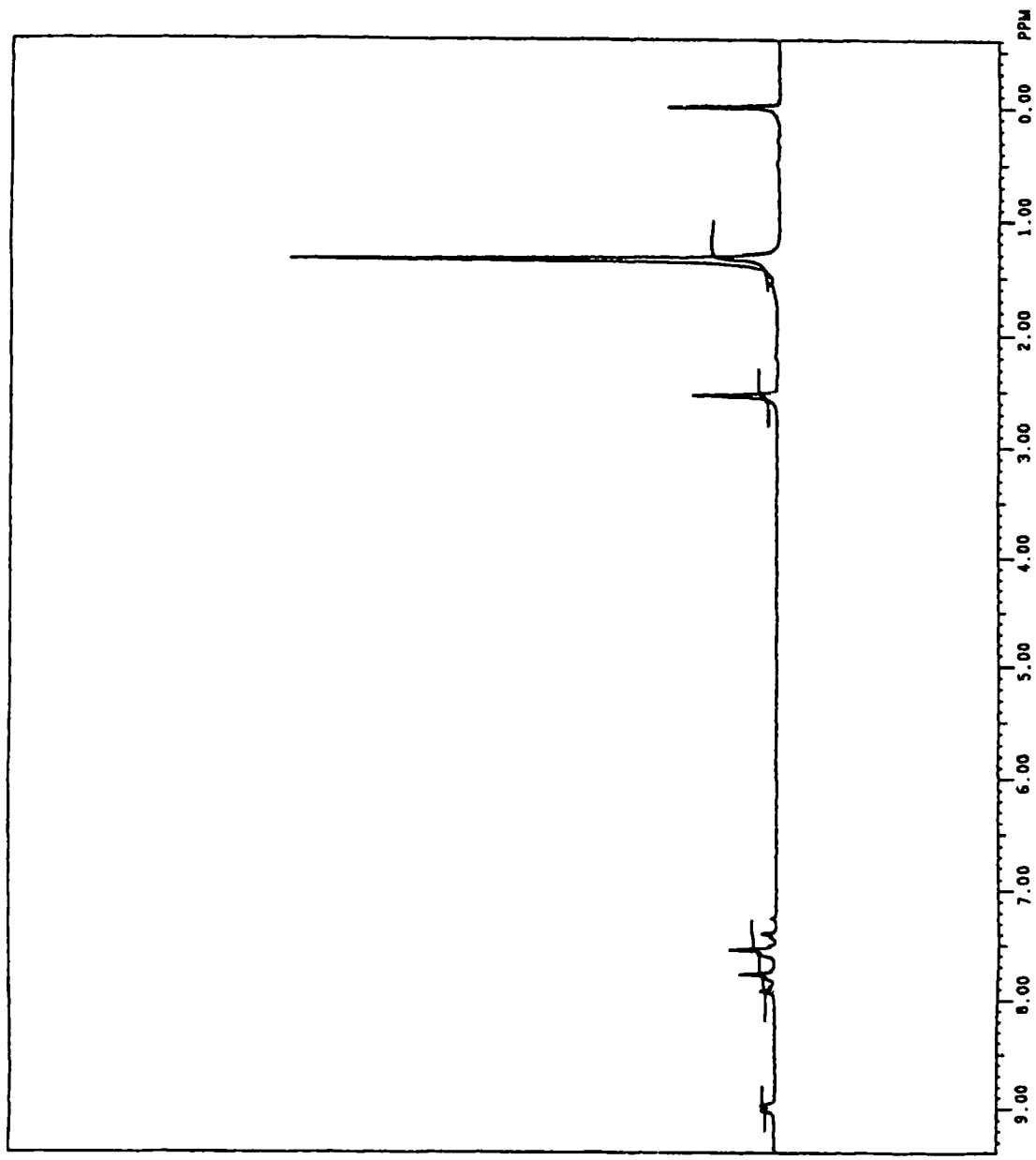
FIG. 8 is a $^1$H-NMR spectrum of the compound represented by the chemical formula (10).
Figure 9:
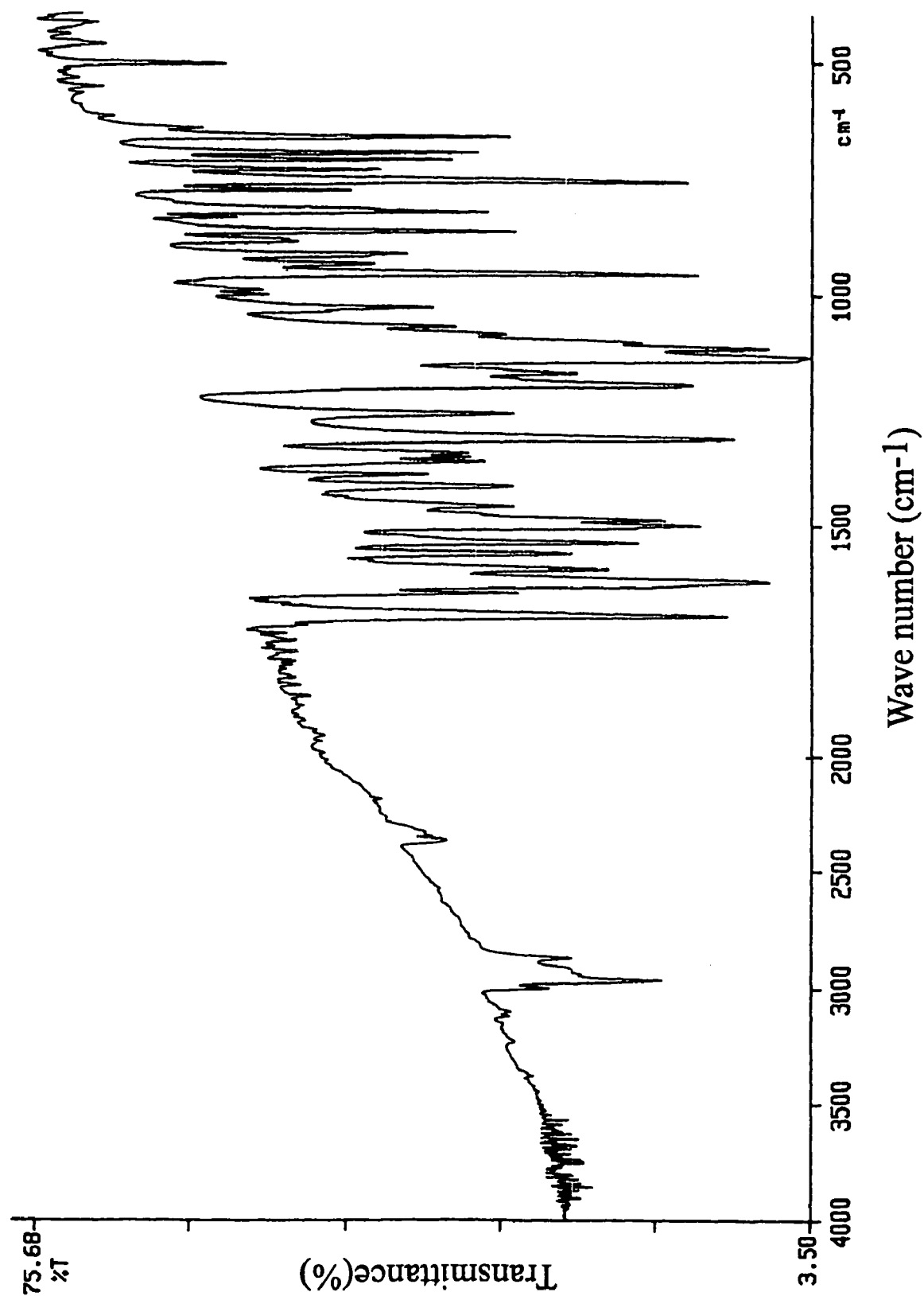
FIG. 9 is an IR spectrum of a compound represented by the chemical formula (11).
Figure 10:
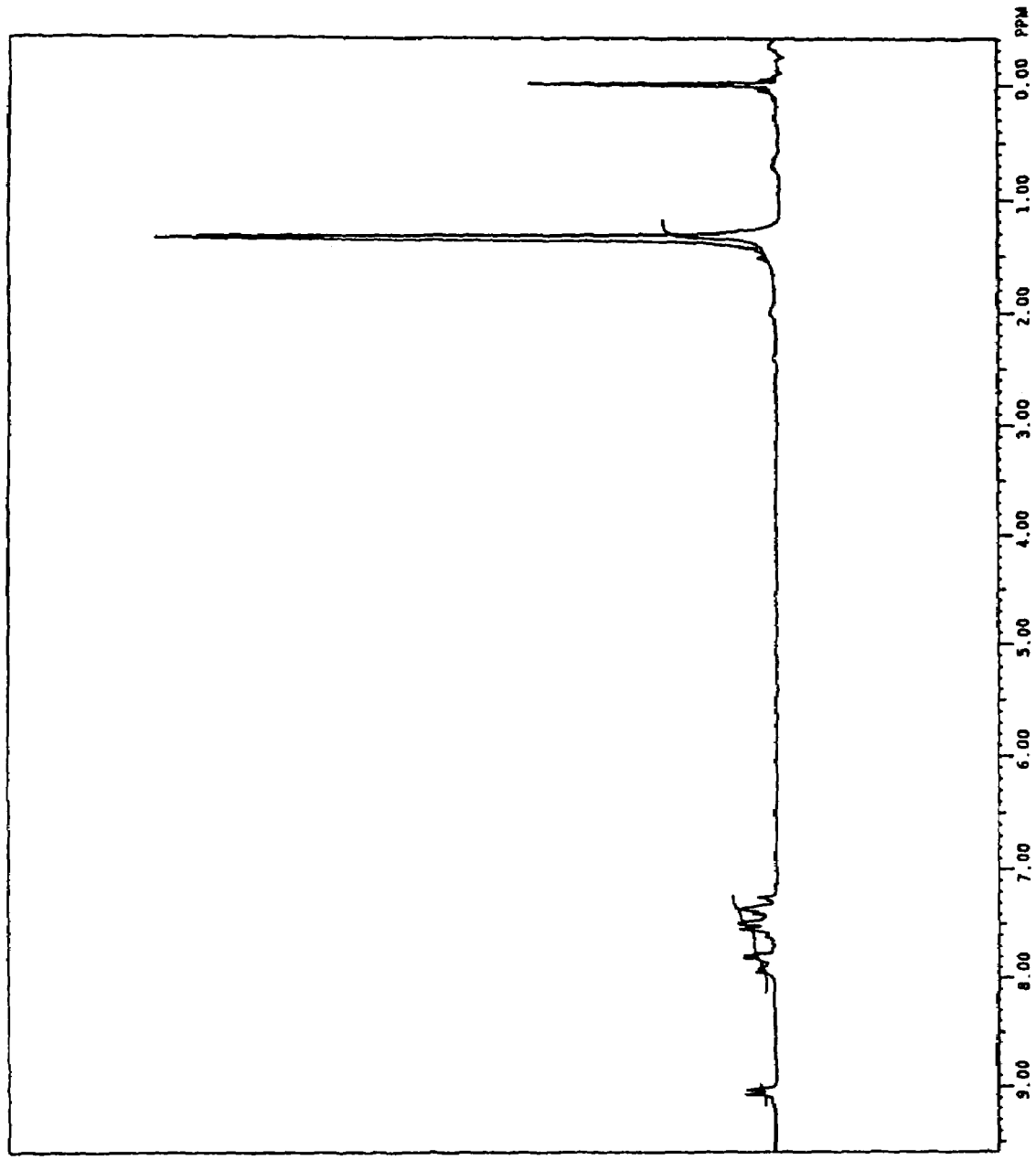
FIG. 10 is a $^1$H-NMR spectrum of the compound represented by the chemical formula (11).
Figure 11:
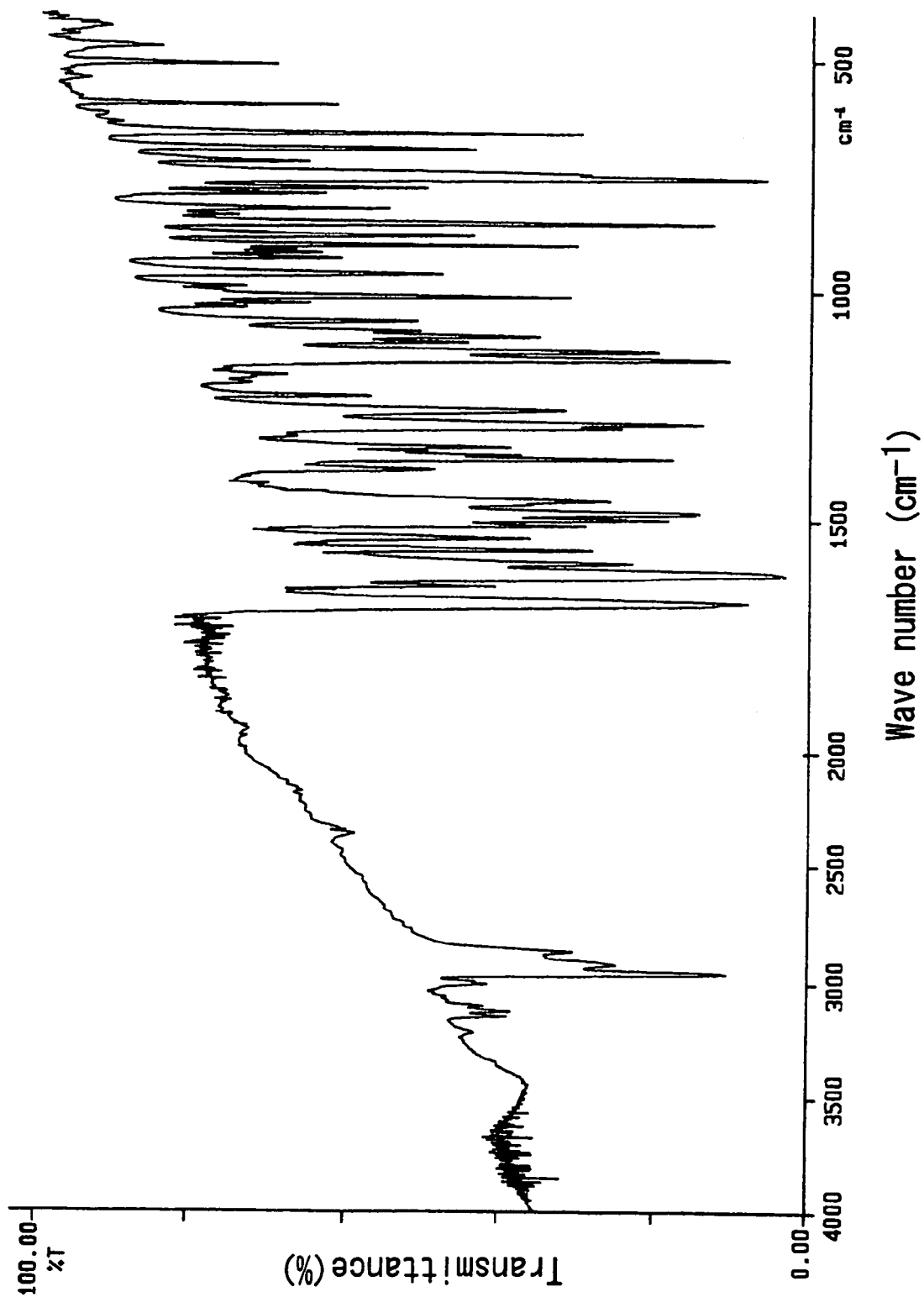
FIG. 11 is an IR spectrum of a compound represented by the chemical formula (12).
Figure 12:
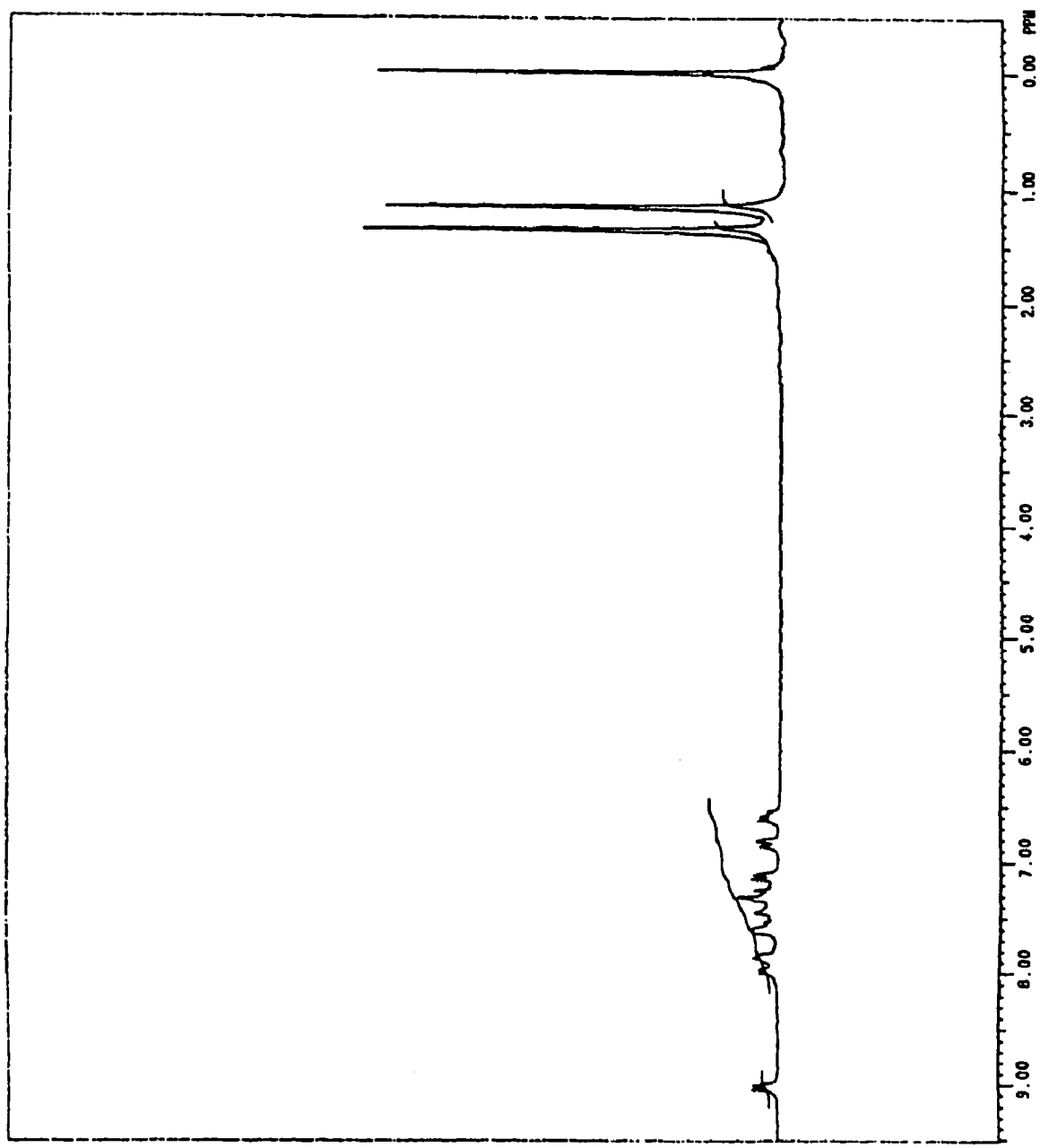
FIG. 12 is a $^1$H-NMR spectrum of the compound represented by the chemical formula (12).
Figure 13:
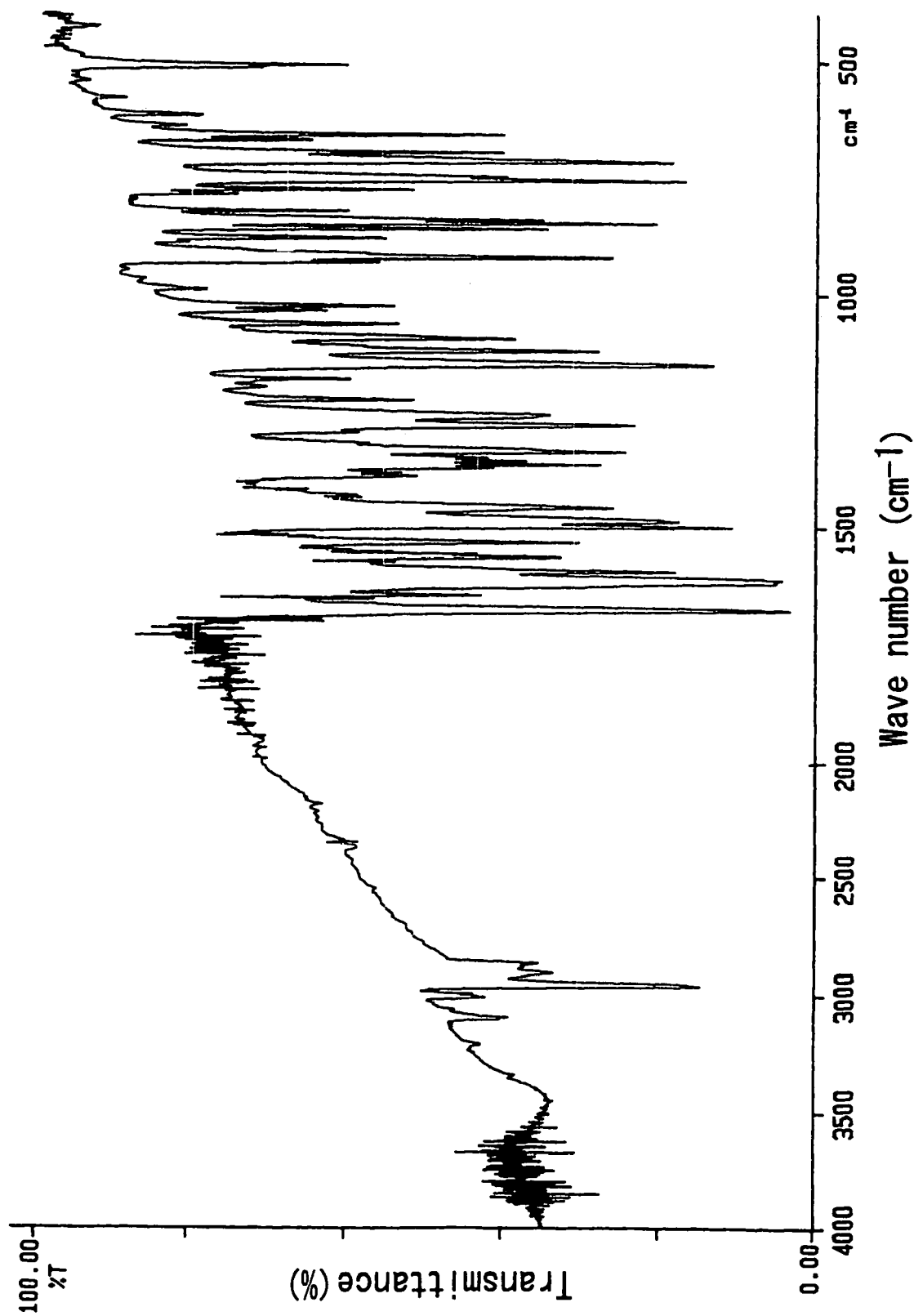
FIG. 13 is an IR spectrum of a compound represented by the chemical formula (13).
Figure 14:
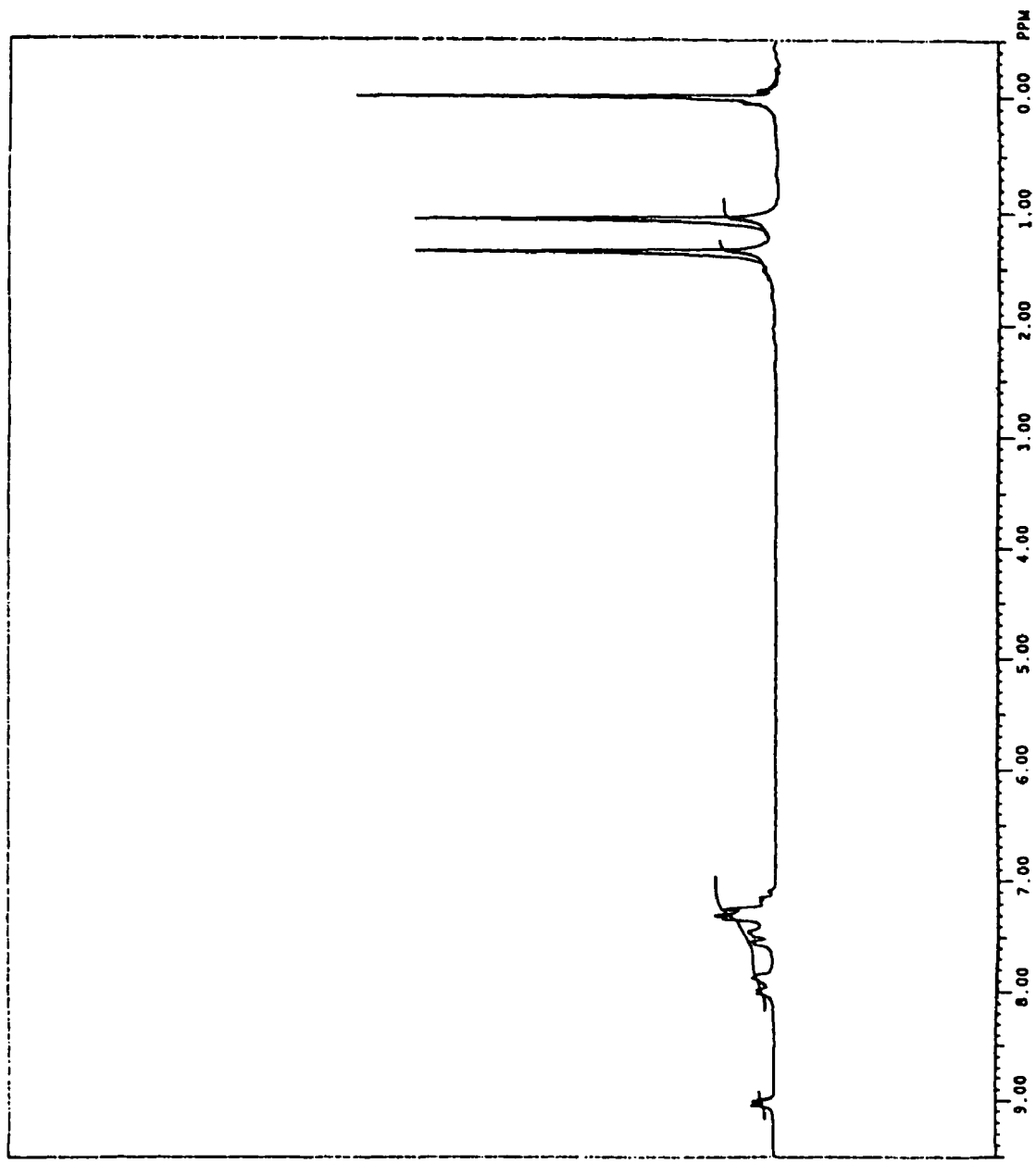
FIG. 14 is a $^1$H-NMR spectrum of the compound represented by the chemical formula (13).
Figure 15:
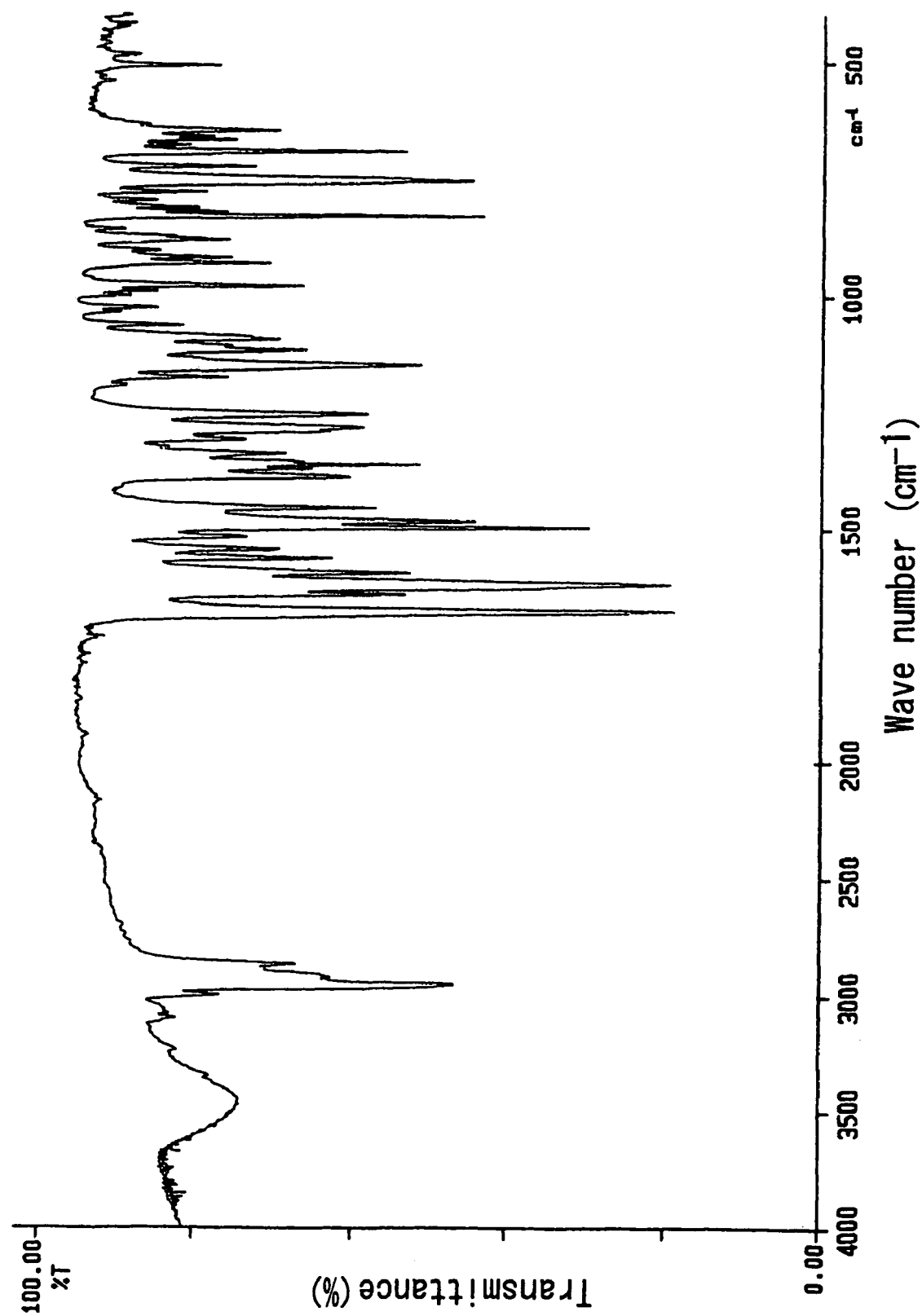
FIG. 15 is an IR spectrum of a compound represented by the chemical formula (14).
Figure 16:
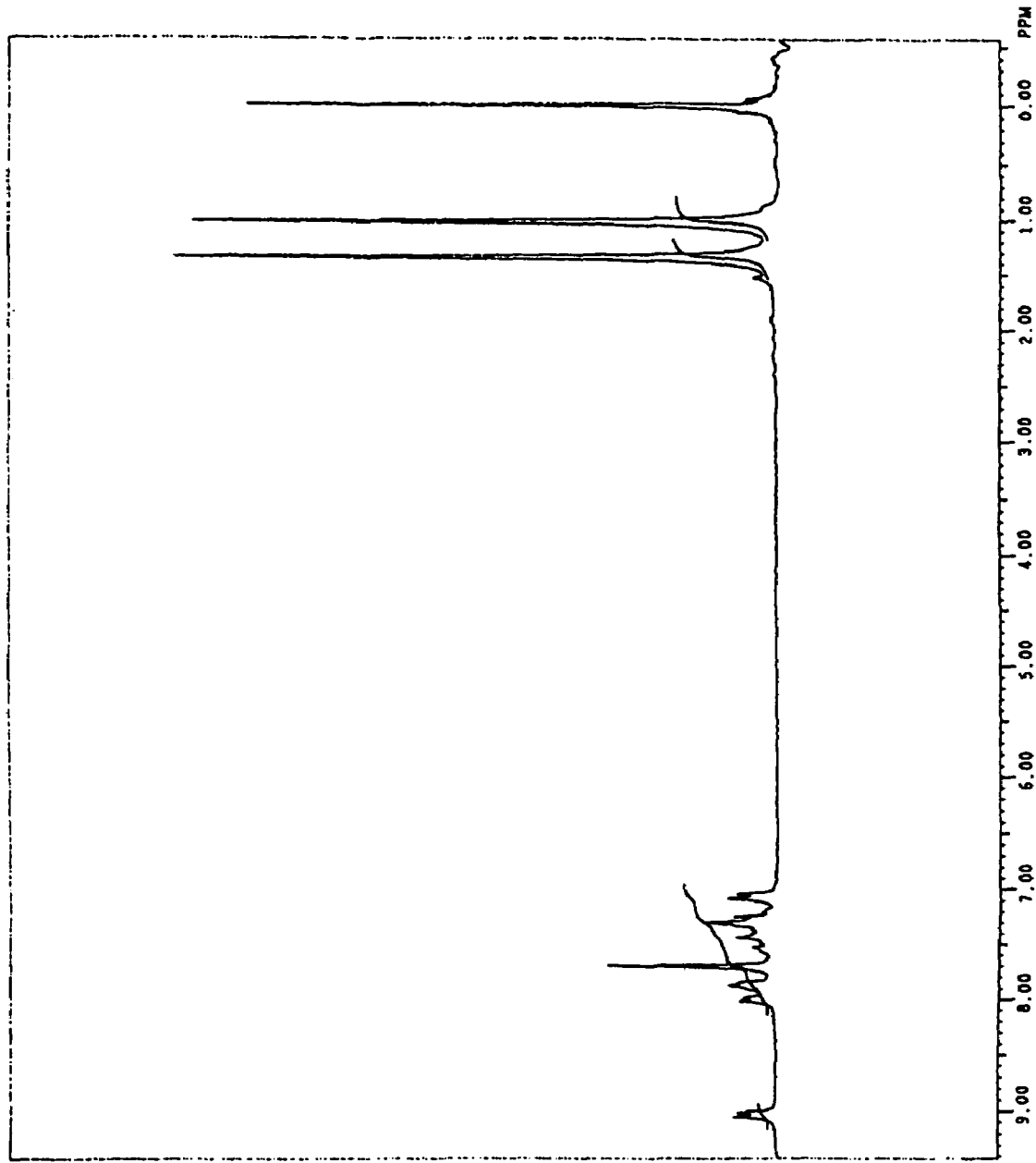
FIG. 16 is a $^1$H-NMR spectrum of the compound represented by the chemical formula (14).
Figure 17:
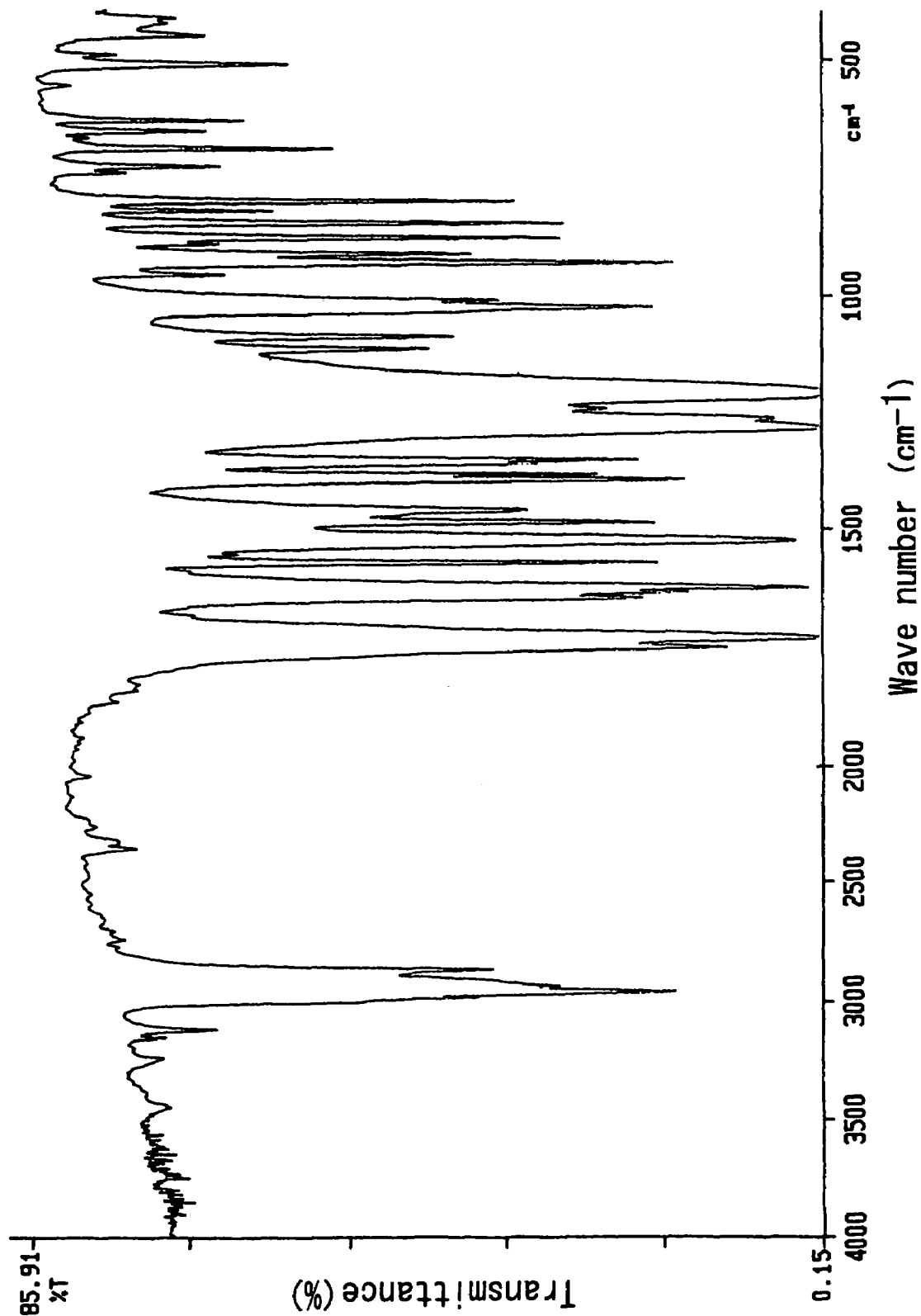
FIG. 17 is an IR spectrum of a compound represented by the chemical formula (15).
Figure 18:
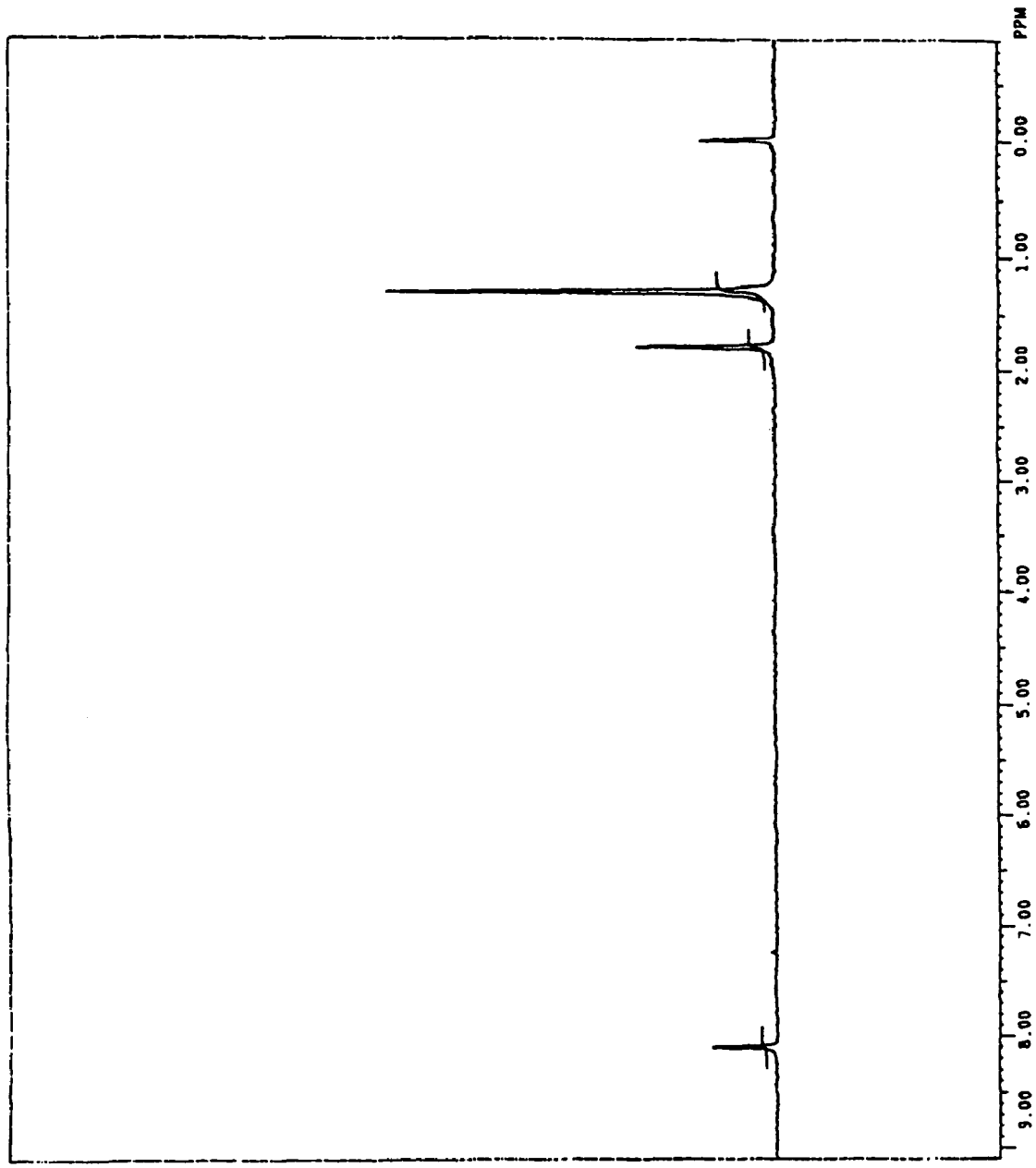
FIG. 18 is a $^1$H-NMR spectrum of the compound represented by the chemical formula (15).
Figure 19:
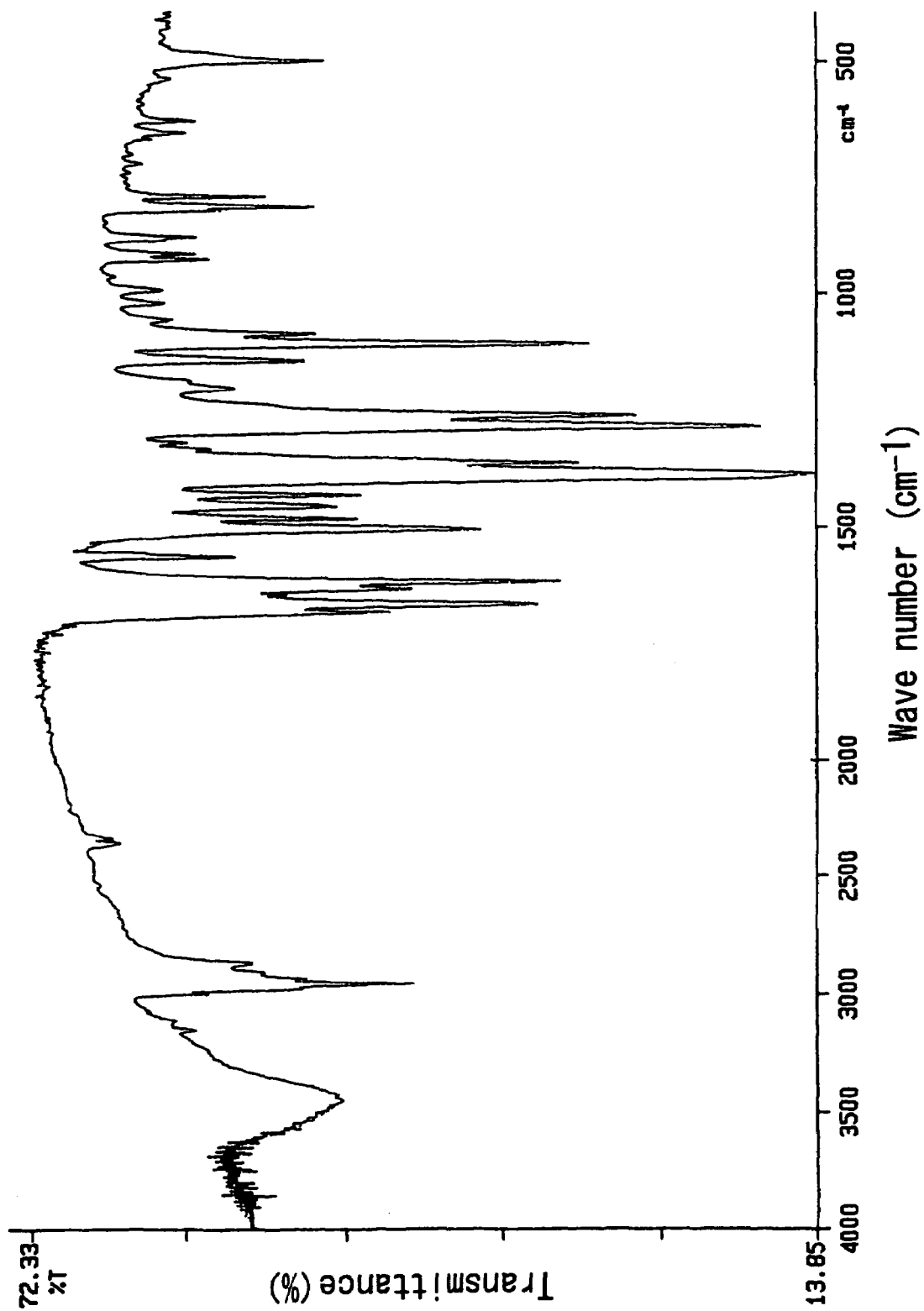
FIG. 19 is an IR spectrum of a compound represented by the chemical formula (16).
Figure 20:
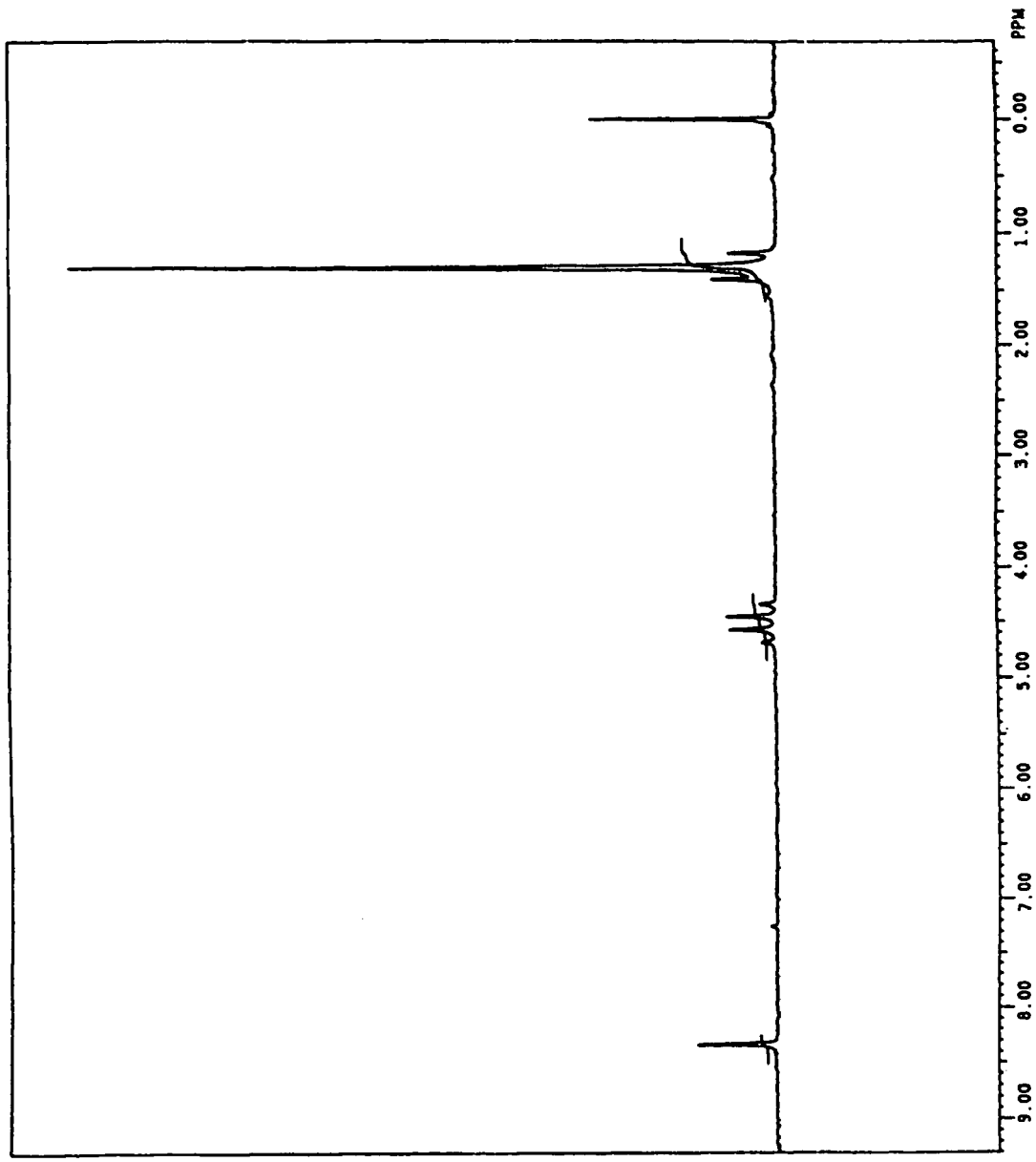
FIG. 20 is a $^1$H-NMR spectrum of the compound represented by the chemical formula (16).

Throughout the figures, the reference numeral 1 denotes an electroconductive substrate; the reference numeral 2 denotes a charge-generation layer; the reference numeral 3 denotes a charge-transfer layer; the reference numeral 4 denotes a photosensitive layer; the reference numerals 11 and 12 each denote an electrophotographic photoreceptor; the reference numeral 21 denotes an organic electroluminescence element; the reference numeral 22 denotes a first electrode; the reference numeral 25 denotes a luminescent layer; and the reference numeral 26 denotes a second electrode.

DETAILED DESCRIPTION OF PREFERRED EMBODIMENTS

The ring structure represented by W exhibits strong acidity and thus strong electron acceptability. Given this, the present inventors have designed a novel molecular skeleton in which the ring represented by W is connected via a double bond to a quinone ring, which is generally known to exhibit a strong electron acceptability. The dipole moment of this molecular skeleton must be large enough so that the generation of stable radicals, as in the case of diphenoquinone, is prevented.

The dipole moment of the molecular skeleton can readily be calculated by the molecular orbital method to be compared. Specifically, the molecular skeleton has a dipole moment (debye) of 0.001 or larger, preferably 0.01 or larger, and more preferably 0.1 or larger as determined by MOPAC/AM1 using the molecular skeleton bearing no substituents. In this manner, the resulting radicals have relatively short lives and are thus less likely to form electric traps. As a result, electron transfer can take place even in a low electric field, and the electron mobility is significantly enhanced in a strong electric field, as is the efficiency of electron movement.

The two interconnected ring structures, namely, the 6-membered ring and the ring represented by W, make the molecular skeleton of the above-described compound larger than that of the compound of the formula (24). This ensures a larger distance along which electrons can travel and thus facilitates movement of electrons within the molecule. As a result, the compound exhibits a high electron mobility.

In contrast to diphenoquinone compounds, asymmetric configuration of its conjugated system ensures the above compound's weak ability to exhibit color, so that it hardly absorbs light. Furthermore, the ring represented by W attached to one end of the quinone ring makes its molecular structure asymmetric. This facilitates the compatibility of the compound with resin, so that it can be dispersed in resin at a high concentration. These functions can readily be varied as desired by using different combinations of substituents. In this manner, it is possible to optimize the compatibility with resin or control the speed or the amount of electron movement.

In a preferred embodiment, the present invention provides a compound represented by the following general formula (2):

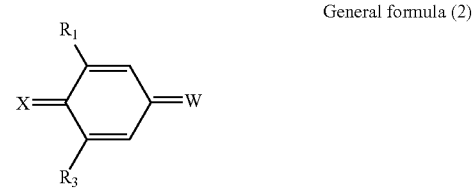

General formula (2)

wherein $R_1$ and $R_3$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and W is a 4- to 8-membered ring and has the structure shown in the following general formula (2') that replaces the general formula (2) above:

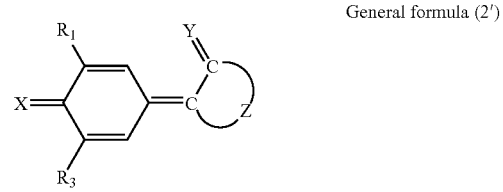

General formula (2')

wherein Y is oxygen or sulfur, and Z is a structure that has 2 or more atoms and forms a part of the ring.

Introduction of at least one alkyl group having 1 to 6 carbon atoms or at least one phenyl group into the substituents $R_1$ and $R_3$ can provide the molecular skeleton with the effect to push out electrons. In this manner, the polarization of the molecule, and thus the electron mobility within the molecule, is increased. The substituents that exhibit high compatibility with resin may be used in combination.

In a particularly preferred embodiment, the present invention provides a compound represented by the following general formula (3):

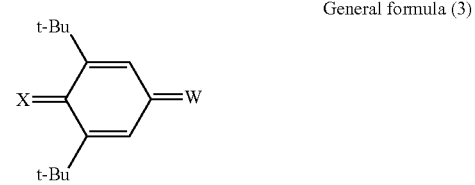

General formula (3)

wherein X is selected from the group consisting of oxygen, sulfur, and $=C(CN)_2$; and W is a 4- to 8-membered ring and has the structure shown in the following general formula (3') that replaces the general formula (3) above:

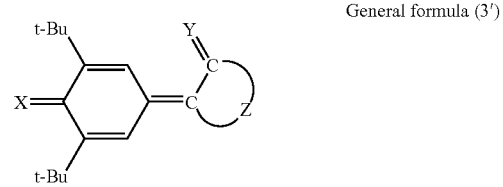

General formula (3')

wherein Y is oxygen or sulfur, and Z is a structure that has 2 or more atoms and forms a part of the ring.

Introduction of the bulky t-Bu group into the quinone ring can increase the compatibility with resin and provide the molecular skeleton with the effect to push out electrons. In this manner, the polarization of the molecule is increased and a compound with significantly increased electron mobility is obtained.

The present invention provides a compound represented by the following general formula (4):

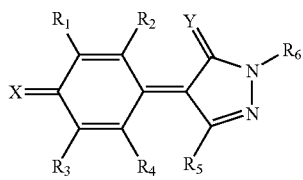

General formula (4)

wherein $R_1$ through $R_6$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and Y is oxygen or sulfur.

By introducing a phenyl, thienyl, or furil group, each being an aromatic 6 π electron system, into the substituent $R_5$ in the general formula (4) above, the molecular skeleton can be stabilized.

The present invention provides a compound represented by the following general formula (5):

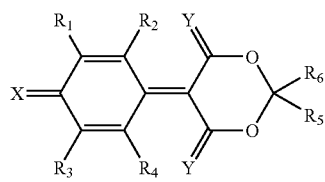

General formula (5)

wherein $R_1$ through $R_6$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and Y is oxygen or sulfur.

The present invention provides a compound represented by the following general formula (6):

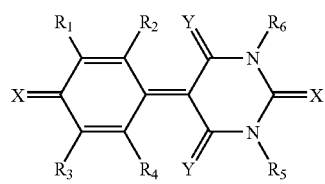

General formula (6)

wherein $R_1$ through $R_6$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and Y is oxygen or sulfur.

The present invention provides a compound represented by the following general formula (44):

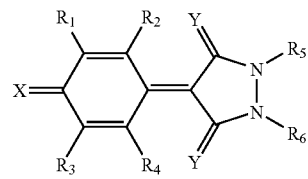

General formula (44)

wherein $R_1$ through $R_6$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and Y is oxygen or sulfur.

The present invention provides a compound represented by the following chemical formula (7):

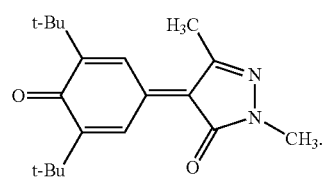

Chemical formula (7)

The present invention provides a compound represented by the following chemical formula (8):

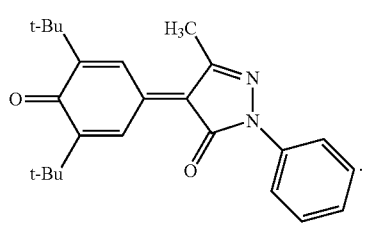

Chemical formula (8)

The present invention provides a compound represented by the following chemical formula (9):

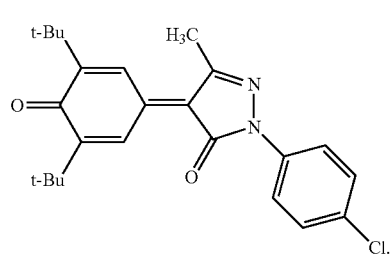

Chemical formula (9)

The present invention provides a compound represented by the following chemical formula (10):

Chemical formula (10)

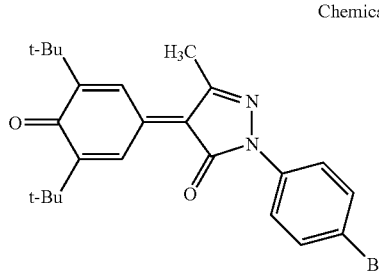

The present invention provides a compound represented by the following chemical formula (11):

Chemical formula (11)

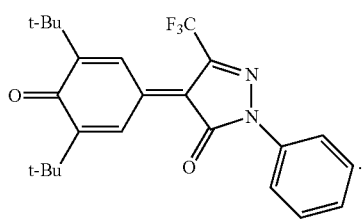

The present invention provides a compound represented by the following chemical formula (12):

Chemical formula (12)

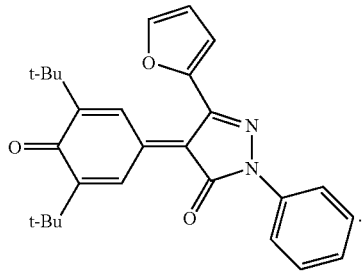

The present invention provides a compound represented by the following chemical formula (13):

Chemical formula (13)

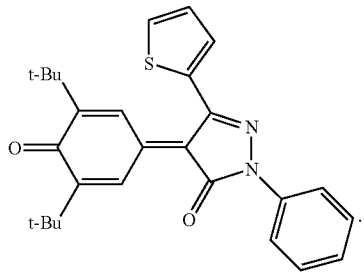

The present invention provides a compound represented by the following chemical formula (14):

Chemical formula (14)

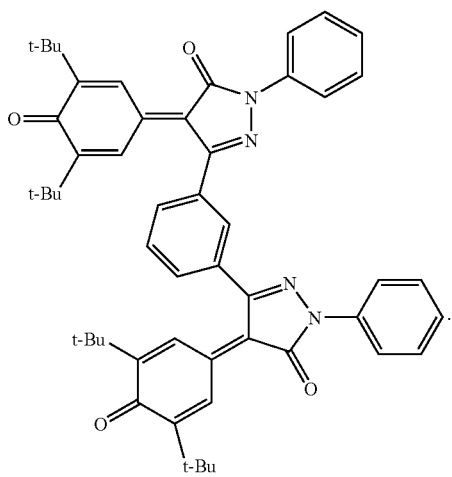

The present invention provides a compound represented by the following chemical formula (15):

Chemical formula (15)

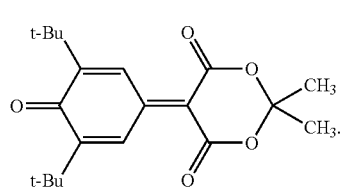

The present invention provides a compound represented by the following chemical formula (16):

Chemical formula (16)

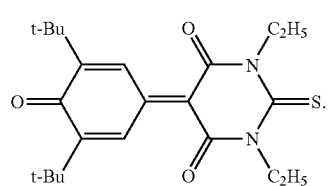

The present invention provides a compound represented by the following chemical formula (29):

Chemical formula (29)

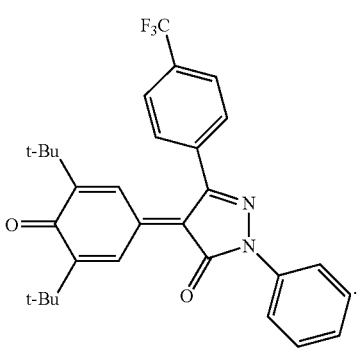

The present invention provides a compound represented by the following chemical formula (30):

Chemical formula (30)

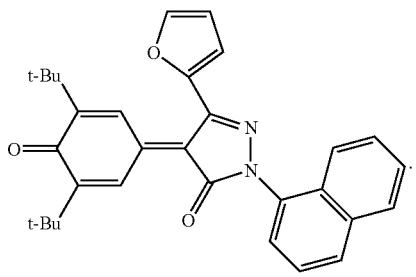

The present invention provides a compound represented by the following chemical formula (31):

Chemical formula (31)

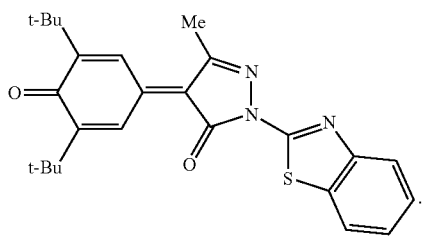

The present invention provides a compound represented by the following chemical formula (32):

Chemical formula (32)

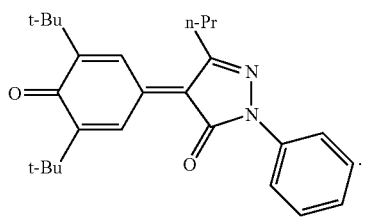

The present invention provides a compound represented by the following chemical formula (33):

Chemical formula (33)

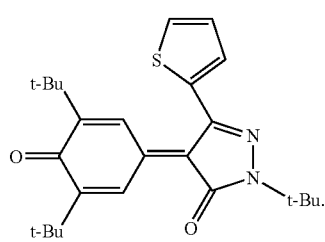

The present invention provides a compound represented by the following chemical formula (34):

Chemical formula (34)

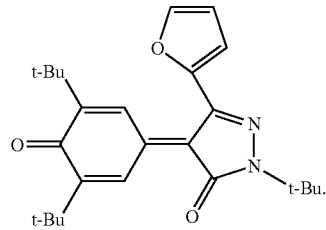

The present invention provides a compound represented by the following chemical formula (35):

Chemical formula (35)

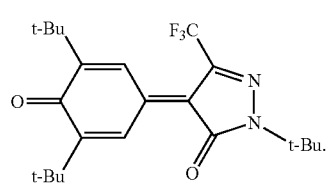

The present invention provides a compound represented by the following chemical formula (36):

Chemical formula (36)

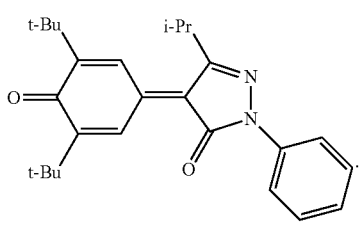

The present invention provides a compound represented by the following chemical formula (37):

Chemical formula (37)

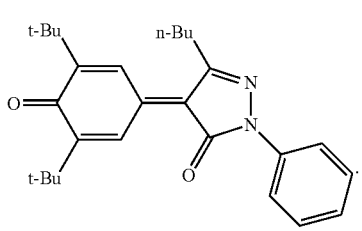

The present invention provides a compound represented by the following chemical formula (38):

Chemical formula (38)

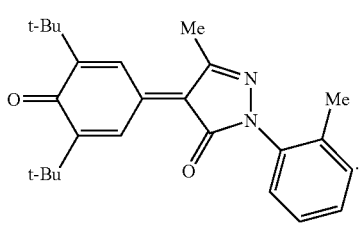

The present invention provides a compound represented by the following chemical formula (39):

Chemical formula (39)

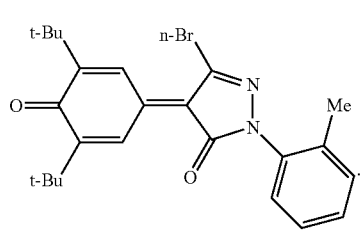

The present invention provides a compound represented by the following chemical formula (40):

Chemical formula (40)

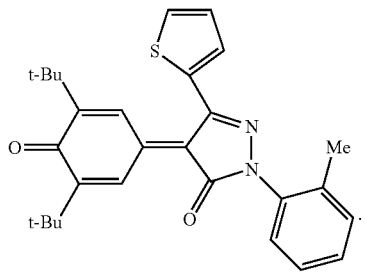

The present invention provides a compound represented by the following chemical formula (41):

Chemical formula (41)

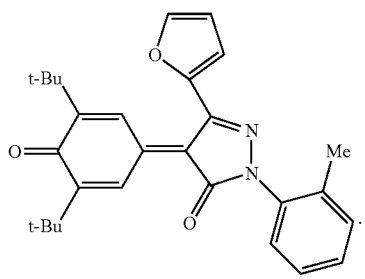

The present invention provides a compound represented by the following chemical formula (42):

Chemical formula (42)

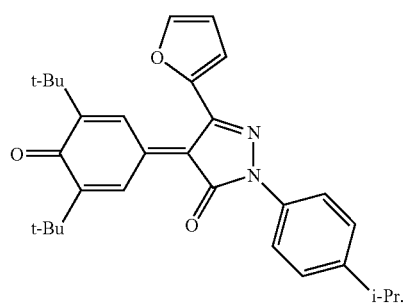

The present invention provides a compound represented by the following chemical formula (43):

Chemical formula (43)

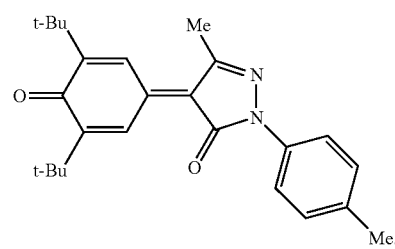

The present invention provides a compound represented by the following chemical formula (45):

Chemical formula (45)

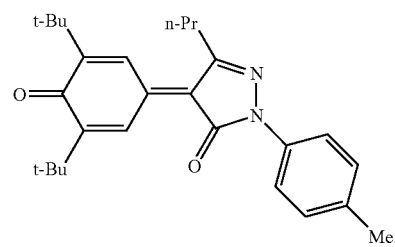

The present invention provides a compound represented by the following chemical formula (46):

Chemical formula (46)

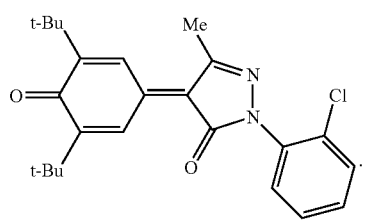

The present invention provides a compound represented by the following chemical formula (47):

Chemical formula (47)

The present invention provides a compound represented by the following chemical formula (48):

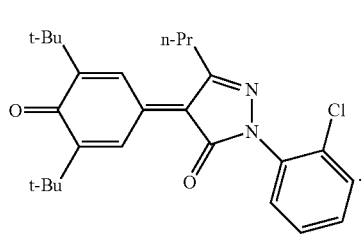

Chemical formula (48)

The present invention provides a compound represented by the following chemical formula (49):

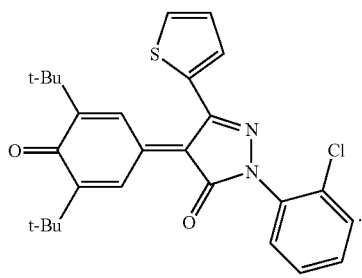

Chemical formula (49)

The present invention provides a compound represented by the following chemical formula (50):

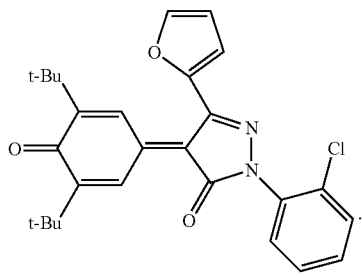

Chemical formula (50)

The present invention provides a compound represented by the following chemical formula (51):

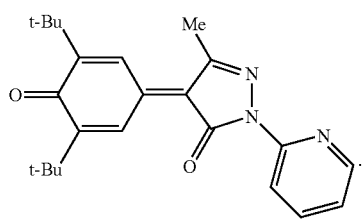

Chemical formula (51)

The present invention provides a compound represented by the following chemical formula (52):

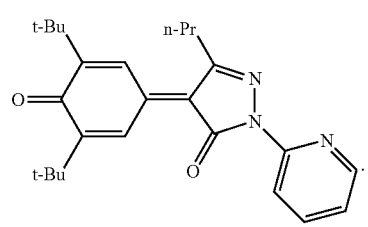

Chemical formula (52)

The present invention provides a compound represented by the following chemical formula (53):

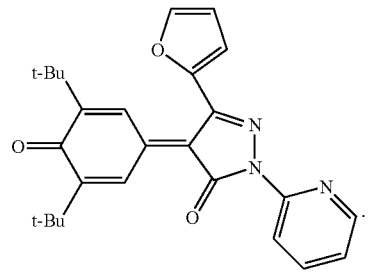

Chemical formula (53)

The present invention provides a compound represented by the following chemical formula (54):

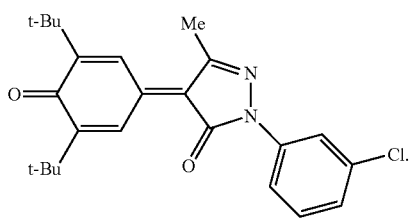

Chemical formula (54)

The present invention provides a compound represented by the following chemical formula (55):

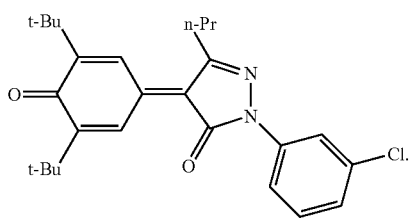

Chemical formula (55)

The present invention provides a compound represented by the following chemical formula (56):

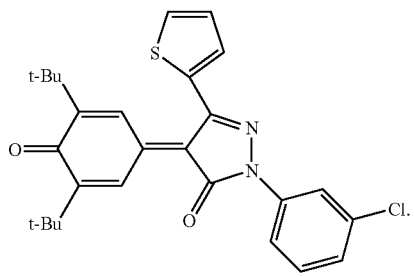

Chemical formula (56)

The present invention provides a compound represented by the following chemical formula (57):

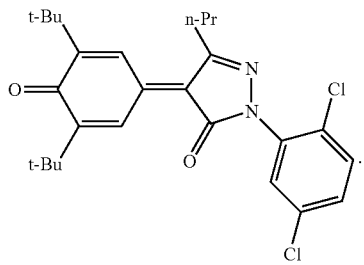

Chemical formula (57)

The present invention provides a compound represented by the following chemical formula (58):

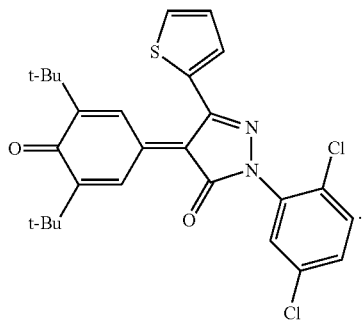

Chemical formula (58)

The present invention provides a compound represented by the following chemical formula (59):

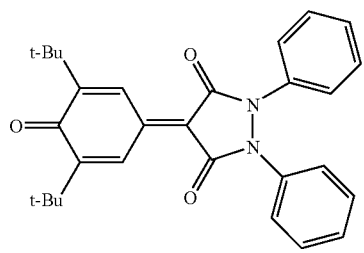

Chemical formula (59)

The present invention provides a compound represented by the following chemical formula (60):

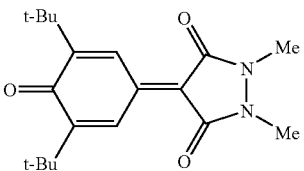

Chemical formula (60)

In each of the chemical formulae (7) through (16), (29) through (43), and (45) through (60), t-Bu represents a tertiary butyl group (($CH_3$)$_3$C—), n-Bu represents a straight-chained butyl group ($CH_3CH_2CH_2CH_2$—), Me represents a methyl group ($CH_3$—), n-Pr represents a straight chained propyl group ($CH_3CH_2CH_2$—), and i-Pr represents an iso-propyl group (($CH_3$)$_2$CH—).

The present invention provides a process for producing a compound represented by the following general formula (1):

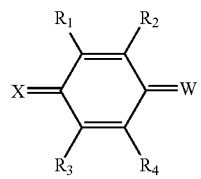

General formula (1)

wherein $R_1$ to $R_4$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and =C(CN)$_2$; and W is a 4- to 8-membered ring and has the structure shown in the following general formula (1') that replaces the general formula (1) above:

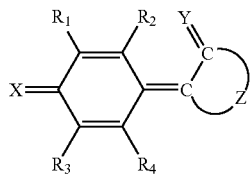

General formula (1')

wherein Y is oxygen or sulfur, and Z is a structure that has 2 or more atoms and forms a part of the ring, the process involving the step of reacting in the presence of a base catalyst a benzoquinone compound represented by the following general formula (17):

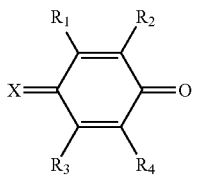

General formula (17)

wherein $R_1$ to $R_4$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; and X is selected from the group consisting of oxygen, sulfur, and $=C(CN)_2$, with a compound having an active methylene represented by the following general formula (18):

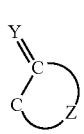

General formula (18)

wherein the compound is a 4- to 8-membered ring; Y is oxygen or sulfur; and Z is a structure that has 2 or more atoms and forms a part of the ring. In this manner, the electron-transfer compound can be readily produced. A solvent which is inert against benzoquinone compound and the compound having an active methylene may be added along with the base catalyst to adjust the reaction rate.

The present invention provides a process for producing a compound represented by the following general formula (2):

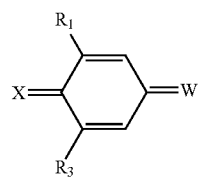

General formula (2)

wherein $R_1$ and $R_3$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and W is a 4- to 8-membered ring and has the structure shown in the following general formula (2') that replaces the general formula (2) above:

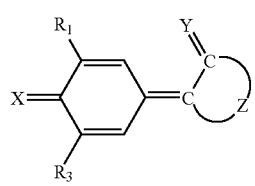

General formula (2')

wherein Y is oxygen or sulfur, and Z is a structure that has 2 or more atoms and forms a part of the ring, the process involving the step of reacting in the presence of a base catalyst a benzoquinone compound represented by the following general formula (19):

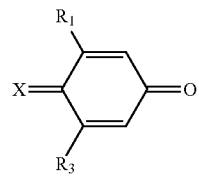

General formula (19)

wherein $R_1$ and $R_3$ are each independently selected from the group consisting of hydrogen, alkyl with 1 to 6 carbon atoms, and phenyl; and X is selected from the group consisting of oxygen, sulfur, and $=C(CN)_2$, with a compound having an active methylene represented by the following general formula (18):

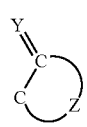

General formula (18)

wherein the compound is a 4- to 8-membered ring; Y is oxygen or sulfur; and Z is a structure having 2 or more atoms and forms a part of the ring.

The present invention provides a process for producing a compound represented by the following general formula (3):

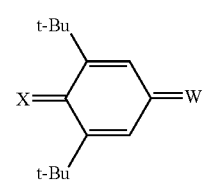

General formula (3)

wherein X is selected from the group consisting of oxygen, sulfur, and $=C(CN)_2$; and W is a 4- to 8-membered ring and has the structure shown in the following general formula (3') that replaces the general formula (3) above:

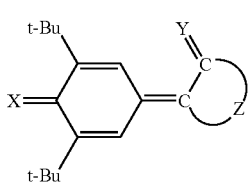

General formula (3')

wherein Y is oxygen or sulfur, and Z is a structure that has 2 or more atoms and forms apart of the ring, the process involving the step of reacting in the presence of a base catalyst a benzoquinone compound represented by the following general formula (20):

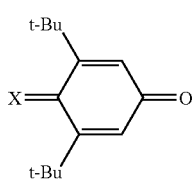

General formula (20)

wherein X is selected from the group consisting of oxygen, sulfur, and =C(CN)$_2$, with a compound having an active methylene represented by the following general formula (18):

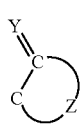

General formula (18)

wherein the compound is a 4- to 8-membered ring; Y is oxygen or sulfur; and Z is a structure having 2 or more atoms and forms a part of the ring.

The present invention provides a process for producing a compound represented by the following general formula (4):

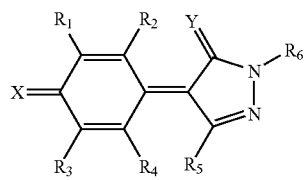

General formula (4)

wherein $R_1$ through $R_6$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and =C(CN)$_2$; and Y is oxygen or sulfur, the process involving the step of reacting in the presence of a base catalyst a benzoquinone compound represented by the following general formula (17):

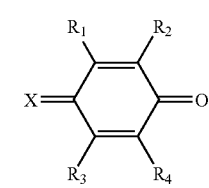

General formula (17)

wherein $R_1$ through $R_4$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; and X is selected from the group consisting of oxygen, sulfur, and =C(CN)$_2$, with a compound having an active methylene represented by the following general formula (21):

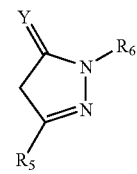

General formula (21)

wherein $R_5$ and $R_6$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; and Y is oxygen or sulfur.

The present invention provides a process for producing a compound represented by the following general formula (5):

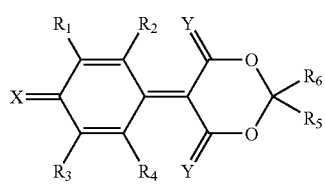

General formula (5)

wherein $R_1$ through $R_6$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and =C(CN)$_2$; and Y is oxygen or sulfur, the process involving the step of reacting in the presence of a base catalyst a benzoquinone compound represented by the following general formula (17):

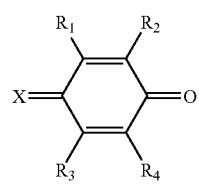

General formula (17)

wherein $R_1$ through $R_4$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; and X is selected from the group consisting of oxygen, sulfur, and =C(CN)$_2$, with a compound having an active methylene represented by the following general formula (22):

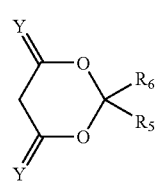

General formula (22)

wherein $R_5$ and $R_6$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; and Y is oxygen or sulfur.

The present invention provides a process for producing a compound represented by the following general formula (6):

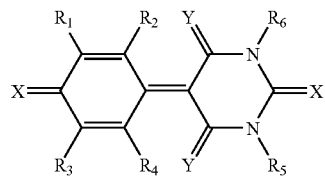

General formula (6)

wherein $R_1$ through $R_6$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and Y is oxygen or sulfur, the process involving the step of reacting in the presence of a base catalyst a benzoquinone compound represented by the following general formula (17):

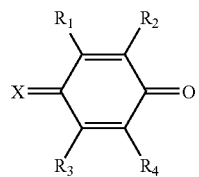

General formula (17)

wherein $R_1$ through $R_4$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; and X is selected from the group consisting of oxygen, sulfur, and $=C(CN)_2$, with a compound having an active methylene represented by the following general formula (23):

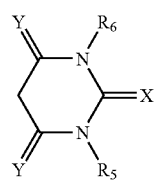

General formula (23)

wherein $R_5$ and $R_6$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and Y is oxygen or sulfur.

The present invention provides a process for producing a compound represented by the following general formula (44):

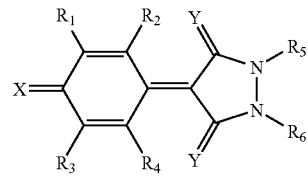

General formula (44)

wherein $R_1$ through $R_6$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and Y is oxygen or sulfur, the process involving the step of reacting in the presence of a base catalyst a benzoquinone compound represented by the following general formula (17):

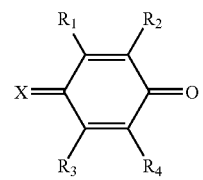

General formula (17)

wherein $R_1$ through $R_4$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; and X is selected from the group consisting of oxygen, sulfur, and $=C(CN)_2$, with a compound having an active methylene represented by the following general formula (61):

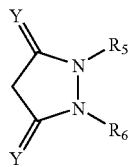

General formula (61)

wherein $R_5$ and $R_6$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, and carboxylic acid; and Y is oxygen or sulfur.

The present invention provides a process for producing a compound in which the benzoquinone compound is reacted with the compound having an active methylene in the presence of the base catalyst and one or a mixture of two or more solvents selected from the group consisting of water, alcohol, and saturated aliphatic hydrocarbon solvent.

The present invention provides a process for producing a compound in which the benzoquinone compound is reacted with the compound having an active methylene in the presence of the base catalyst and a solvent that needs to be used in amounts of 50 ml or more to dissolve 1 g of the compound of the general formulae (1) through (6) and (44).

The present invention provides an electron-transfer agent comprising a resin containing as a charge-transfer material a compound represented by the following general formula (1):

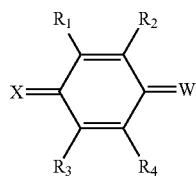

General formula (1)

wherein $R_1$ through $R_4$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and W is a 4- to 8-membered ring and has the structure shown in the following general formula (1') that replaces the general formula (1) above:

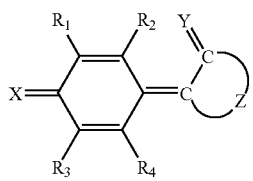

General formula (1')

wherein Y is oxygen or sulfur, and Z is a structure that has 2 or more atoms and forms a part of the ring.

The present invention provides an electron-transfer agent comprising a resin containing as a charge-transfer material a compound represented by the following general formula (2):

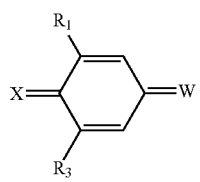

General formula (2)

wherein $R_1$ and $R_3$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and W is a 4- to 8-membered ring having the structure shown in the following general formula (2') that replaces the general formula (2) above:

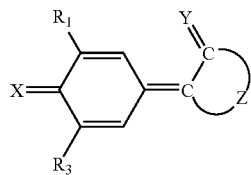

General formula (2')

wherein Y is oxygen or sulfur, and Z is a structure that has 2 or more atoms and forms a part of the ring.

The present invention provides an electron-transfer agent comprising a resin containing as a charge-transfer material a compound represented by the following general formula (3):

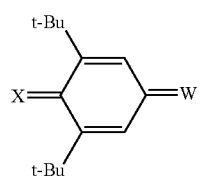

General formula (3)

wherein X is selected from the group consisting of oxygen, sulfur, and $=C(CN)_2$; and W is a 4- to 8-membered ring and has the structure shown in the following general formula (3') that replaces the general formula (3) above:

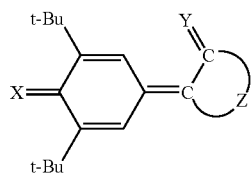

General formula (3')

wherein Y is oxygen or sulfur, and Z is a structure that has 2 or more atoms and forms a part of the ring.

The present invention provides an electrophotographic photoreceptor comprising an electroconductive substrate having at least a photosensitive layer disposed thereon, wherein the photosensitive layer contains as a charge-transfer material a compound represented by the following general formula (1):

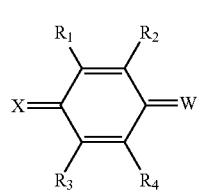

General formula (1)

wherein $R_1$ through $R_4$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and =C(CN)$_2$; and W is a 4- to 8-membered ring and has the structure shown in the following general formula (1') that replaces the general formula (1) above:

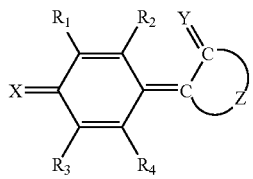

General formula (1')

wherein Y is oxygen or sulfur, and Z is a structure that has 2 or more atoms and forms a part of the ring.

As described above, the use of the compound, which has a high electron mobility and high compatibility with resin, makes it possible to provide highly sensitive electrophotographic photoreceptors.

The present invention provides an electrophotographic photoreceptor, comprising an electroconductive substrate having at least one photosensitive layer disposed thereon, wherein the photosensitive layer contains as a charge-transfer material a compound represented by the following general formula (2):

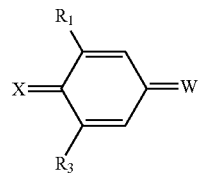

General formula (2)

wherein R$_1$ and R$_3$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and =C(CN)$_2$; and W is a 4- to 8-membered ring and has the structure shown in the following general formula (2') that replaces the general formula (2) above:

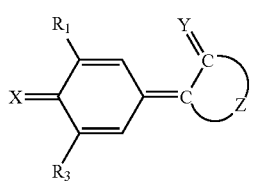

General formula (2')

wherein Y is oxygen or sulfur, and Z is a structure that has 2 or more atoms and forms a part of the ring.

As described above, the use of the compound, which has a high electron mobility and high compatibility with resin, makes it possible to provide electrophotographic photoreceptors with even higher sensitivity.

The present invention provides an electrophotographic photoreceptor comprising an electroconductive substrate having at least a photosensitive layer disposed thereon, wherein the photosensitive layer contains as a charge-transfer material a compound represented by the following general formula (3):

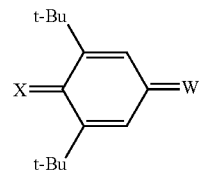

General formula (3)

wherein X is selected from the group consisting of oxygen, sulfur, and =C(CN)$_2$; and W is a 4- to 8-membered ring and has the structure shown in the following general formula (3') that is to replace the general formula (3) above:

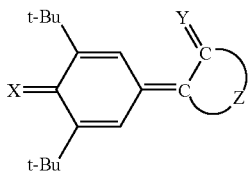

General formula (3')

wherein Y is oxygen or sulfur, and Z is a structure that has 2 or more atoms and forms a part of the ring.

As described above, the use of the compound, which has a high electron mobility and high compatibility with resin, makes it possible to provide extremely sensitive electrophotographic photoreceptors.

The present invention provides an organic electroluminescence element including an organic film that can at least emit light and is disposed between a pair of electrodes, wherein the organic film contains a compound represented by the following general formula (1):

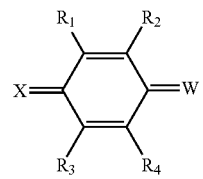

General formula (1)

wherein R$_1$ to R$_4$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and =C(CN)$_2$; and W is a 4- to 8-membered ring and has the structure shown in the following general formula (1') that replaces the general formula (1) above:

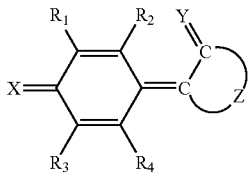

General formula (1')

wherein Y is oxygen or sulfur, and Z is a structure that has 2 or more atoms and forms a part of the ring.

The present invention provides an organic electroluminescence element including an organic film that can at least emit light and is arranged between a pair of electrodes, wherein the organic film contains a compound represented by the following general formula (2):

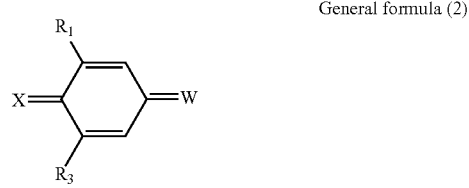

General formula (2)

wherein $R_1$ and $R_3$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and W is a 4- to 8-membered ring and has the structure shown in the following general formula (2') that replaces the general formula (2) above:

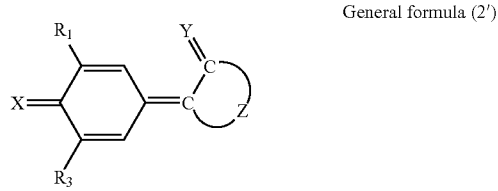

General formula (2')

wherein Y is oxygen or sulfur, and Z is a structure that has 2 or more atoms and forms a part of the ring.

The present invention provides an organic electroluminescence element including an organic film that can at least emit light and is arranged between a pair of electrodes, wherein the organic film contains a compound represented by the following general formula (3):

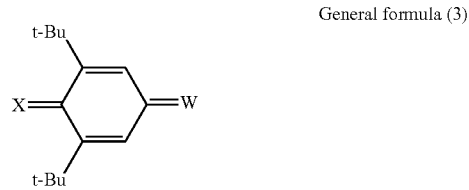

General formula (3)

wherein X is selected from the group consisting of oxygen, sulfur, and $=C(CN)_2$; and W is a 4- to 8-membered ring and has the structure shown in the following general formula (3') that replaces the general formula (3) above:

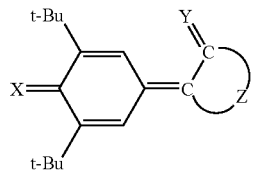

General formula (3')

wherein Y is oxygen or sulfur, and Z is a structure that has 2 or more atoms and forms a part of the ring.

The substituent represented by W in the general formulae (1) through (3) above does not include those represented by the following general formula (28):

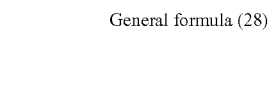

General formula (28)

wherein R' is selected from the group consisting of hydrogen, cyano, nitro, halogen, hydroxyl, alkyl, allyl, amide, amino, acyl, alkenyl, alkynyl, carboxyl, carbonyl, and carboxylic acid.

As described above, not only does the compound of the present invention exhibit a high electron mobility, but it also makes it possible to design a proper molecular structure depending on functions required for the material for an electrophotographic photoreceptor or organic electroluminescence element that makes use of electron-transfer materials.

In cases where the substituents $R_1$ through $R_6$ in the above general formulae (1) through (6) and (44) are each selected from alkyl, aryl, heterocyclic ring, ester, alkoxy, aralkyl, allyl, amide, amino, acyl, alkenyl, alkynyl, carboxyl, carbonyl, and carboxylic acid, these substituents may be modified by other substituents. The modified substituents are also encompassed by the scope of the present invention. Among the substituents $R_1$ through $R_6$, $R_1$ and $R_2$ may link together to form a ring, as may $R_3$ and $R_4$.

The substituents $R_1$ through $R_6$ may be different from one another, or two or more of the substituents $R_1$ through $R_6$ may be identical to one another.

The substituent W, a 4- to 8-membered cyclic compound shown in the general formulae (1) through (3), may condense with other cyclic compounds and may form a fused ring. These fused rings are also encompassed by the scope of the present invention. The present invention further encompasses the case where the structure Z includes one or more of heteroatoms, the case where the structure Z consists only of carbon atoms, and the case where the structure Z is modified by a substituent.

Preferred embodiments of electron-transfer compounds, processes for producing the electron-transfer compounds, and electron-transfer agents of the present invention, as well as application examples thereof, will now be described in detail with reference to Tables A through AC mentioned below.

1. Description of Compounds

An electron-transfer compound in accordance with the present invention has a novel molecular skeleton in which an active methylene group of a cyclic compound that bears the active methylene is attached to a quinone ring via a double bond. The structure of the compound is shown by the following general formula (1):

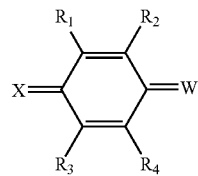

General formula (1)

wherein $R_1$ through $R_4$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and W is a 4- to 8-membered ring and has the structure shown in the following general formula (1') that replaces the general formula (1) above:

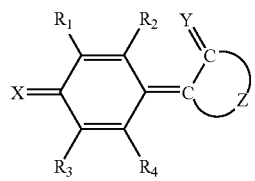

General formula (1')

wherein Y is oxygen or sulfur, and Z is a structure that has 2 or more atoms and forms a part of the ring.

While specific examples of the electron-transfer compound are described below, they are not intended to limit the scope of the invention in any way. Tables A(1) through A(18) list structures of the compounds shown by the general formulae (101) through (314), each having six substituents, $R_1$ through $R_6$, whereas Tables A(19) through A(26) list structures of the compounds shown by the general formulae (315) through (423), each having five substituents, $R_1$ through $R_5$.

Table B is a list showing substituents S1 through S23, which can be independently used as the substituents $R_1$ through $R_6$, or $R_1$ through $R_5$, in the general formulae (101) through (423).

Tables C(1) through C(6) each show possible combinations of the six substituents $R_1$ through $R_6$ for the compounds of the general formulae (101) through (314), whereas Tables C(7) through C(11) each show possible combinations of the five substituents $R_1$ through $R_5$ for the compounds of the general formulae (315) through (423).

2. Description of Production Process

A production process in accordance with the present invention involves reacting a benzoquinone compound with a compound having an active methylene in the presence of a base catalyst. The benzoquinone compound for use in the process of the present invention has the structure represented by the following general formula (17):

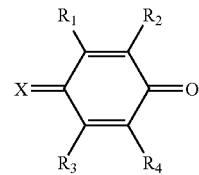

General formula (17)

wherein $R_1$ to $R_4$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; and X is selected from the group consisting of oxygen, sulfur, and $=C(CN)_2$.

Preferably, $R_2$ and $R_4$ each are a hydrogen atom in the general formula (17), as shown by the following general formula (19):

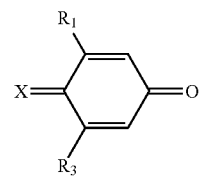

General formula (19)

wherein $R_1$ and $R_3$ are each independently selected from the group consisting of hydrogen, alkyl having 1 to 6 carbon atoms, and phenyl; and X is selected from the group consisting of oxygen, sulfur, and $=C(CN)_2$.

Preferably, $R_1$ and $R_3$ in the general formula (19) each are a t-Bu group, as shown by the following general formula (20):

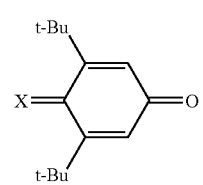

General formula (20)

wherein X is selected from the group consisting of oxygen, sulfur, and $=C(CN)_2$.

The compound having an active methylene for use in the process of the present invention has the structure represented by the following general formula (18):

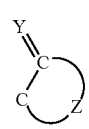

General formula (18)

wherein the compound is a 4- to 8-membered ring; Y is oxygen or sulfur; and Z is a structure that has 2 or more atoms and forms a part of the ring. Preferably, the compound having an active methylene of the general formula (18) is a compound represented by the following general formula (21):

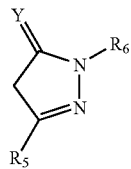

General formula (21)

wherein $R_5$ and $R_6$ are each independently selected from the group consisting of hydrogen, cyano, nitro, halogen, hydroxyl, alkyl, aryl, heterocyclic ring, ester, alkoxy, aralkyl, allyl, amide, amino, acyl, alkenyl, alkynyl, carboxyl, carbonyl, and carboxylic acid; and Y is oxygen or sulfur.

It is also preferred that the compound having an active methylene of the general formula (18) be a compound represented by the following general formula (22):

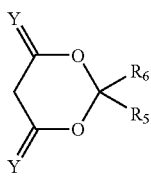

General formula (22)

wherein $R_5$ and $R_6$ are each independently selected from the group consisting of hydrogen, cyano, nitro, halogen, hydroxyl, substituted or unsubstituted alkyl, aryl, heterocyclic ring, ester, alkoxy, aralkyl, allyl, amide, amino, acyl, alkenyl, alkynyl, carboxyl, carbonyl, and carboxylic acid; and Y is oxygen or sulfur.

It is also preferred that the compound having an active methylene of the general formula (18) be a compound represented by the following general formula (23):

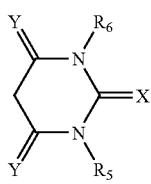

General formula (23)

wherein $R_5$ and $R_6$ are each independently selected from the group consisting of hydrogen, cyano, nitro, halogen, hydroxyl, substituted or unsubstituted alkyl, aryl, heterocyclic ring, ester, alkoxy, aralkyl, allyl, amide, amino, acyl, alkenyl, alkynyl, carboxyl, carbonyl, and carboxylic acid; X is selected from the group consisting of oxygen, sulfur, and $=C(CN)_2$; and Y is oxygen or sulfur.

Examples of organic base catalysts that can serve as the base catalyst for use in the process of the present invention include primary amines, such as methylamine, ethylamine, propylamine, and butylamine; secondary amines, such as dimethylamine, diethylamine, methylethylamine, dipropylamine, and dibutylamine; tertiary amines, such as trimethylamine, dimethylethylamine, methyldiethylamine, dimethylpropylamine, triethylamine, methylethylpropylamine, diethylpropylamine, dipropylmethylamine, ethyldipropylamine, and tributylamine; cyclic amines, such as pyridine, 2,6-dimethylpyridine, quinoline, 1,8-diazabicyclo[5.4.0]undec-7-ene (DBU), 1,5-diazabicyclo[4.3.0]non-5-ene, and 1,4-diazabicyclo[2.2.2]octane; metal alkoxides, such as sodium methoxide, potassium methoxide, and butyl lithium; and metal amides, such as sodium amide and potassium amide.

Examples of inorganic base catalysts that can serve as the base catalyst for use in the present invention include basic gases such as ammonia, alkali metals such as sodium, potassium and lithium, metal hydroxides such as sodium hydroxide, potassium hydroxide and calcium hydroxide, metal salts such as sodium carbonate and potassium carbonate. Among these bases, those having a base dissociation constant greater than that of pyridine are preferred since they can accelerate the reaction significantly. The base catalyst may be used as a mixture of two or more base catalysts.

The base catalyst may be used together with an inert solvent. Examples of the inert solvent include alcohols such as methanol, ethanol, 1-propanol, 2-propanol, butanol and ethylene glycol, saturated aliphatic hydrocarbons such as hexane, heptane, octane, cyclohexane and cycloheptane, aromatic hydrocarbons such as benzene, toluene and xylene, chloride-containing hydrocarbons such as dichloromethane, dichloroethane, chloroform, carbon tetrachloride and chlorobenzene, ethers such as diethylether, diisopropylether, tetrahydrofuran (THF), dioxane and methoxyethanol, ketones such as acetone, methyl ethyl ketone, methyl isobutyl ketone and cyclohexanone, esters such as ethyl formate, propyl formate, methyl acetate, ethyl acetate, propyl acetate, butyl acetate and methyl propionate, and N-methylpyrrolidone. These inert solvents may be used independently or as a mixture of two or more solvents.

While the reaction may proceed at low temperatures depending on the type of the base catalyst used, it is preferably carried out at room temperature or above to reduce the reaction time. The reaction system may be heated or cooled depending on the conditions of the reaction. While it depends on the type of the materials used, the reaction may require stirring so that it can take place, or in some cases the reaction may proceed by simply allowing the mixture of the materials to stand still.

3. Description of Electron-Transfer Agent

An electron-transfer agent of the present invention comprises a resin and the electron-transfer compound. Examples of the resin for use in the electron-transfer agent include polycarbonate resin, styrene resin, acrylic resin, styrene-acrylic resin, ethylene-vinyl acetate resin, polypropylene resin, vinyl chloride resin, chlorinated polyether, vinyl chloride-vinyl acetate resin, polyester resin, nylon resin, vinyl acetate resin, furan resin, nitrile resin, alkyd resin, polyacetal resin, polymethylpentene resin, polyamide resin, polyurethane resin, epoxy resin, polyarylate resin, diarylate resin, polysulfone resin, polyethersulfone resin, polyarylsulfone resin, silicone resin, ketone resin, polyvinylbutyral resin, polyether resin, phenol resin, EVA (ethylene-vinyl acetate copolymer) resin, ACS (acrylonitrile-chlorinated polyethylene-styrene)resin, ABS (acrylonitrile-butadiene-styrene) resin, polyimide resin and epoxyarylate.

These resins may be used independently, as a copolymer of these resins or as a mixture of two or more resins.

Preferably, the resins with different molecular weights may be mixed together in order to enhance the hardness and wear-resistance.

The electron-transfer agent of the present invention contains the resin and the compound of the general formula (1), and the compound is dispersed in the resin.

When the preferred compound of the general formula (2) is used, it enhances the electron mobility, whereas when the particularly preferred compound of the general formula (3) is used, it enhances the electron mobility and the compatibility with the resin. In addition, these electron-transfer agents may be used as high-performance materials in various applications, including electrophotographic photoreceptors, electroconductive agents, charge-controlling agents, EL elements, photoelectric conversion elements, sensitizing agents for photochemical reactions, and high electroconductivity materials using charge-transfer complexes.

4. Description of Application Examples a. Description of Electrophotographic Photoreceptor An electrophotographic photoreceptor of the present invention includes an electroconductive substrate and a photosensitive layer disposed thereon. The photosensitive layer contains the electron-transfer compound as a charge-transfer material.

Figure 21:
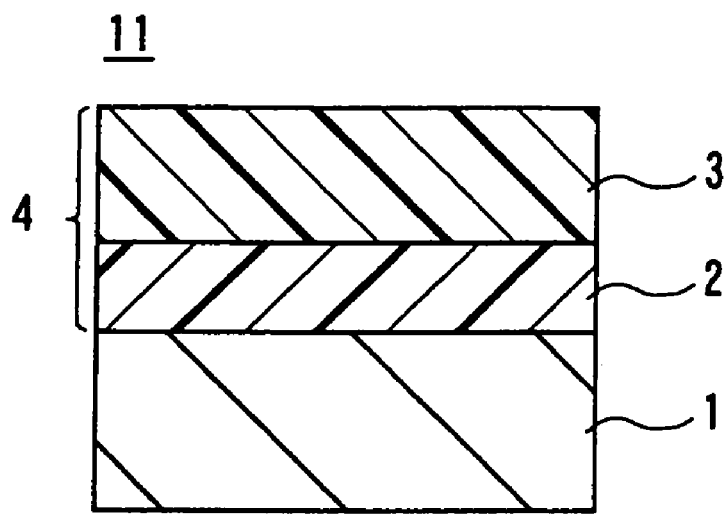
FIG. 21 is a cross-sectional view showing one example of a multi-layered electrophotographic photoreceptor.
Figure 22:
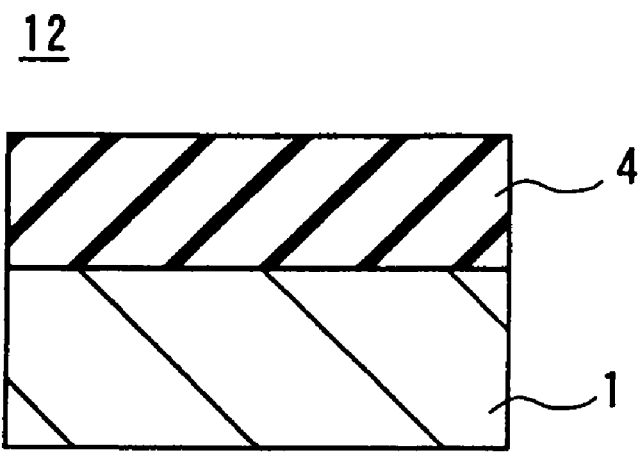
FIG. 22 is a cross-sectional view showing one example of a single-layered electrophotographic photoreceptor.

An exemplary electrophotographic photoreceptor of the present invention is denoted by reference numeral 11 in FIG. 21 and by reference numeral 12 in FIG. 22. The electrophotographic photoreceptor 11 is of a multi-layered type, whereas the electrophotographic photoreceptor 12 is of a single-layered type. The electrophotographic photoreceptors 11 and 12 each show one embodiment in which organic film containing the compound of the present invention is used in a photosensitive layer.

Referring to FIG. 21, the electrophotographic photoreceptor 11 includes a cylindrical electroconductive substrate 1. A charge-generation layer 2 and a charge-transfer layer 3 are disposed on the electroconductive substrate 1 in this order. The charge-generation layer 2 and the charge-transfer layer 3 together form a photosensitive layer 4.

The charge-generation layer 2 as shown in FIG. 21 includes at least a charge-generation material and may be formed by depositing the charge-generation material, by making use of a binder resin, on the electroconductive substrate 1 as a foundation.

Although the charge-generation layer 2 may be formed by using various methods, including conventional methods, it is preferably formed by dispersing or dissolving, along with the binder resin, the charge-generation material into a proper solvent so as to make a coating solution, coating the electroconductive substrate 1, which serves as a foundation, with the coating solution, and then drying the coating. Alternatively, the charge-generation layer 2 may be formed by vacuum-depositing the charge-generation material on the substrate.

The charge-transfer layer 3 includes at least a charge-transfer material, which will be described later, and may be formed by, for example, depositing the charge-transfer material, by making use of a binder resin, on the charge-generation layer 2 as the foundation for the charge-transfer layer 3. Although the charge-transfer layer 3 may be formed by using various methods, including conventional methods, it is typically formed by dispersing or dissolving, along with the binder resin, the charge-transfer material into a proper solvent so as to make a coating solution, coating the charge-generation layer 2, which serves as a foundation, with the coating solution, and then drying the coating.

Referring now to FIG. 22, one example of the single-layered electrophotographic photoreceptor is denoted by reference numeral 12. With the same numerals assigned to the same components as those in the electrophotographic photoreceptor 11 of the first example, the electrophotographic photoreceptor 12 includes a single-layered photosensitive layer 4 formed on the electroconductive substrate 1. The photosensitive layer 4 contains the charge-generation material and the charge-transfer material.

Although the photosensitive layer 4 may be formed by using various methods, including conventional methods, it is preferably formed by dispersing or dissolving, along with the binder resin, the charge-generation material into a proper solvent and then dissolving the charge-transfer material so as to make a coating solution, coating the electroconductive substrate 1, which serves as a foundation, with the coating solution, and then drying the coating. The charge-generation material and the charge-transfer material will be described later.

The electroconductive substrate 1 for use in the present invention may be formed of various electroconductive materials and may be of any material and shape. For example, it may be a metal article of a metal or an alloy of metals, including aluminum, magnesium, brass, stainless steel, nickel, chromium, titanium, gold, silver, copper, tin, platinum, molybdenum and indium; it may be a plastic plate or film with an electroconductive material, such as the aforementioned metal or carbon, vapor-deposited or plated thereon to impart conductivity; or it may be an electroconductive glass plate coated with tin oxide, indium oxide, aluminum iodide or copper iodide.

Cylindrical aluminum tubes are commonly used, and may or may not be surface-treated by aluminum-anodizing. A resin layer may be deposited on the surface of the aluminum tube, or on the anodized aluminum layer in the case of the surface-treated tube.

The resin layer is provided for the purposes of enhancing adhesion, serving as a barrier to prevent electric current from flowing from the substrate, and covering surface defects of the substrate. Various types of resin can be used in the resin layer, including polyethylene resin, acrylic resin, epoxy resin, polycarbonate resin, polyurethane resin, vinyl chloride resin, vinyl acetate resin, polyvinylbutyral resin, polyamide resin and nylon resin.

The resin layer may be formed solely of a single resin, or it may be formed of a mixture of two or more resins or in conjunction with the aluminum-anodizing treatment. Further, metal compounds, metal oxides, carbon, silica, resin powder and other materials may be dispersed in the resin layer. In addition, various pigments, electron acceptors and electron donors may be added in order to improve characteristics of the resin layer.

Examples of the charge-generation material for use in the present invention include selenium, selenium-tellurium, selenium-arsenic, amorphous silicon, phthalocyanine pigments, monoazo pigments, trisazo pigments, polyazo pigments, indigo pigments, toluidine pigments, pyrazoline pigments, perylene pigments, quinacridone pigments and pyrylium salts. Among these, disazo pigments and phthalocyanine pigments are particularly preferred in order to obtain a high sensitivity because they are highly compatible with the compound of the present invention.

Of the phthalocyanine pigments, particularly preferred are oxytitanium phthalocyanine, copper phthalocyanine, metal-free phthalocyanine, hydroxygallium phthalocyanine, and diol adducts of oxytitanium phthalocyanine, each of which shows high absorption at longer wavelengths. These charge-generation materials may be used independently or as a mixture of two or more materials in order to obtain optimum wavelengths at which the photosensitivity peaks or has increased sensitivity.

Examples of the binder resins that can be used to form the photosensitive layer 4 include polycarbonate resin, styrene resin, acrylic resin, styrene-acrylic resin, ethylene-vinyl acetate resin, polypropylene resin, vinyl chloride resin, chlorinated polyether, vinyl chloride-vinyl acetate resin, polyester resin, nylon resin, vinyl acetate resin, furan resin, nitrile resin, alkyd resin, polyacetal resin, polymethylpentene resin, polyamide resin, polyurethane resin, epoxy resin, polyarylate resin, diarylate resin, polysulfone resin, polyethersulfone resin, polyarylsulfone resin, silicone resin, ketone resin, polyvinylbutyral resin, polyether resin, phenol resin, EVA (ethylene-vinyl acetate copolymer) resin, ACS (acrylonitrile-chlorinated polyethylene-styrene)resin, ABS (acrylonitrile-butadiene-styrene) resin, polyimide resin and epoxy arylate.

These resins may be used independently or as a mixture or a copolymer of two or more resins. Preferably, the resins with different molecular weights may be mixed together in order to enhance the hardness and wear-resistance. The binder resin can be used in each of the charge-generation layer 2 and the charge-transfer layer 3 in the multi-layered photoreceptor shown in FIG. 21.

Examples of the solvent for use in the coating solution include alcohols such as methanol, ethanol, 1-propanol, 2-propanol and butanol, saturated aliphatic hydrocarbons such as pentane, hexane, heptane, octane, cyclohexane and cycloheptane, aromatic hydrocarbons such as toluene and xylene, chloride-containing hydrocarbons such as dichloromethane, dichloroethane, chloroform, and chlorobenzene, ethers such as dimethylether, diethylether, tetrahydrofuran (THF) and methoxyethanol, ketones such as acetone, methyl ethyl ketone, methyl isobutyl ketone and cyclohexanone, esters such as ethyl formate, propyl formate, methyl acetate, ethyl acetate, propyl acetate, butyl acetate and methyl propionate, N,N-dimethylformamide and dimethylsulfoxide. These solvents may be used independently or as a mixture of two or more solvents.

In the electrophotographic photoreceptor of the present invention, the photosensitive layer 4 contains as a charge-transfer material the compound of the general formula (1). The compound is preferable since it has a high electron mobility, has reduced ability to exhibit colors and can be dispersed in the photosensitive layer at a high concentration. When the preferred compound of the general formula (2) is used, it enhances the electron mobility, whereas when the particularly preferred compound of the general formula (3) is used, it also enhances the compatibility with the resin.

Other charge-transfer materials may also be added to the electrophotographic photoreceptor of the present invention. In such a case, the sensitivity is increased and the residual potential is decreased, with the result that characteristics of the electrophotographic photoreceptor of the present invention are improved.

An electroconductive high molecular compound as a charge-transfer material may be added to the electrophotographic photoreceptor for the purpose of improving the characteristics of the photoreceptor. Examples of the electroconductive polymer include polyvinylcarbazole, halogenated polyvinylcarbazole, polyvinylpyrene, polyvinylindoloquinoxaline, polyvinylbenzothiophene, polyvinylanthracene, polyvinylacridine, polyvinylpyrazoline, polyacetylene, polythiophene, polypyrrole, polyphenylene, polyphenylene vinylene, polyisothianaphtene, polyaniline, polydiacetylene, polyheptadiene, polypyridinediyl, polyquinoline, polyphenylenesulfide, polyferrocenylene, polyperinaphthylene, and polyphthalocyanine.

Low molecular compounds may also be used for this purpose, including trinitrofluorenon, tetracyanoethylene, tetracyanoquinodimethane, quinone, diphenoquinone, naphthoquinone, anthraquinone and derivatives thereof, polycyclic aromatic compounds such as anthracene, pyrene and phenanthrene, nitrogen-containing heterocyclic compounds such as indole, carbazole and imidazole, fluorenone, fluorene, oxadiazole, oxazole, pyrazoline, hydrazone, triphenylmethane, triphenylamine, enamine, stilbene and butadiene compounds.

Also used are polymeric solid electrolytes obtained by doping polymers, such as polyethyleneoxide, polypropyleneoxide, polyacrylonitrile, poly methacrylic acid, with metal ions such as Li ions. Further, an organic electron-transfer complex may also be used that consists of an electron donor compound and an electron acceptor compound as represented by tetrathiafulvalene-tetracyanoquinodimethane. These compounds may be added independently or as a mixture of two or more compounds to obtain desired photosensitive characteristics.

In order to improve photosensitive characteristics, durability or mechanical properties of the photoreceptor of the present invention, antioxidants, UV-absorbing agents, radical scavengers, softeners, hardeners or cross-linking agents may be added to the coating solution for producing the photoreceptor of the present invention, provided that these agents do not affect the characteristics of the electrophotographic photoreceptor.

The finished appearance of the photoreceptor and the life of the coating solution are improved by further adding dispersion stabilizers, anti-settling agents, anti-flooding agents, leveling agents, anti-foaming agents, thickeners and flatting agents.

In addition, a surface-protection layer may be provided on the photosensitive layer 4. The surface-protection layer may be organic film formed of epoxy resin, melamine resin, polyvinylformal resin, polycarbonate resin, fluororesin, polyurethane resin or silicone resin, or it may be film formed of siloxane structure resulting from hydrolysis of silane coupling agents. In this manner, the durability of the photoreceptor is enhanced. The surface-protection layer may serve to improve functions other than the durability.

b. Description of Organic Electroluminescence Elements

An organic electroluminescence element of the present invention includes a pair of electrodes and a layer disposed between the electrodes, and containing at least one luminescent substance. The electroluminescence element contains the compound represented by the general formula (1) as a compound to impart the electron mobility.

An organic electroluminescence element is an element in which a single layer or multiple layers of organic film (luminescent layer) are disposed between a pair of electrodes.

Figure 23:
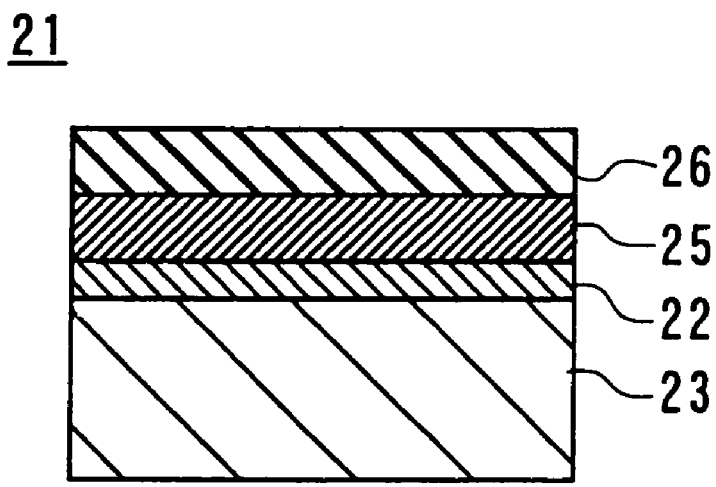
FIG. 23 is a cross-sectional view showing one example of an organic electroluminescence element.
Figure 24:
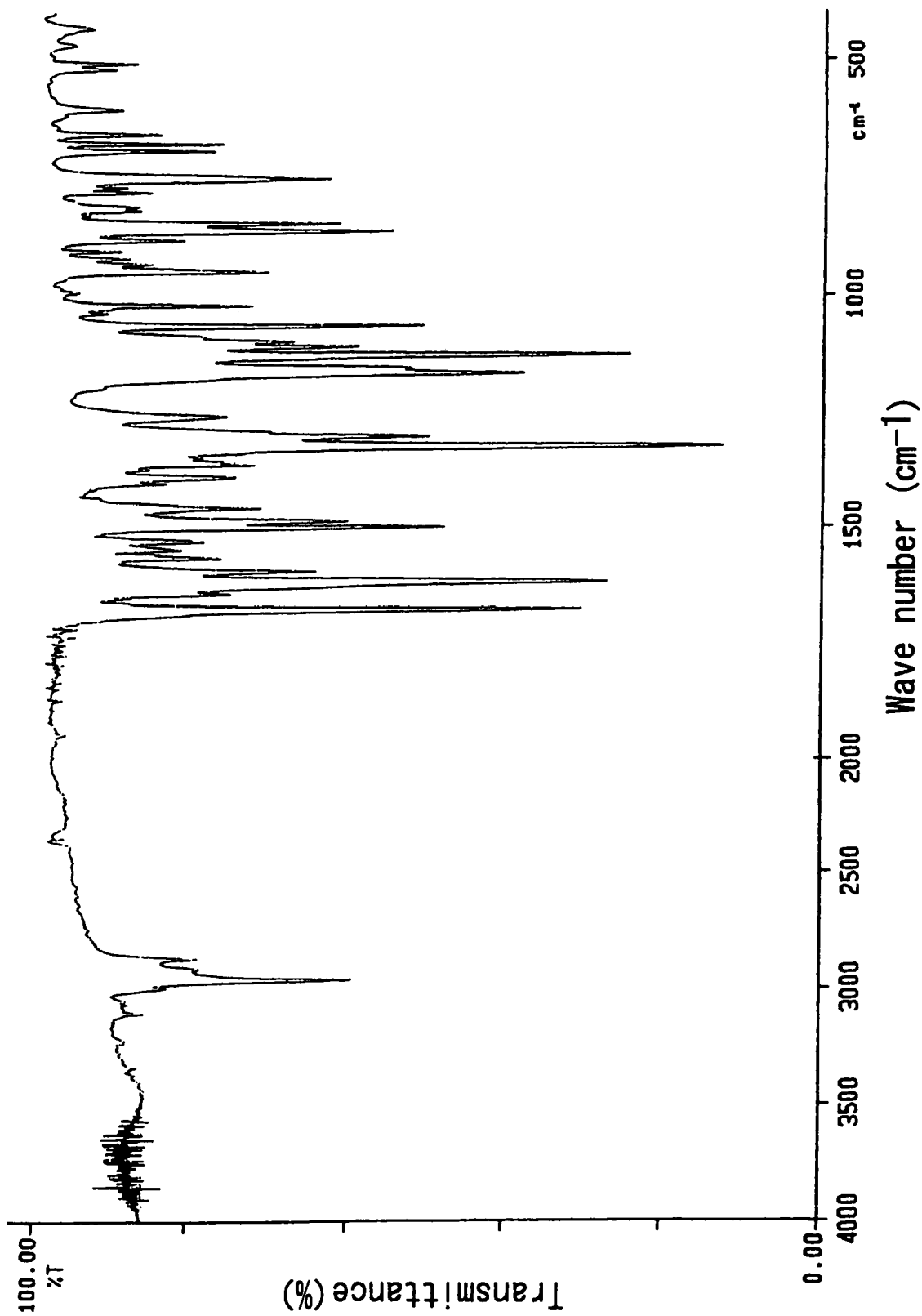
FIG. 24 is an IR spectrum of a compound represented by the chemical formula (29).
Figure 25:
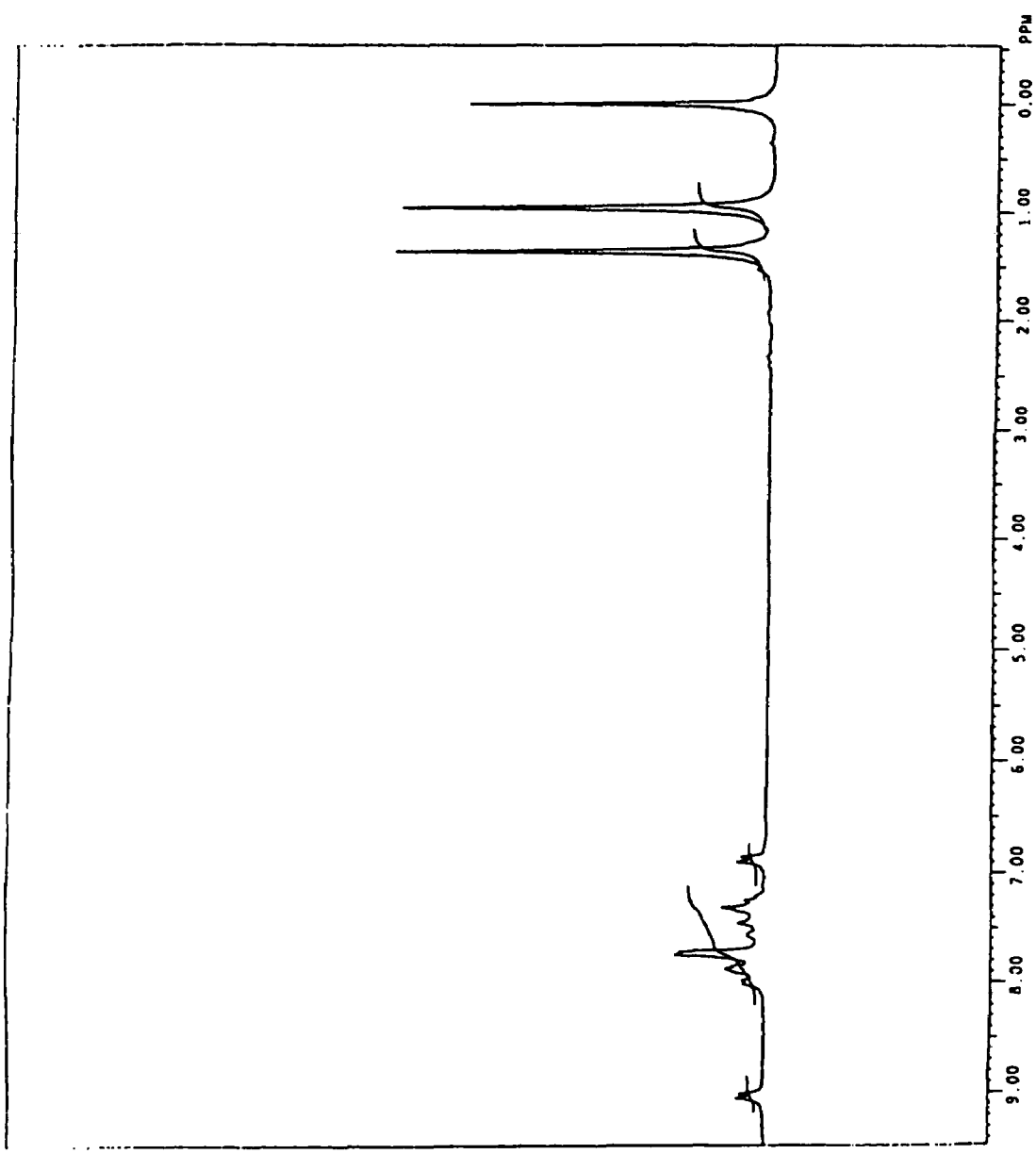
FIG. 25 is a $^1$H-NMR spectrum of the compound represented by the chemical formula (29).
Figure 26:
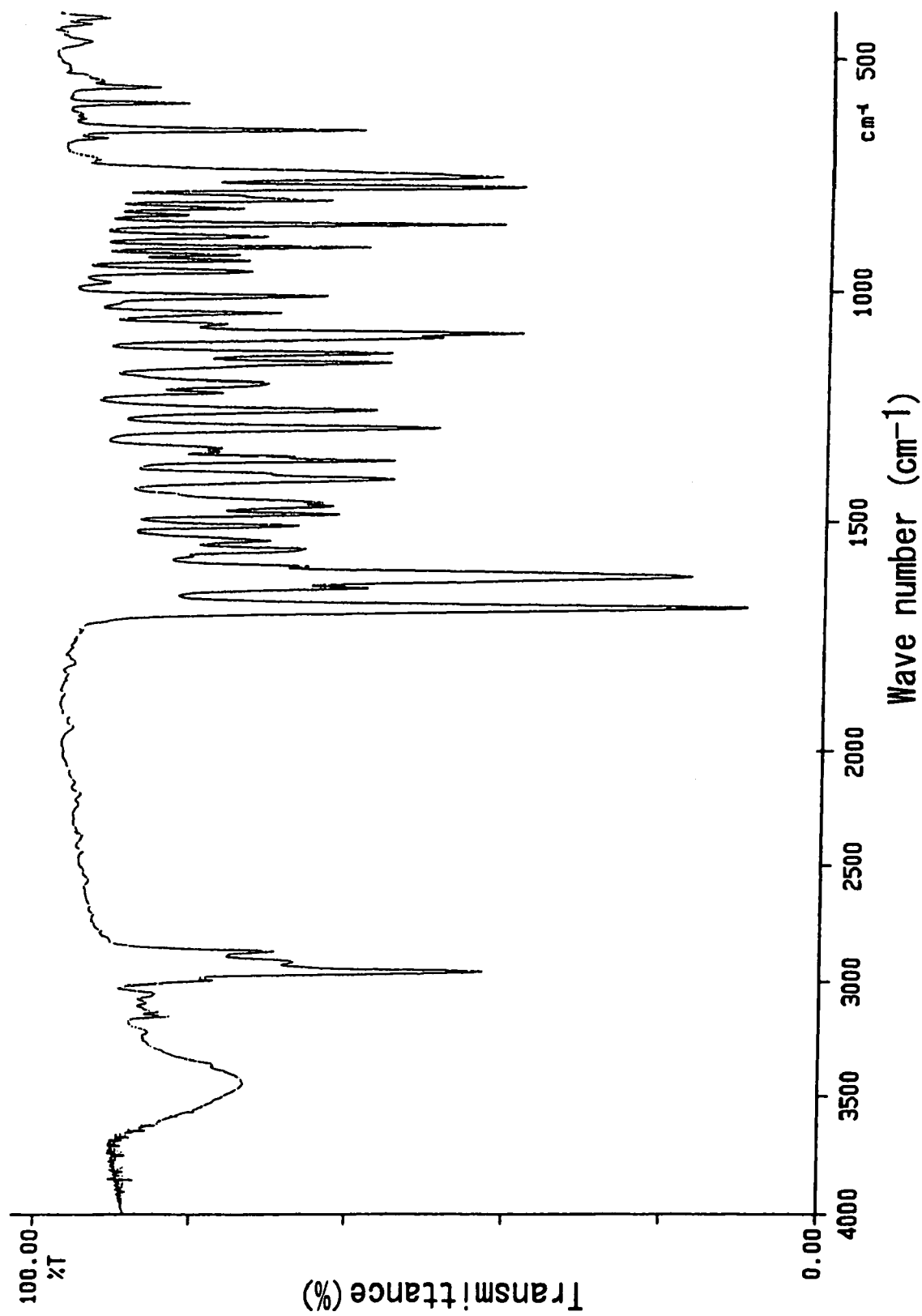
FIG. 26 is an IR spectrum of a compound represented by the chemical formula (30).
Figure 27:
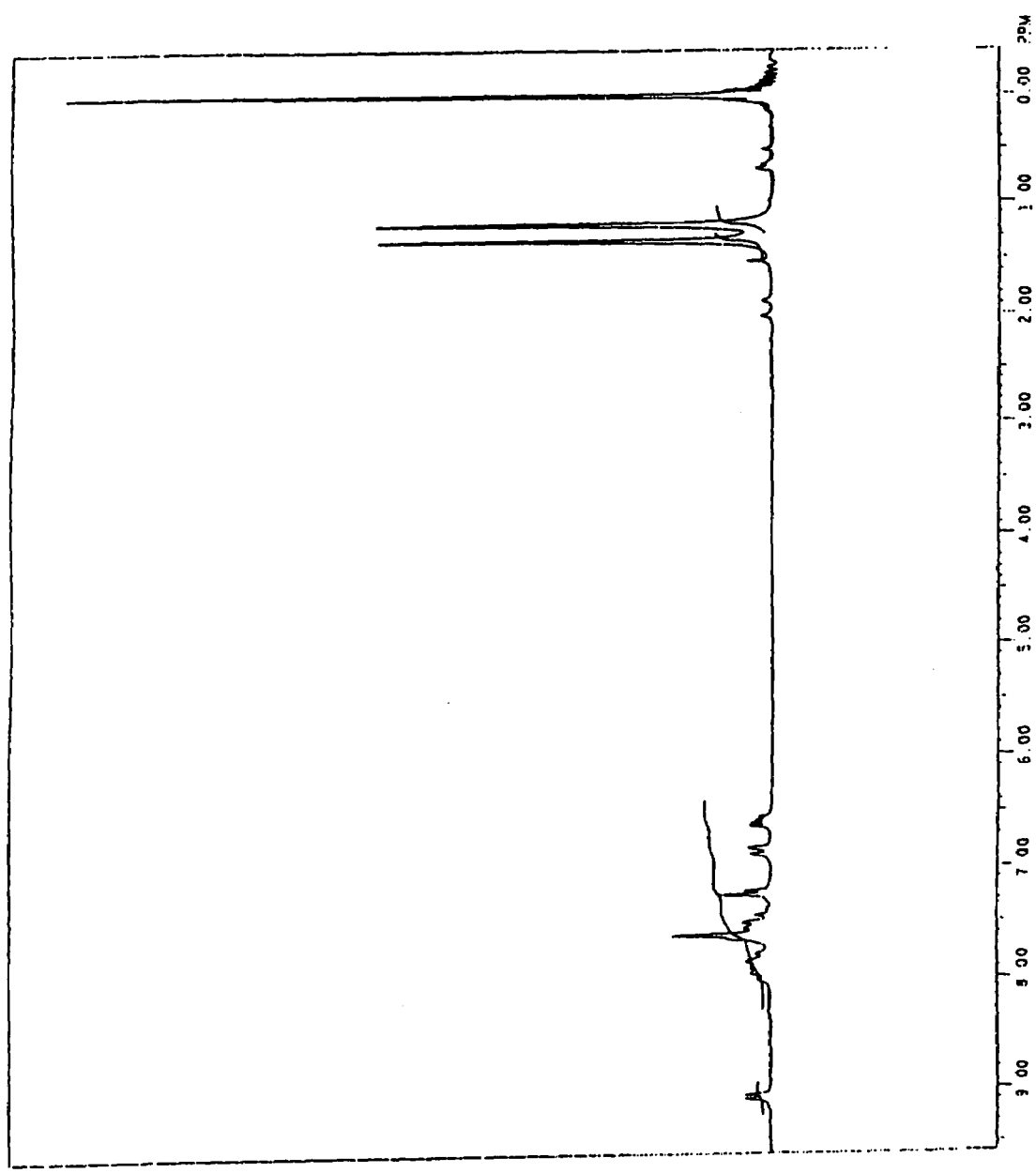
FIG. 27 is a $^1$H-NMR spectrum of the compound represented by the chemical formula (30).
Figure 28:
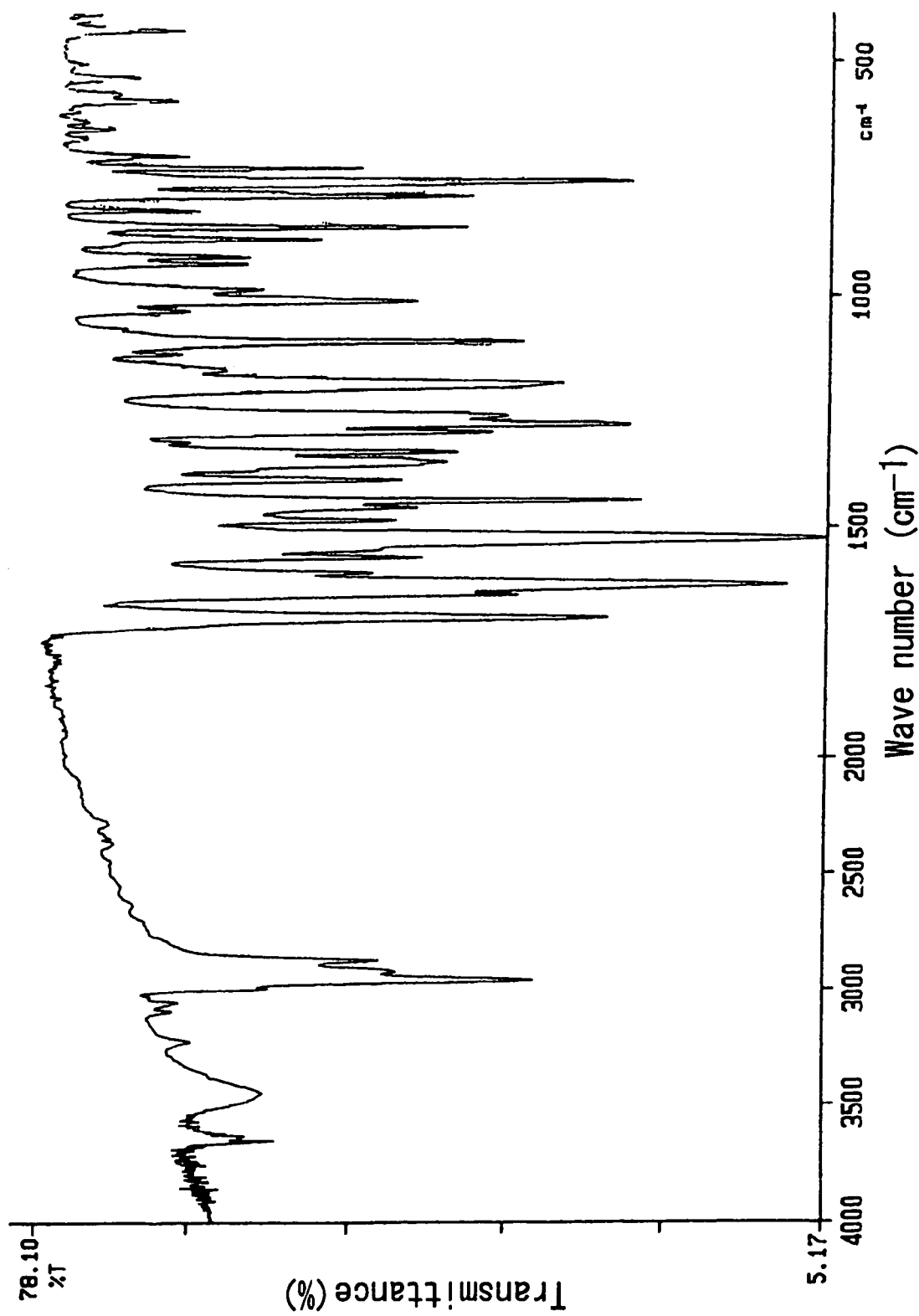
FIG. 28 is an IR spectrum of a compound represented by the chemical formula (31).
Figure 29:
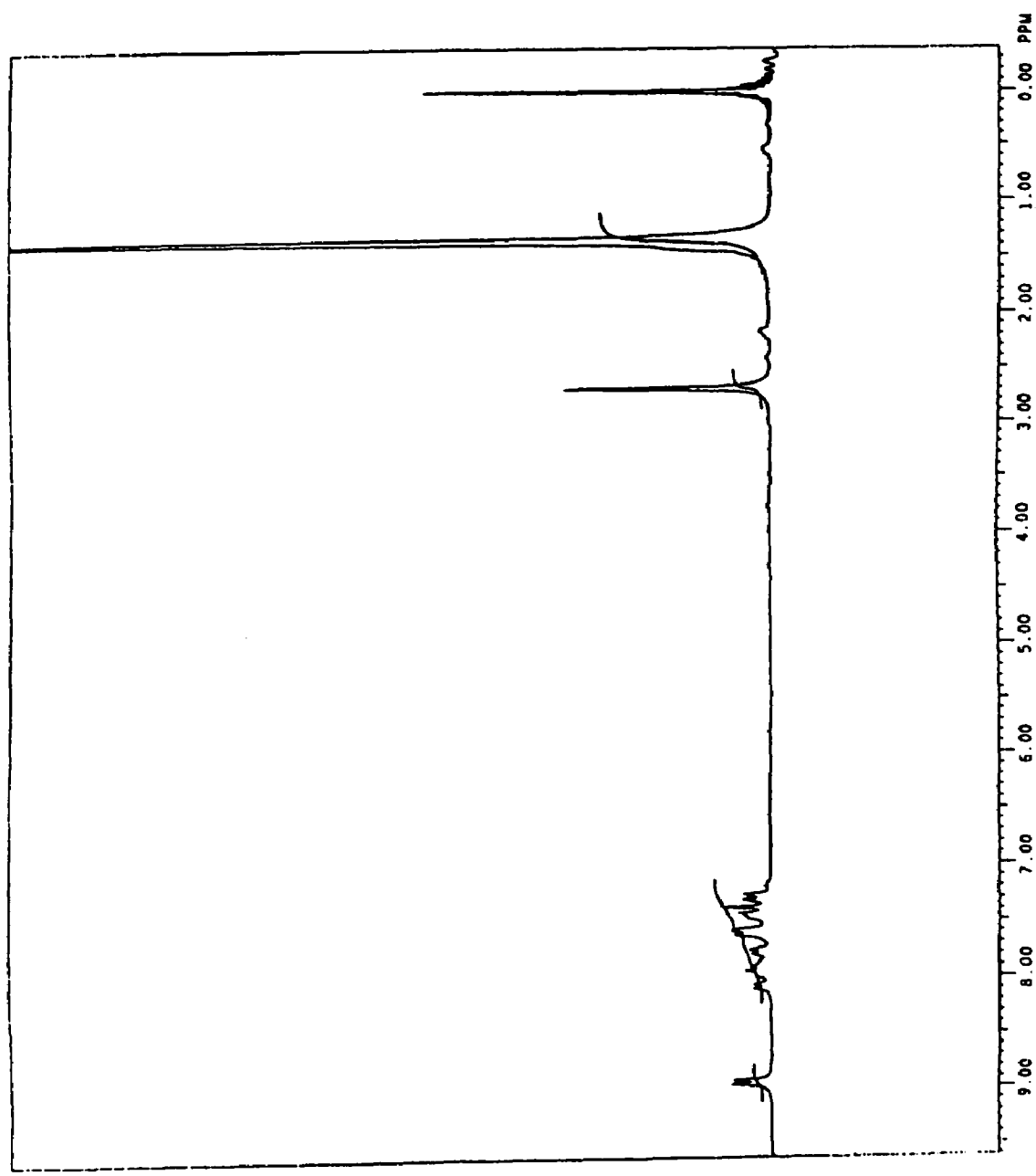
FIG. 29 is a $^1$H-NMR spectrum of the compound represented by the chemical formula (31).
Figure 30:
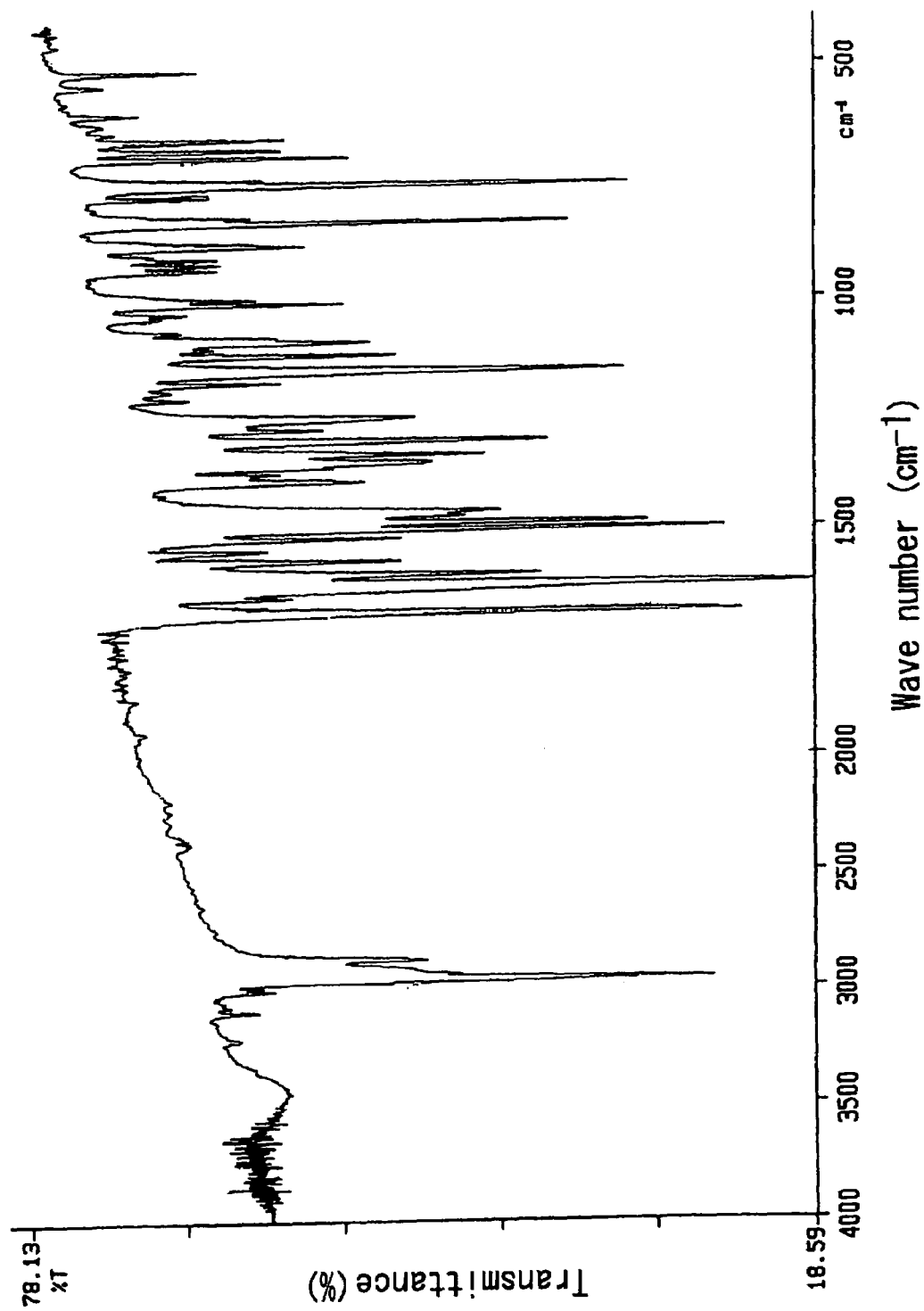
FIG. 30 is an IR spectrum of a compound represented by the chemical formula (32).
Figure 31:
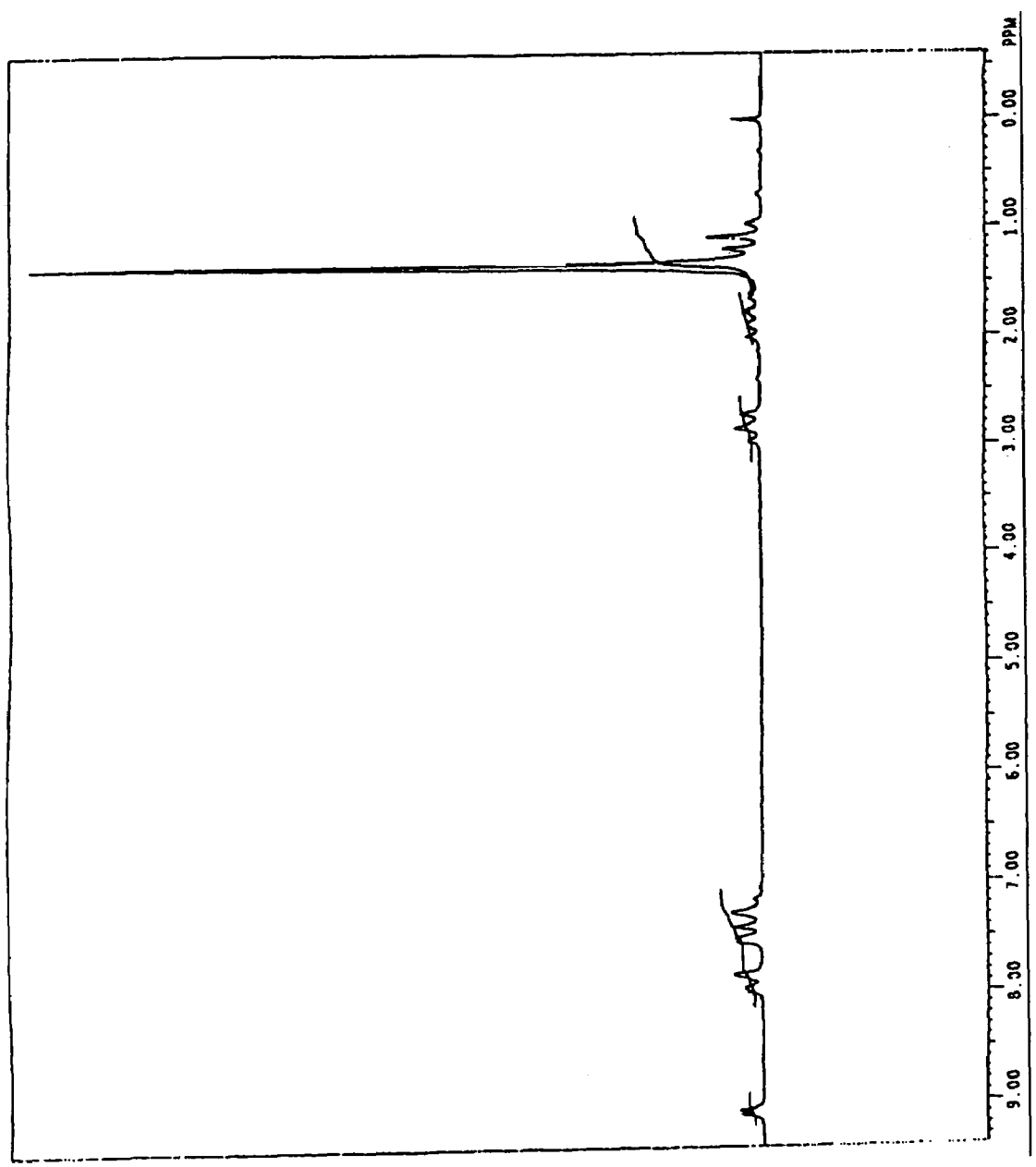
FIG. 31 is a $^1$H-NMR spectrum of the compound represented by the chemical formula (32).
Figure 32:
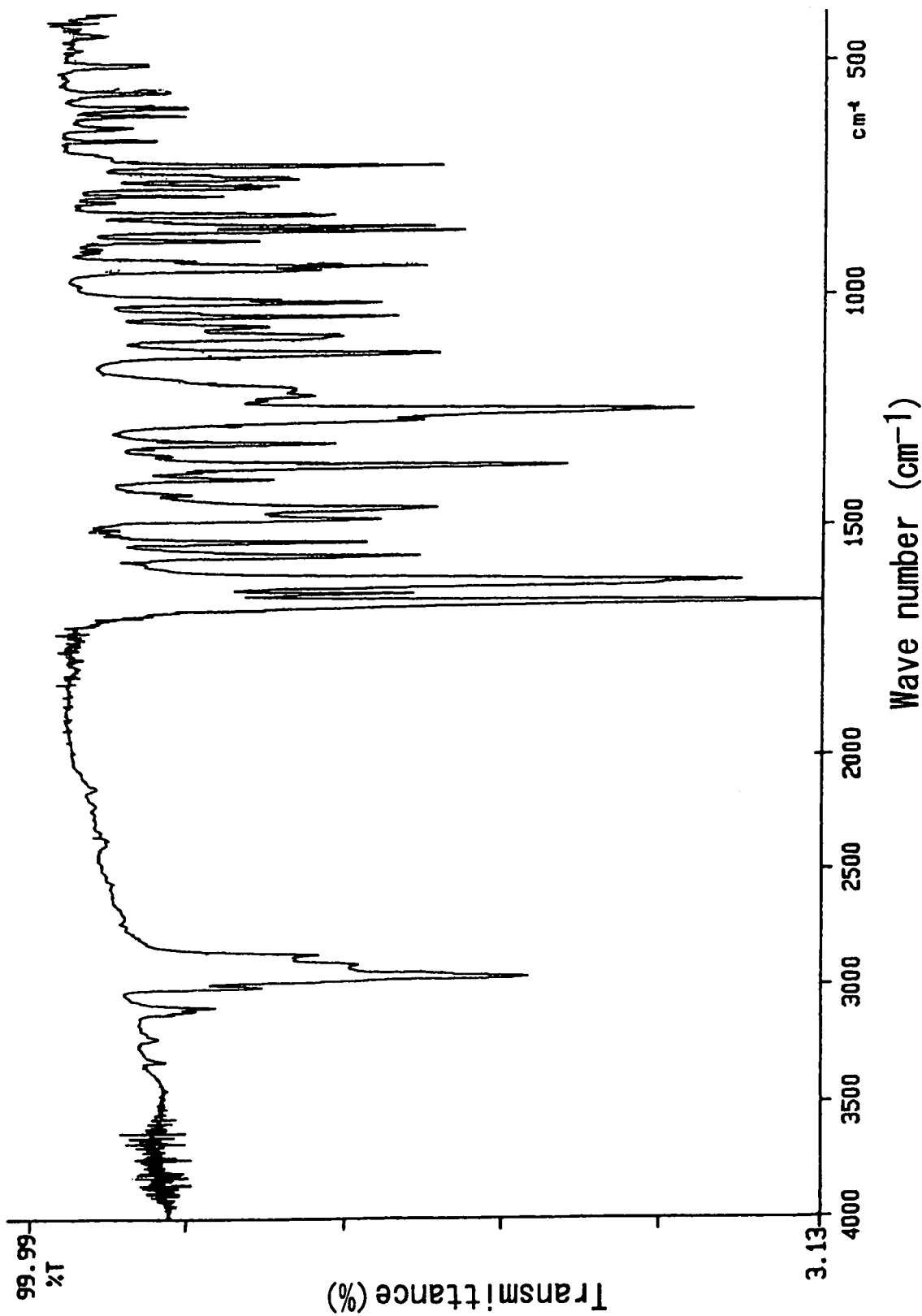
FIG. 32 is an IR spectrum of a compound represented by the chemical formula (33).
Figure 33:
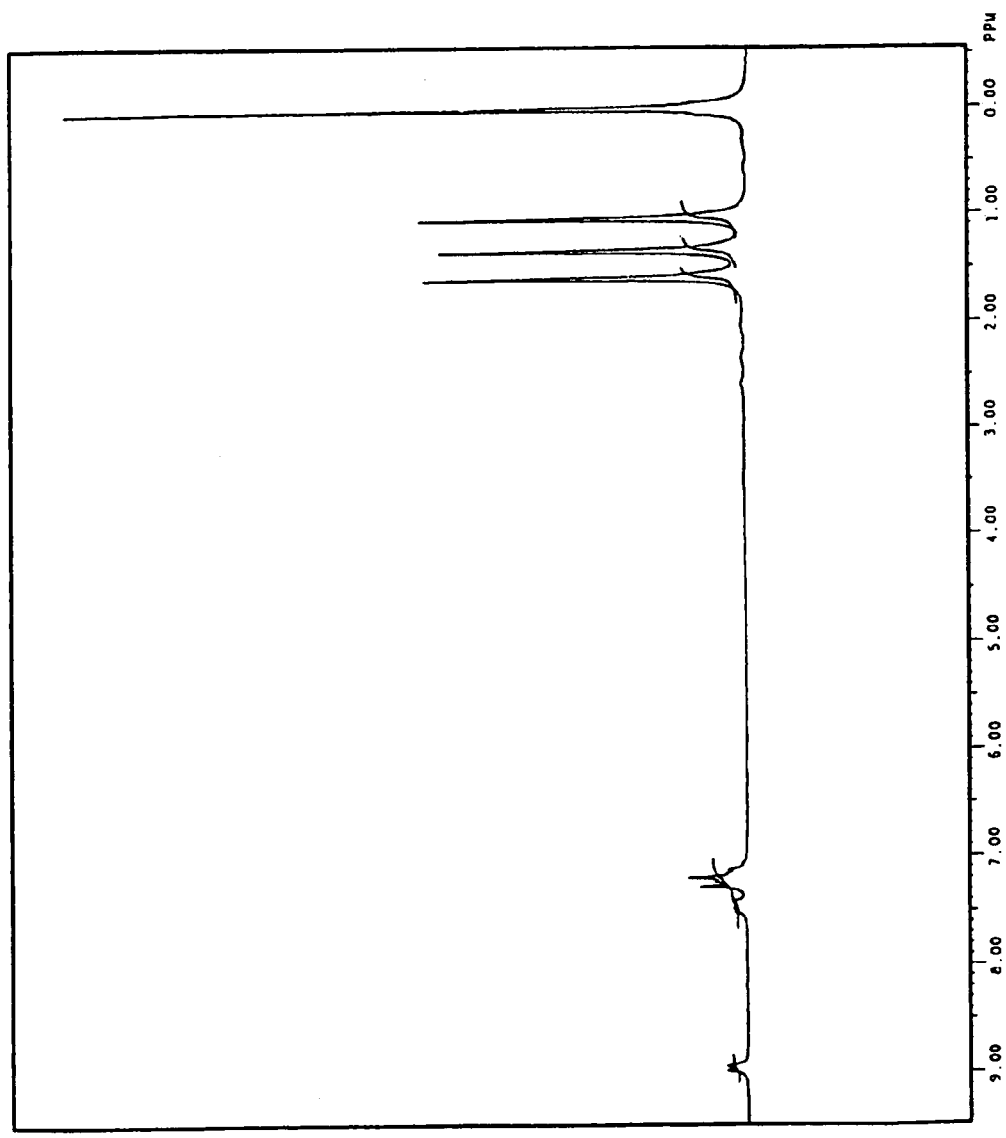
FIG. 33 is a $^1$H-NMR spectrum of the compound represented by the chemical formula (33).
Figure 34:
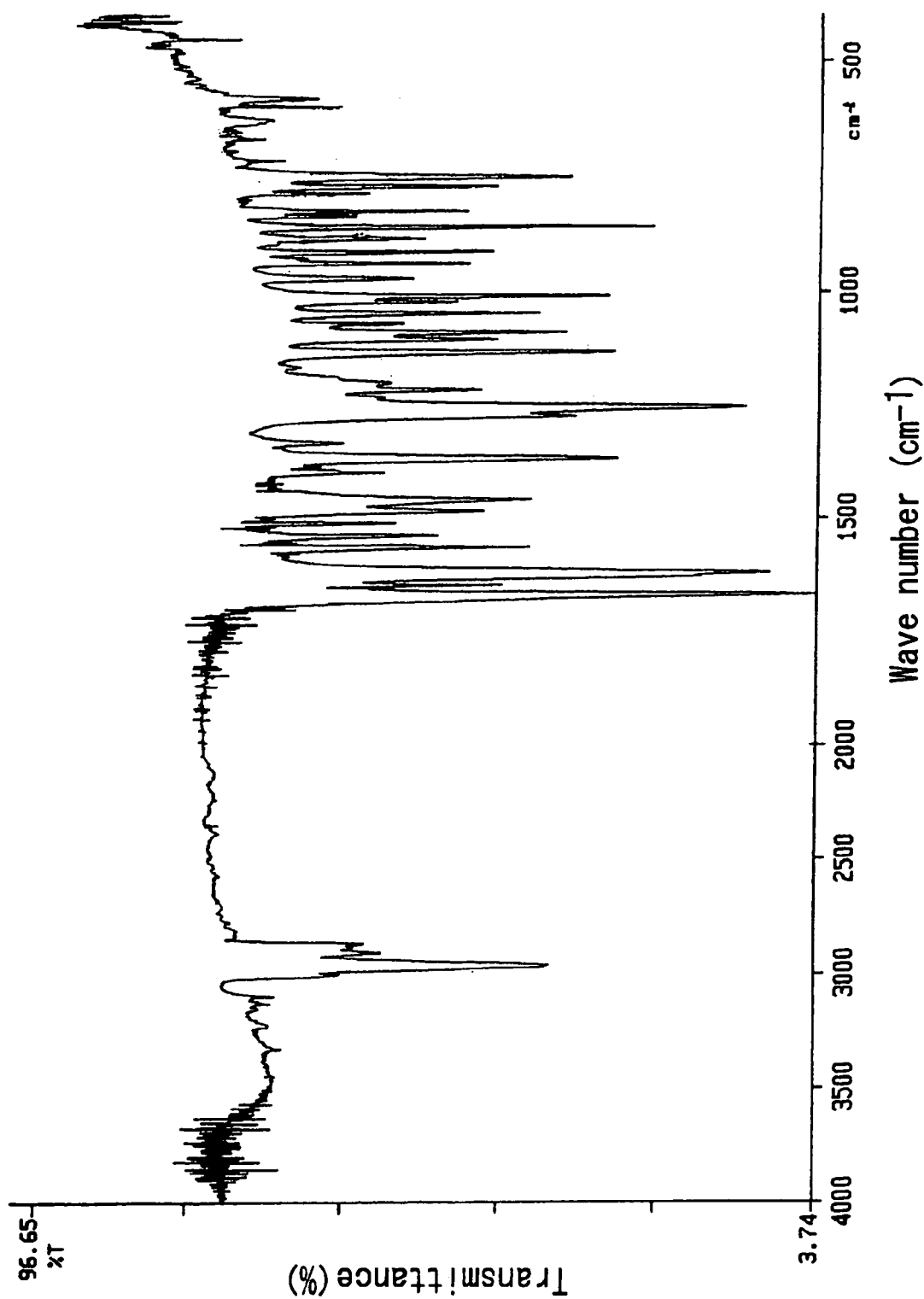
FIG. 34 is an IR spectrum of a compound represented by the chemical formula (34).
Figure 35:
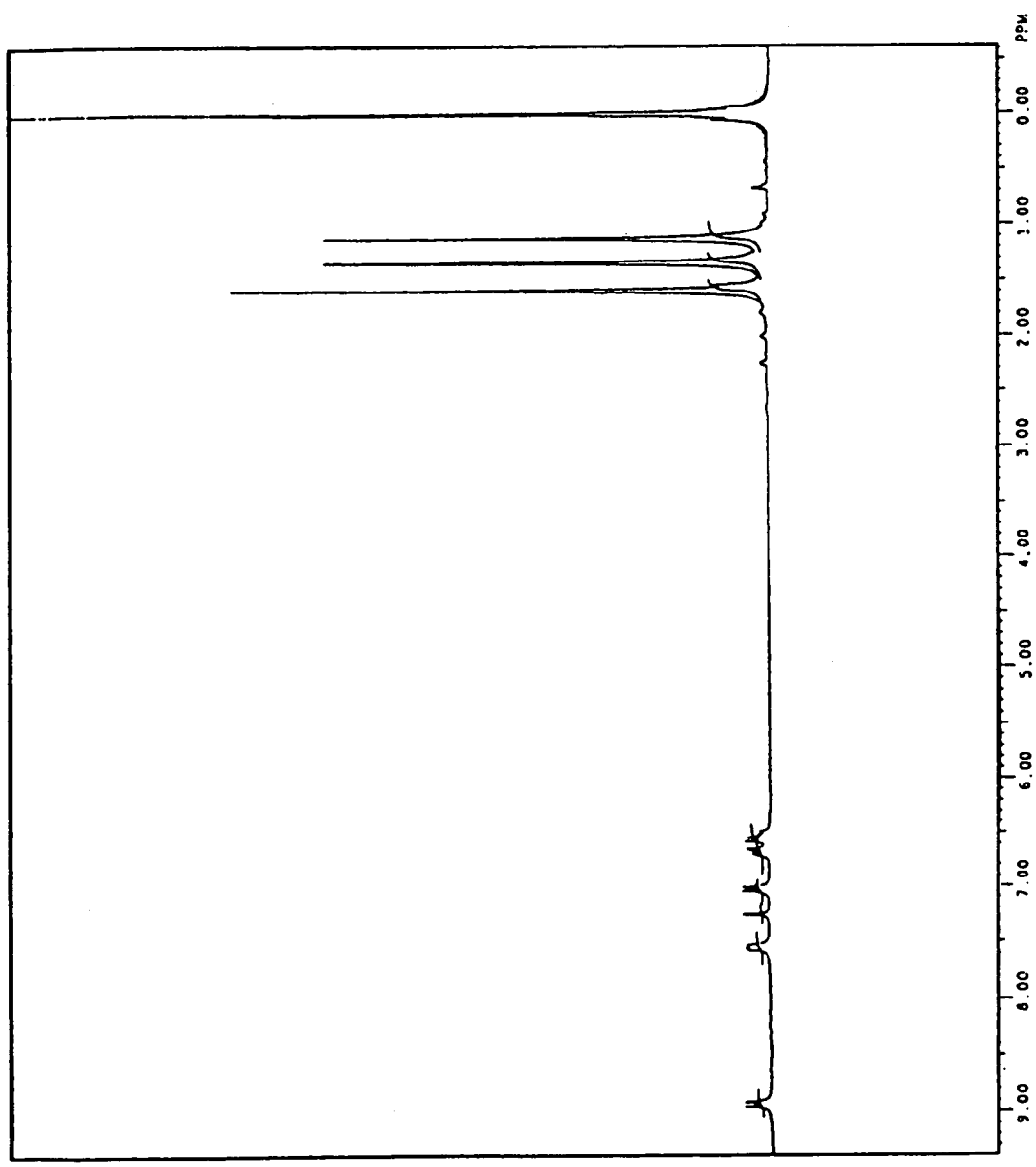
FIG. 35 is a $^1$H-NMR spectrum of the compound represented by the chemical formula (34).
Figure 36:
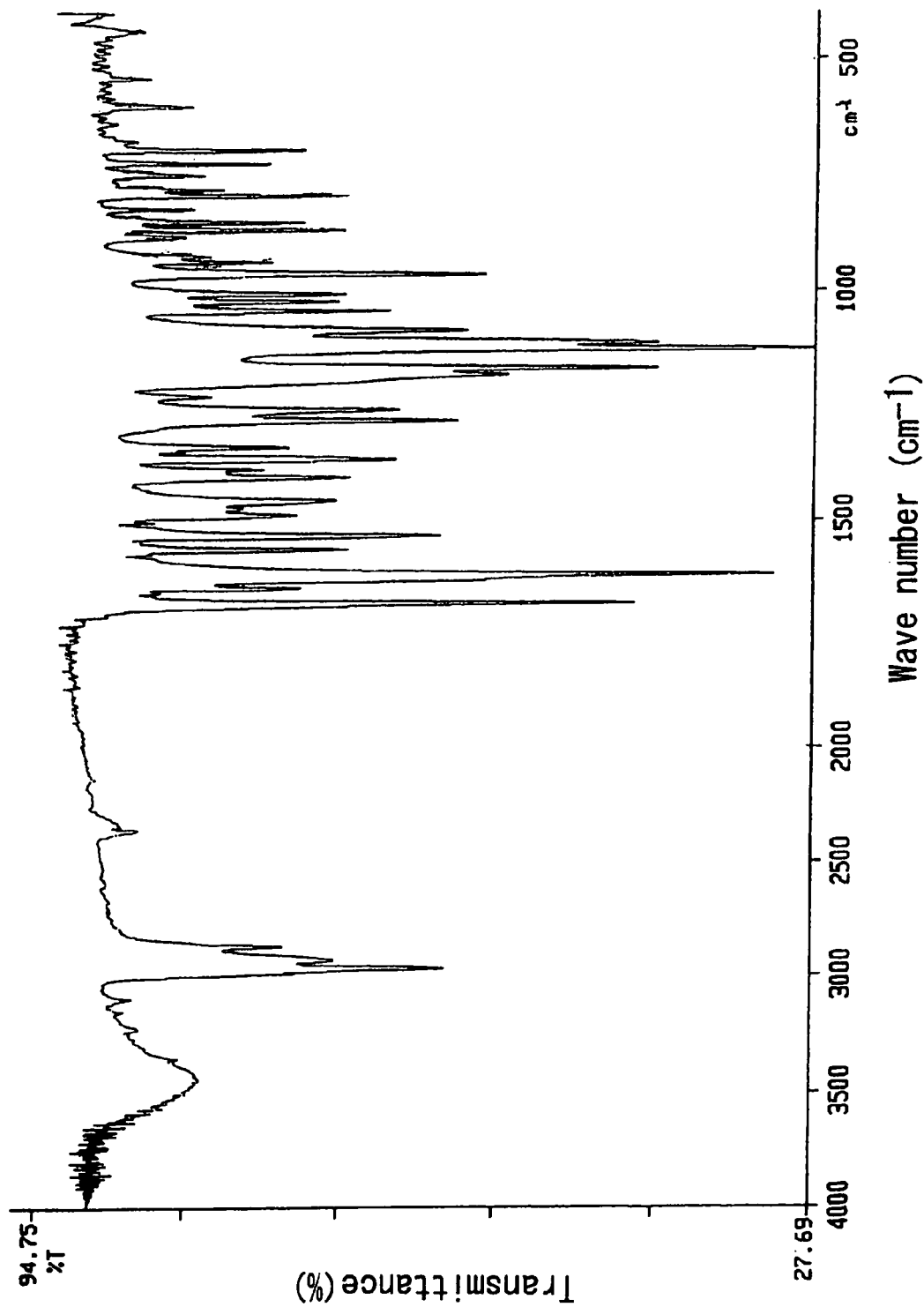
FIG. 36 is an IR spectrum of a compound represented by the chemical formula (35).
Figure 37:
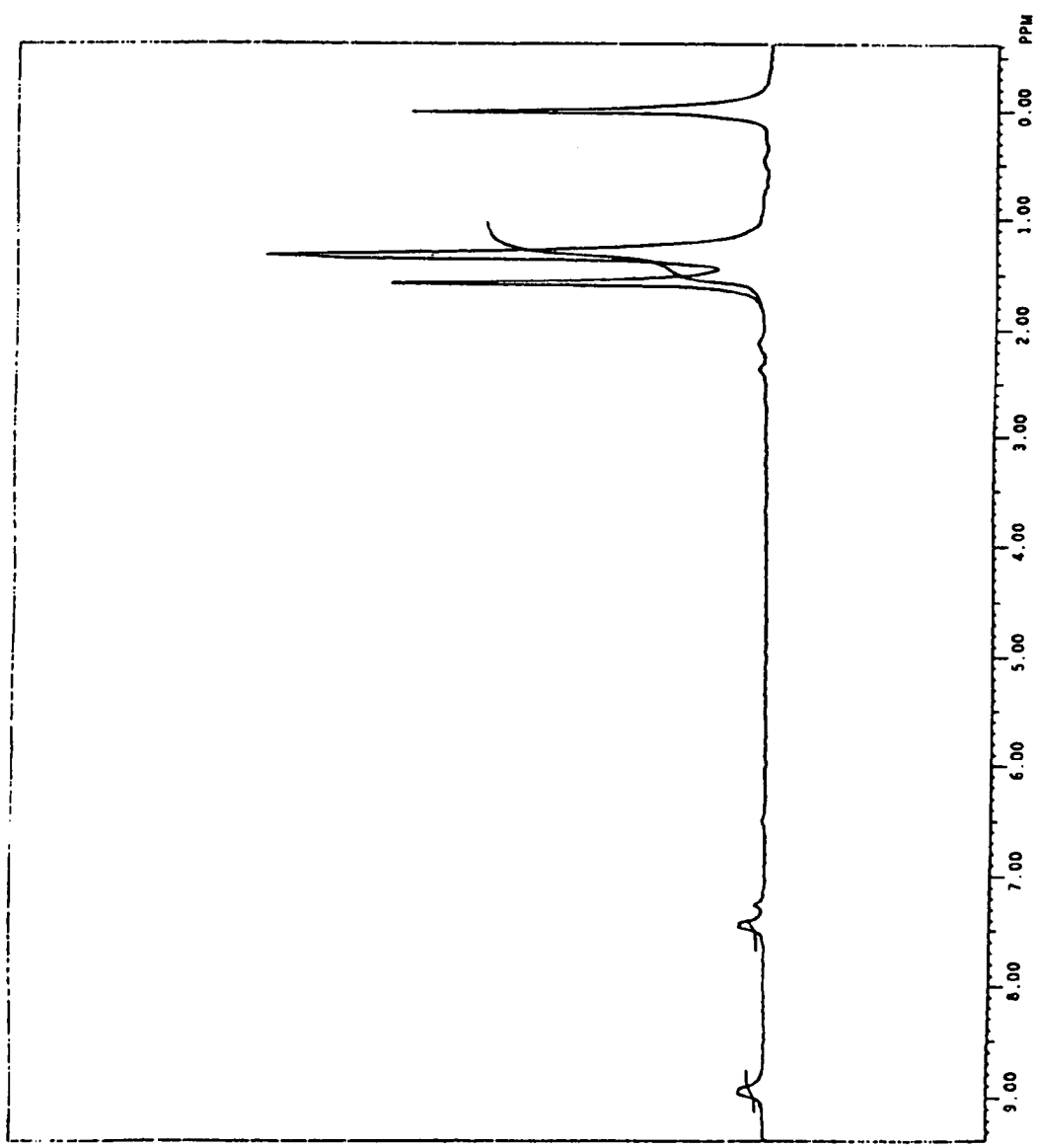
FIG. 37 is a $^1$H-NMR spectrum of the compound represented by the chemical formula (35).
Figure 38:
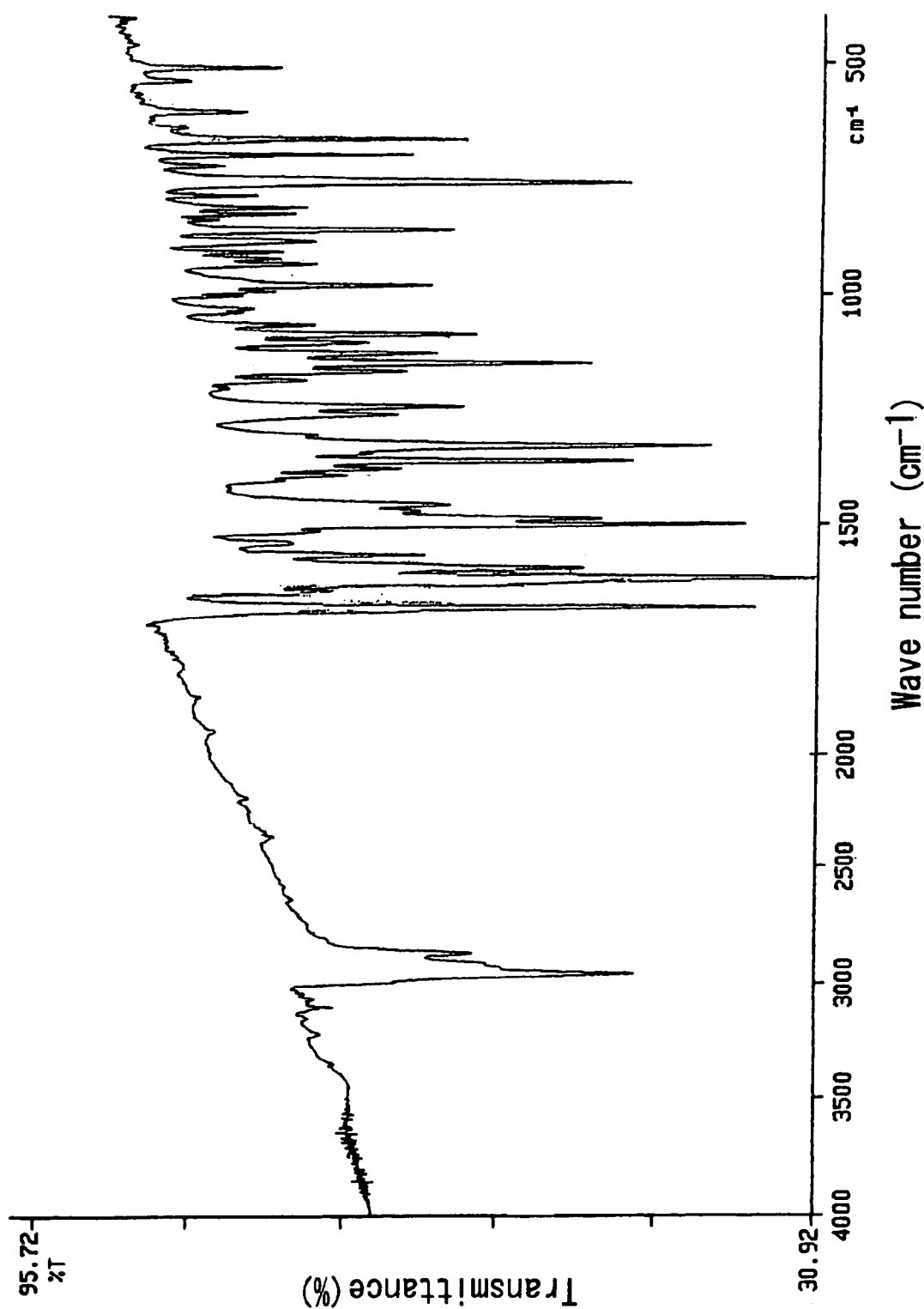
FIG. 38 is an IR spectrum of a compound represented by the chemical formula (36).
Figure 39:
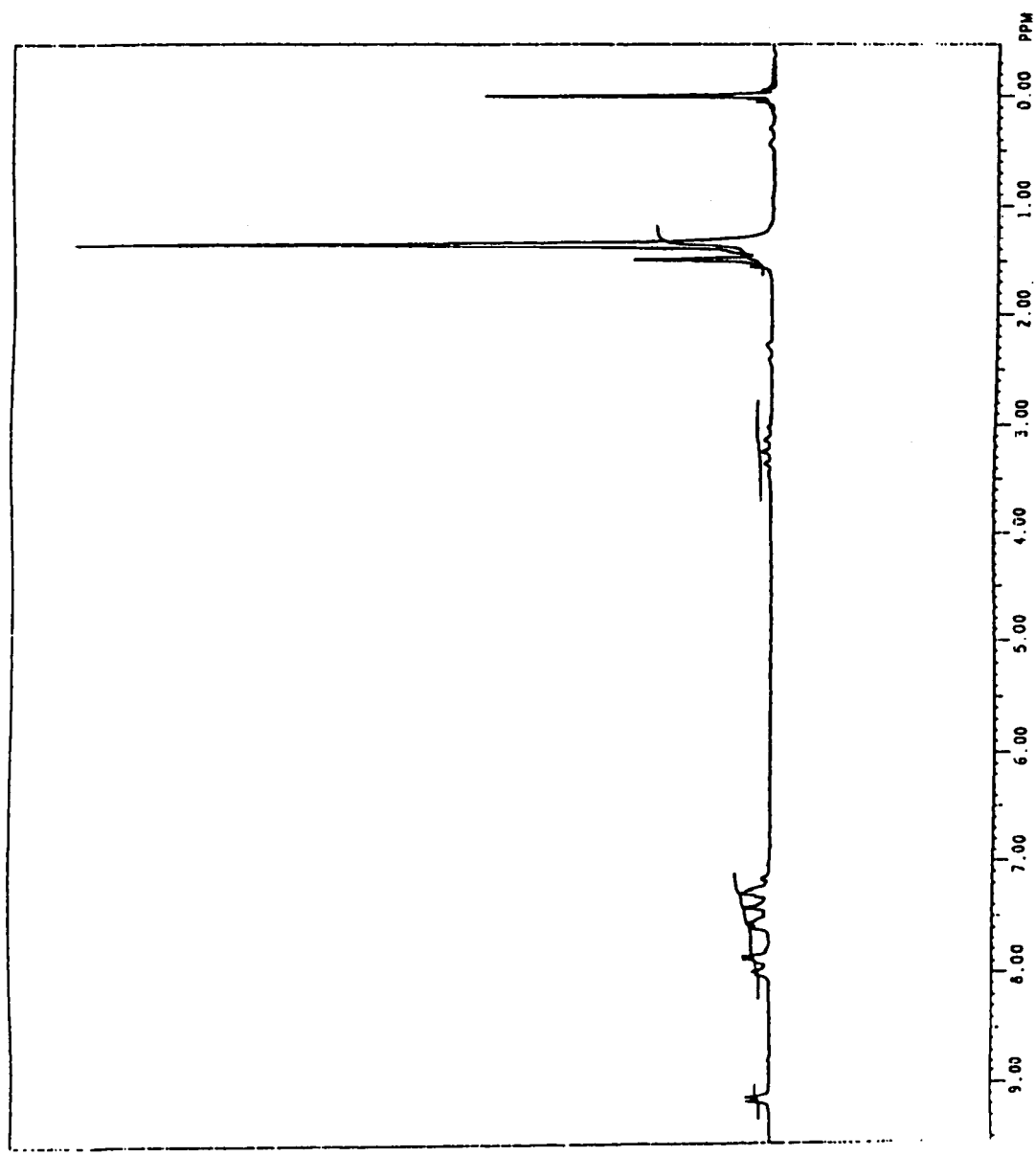
FIG. 39 is a $^1$H-NMR spectrum of the compound represented by the chemical formula (36).
Figure 40:
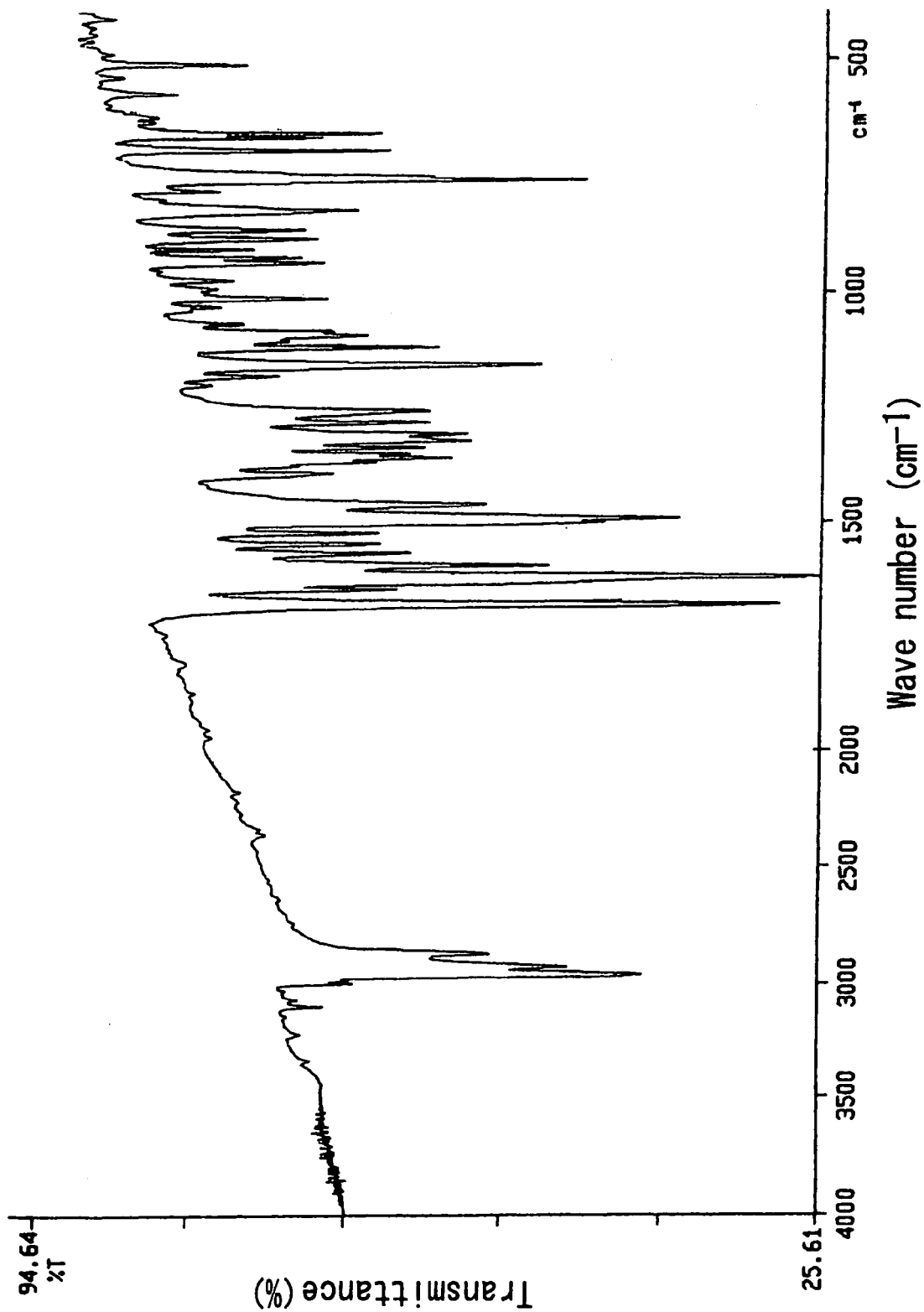
FIG. 40 is an IR spectrum of a compound represented by the chemical formula (37).
Figure 41:
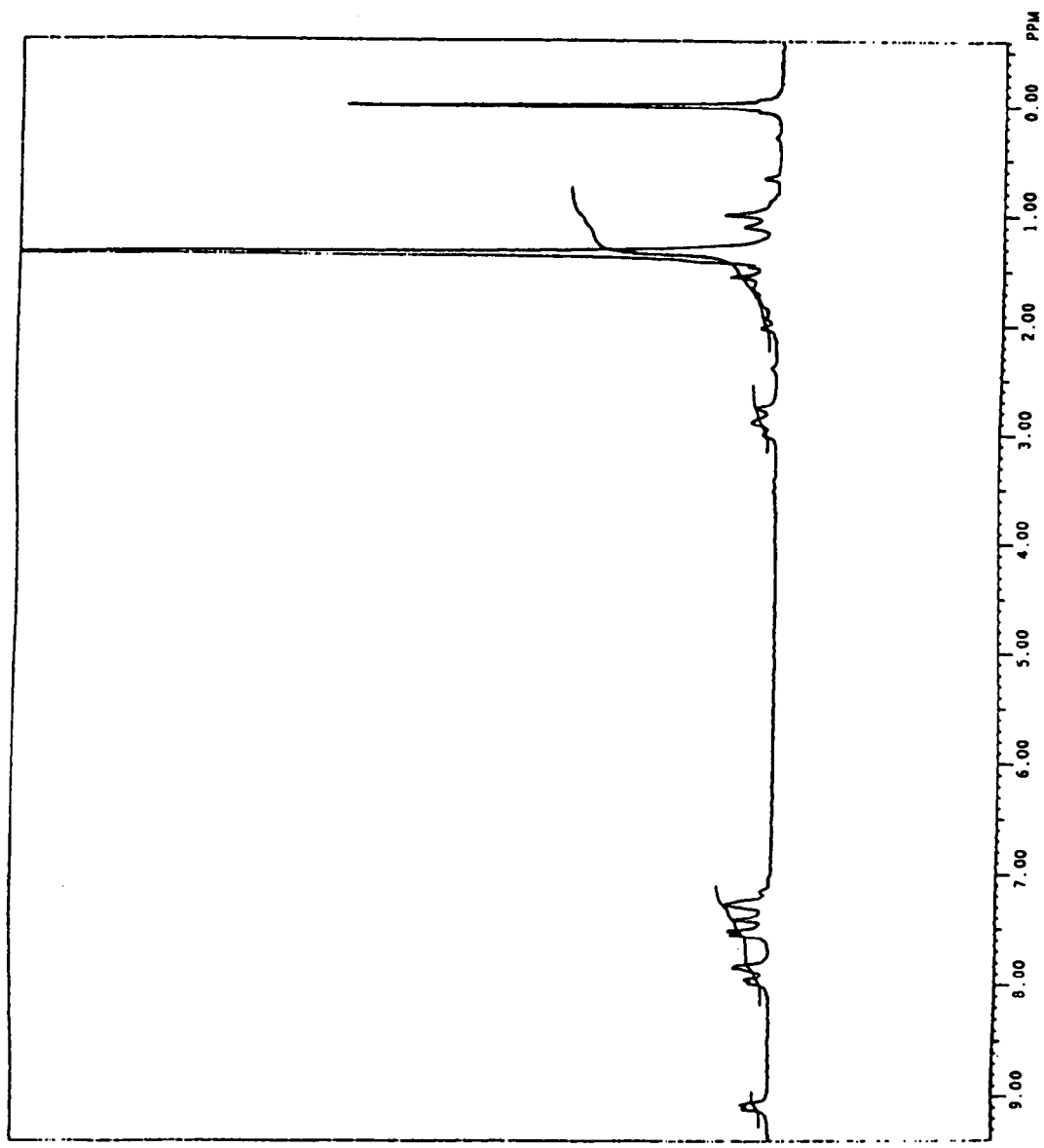
FIG. 41 is a $^1$H-NMR spectrum of the compound represented by the chemical formula (37).
Figure 42:
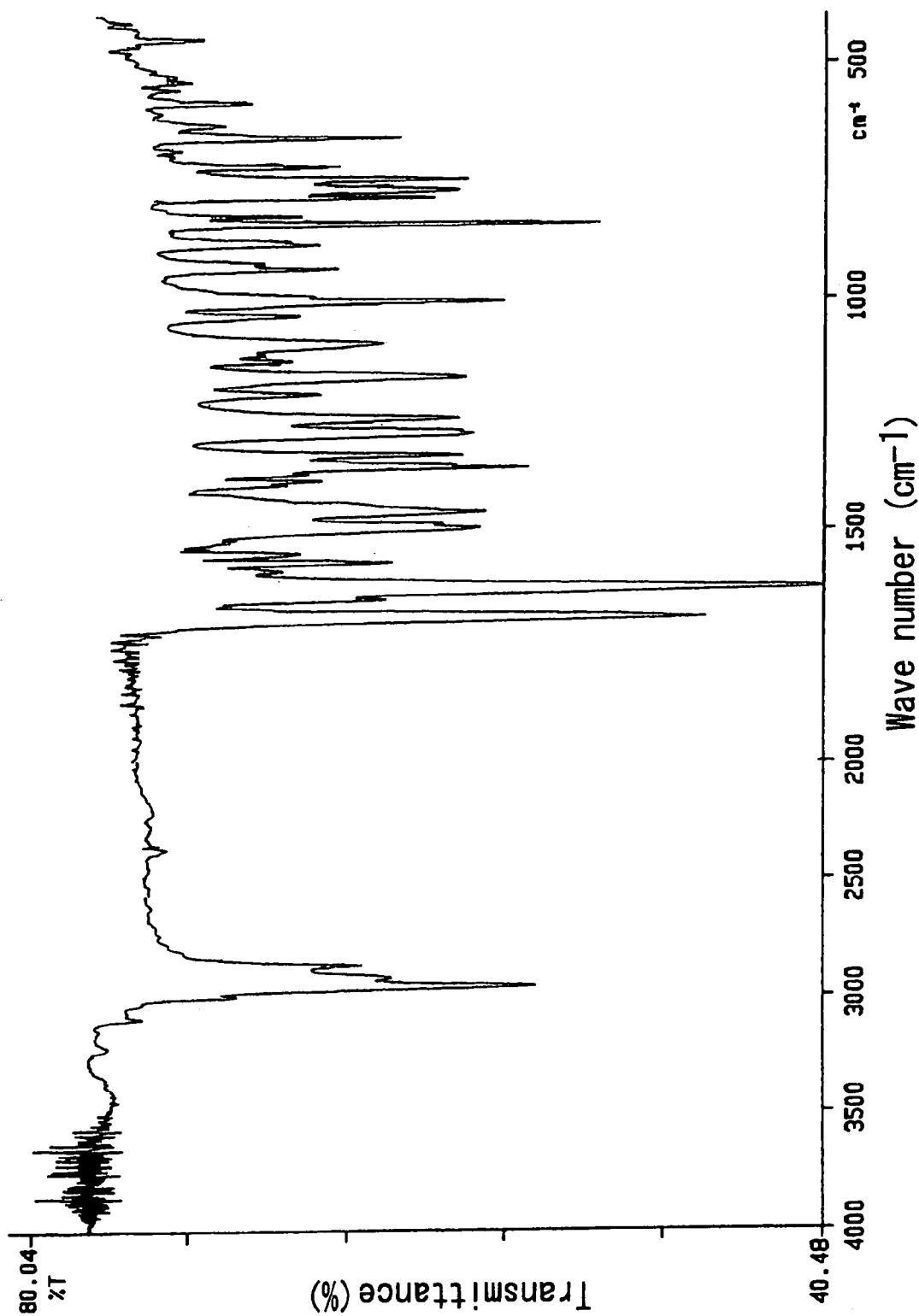
FIG. 42 is an IR spectrum of a compound represented by the chemical formula (38).
Figure 43:
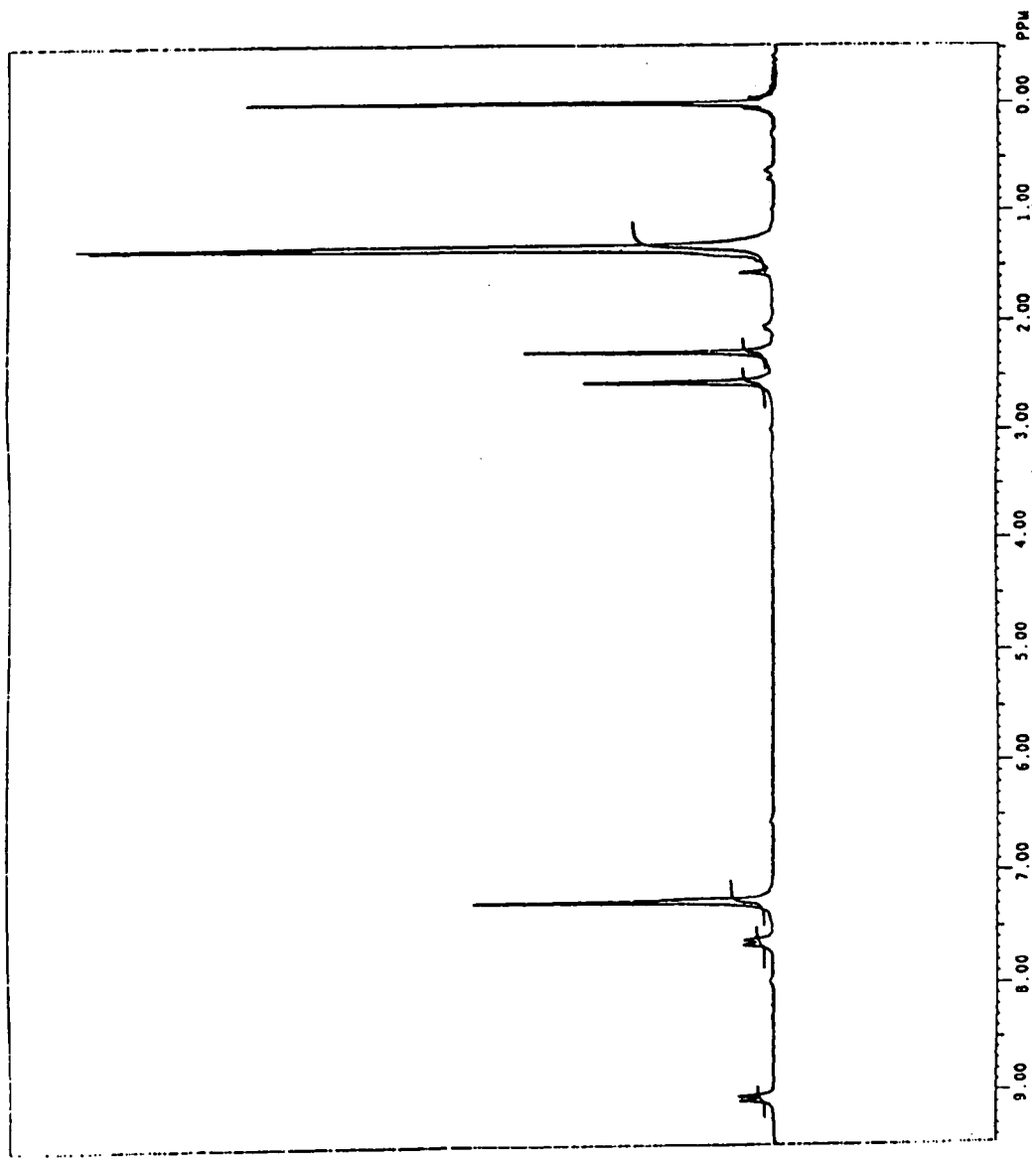
FIG. 43 is a $^1$H-NMR spectrum of the compound represented by the chemical formula (38).
Figure 44:
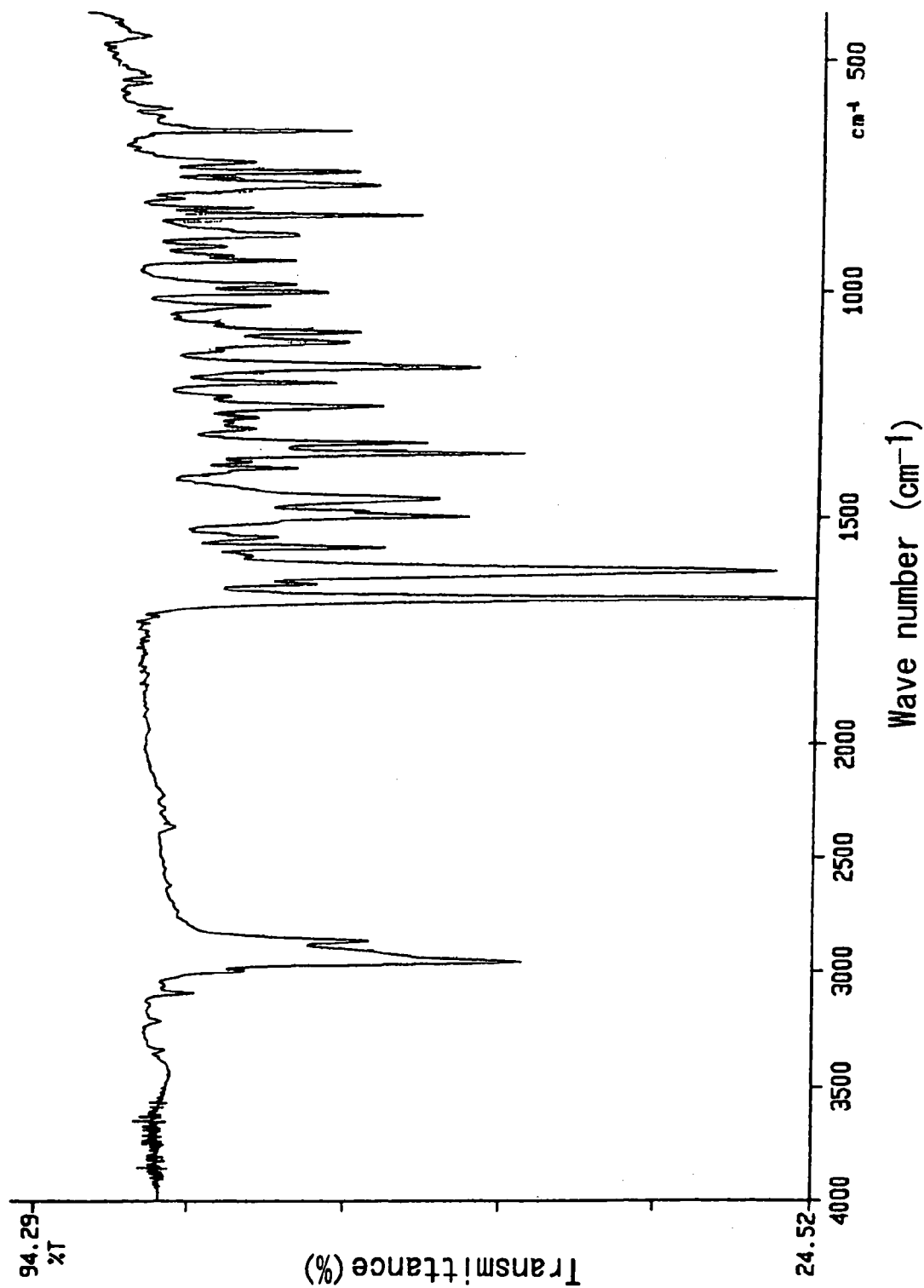
FIG. 44 is an IR spectrum of a compound represented by the chemical formula (39).
Figure 45:
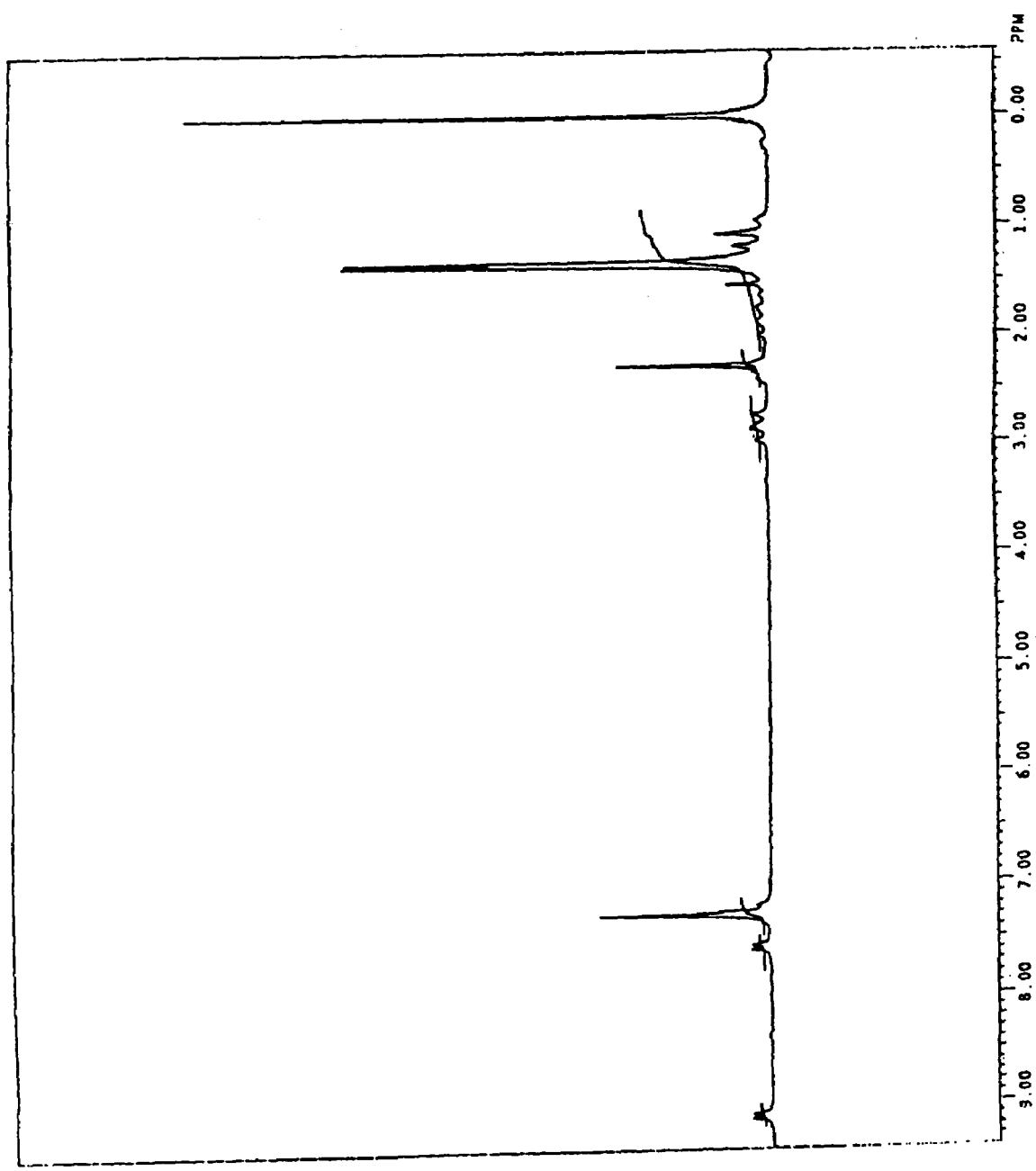
FIG. 45 is a $^1$H-NMR spectrum of the compound represented by the chemical formula (39).
Figure 46:
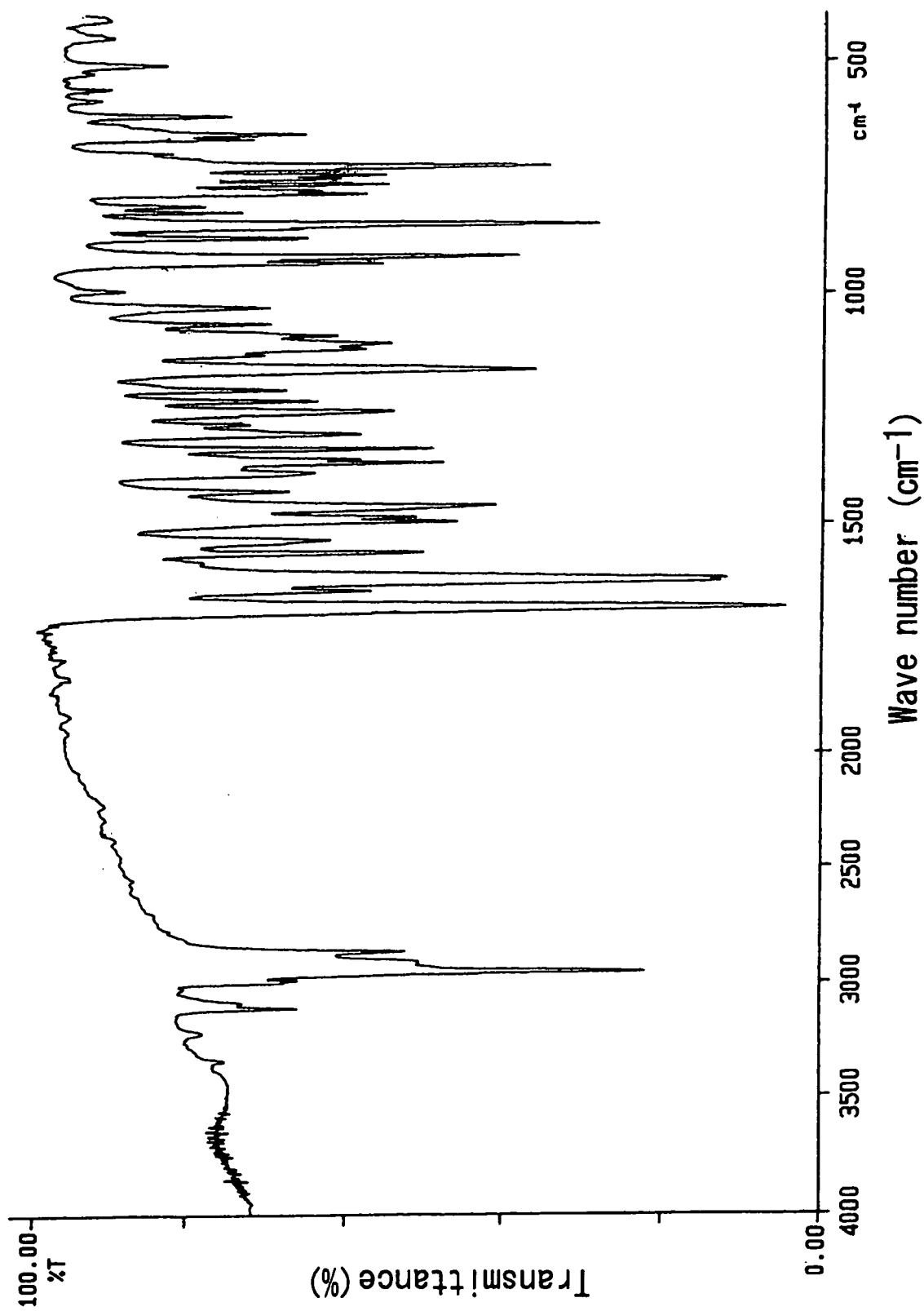
FIG. 46 is an IR spectrum of a compound represented by the chemical formula (40).
Figure 47:
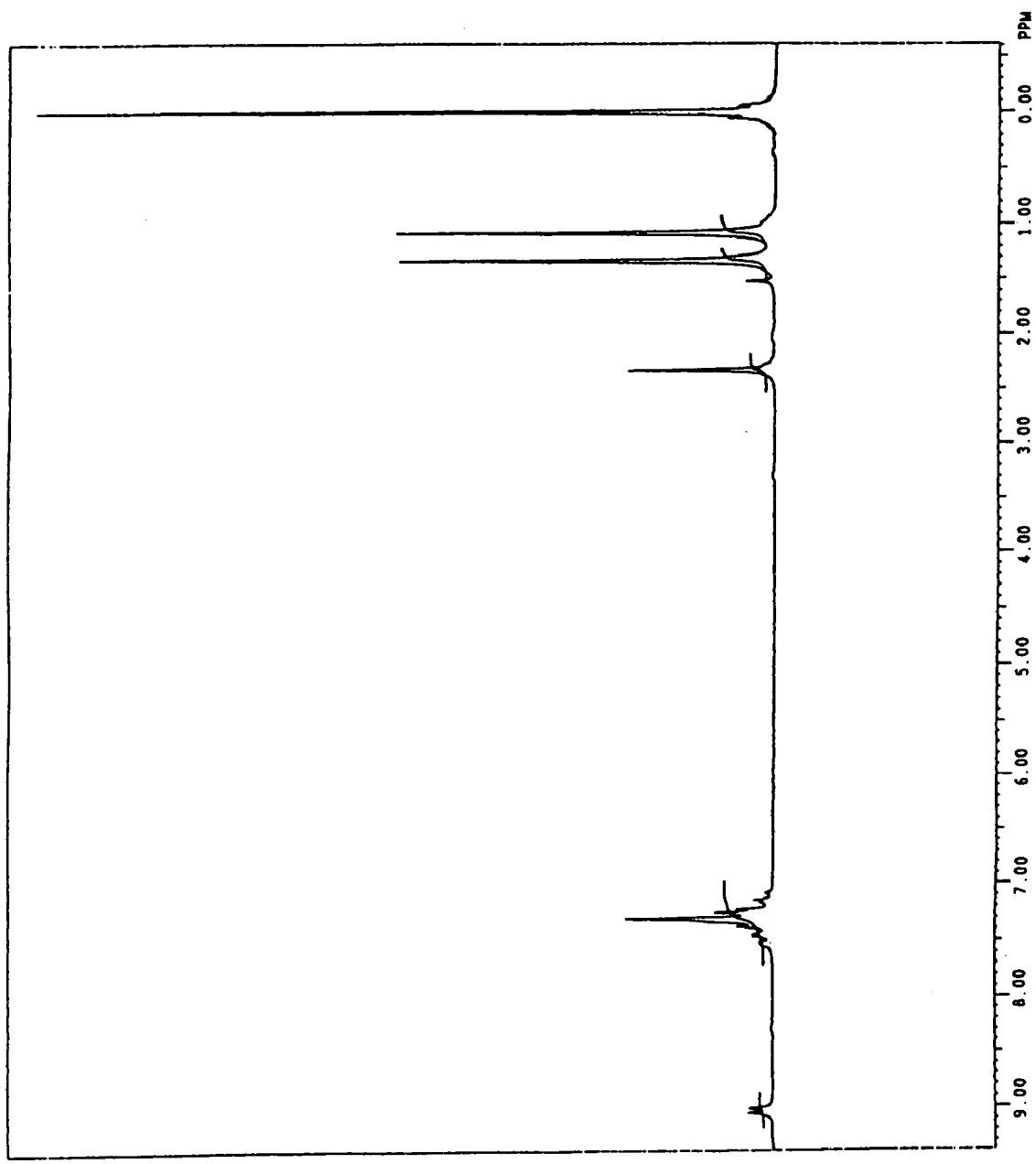
FIG. 47 is a $^1$H-NMR spectrum of the compound represented by the chemical formula (40).
Figure 48:
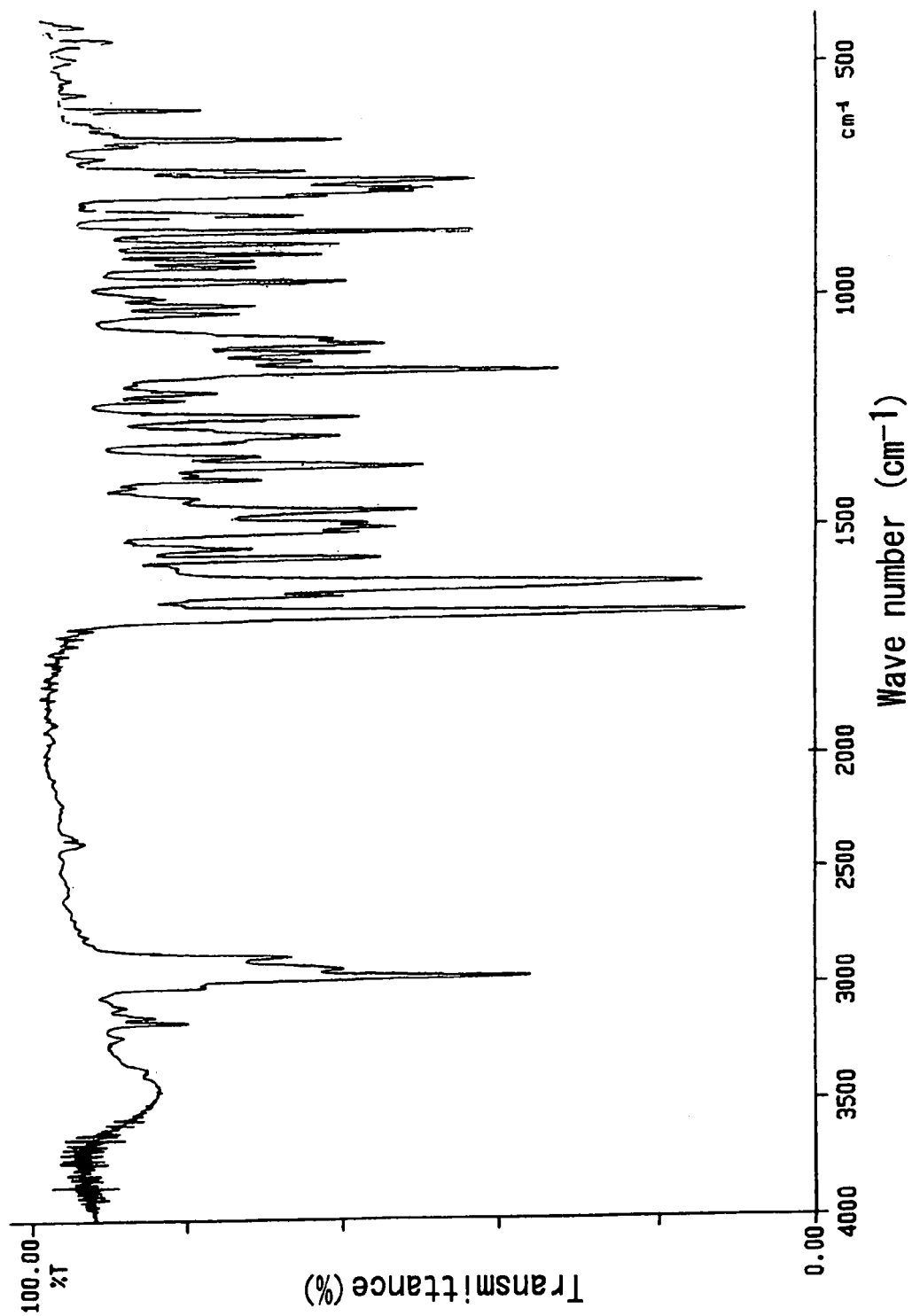
FIG. 48 is an IR spectrum of a compound represented by the chemical formula (41).
Figure 49:
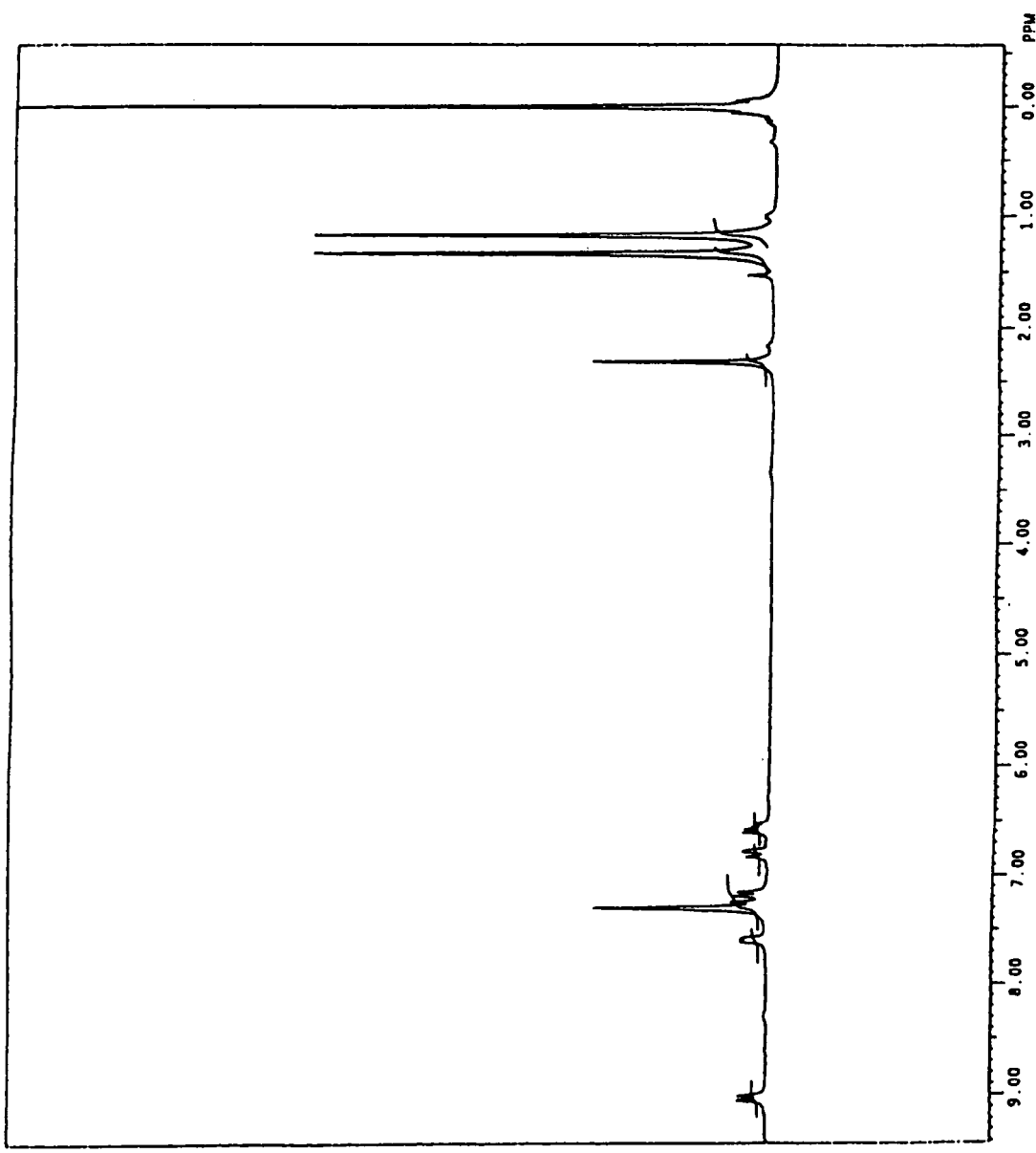
FIG. 49 is a $^1$H-NMR spectrum of the compound represented by the chemical formula (41).
Figure 50:
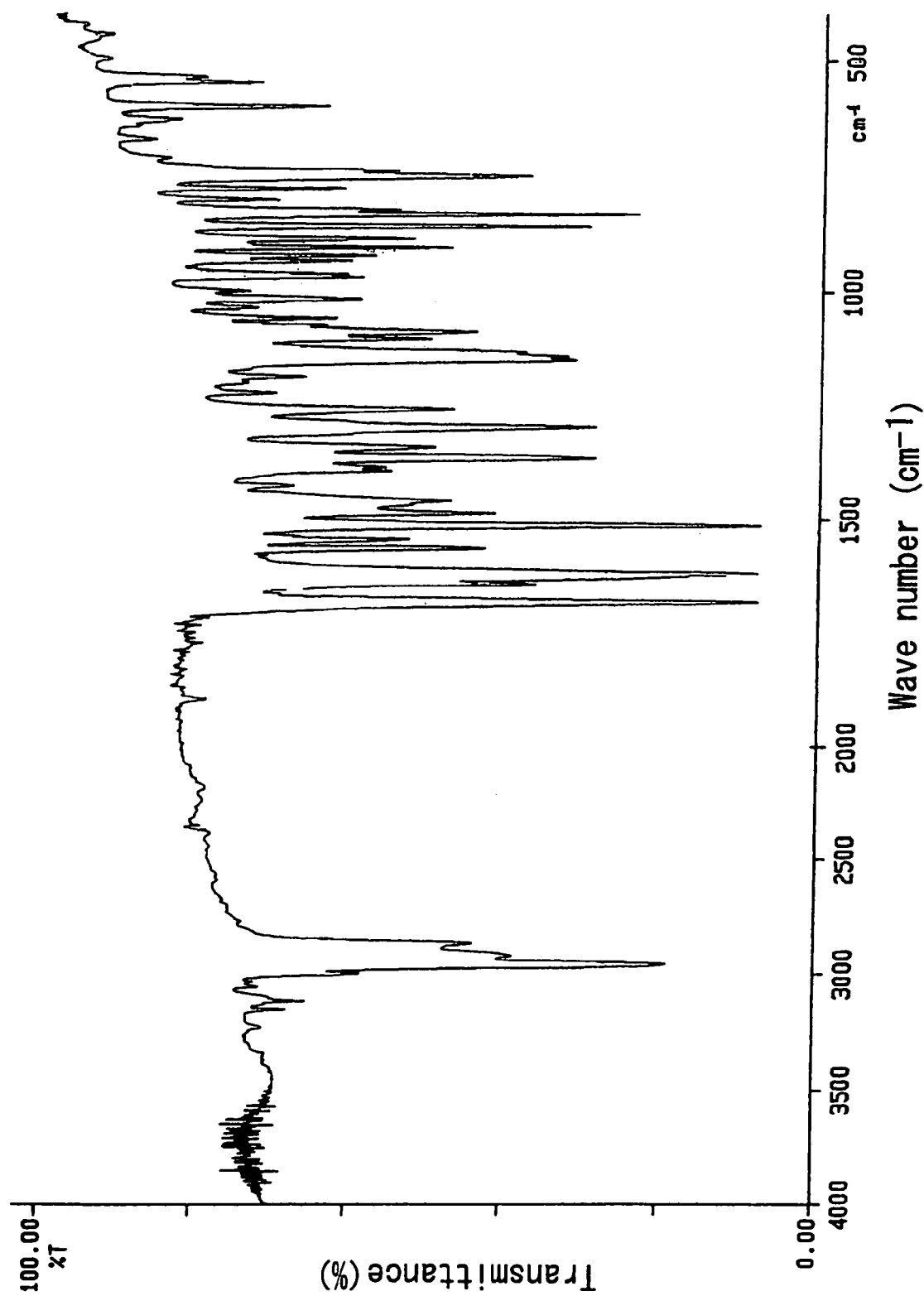
FIG. 50 is an IR spectrum of a compound represented by the chemical formula (42).
Figure 51:
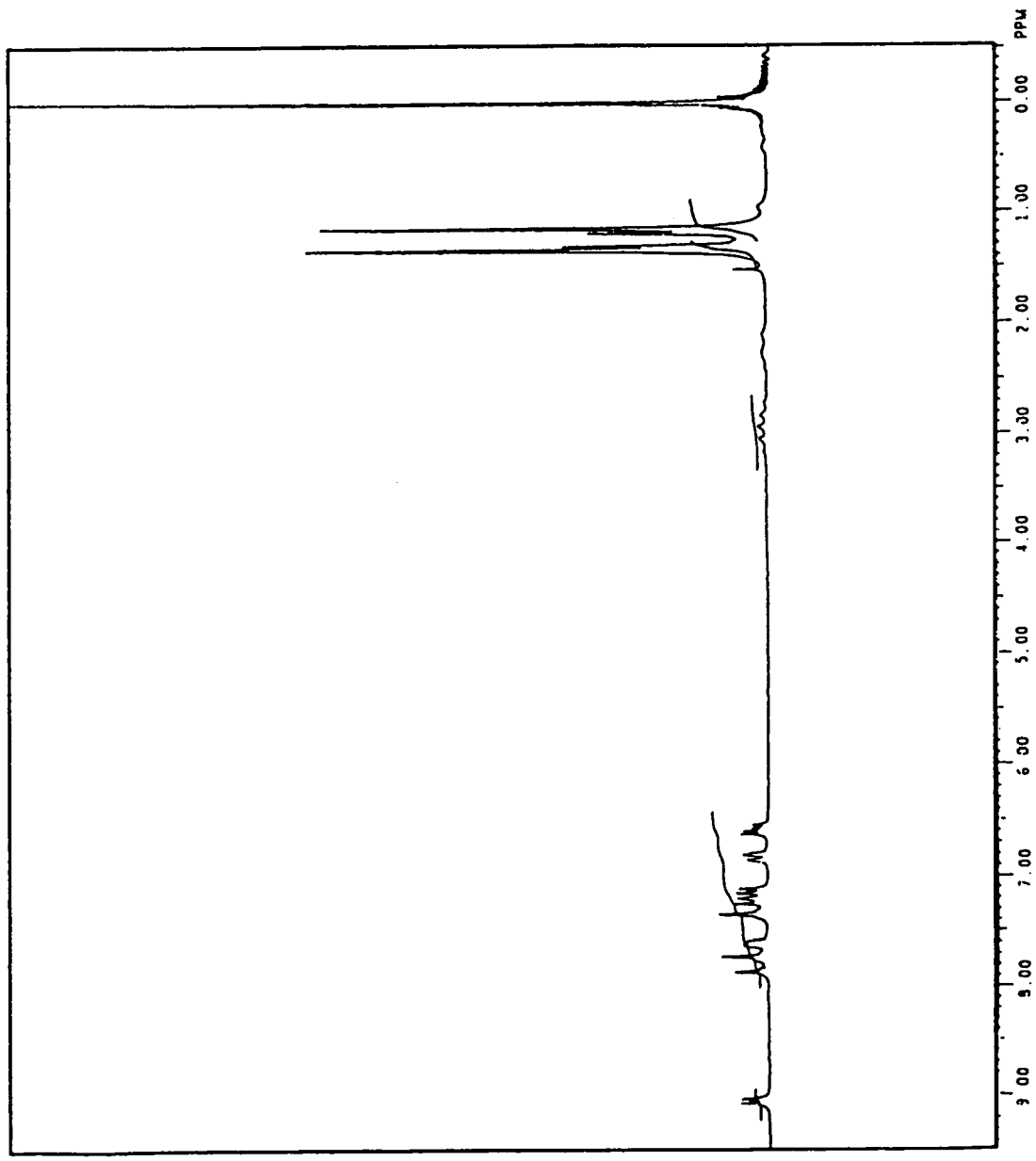
FIG. 51 is a $^1$H-NMR spectrum of the compound represented by the chemical formula (42).
Figure 52:
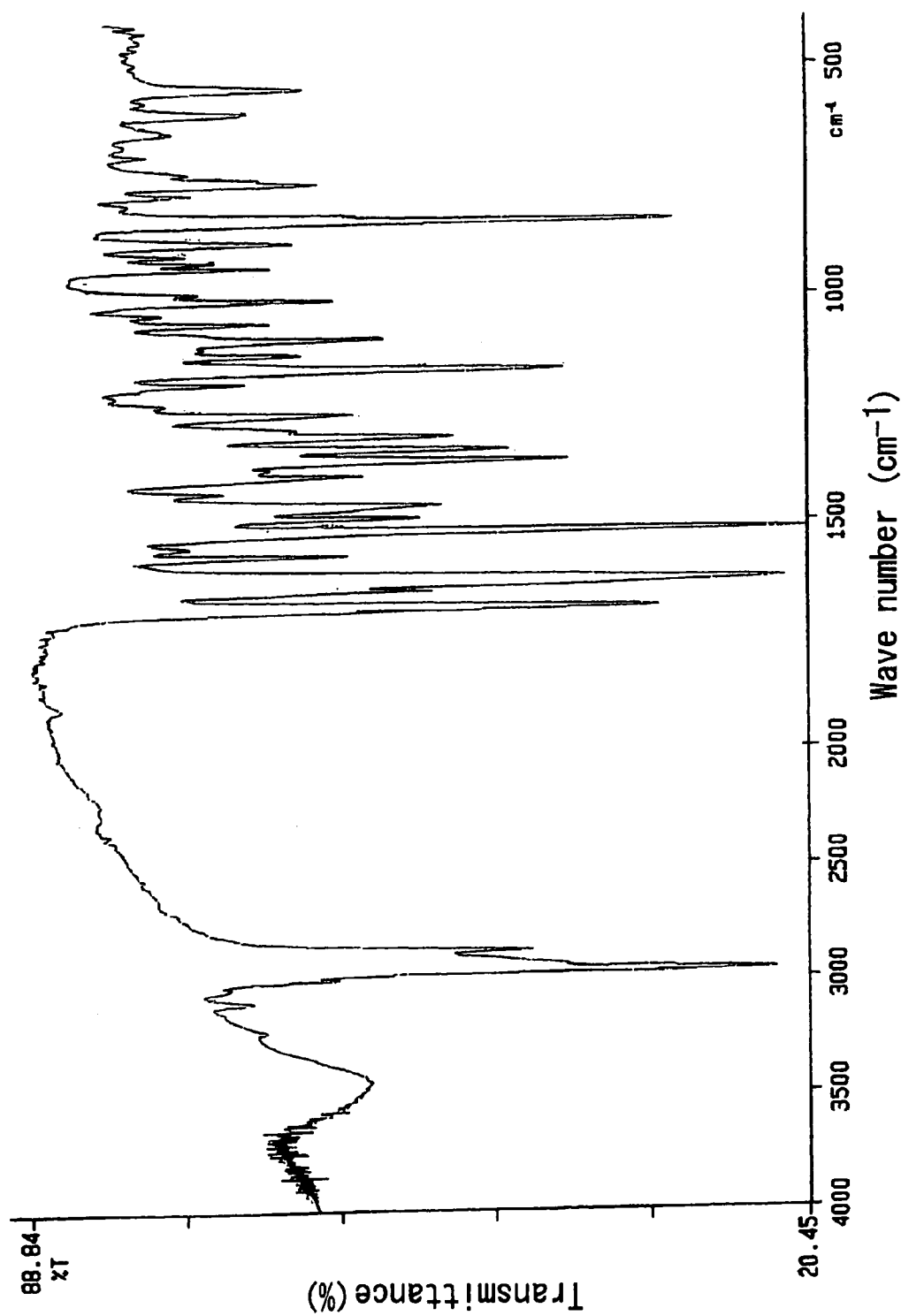
FIG. 52 is an IR spectrum of a compound represented by the chemical formula (43).
Figure 53:
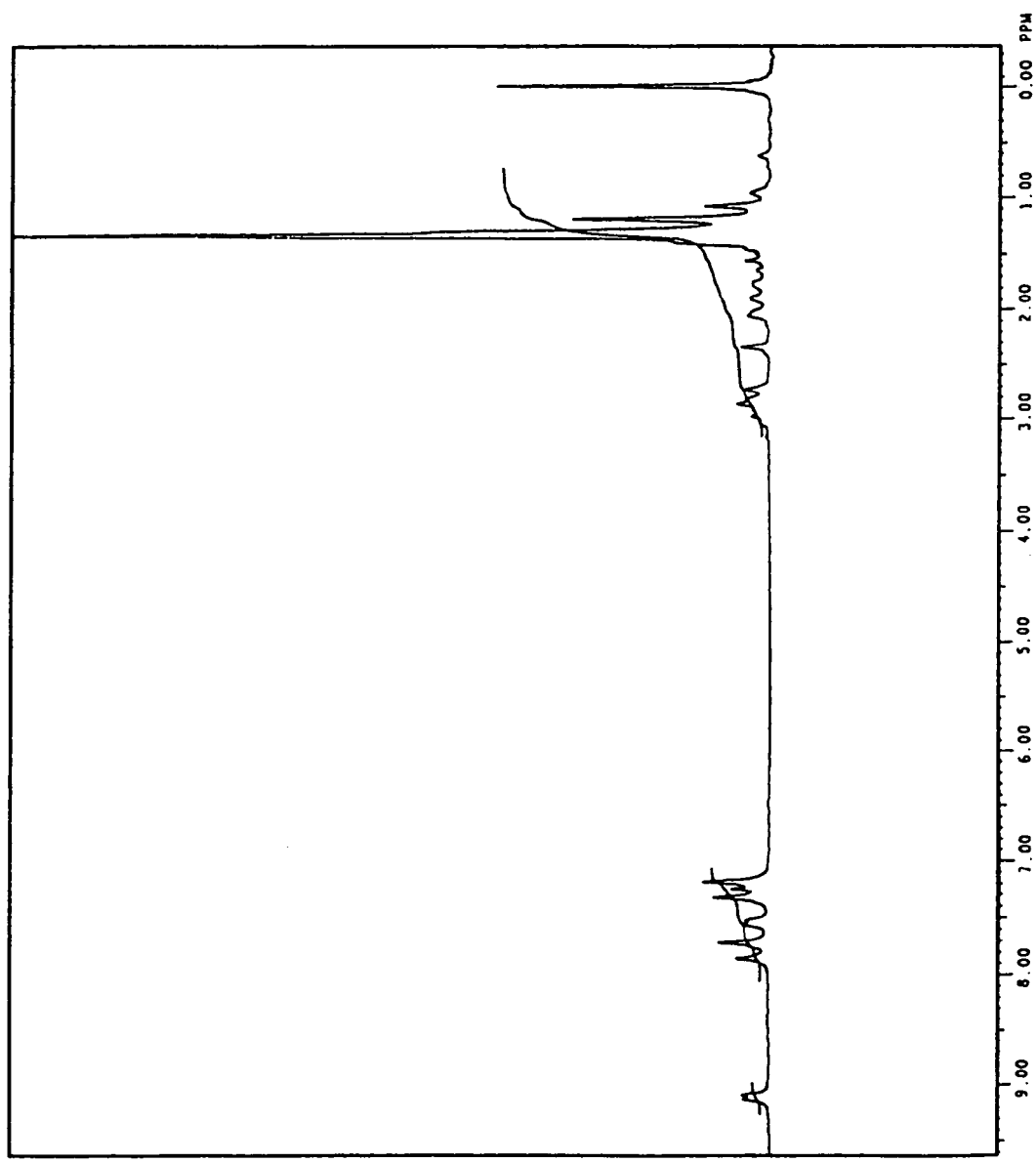
FIG. 53 is a $^1$H-NMR spectrum of the compound represented by the chemical formula (43).
Figure 54:
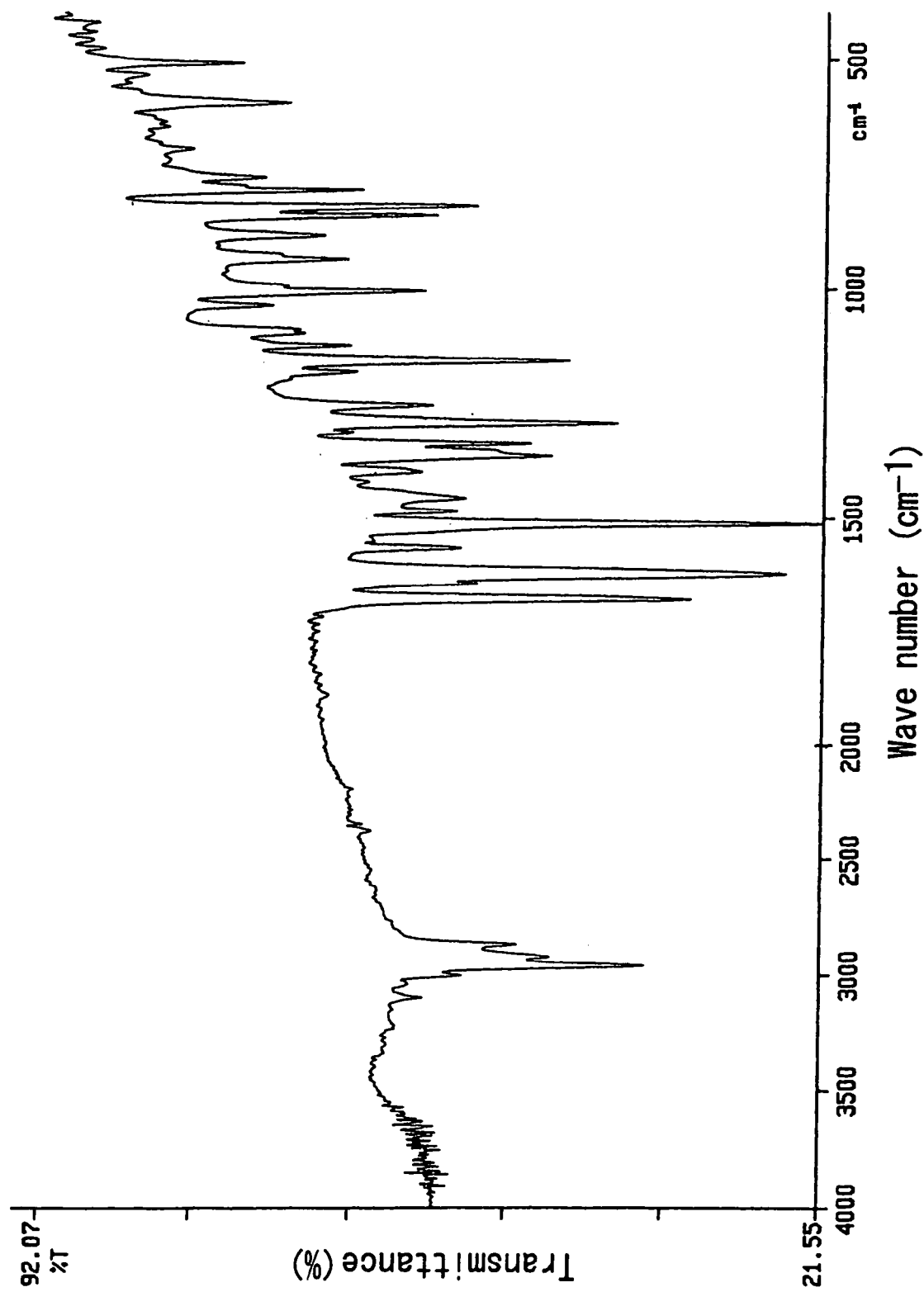
FIG. 54 is an IR spectrum of a compound represented by the chemical formula (45).
Figure 55:
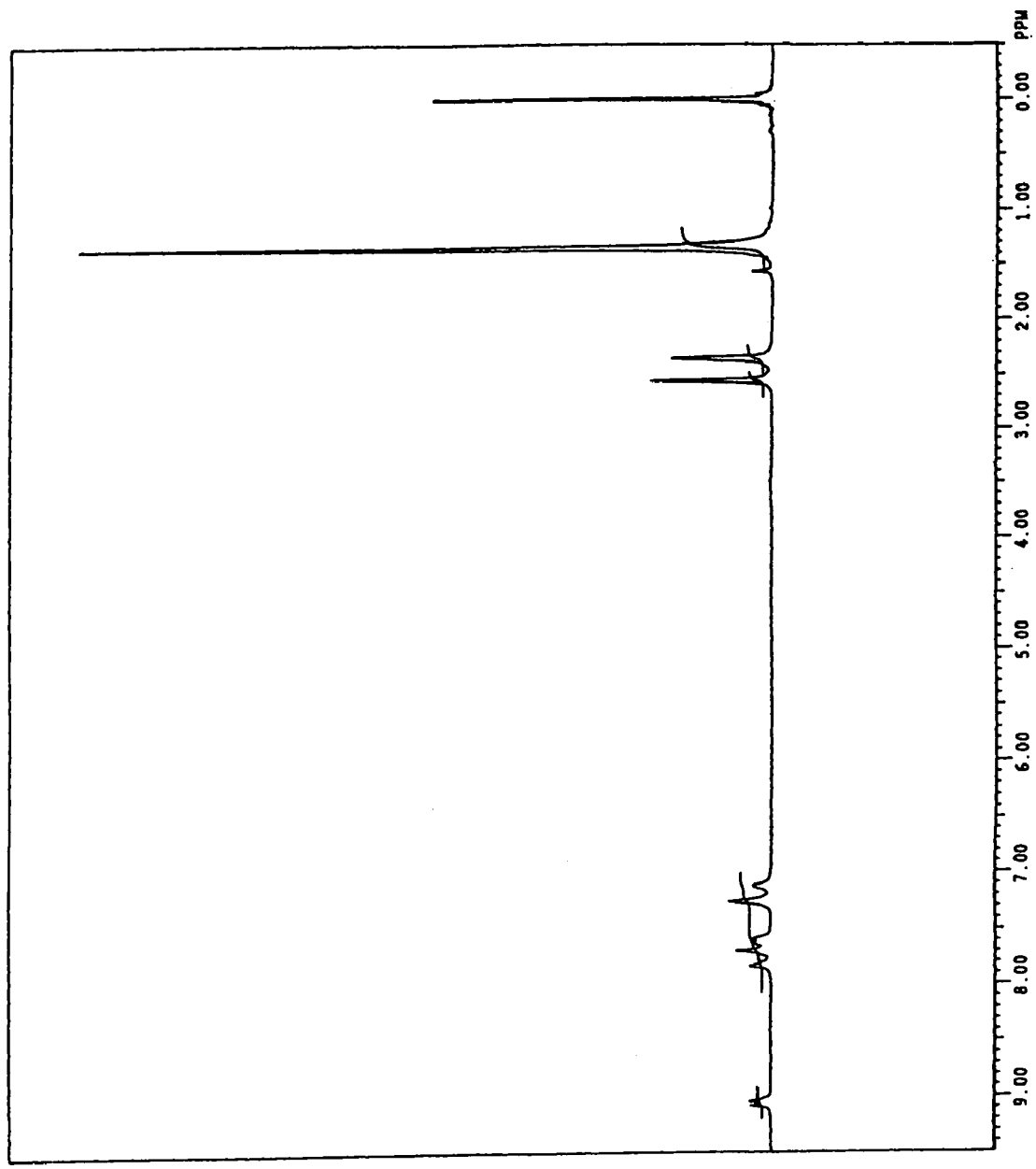
FIG. 55 is a $^1$H-NMR spectrum of the compound represented by the chemical formula (45).
Figure 56:
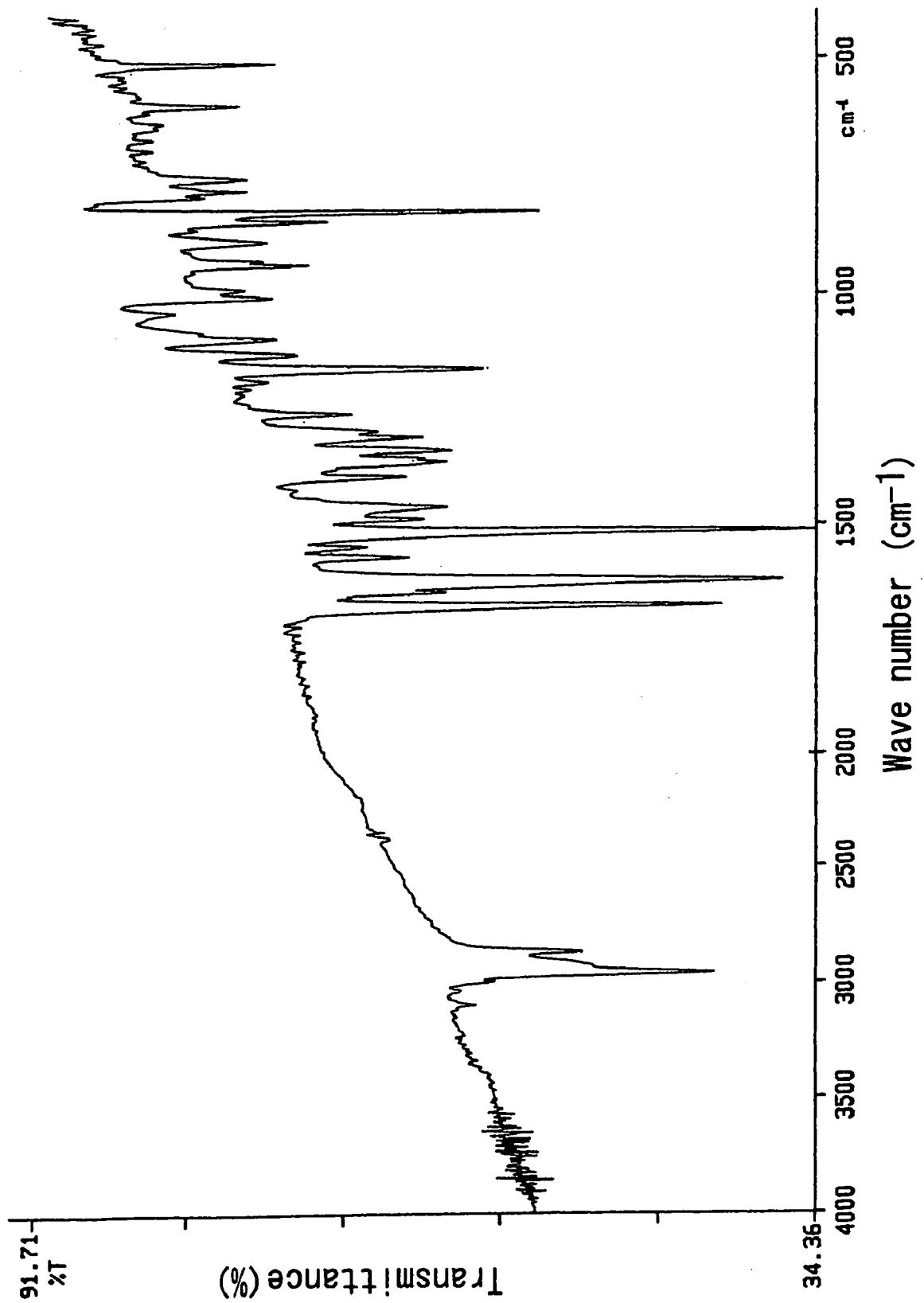
FIG. 56 is an IR spectrum of a compound represented by the chemical formula (46).
Figure 57:
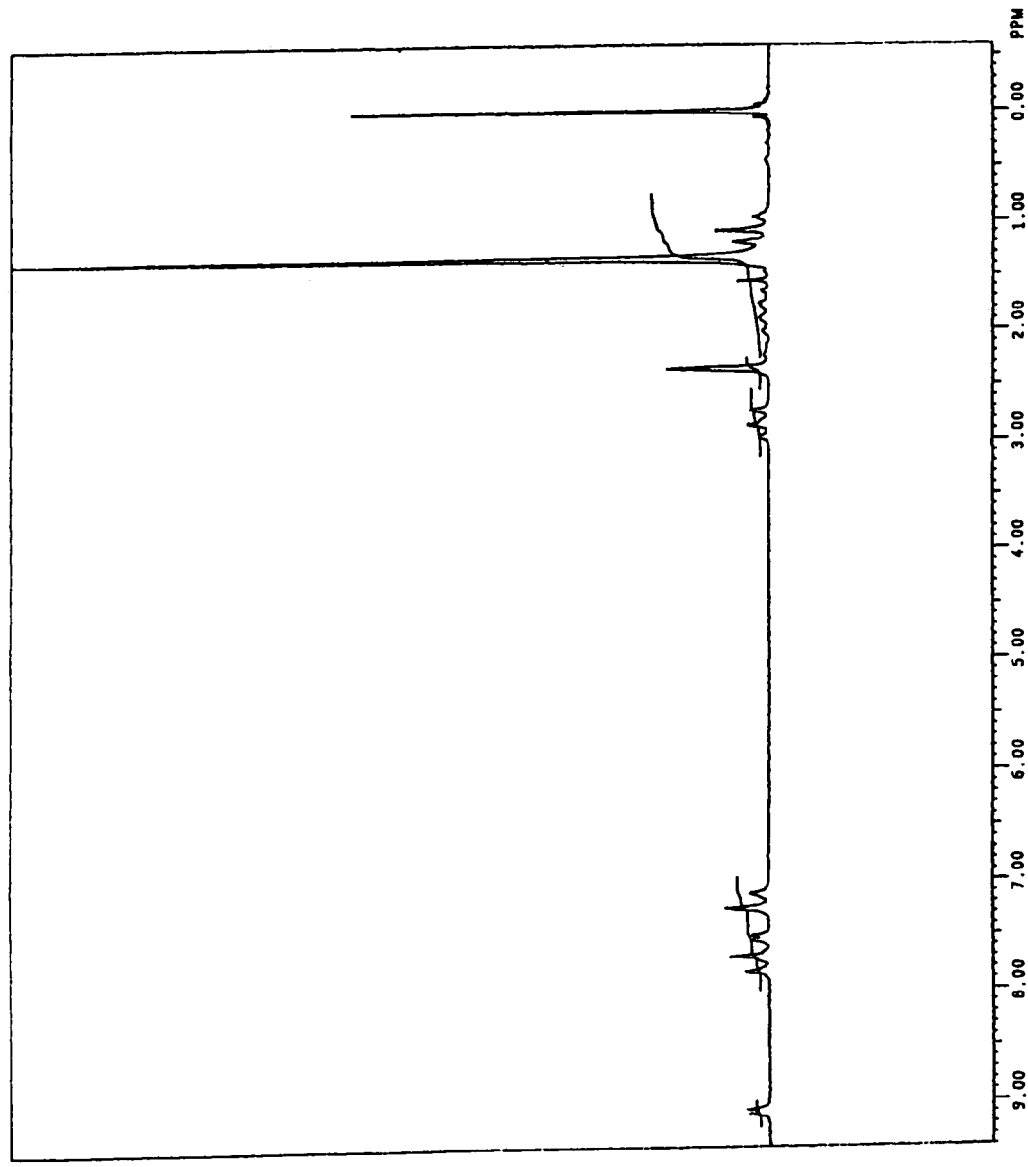
FIG. 57 is a $^1$H-NMR spectrum of the compound represented by the chemical formula (46).
Figure 58:
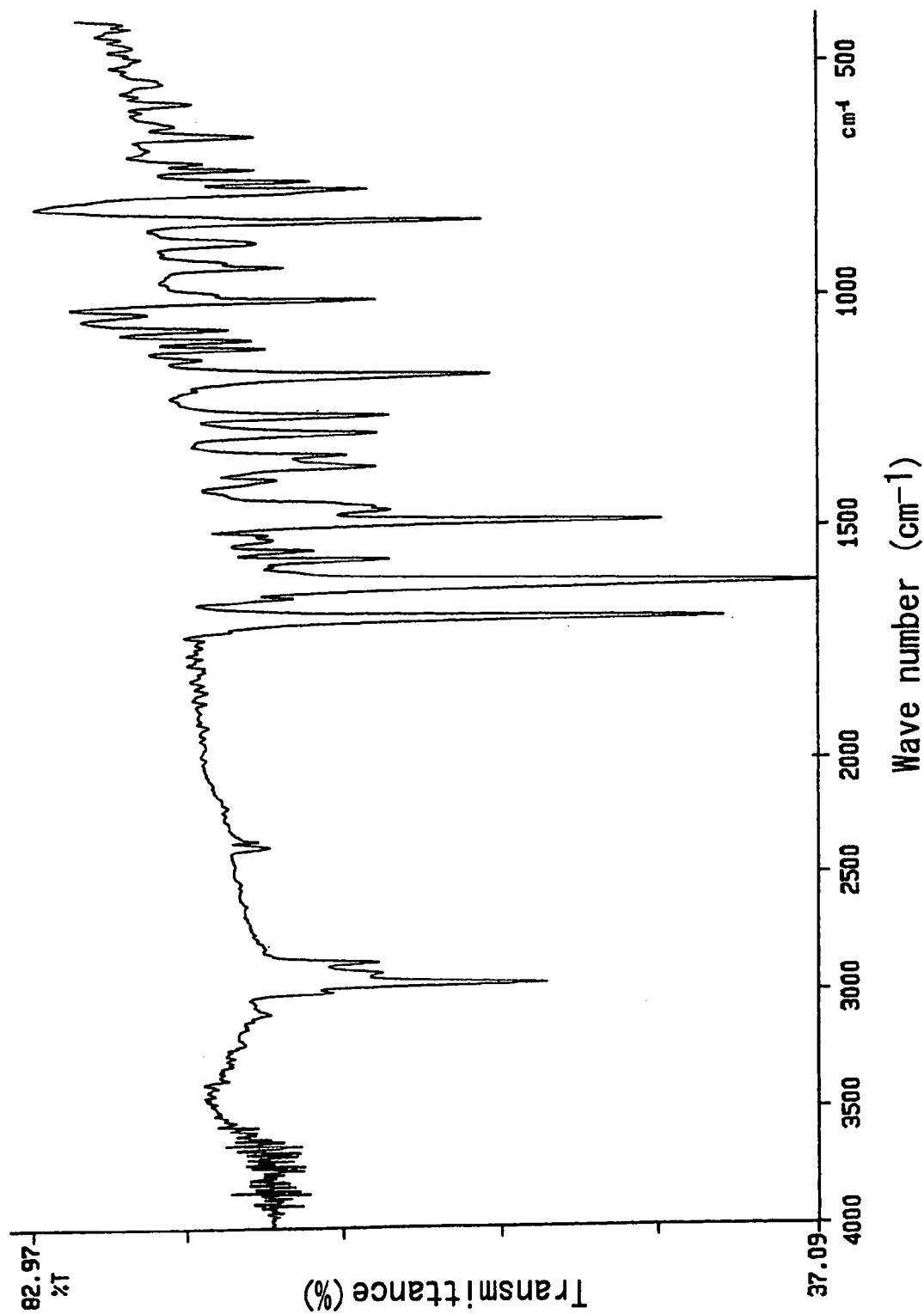
FIG. 58 is an IR spectrum of a compound represented by the chemical formula (47).
Figure 59:
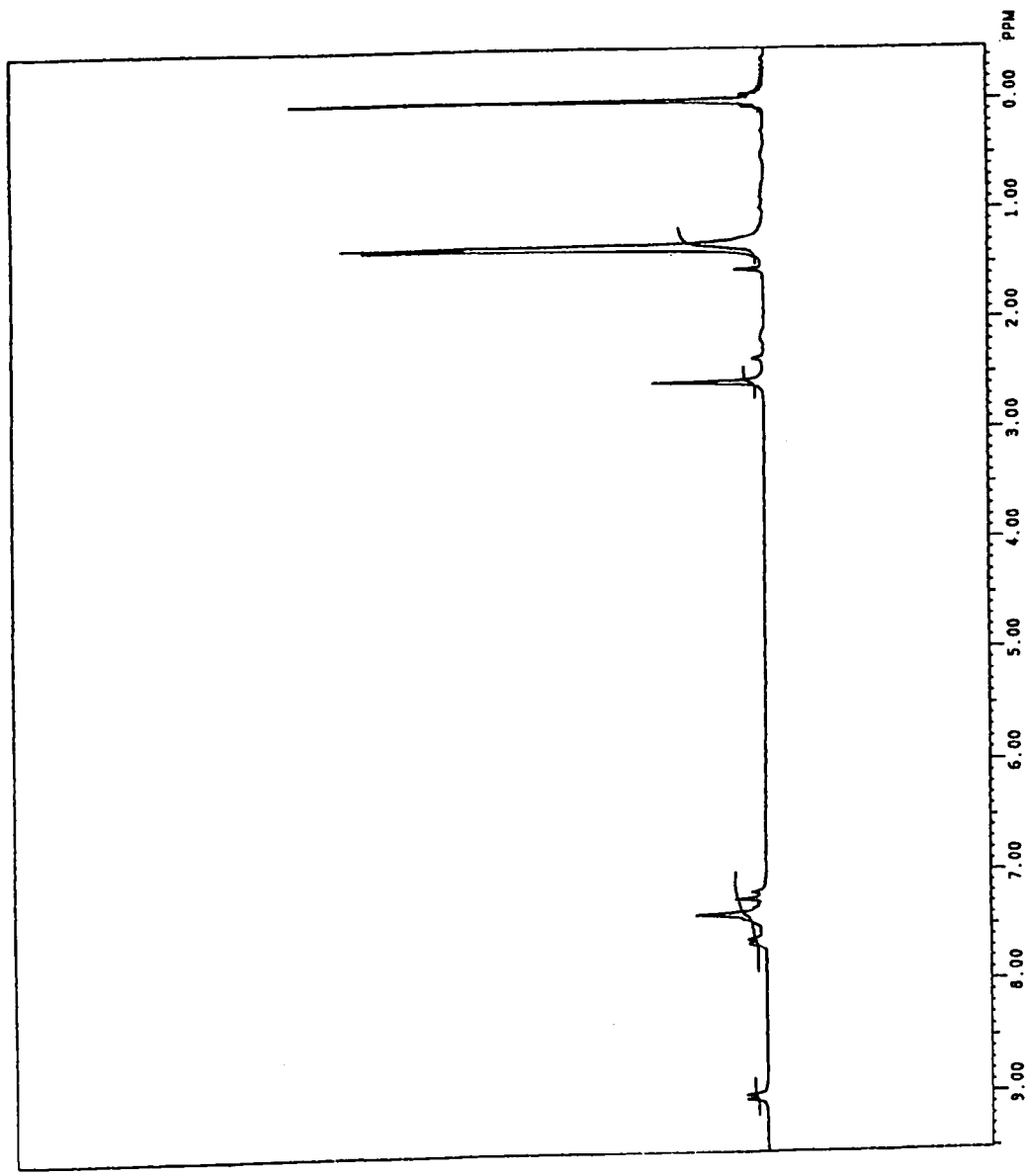
FIG. 59 is a $^1$H-NMR spectrum of the compound represented by the chemical formula (47).
Figure 60:
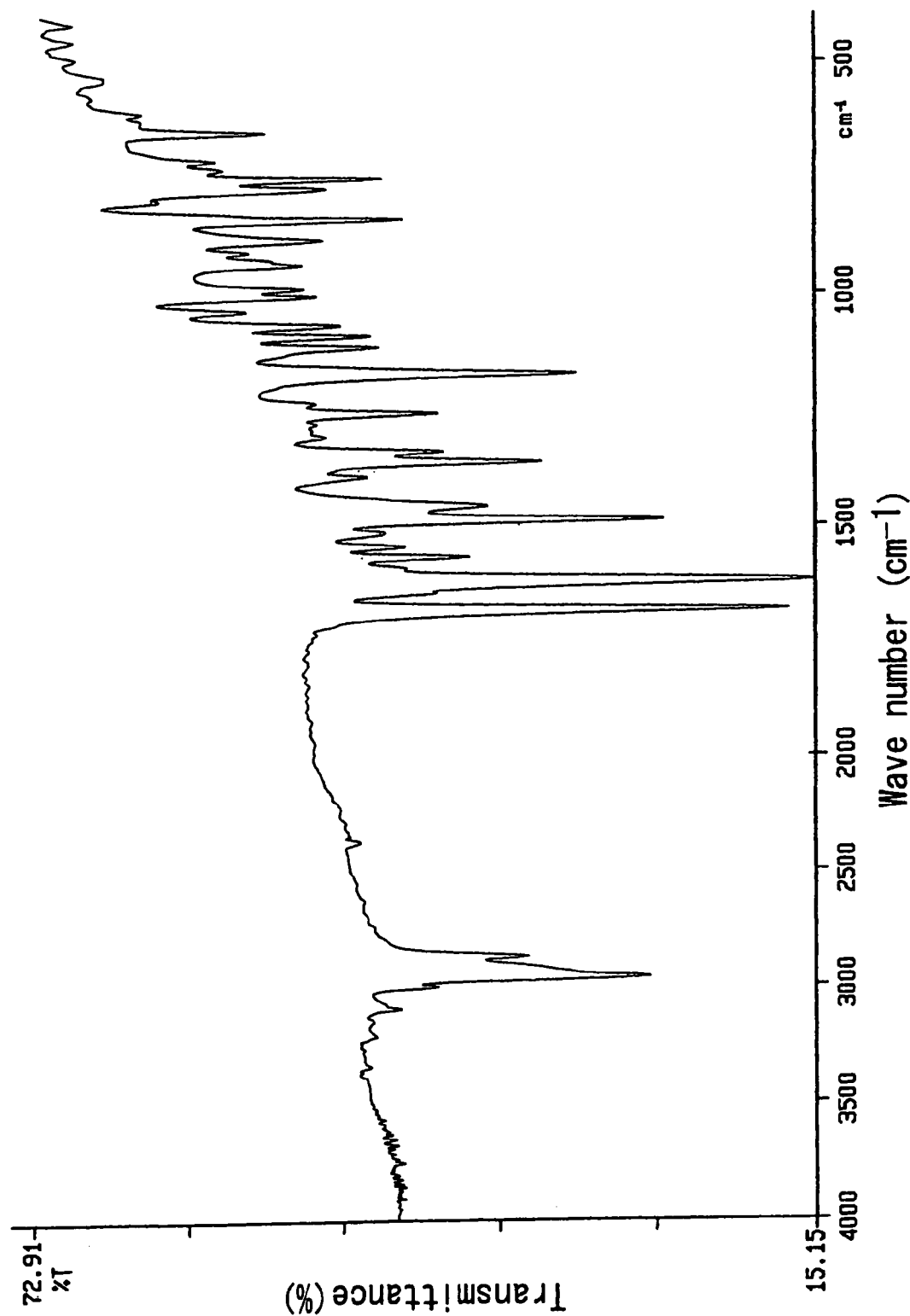
FIG. 60 is an IR spectrum of a compound represented by the chemical formula (48).
Figure 61:
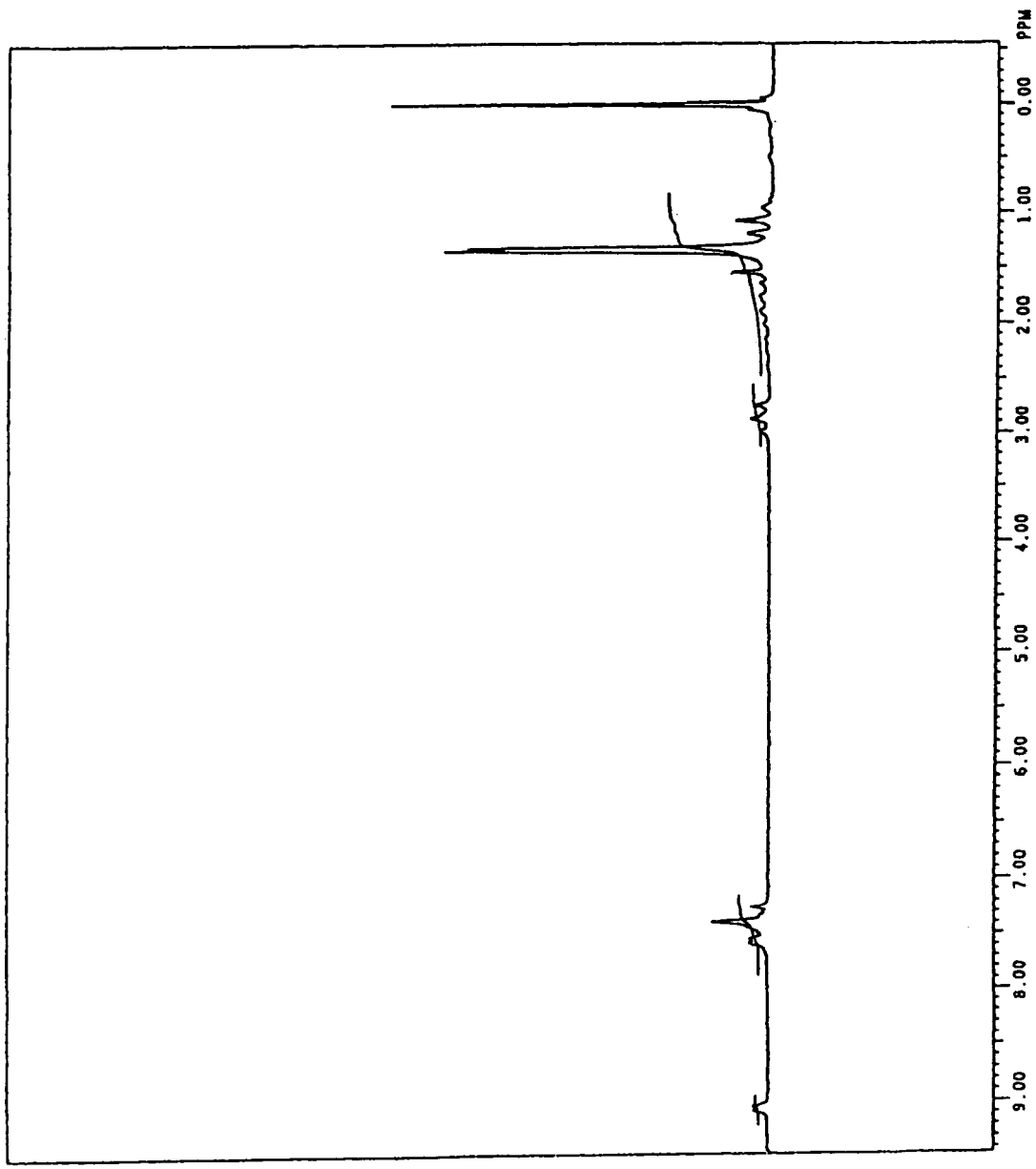
FIG. 61 is a $^1$H-NMR spectrum of the compound represented by the chemical formula (48).
Figure 62:
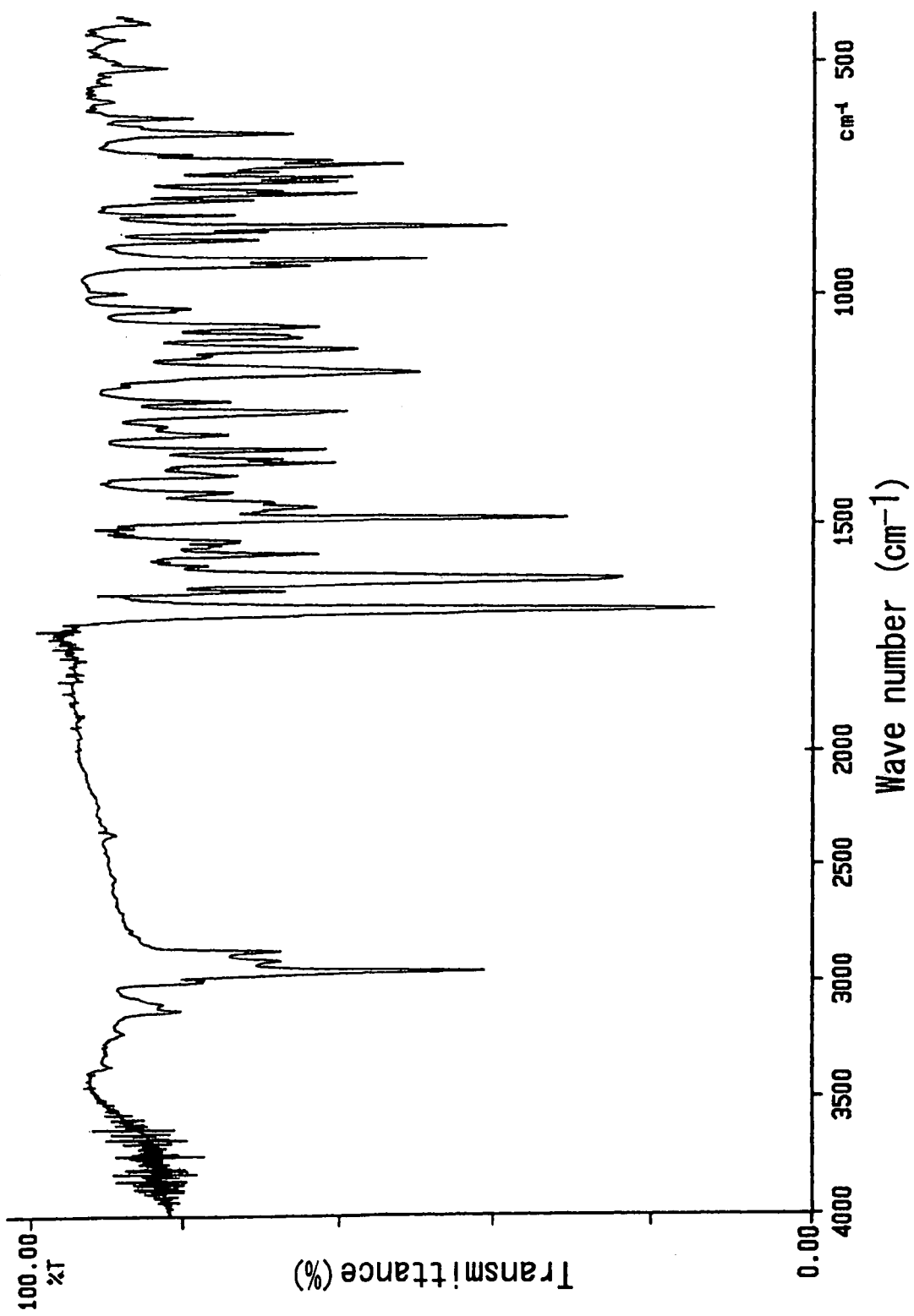
FIG. 62 is an IR spectrum of a compound represented by the chemical formula (49).
Figure 63:
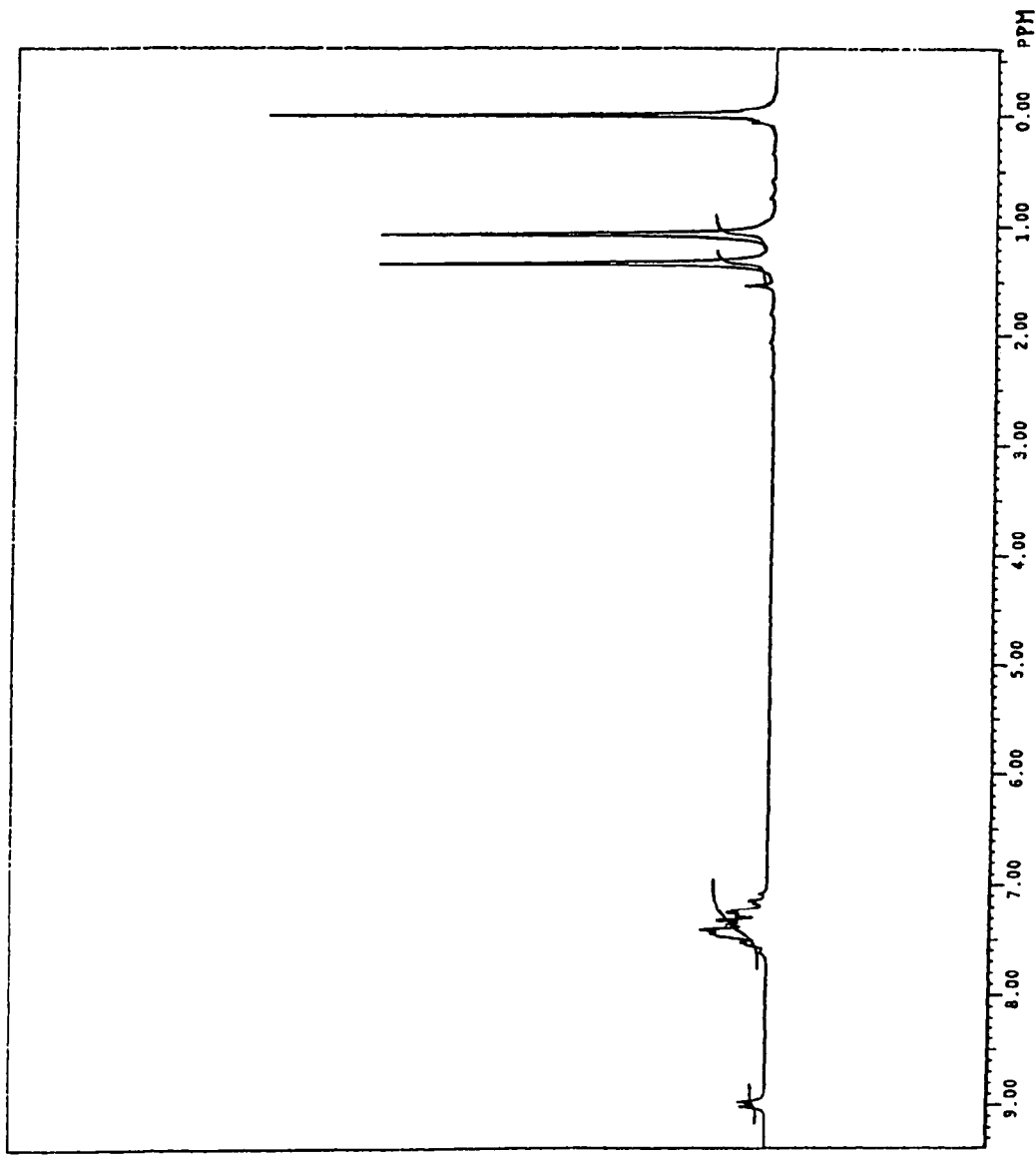
FIG. 63 is a $^1$H-NMR spectrum of the compound represented by the chemical formula (49).
Figure 64:
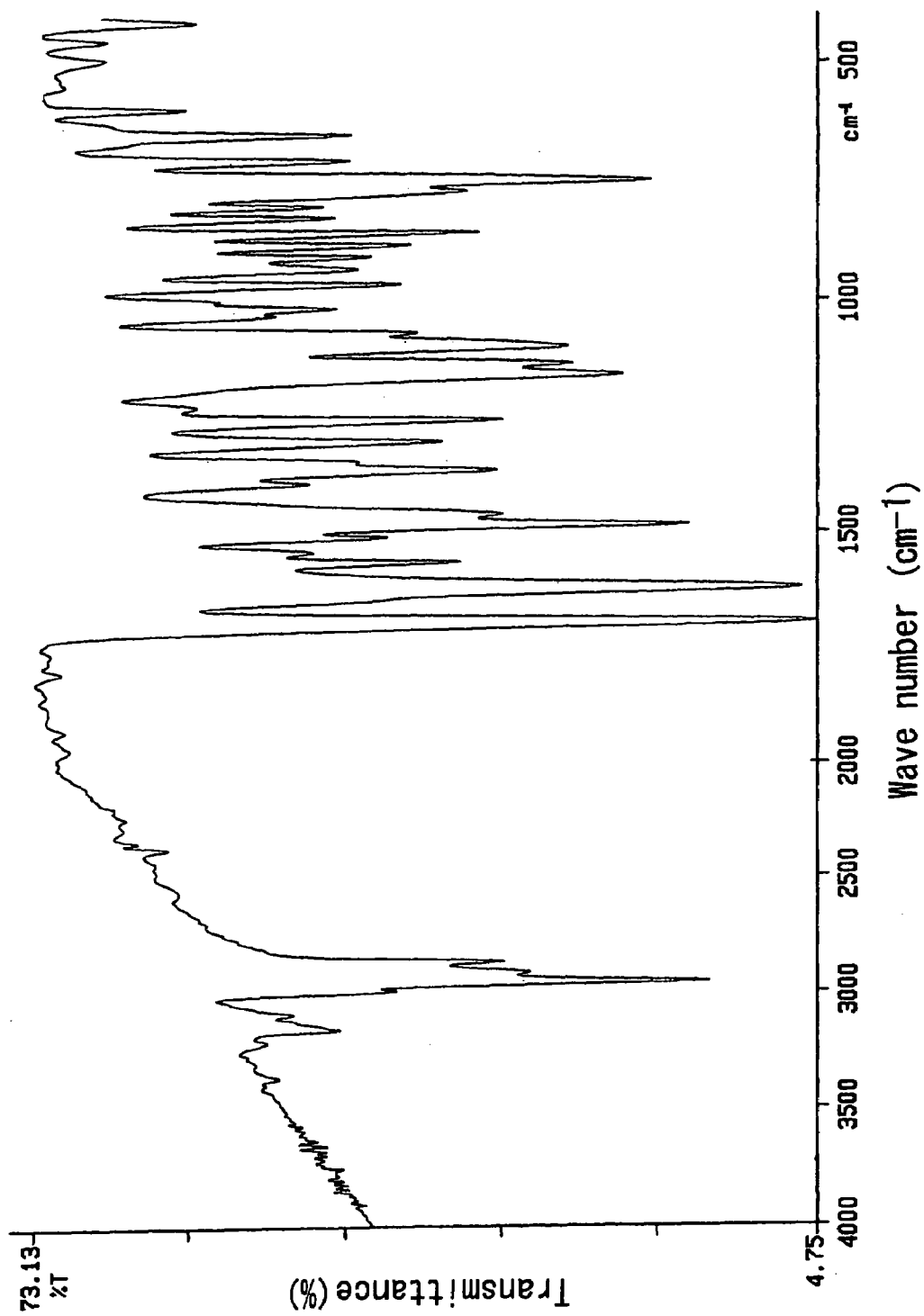
FIG. 64 is an IR spectrum of a compound represented by the chemical formula (50).
Figure 65:
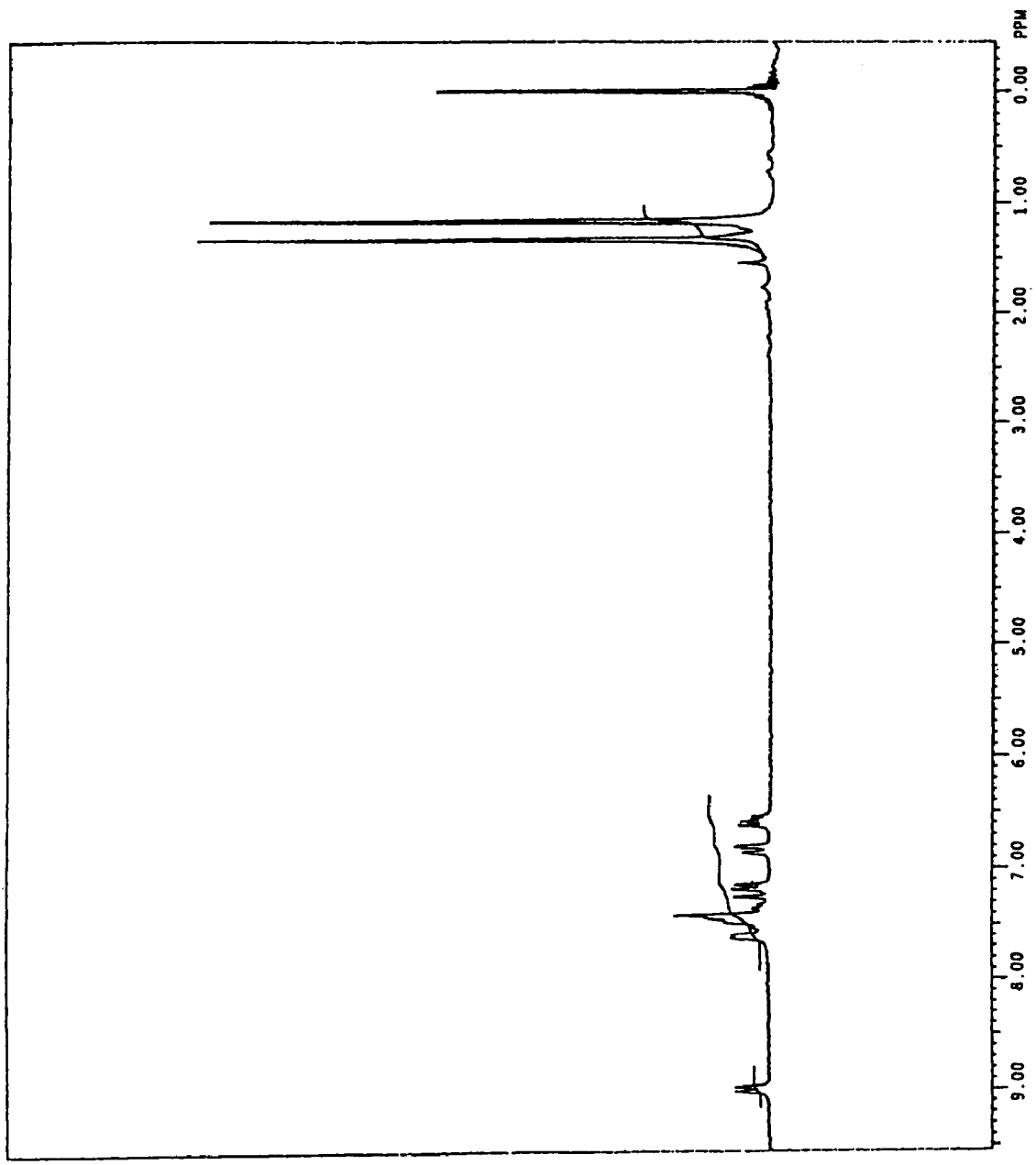
FIG. 65 is a $^1$H-NMR spectrum of the compound represented by the chemical formula (50).
Figure 66:
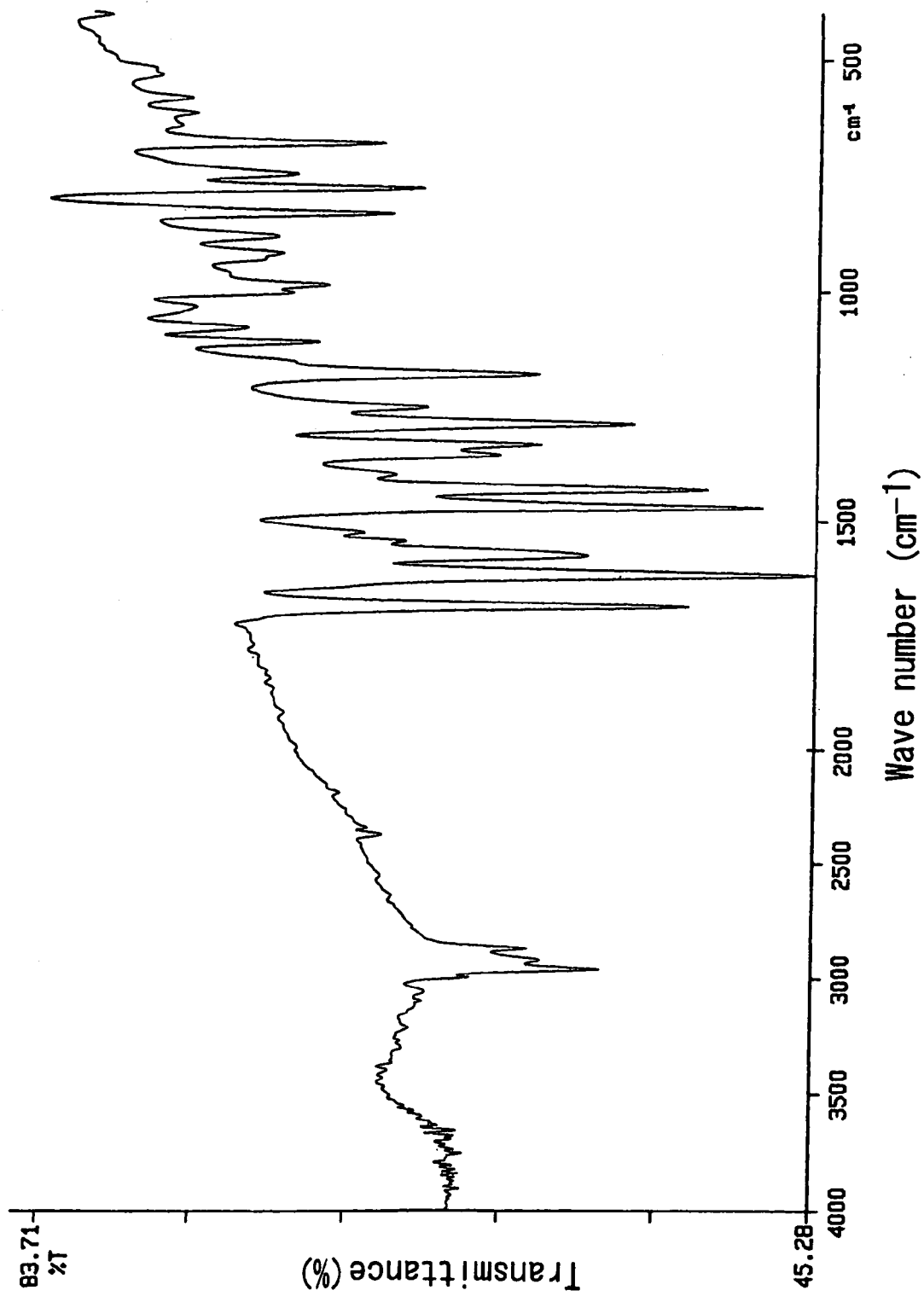
FIG. 66 is an IR spectrum of a compound represented by the chemical formula (51).
Figure 67:
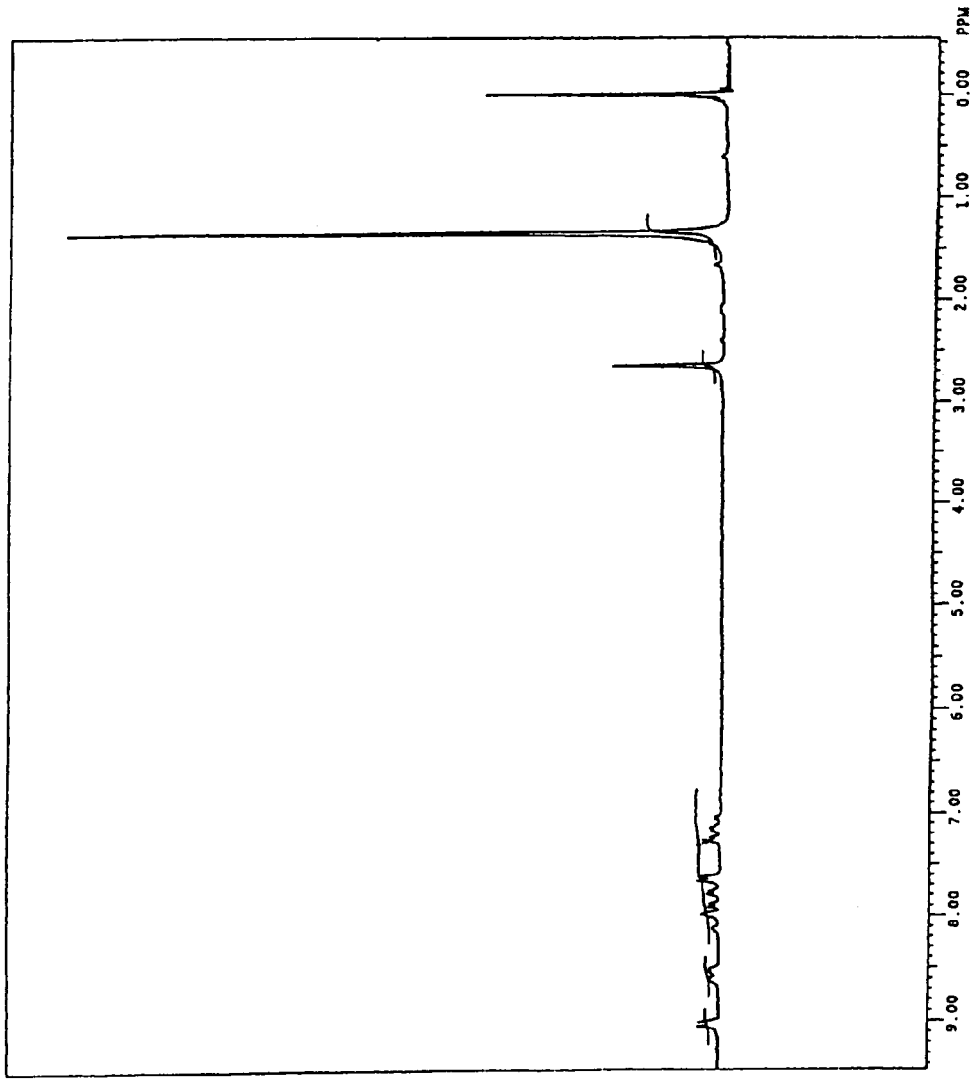
FIG. 67 is a $^1$H-NMR spectrum of the compound represented by the chemical formula (51).
Figure 68:
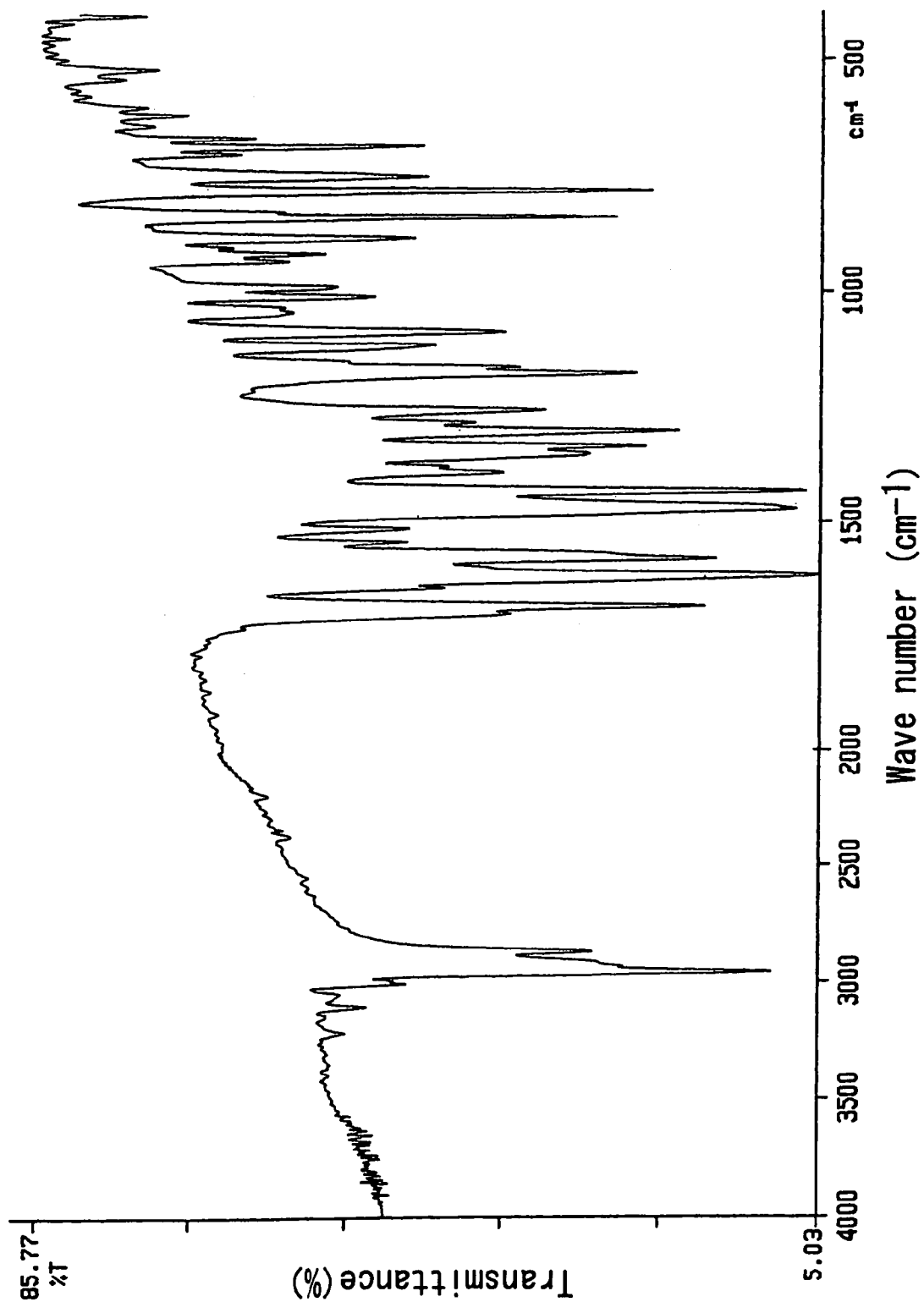
FIG. 68 is an IR spectrum of a compound represented by the chemical formula (52).
Figure 69:
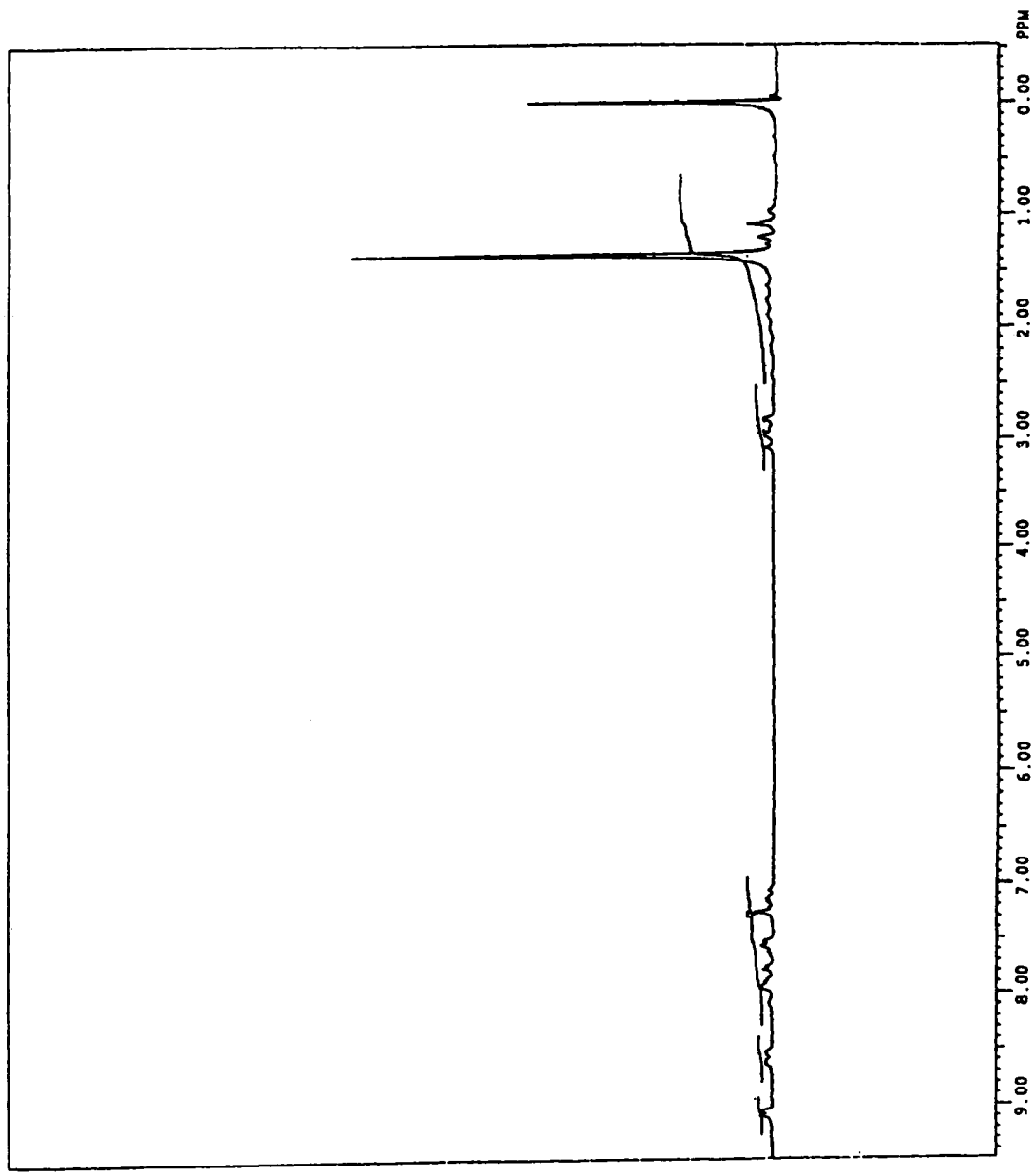
FIG. 69 is a $^1$H-NMR spectrum of the compound represented by the chemical formula (52).
Figure 70:
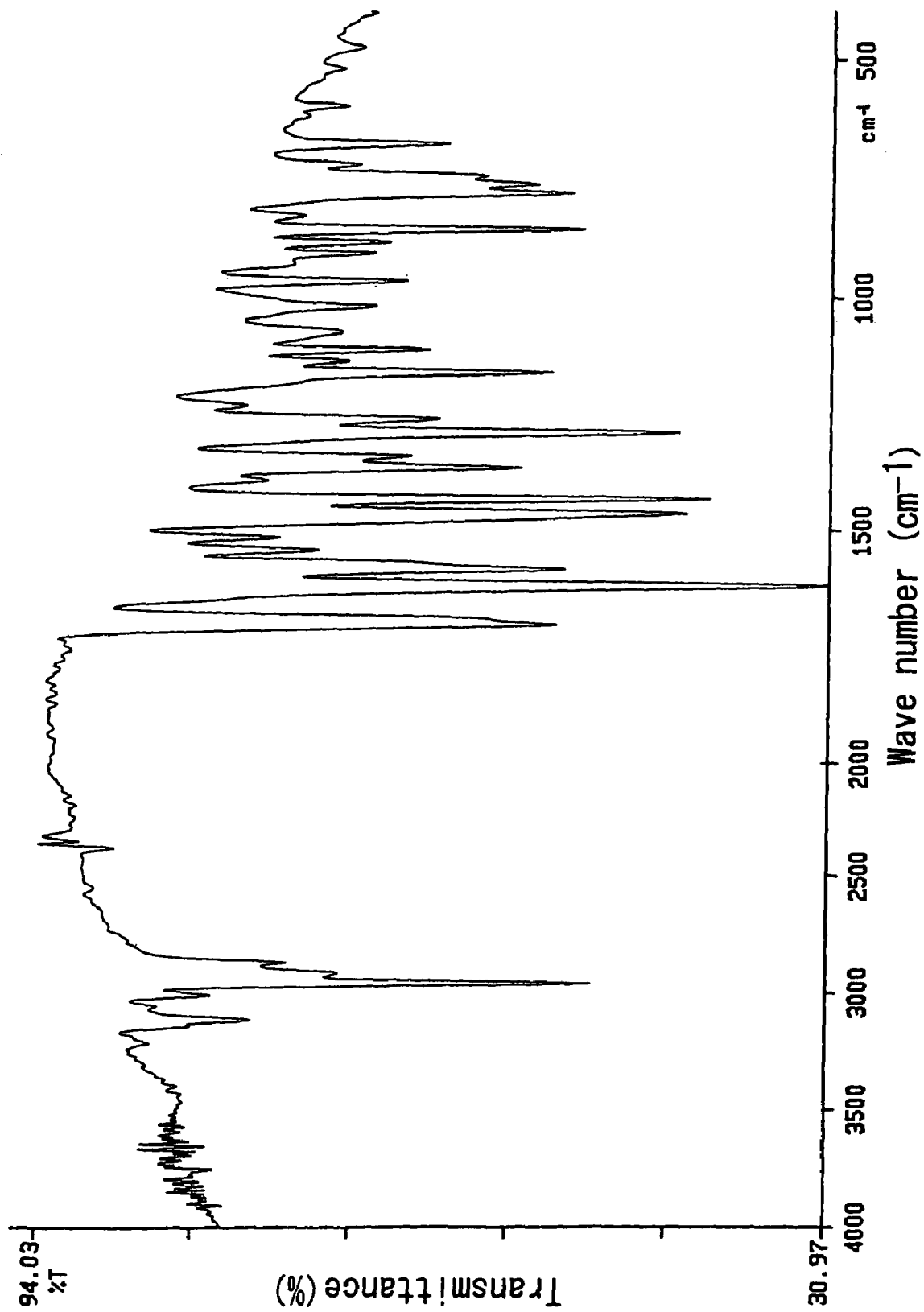
FIG. 70 is an IR spectrum of a compound represented by the chemical formula (53).
Figure 71:
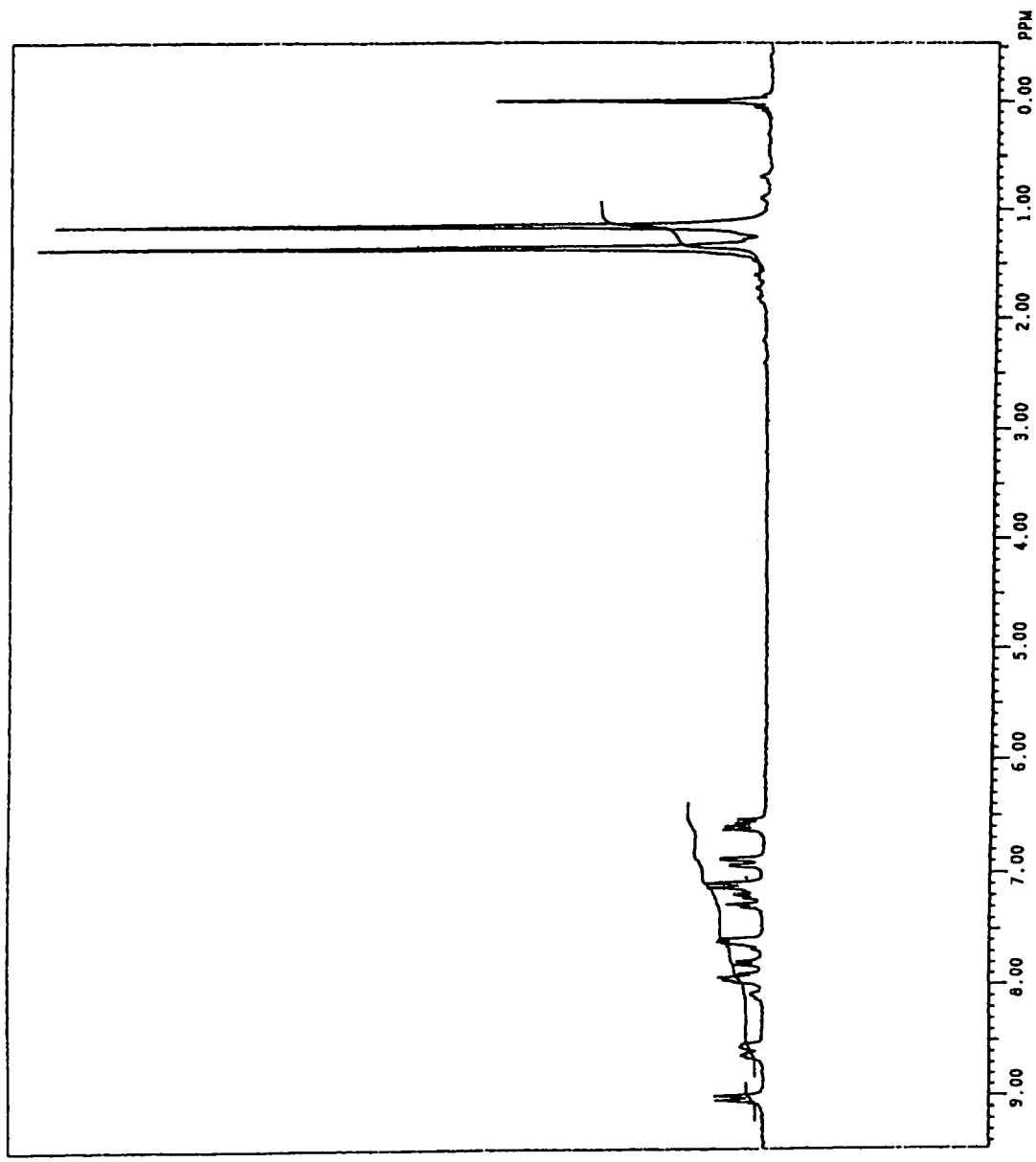
FIG. 71 is a $^1$H-NMR spectrum of the compound represented by the chemical formula (53).
Figure 72:
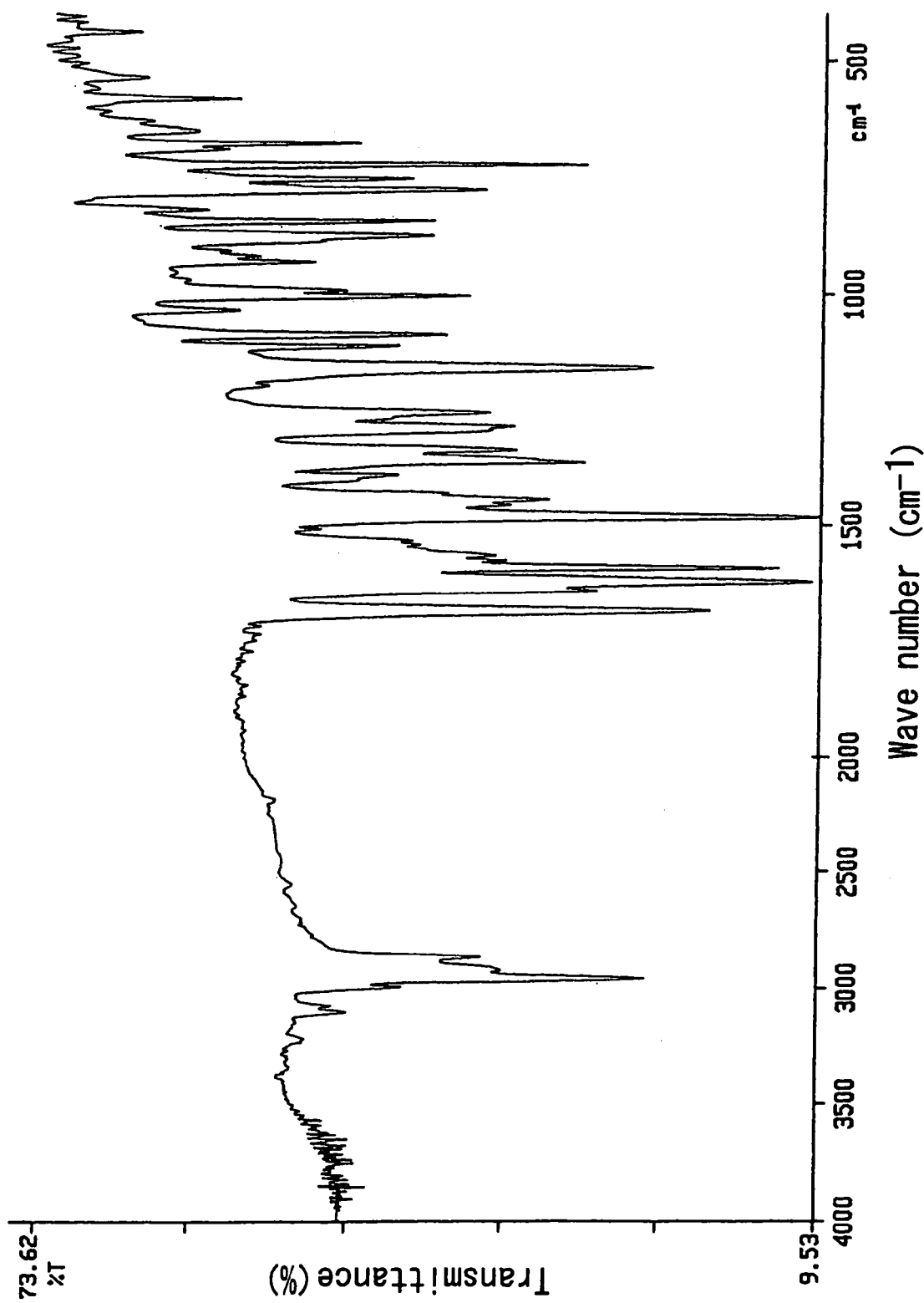
FIG. 72 is an IR spectrum of a compound represented by the chemical formula (54).
Figure 73:
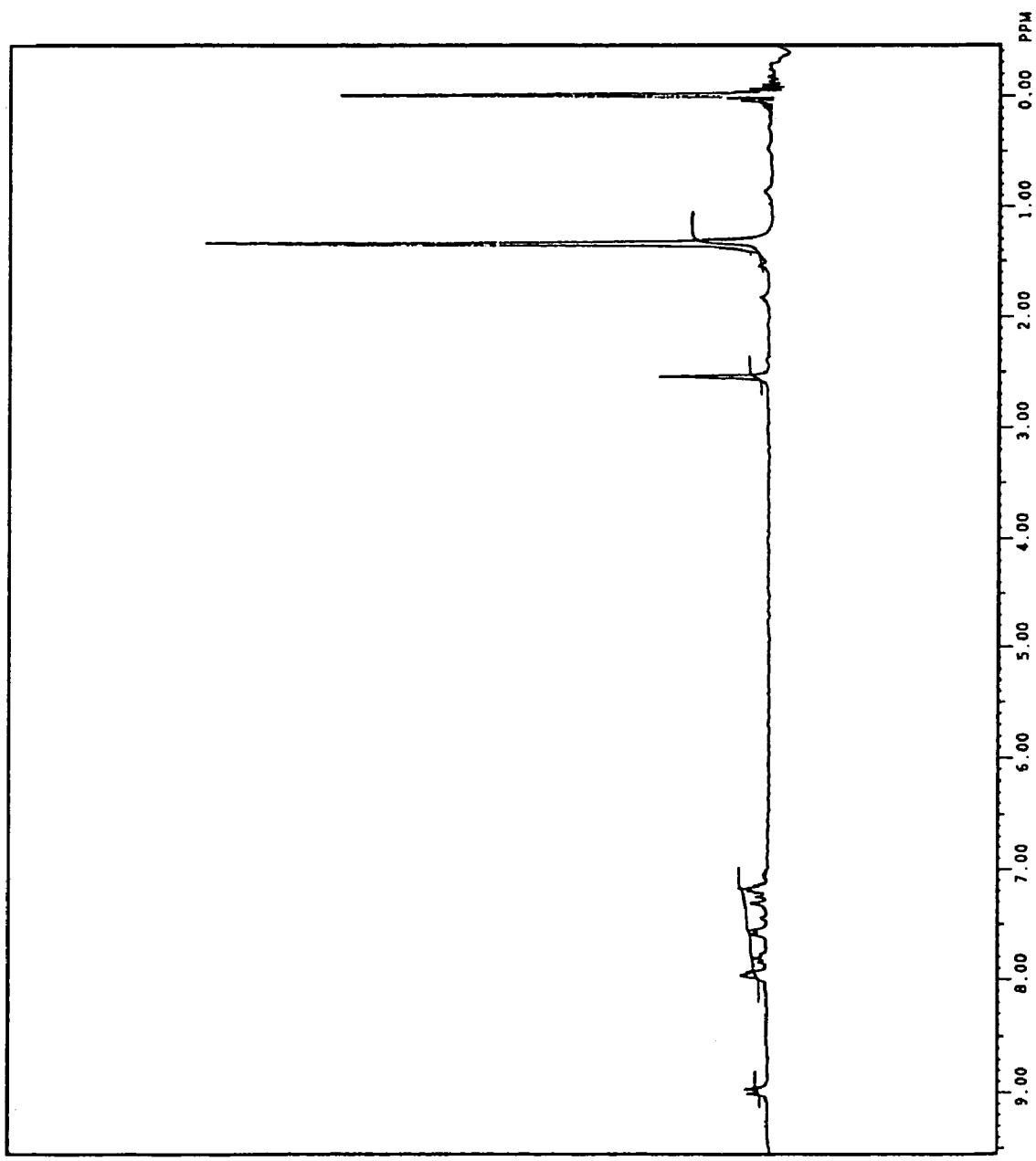
FIG. 73 is a $^1$H-NMR spectrum of the compound represented by the chemical formula (54).
Figure 74:
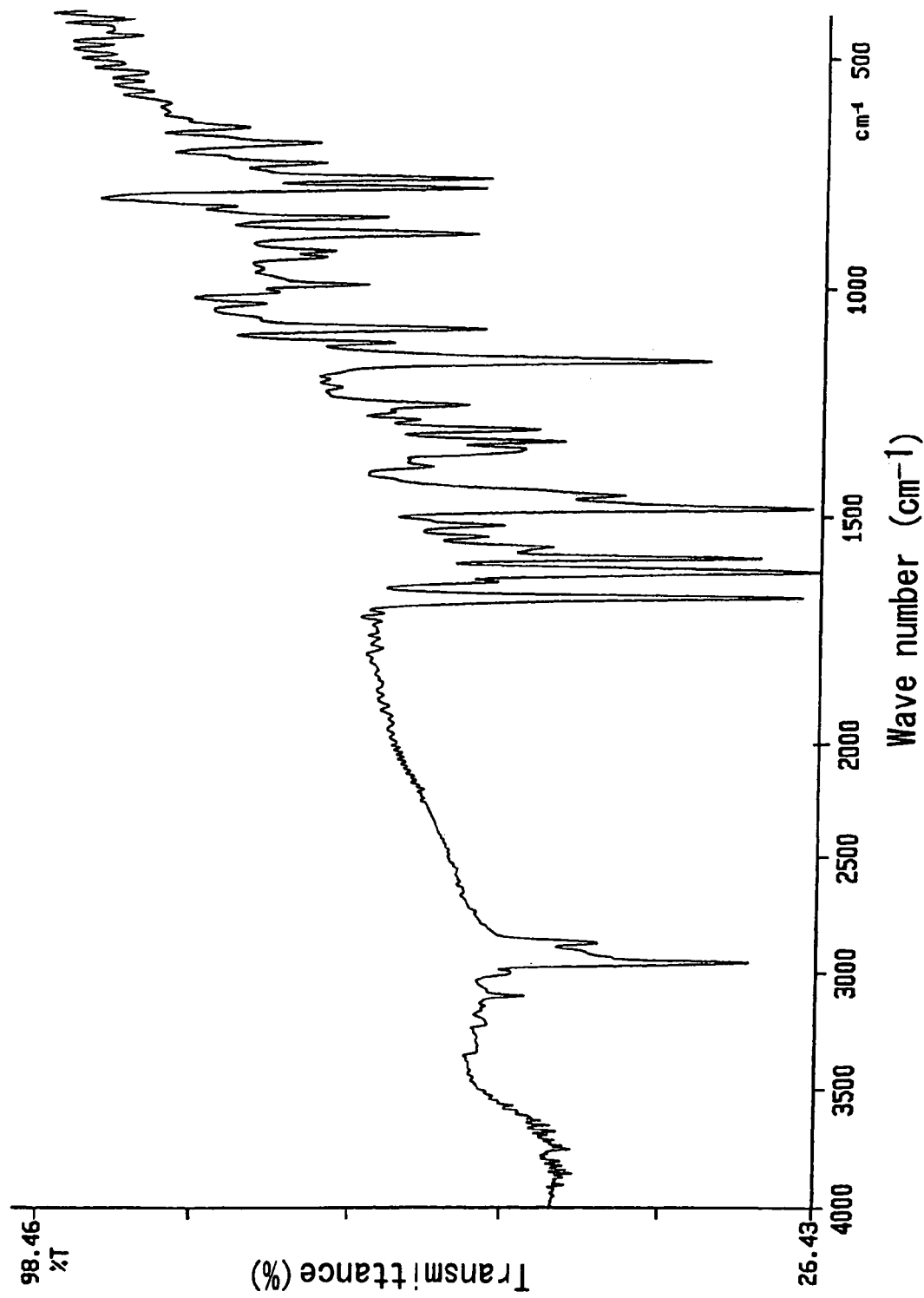
FIG. 74 is an IR spectrum of a compound represented by the chemical formula (55).
Figure 75:
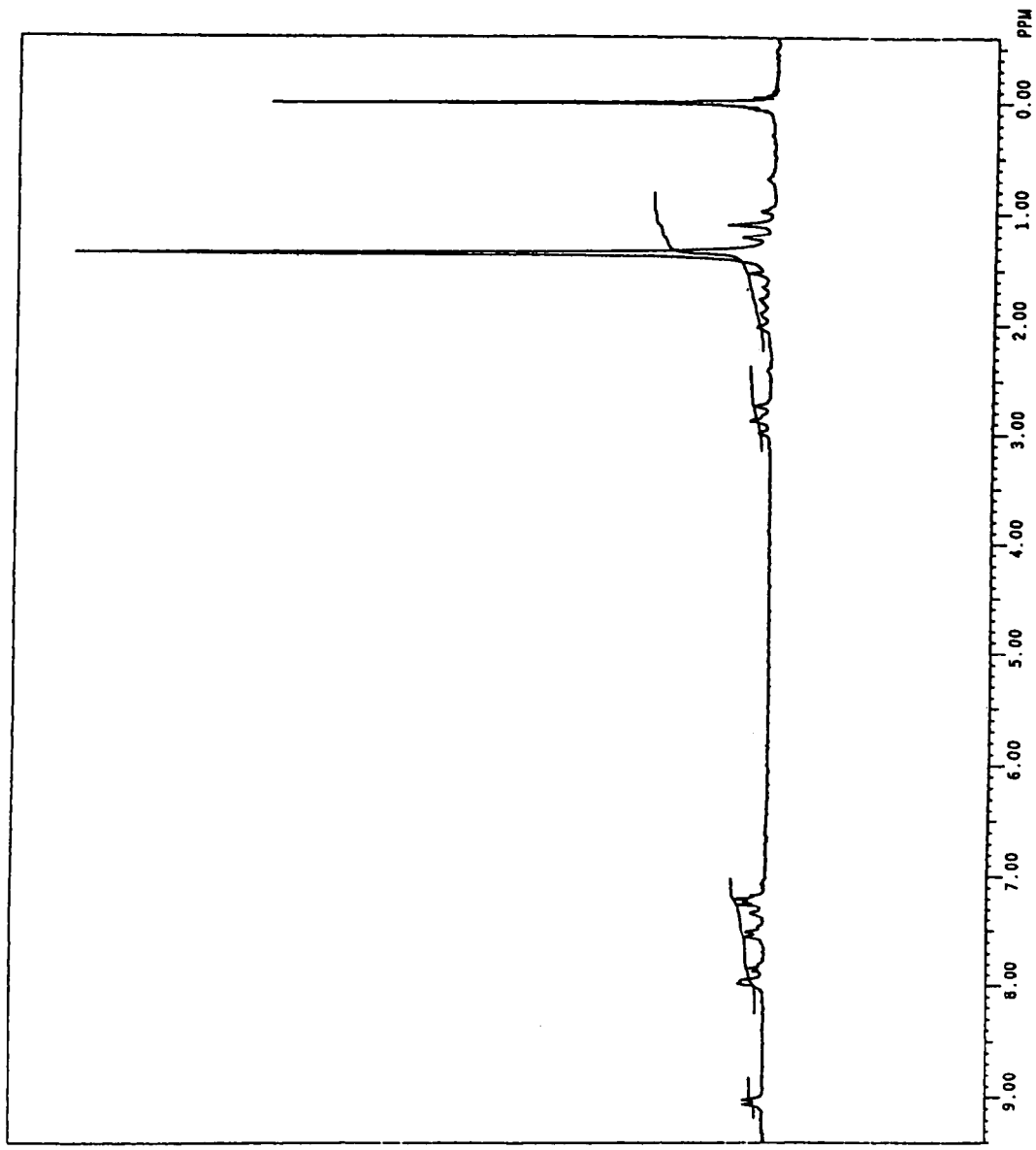
FIG. 75 is a $^1$H-NMR spectrum of the compound represented by the chemical formula (55).
Figure 76:
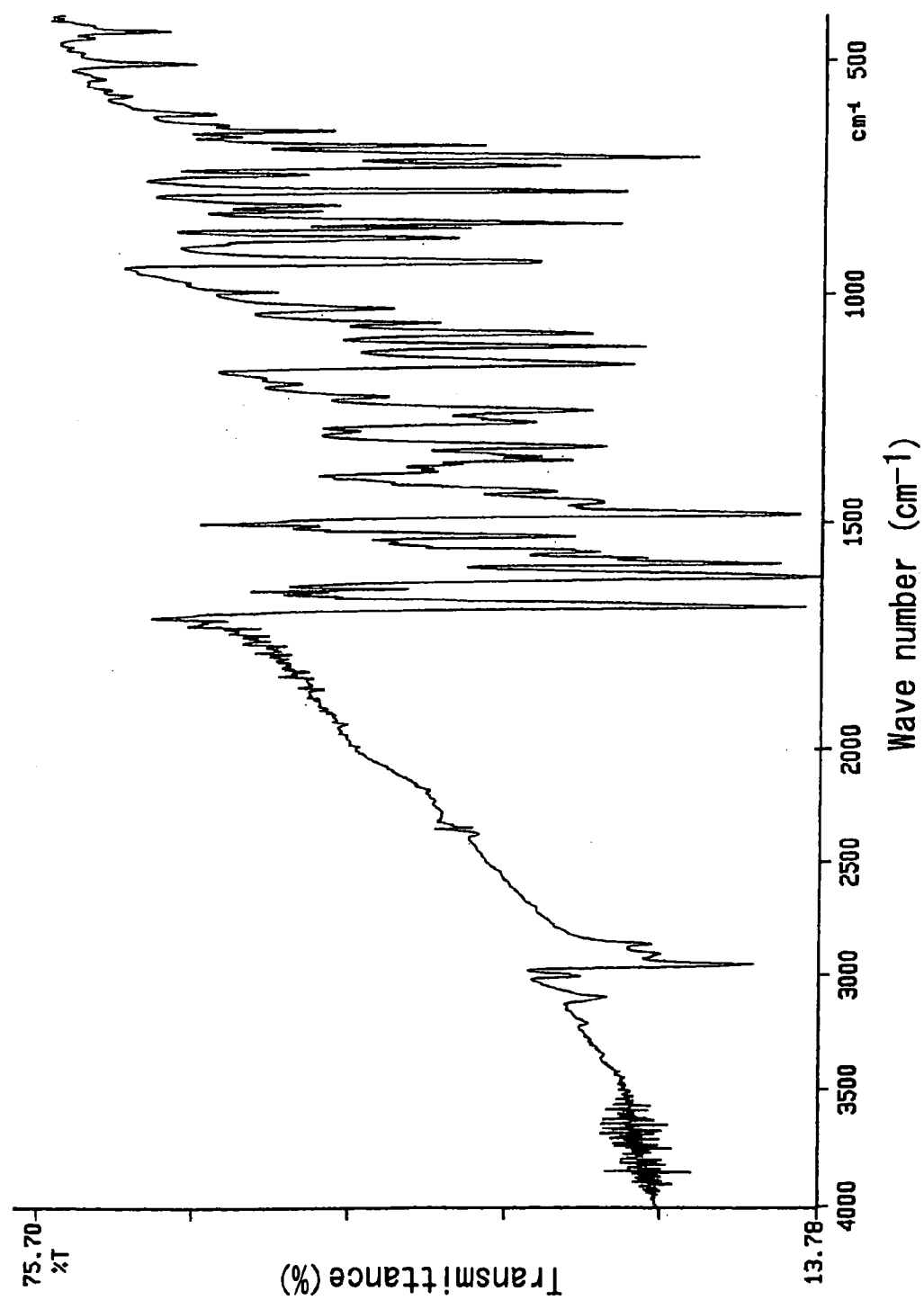
FIG. 76 is an IR spectrum of a compound represented by the chemical formula (56).
Figure 77:
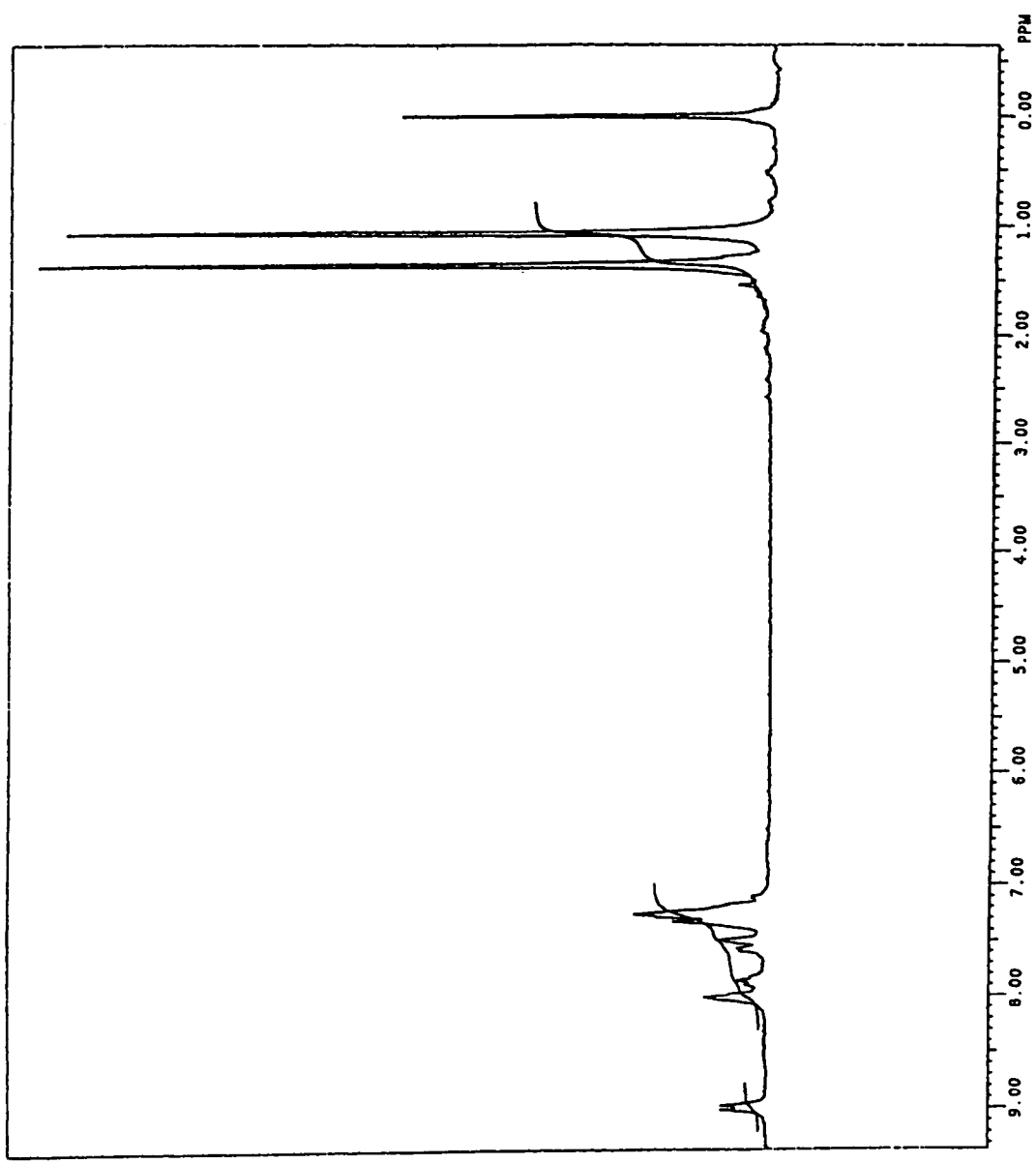
FIG. 77 is a $^1$H-NMR spectrum of the compound represented by the chemical formula (56).
Figure 78:
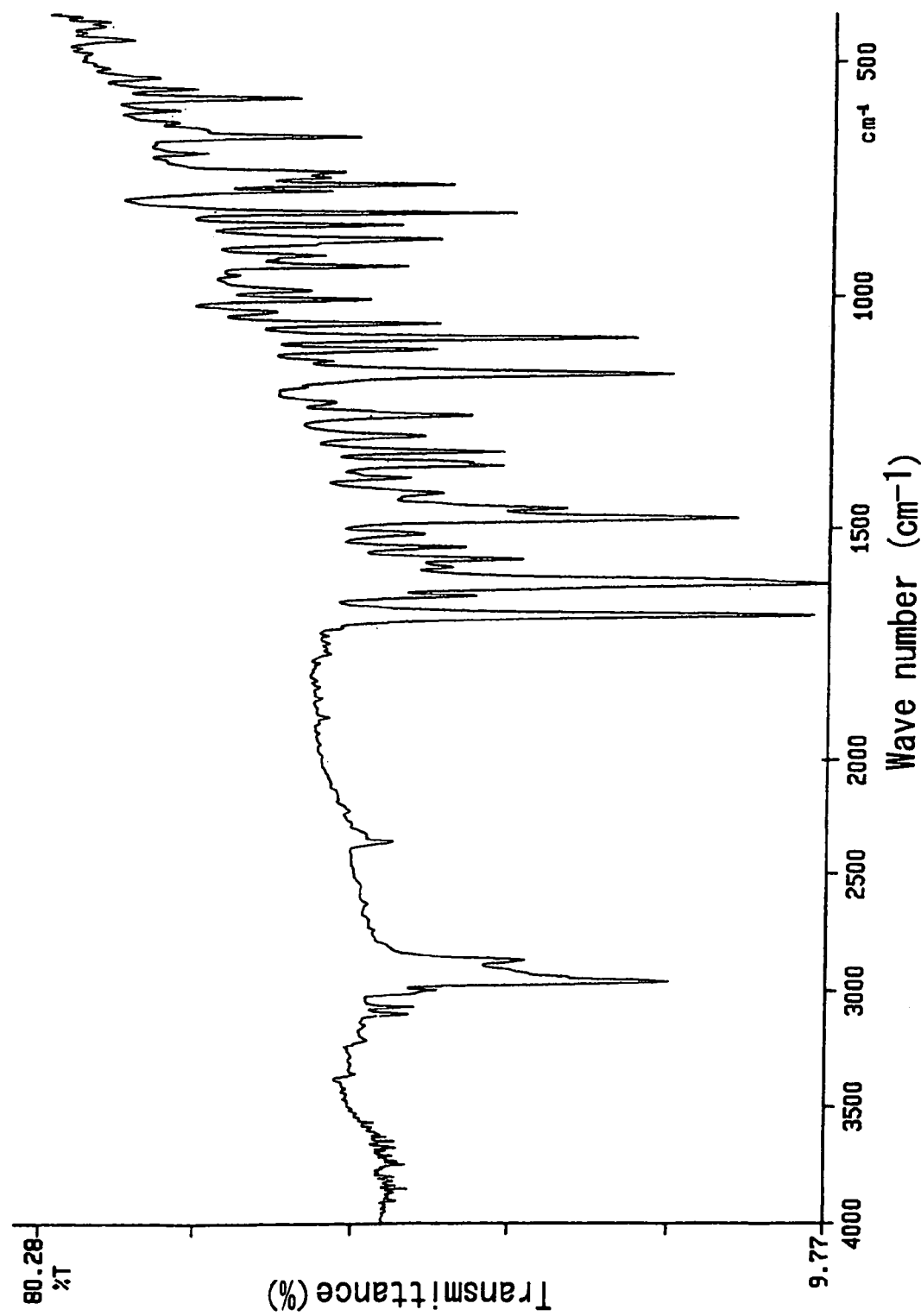
FIG. 78 is an IR spectrum of a compound represented by the chemical formula (57).
Figure 79:
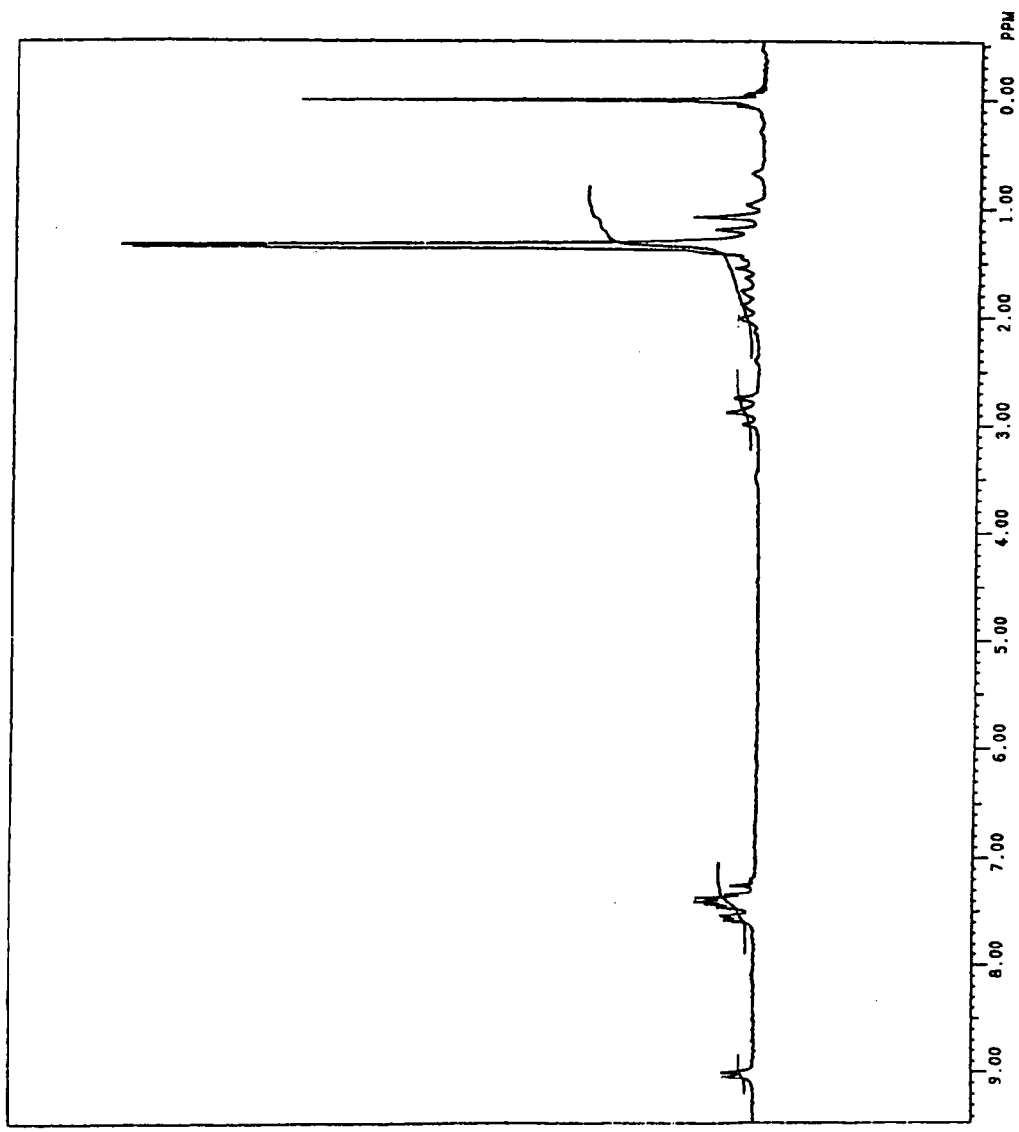
FIG. 79 is a $^1$H-NMR spectrum of the compound represented by the chemical formula (57).
Figure 80:
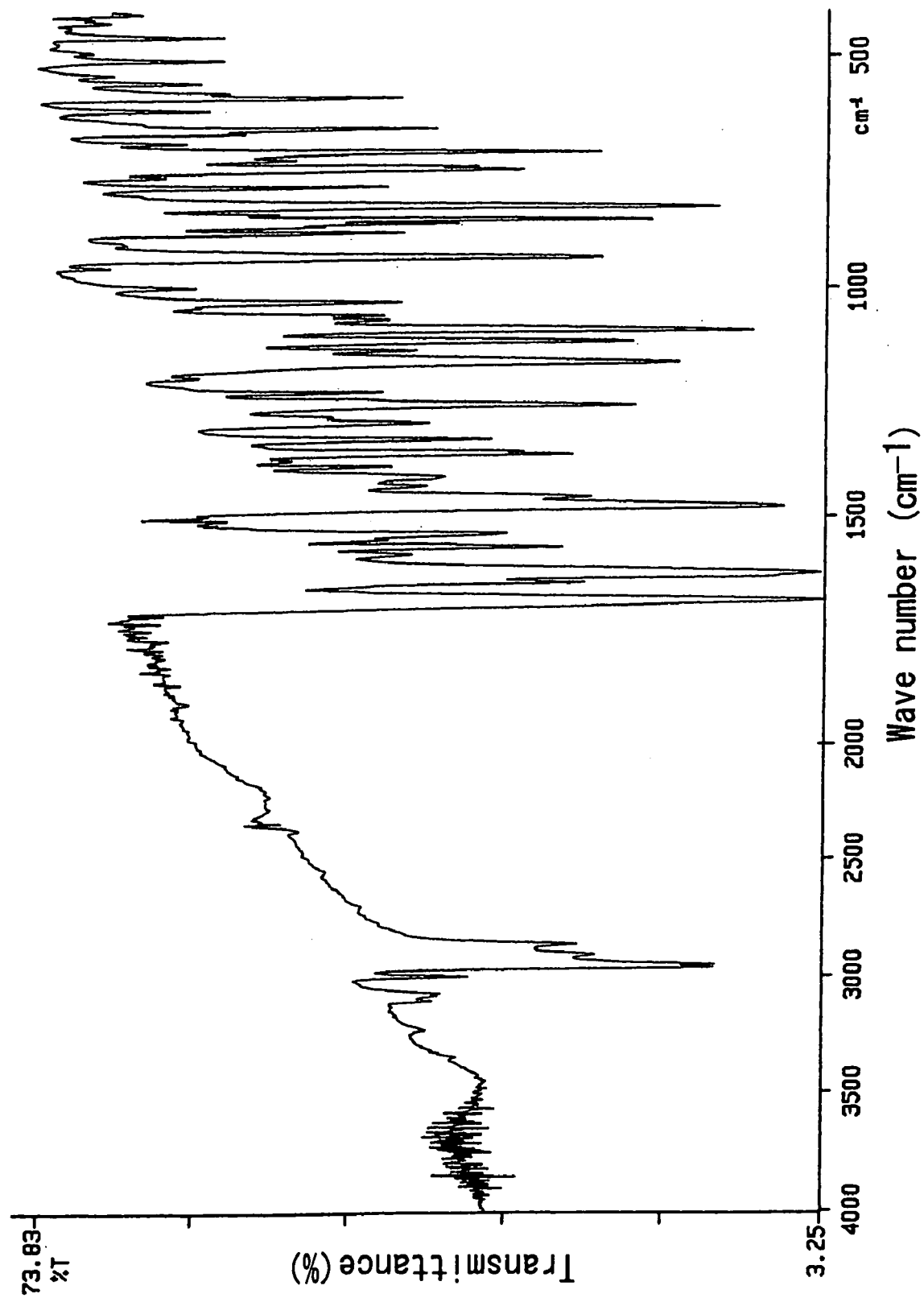
FIG. 80 is an IR spectrum of a compound represented by the chemical formula (58).
Figure 81:
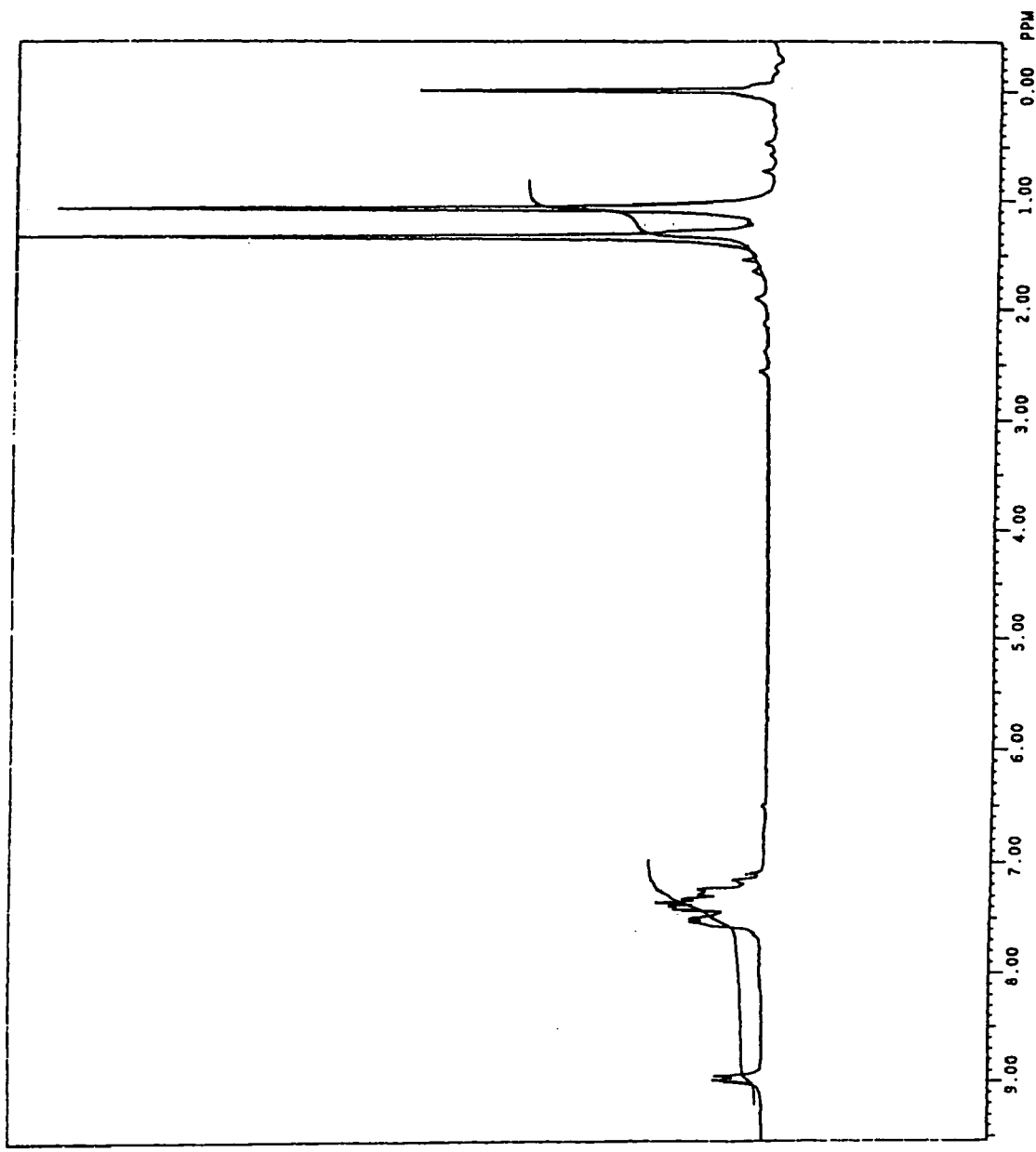
FIG. 81 is a $^1$H-NMR spectrum of the compound represented by the chemical formula (58).
Figure 82:
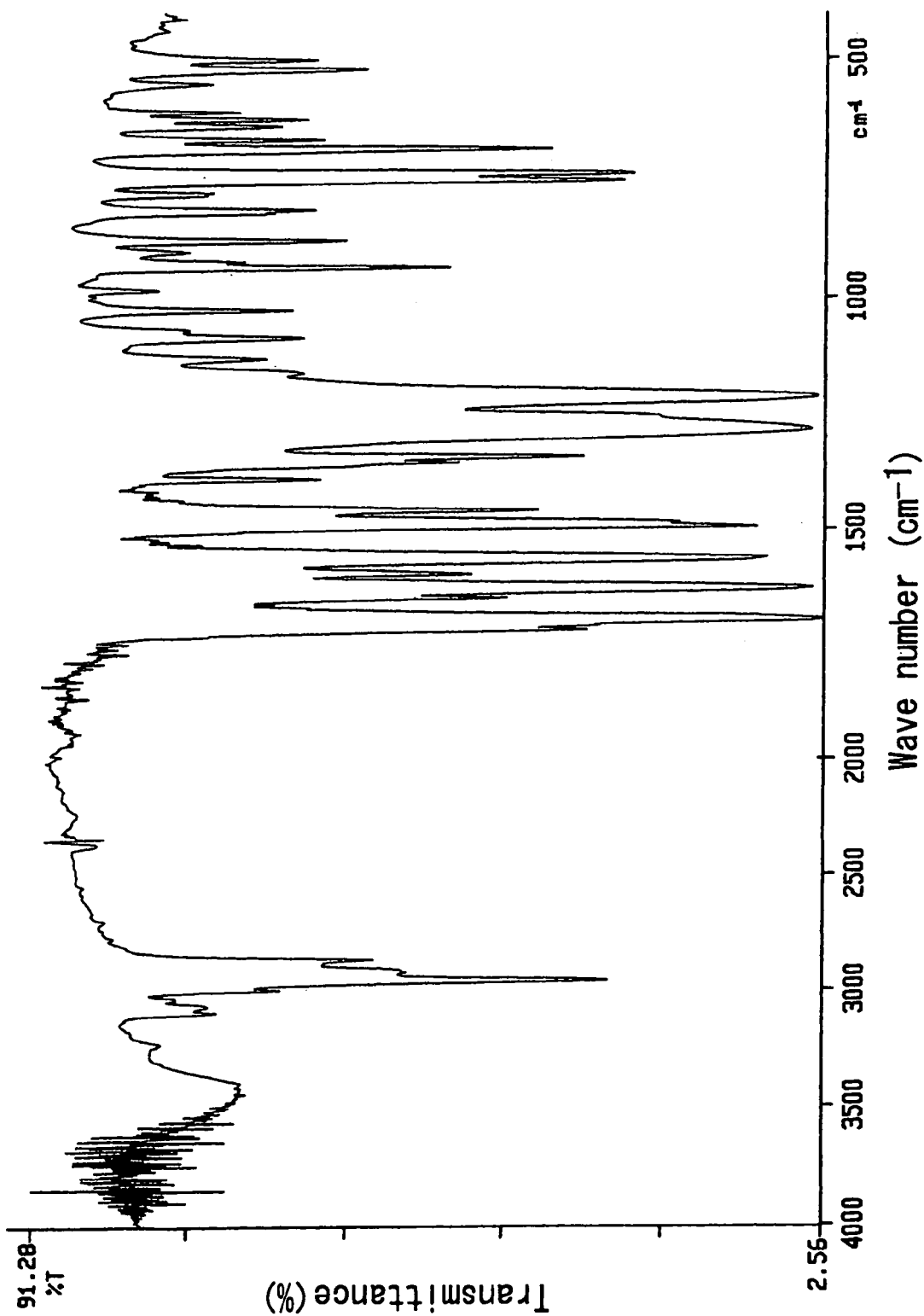
FIG. 82 is an IR spectrum of a compound represented by the chemical formula (59).
Figure 83:
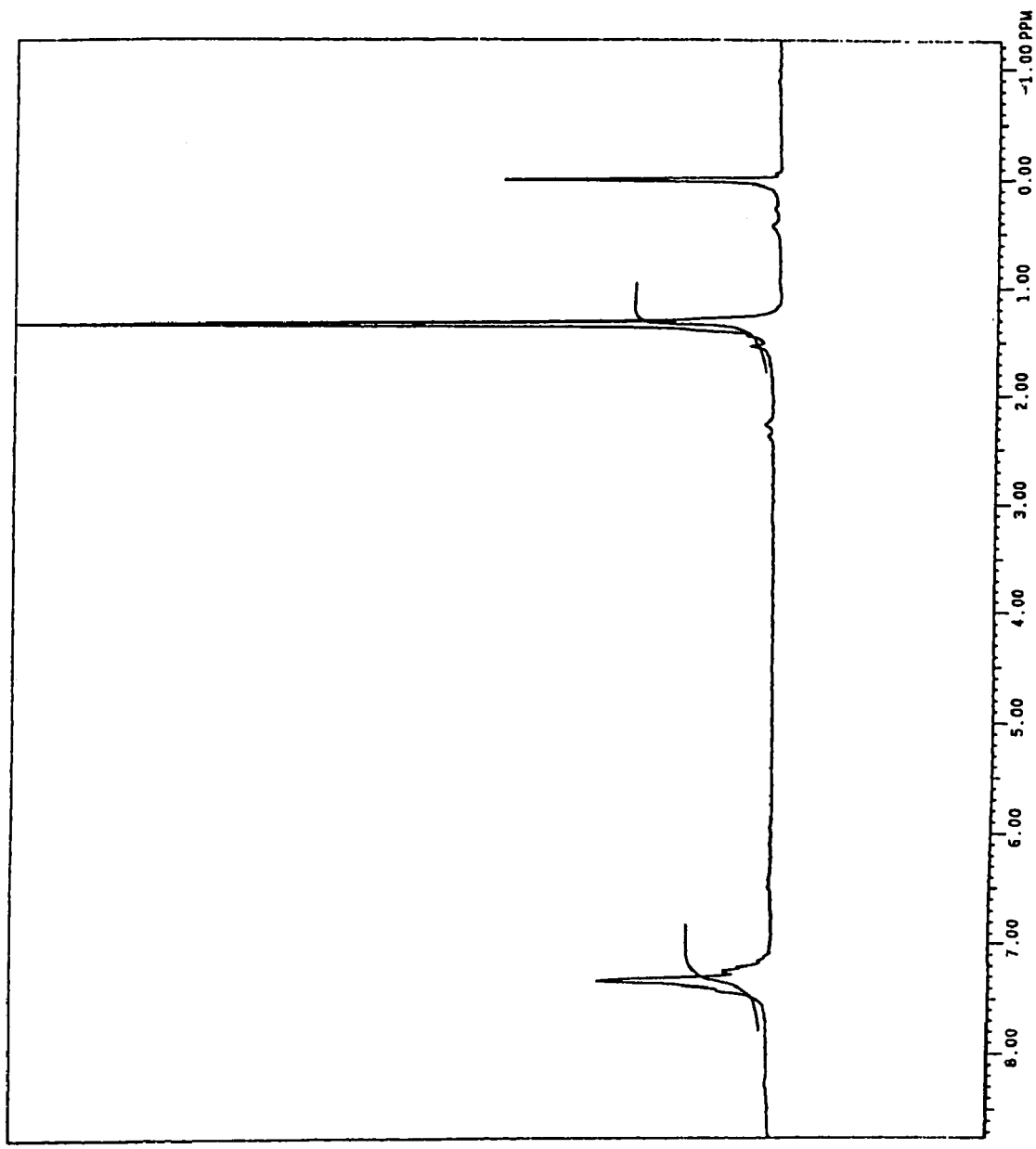
FIG. 83 is a $^1$H-NMR spectrum of the compound represented by the chemical formula (59).
Figure 84:
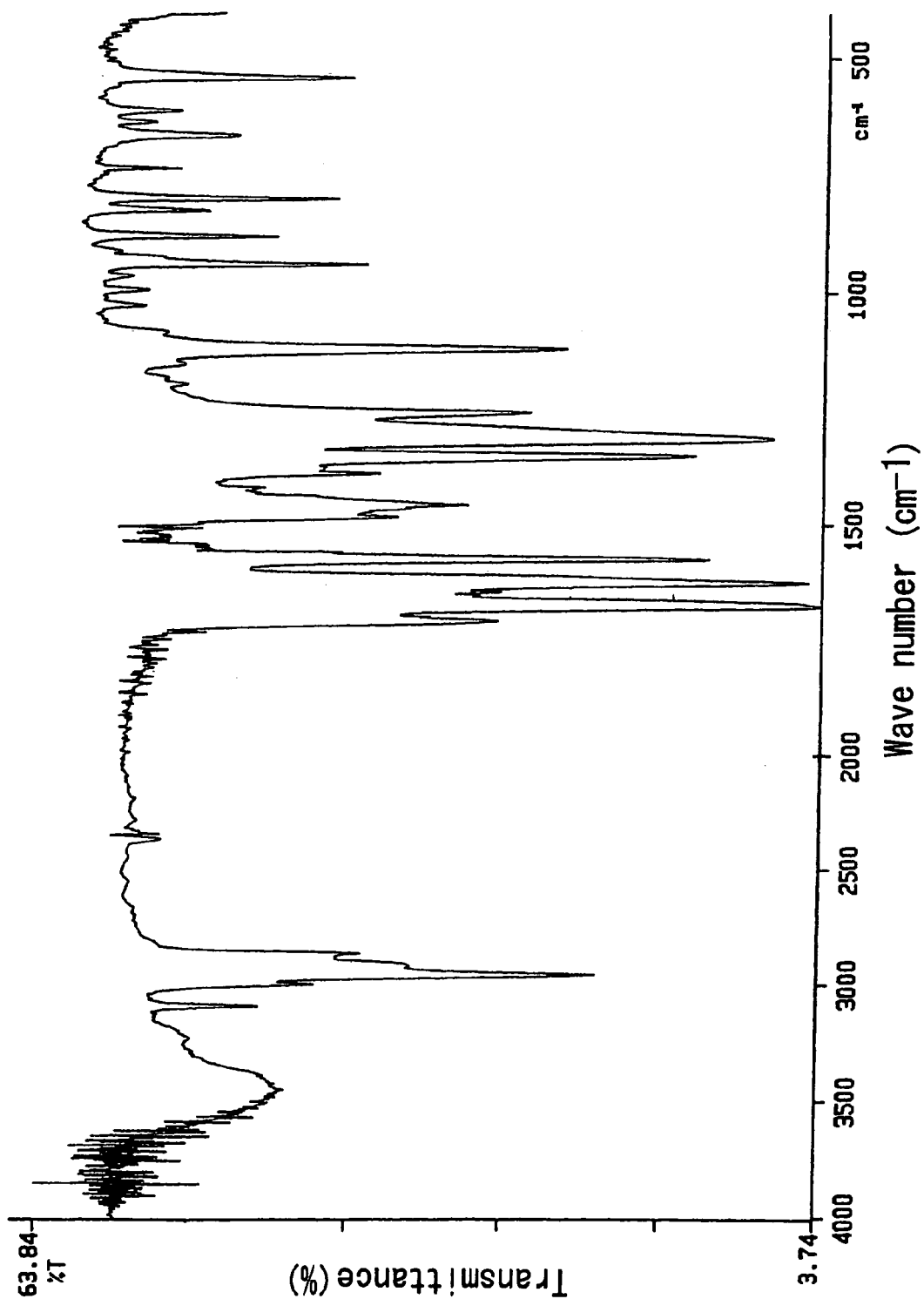
FIG. 84 is an IR spectrum of a compound represented by the chemical formula (60).
Figure 85:
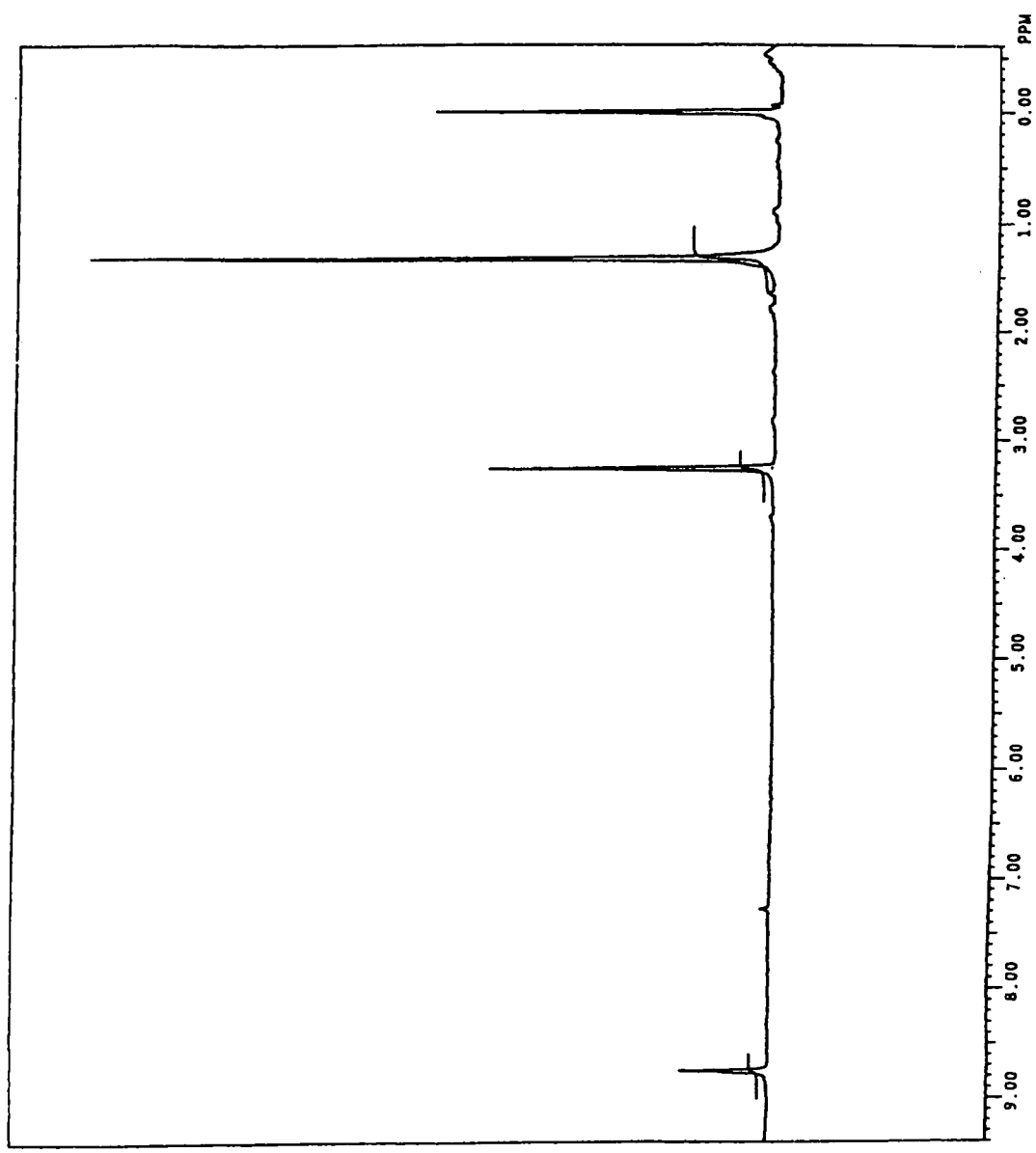
FIG. 85 is a $^1$H-NMR spectrum of the compound represented by the chemical formula (60).

Referring to FIG. 23, an exemplary organic electroluminescence element is denoted by reference numeral 21. The organic electroluminescence element 21 includes a glass substrate 23, a first electrode (ITO electrode) 22 formed of indium-tin oxide (ITO) and deposited on one surface of the glass substrate 23, a luminescent layer 25 closely arranged on one surface of the first electrode 22, and a second electrode 26 closely arranged on a surface of the luminescent layer 25 that is opposite the first electrode 22.

The luminescent layer 25 contains a luminescent material and may further contain a hole-transfer material for transporting holes injected from the anode (the first electrode 22) to the luminescent material or an electron-transfer material for transporting electrons moving from the cathode (the second electrode 26) to the luminescent material. The luminescent material may have the ability to move holes or electrons.

When the luminescent layer has a multi-layered structure, the organic electroluminescence element may include a luminescent layer, an electron-transfer layer, and a hole-transfer layer that are laminated on top of one another between the pair of electrodes.

The order of laminating the layers can be changed depending on the purpose of the element.

Examples of the luminescent material include anthracene, naphthalene, phenanthlene, pyrene, tetracene, coronene, chrysene, fluoresceine, perylene, phthaloperylene, naphthaloperylene, perynone, phthaloperynone, naphthaloperynone, diphenylbutadiene, tetraphenylbutadiene, coumarin, oxadiazole, aldadine, bis-benzoxazoline, bis-styrile, pyrazine, cyclopentadiene, metal complexes of quinoline, metal complexes of aminoquinoline, metal complexes of benzoquinoline, imine, diphenylethylene, vinylanthracene, diaminocarbazole, triphenylamine, benzidine-type triphenylamine, styrileamine-type triphenylamine, diaamine-type triphenylaminepyran, thiopyran, polymethine, merocyanine, imidazole-chelated oxynoid compounds, metal complexes of porphyrin, phthalocyanine complexes, rare earth metal complexes, quinacridone, rubrene, and fluorescent dyes for use in dye laser and in brightening.

Examples of the hole-transfer material include phthalocyanine derivatives, naphthalocyanine derivatives, porphyrin derivatives, oxazole, oxadiazole, triazole, imidazole, imidazolone, imidazolethione, pyrazoline, pyrazolone, tetrahydroimidazole, oxazole, oxadiazole, hydrazone, acylhydrazone, polyaryl alkanes, stilbene, butadiene, amine, diamine, triphenylamine, indole, carbazole, triphenylmethane, enamine and their derivatives, and polyvinyl carbazole, polysilane and polymeric materials such as electroconductive polymers.

Aside from the electron-transfer compounds of the present invention, examples of the electron-transfer material include quinolinol complexes, fluorenon, anthraquinodimethane, diphenoquinone, thiopyrandioxide, oxazole, oxadiazole, triazole, imidazole, perylenetetracarboxylic acid, fluorenylidene methane, anthraquinodimethane, anthrone, and derivatives thereof.

Examples of the electroconductive material for use in the anode include carbon, aluminum, brass, stainless steel, chromium, titanium, copper, tin, molybdenum, indium, vanadium, iron, cobalt, nickel, tungsten, silver, gold, platinum, palladium, and alloys thereof, metal oxides for use in ITO substrate and NESA substrate, such as tin oxide, indium oxide, aluminum iodide and copper iodide, and organic electroconductive resins, such as polythiophene and polypyrrole.

Examples of the electroconductive material for use in the cathode include, but are not limited to, magnesium, calcium, tin, lead, titanium, yttrium, lithium, ruthenium, manganese, aluminum and alloys thereof. Typical examples of the alloy include, but are not limited to, magnesium/silver, magnesium/indium, and lithium/aluminum.

The ratio of the alloy is controlled by the temperature, atmosphere, and degree of vacuum of the evaporation source so that a proper ratio is selected. When necessary, each of the anode and the cathode may be formed as a layered structure consisting of two or more layers.

5. Examples

Production examples of the compounds in accordance with the present invention and examples of the electron-transfer agents will now be described in detail, as will the electrophotographic photoreceptors and the organic electroluminescence elements as application examples.

First, examples of one production process of the compound represented by the general formula (1) is described.

PRODUCTION EXAMPLE 1

A mixture of 0.44 g (2 mmols) of 2,6-di-tert-butylbenzoquinone, which served as a benzoquinone compound, 0.23 g (2 mmols) of a pyrazolone compound having an active methylene, and 2 mL pyridine, which served as a base catalyst, was stirred at room temperature to allow the reaction to proceed. The reaction mixture was concentrated and was purified through silica gel column chromatography (developing solvent=hexane:ethyl acetate=10:1) to obtain 2,6-di-tert-butyl-4-(1,3-dimethyl-5-oxo-4-pyrazolilidene)-2,5-cyclohexadiene-1-one, the compound represented by the formula (7), at a yield of 36%. This reaction is shown by the following chemical equation (25):

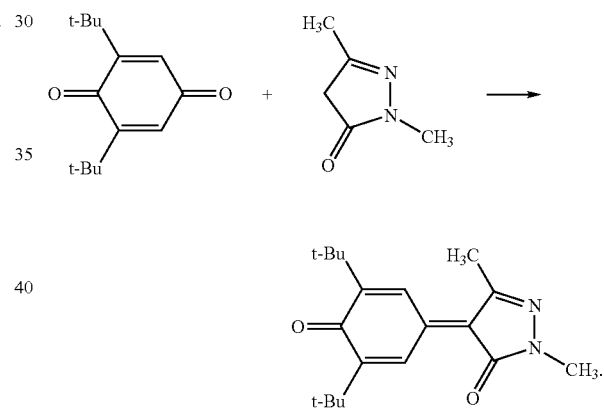

Chemical equation (25)

PRODUCTION EXAMPLE 2

The experiment was carried out in the same manner as in Example 1, except that the base catalyst, pyridine, was replaced by 1,8-diazabicyclo[5.4.0]undec-7-ene (DBU).

The product was obtained at a yield of 35%.

PRODUCTION EXAMPLE 3

The experiment was carried out in the same manner as in Example 1, except that the base catalyst, pyridine, was replaced by trimethylamine. The product was obtained at a yield of 32%.

PRODUCTION EXAMPLE 4

The experiment was carried out in the same manner as in Example 1, except that the base catalyst, pyridine, was replaced by 2,6-dimethylpyridine. The product was obtained at a yield of 35%.

PRODUCTION EXAMPLE 5

The experiment was carried out in the same manner as in Example 1, except that the base catalyst, pyridine, was replaced by tributylamine. The product was obtained at a yield of 30%.

PRODUCTION EXAMPLE 6

The experiment was carried out in the same manner as in Example 1, except that 20 ml ethanol was added as an inert solvent and the base catalyst, pyridine, was replaced by sodium hydroxide. The product was obtained at a yield of 30%.

PRODUCTION EXAMPLES 7 THROUGH 15

Different compounds were used as a compound having an active methylene group. The reaction temperature, reaction time, and yield are shown in Table D(1) for each compound. The structure formula and the name of the compound are shown in Tables D(2) and D(3) for each of the compounds of the formulae (8) through (16) obtained in respective Production Examples.

The melting point and the results of the elemental analysis are shown in Table E for each of the compounds of the formulae (7) through (16) obtained in Production Example 1 and respective Production Examples 7 through 15.

The IR and NMR charts are shown in FIGS. 1 through 20 for each of the compounds of the formulae (7) through (16) obtained in Production Example 1 and in Production Examples 7 through 15.

For IR spectrography, samples were prepared by using the potassium bromide (KBr)-pellet method. For NMR spectrography, deuterated chloroform was used as the sample solvent, and measurements were taken at a frequency of 60 MHz. The horizontal and the vertical axes of the NMR chart indicate chemical shifts and the intensity, respectively.

Comparative Production Example

The experiment was carried out in the same manner as in Example 1, except that the basic solvent, triethylamine, was not used. The reaction did not take place and no product was obtained.

Next, examples of the manner by which the electron mobility of the electron-transfer agent of the present invention was measured are described in conjunction with comparative examples.

EXAMPLE 1

5 g of oxytitanium phthalocyanine was dry-milled together with 50 ml of glass beads for 100 hours on a paint shaker. 50 mL of n-propanol and 5 g of polyvinylbutyral were then added, and the mixture was wet-milled for 1 hour. 100 mL of methyl ethyl ketone solvent was then added to the milled product, and the product was dispersed into the solvent for 10 hours. The resulting dispersion solution was applied to an aluminum-laminated PET film with a bar-coater and was dried to form a 0.5 μm-thick charge-generation layer.

Next, a coating solution was prepared consisting of 8 parts by weight of the compound of the formula (7), 10 parts by weight of polycarbonate and 100 parts by weight of tetrahydrofuran (THF). The coating solution was applied with a bar-coater and was then dried at 80° C. for 1 hour to form a 10 μm-thick charge-transfer layer. Gold was vapor-deposited onto the charge-transfer layer to a thickness of 0.04 μm (40 nm) as an opposed electrode. The electron mobility was measured by applying an electric field to the film and irradiating the film with a laser pulse.

EXAMPLES 2 THROUGH 10

The electron mobility was measured in the same manner as in Example 1 above, except that the compound represented by the formula (7) was replaced by the compound represented by the formula (8) through (16).

COMPARATIVE EXAMPLE 1

The electron mobility was measured in the same manner as in Example 1 above, except that the compound represented by the formula (7) was replaced by the compound represented by the formula (24).

Results

The electron mobilities measured at an electric field of $3.0 \times 10^5$ V/cm are shown in Table F.

As can be seen from Table F, the electron mobility was $1 \times 10^{-8}$ (cm$^2$/V·sec) or higher in each of Examples 1 through 10 and was in each case higher than the electron mobility obtained in Comparative Example 1 ($1 \times 10^{-9}$ (cm$^2$/V·sec)).

While application examples of the present invention are described below with reference to comparative examples, they are not intended to limit the scope of the invention in any way.

Examples of Organic Electroluminescence Elements

APPLICATION EXAMPLE 1

The compound represented by the formula (7) and tris(8-hydroxyquinolinol) aluminum complex were dissolved in chloroform at a ratio of 3:1. The solution was applied by spin-coating to a cleaned glass plate having an ITO electrode to form a 0.07 μm-thick luminescent layer. A 10:1 alloy of magnesium and silver was vapor-deposited onto the luminescent layer to form a 0.2 μm-thick electrode and thus obtain an organic electroluminescence element as shown in FIG. 23.

APPLICATION EXAMPLES 2 THROUGH 10

In each Application Example, an organic electroluminescence element was obtained by replacing the compound of the chemical formula (7) of Application Example 1 with each of the compounds of the chemical formulae (8) through (16). The amount of luminescence that each of the organic electroluminescence elements obtained in Application Examples 1 through 10 emitted when applied a direct current at 5V was shown in Table G.

As can be seen from Table G, the amount of luminescence was 60 (cd/m$^2$) or larger and was sufficiently high in each of Application Examples 1 through 10.

Examples of Electrophotographic Photoreceptors for use in Photocopiers

APPLICATION EXAMPLE 11

10 parts by weight of polycarbonate as a binder resin and 80 parts by weight of THF as a solvent were mixed with 1 part by weight of a dis-azo pigment as a charge-generation material shown by the following chemical formula (26):

Chemical formula (26)

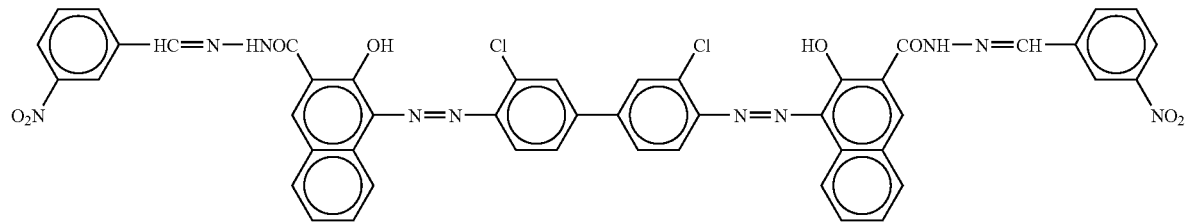

The mixture was kneaded for dispersal for 10 hours in a sand mill. As charge-transfer materials, 9 parts by weight of a triphenyldiamine compound shown by the following chemical formula (27):

Chemical formula (27)

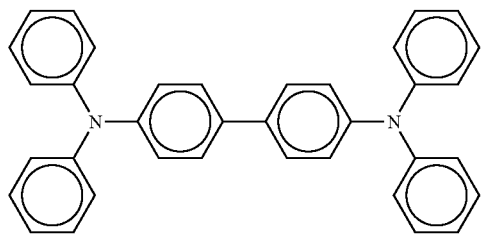

and 2 parts by weight of the compound shown by the formula (7) were dissolved in the mixture to form a coating solution. An aluminum drum as an electroconductive substrate 1 was dipped in this coating solution to apply coating. The drum was then dried at 80° C. for 1 hour to form a 20 μm-thick photosensitive layer 4 that served both to generate charge and to transport charge. In this manner, a single-layered electrophotographic photoreceptor 12 was prepared.

APPLICATION EXAMPLES 12 THROUGH 20

In each Application Example, an electrophotographic photoreceptor was obtained by replacing the compound of the chemical formula (7) of Application Example 11 with each of the compounds of the chemical formulae (8) through (16).

COMPARATIVE EXAMPLE 2

A single-layered electrophotographic photoreceptor was prepared in the same manner as in Example 11, except that the compound represented by the formula (7) was replaced by the compound represented by the formula (24).

Examples of Electrophotographic Photoreceptors for use in Printers

APPLICATION EXAMPLE 21

5 g of oxytitanium phthalocyanine was dry-milled together with 50 ml of glass beads for 100 hours on a paint shaker. 50 mL of n-propanol and 5 g of polyvinylbutyral were then added and the mixture was wet-milled for 1 hour. 100 mL of methyl ethyl ketone solvent was then added to the milled product, and the product was dispersed into the solvent for 10 hours. An aluminum drum as the electroconductive substrate 1 was dipped in the resulting dispersion solution to apply coating. The coating was then dried to form a 0.2 μm-thick charge-generation layer 2.

Next, a coating solution was prepared consisting of 8 parts by weight of the compound of the formula (7), 10 parts by weight of polycarbonate and 100 parts by weight of tetrahydrofuran (THF). The drum with the charge-generation layer 2 formed thereon was dipped in the coating solution to apply coating. The coating was then dried at 80° C. for 1 hour to form a 20 μm-thick charge-transfer layer 3. In this manner, a multi-layered electrophotographic photoreceptor was obtained.

APPLICATION EXAMPLES 22 THROUGH 30

In each Application Example, an electrophotographic photoreceptor was obtained by replacing the compound of the chemical formula (7) of Application Example 21 with each of the compounds of the chemical formulae (8) through (16).

COMPARATIVE EXAMPLE 3

A multi-layered electrophotographic photoreceptor was prepared in the same manner as in Application Example 21 above, except that the compound represented by the formula (7) was replaced by the compound represented by the formula (24).

APPLICATION EXAMPLE 31

A mixture of 1 part by weight of oxytitanium phthalocyanine as a charge-generation material, 10 parts by weight of polycarbonate as a binder resin, and 80 parts by weight of THF as a solvent was kneaded for dispersal for 10 hours in a sand mill. As charge-transfer materials, 9 parts by weight of triphenyldiamine compound shown by the formula (26) and 2 parts by weight of the compound shown by the formula (7) were dissolved in the mixture to form a coating solution. An aluminum drum as an electroconductive substrate 1 was dipped in this coating solution to apply coating. The drum was then dried at 80° C. for 1 hour to form a 20 μm-thick photosensitive layer 4 that served both to generate charge and to transport charge. In this manner, a single-layered electrophotographic photoreceptor was manufactured.

APPLICATION EXAMPLES 32 THROUGH 40

In each Application Example, an electrophotographic photoreceptor was obtained by replacing the compound of the chemical formula (7) of Application Example 31 with each of the compounds of the chemical formulae (8) through (16).

COMPARATIVE EXAMPLE 4

A single-layered electrophotographic photoreceptor was prepared in the same manner as in Example 31, except that the compound represented by the formula (7) was replaced by the compound represented by the formula (24)

APPLICATION EXAMPLE 41

A mixture of 1 part by weight of oxytitanium phthalocyanine as a charge-generation material, 10 parts by weight of polycarbonate as a binder resin, and 80 parts by weight of THF as a solvent was kneaded for dispersal for 10 hours in a sand mill. As charge-transfer materials, 1 part by weight of triphenyldiamine compound shown by the formula (26) and 9 parts by weight of the compound shown by the formula (7) were dissolved in the mixture to form a coating solution. An aluminum drum as an electroconductive substrate 1 was dipped in this coating solution to apply coating. The drum was then dried at 80° C. for 1 hour to form a 20 µm-thick photosensitive layer 4 that served both to generate charge and to transport charge. In this manner, a single-layered electrophotographic photosensitive layer was obtained.

APPLICATION EXAMPLES 42 THROUGH 50

In each Application Example, an electrophotographic photoreceptor was obtained by replacing the compound of the chemical formula (7) of Application Example 41 with each of the compounds of the formulae (8) through (16).

COMPARATIVE EXAMPLE 5

A single-layered electrophotographic photoreceptor was prepared in the same manner as in Application Example 41, except that the compound represented by the formula (7) was replaced by the compound represented by the formula (24).

Conditions for Measurement

A corona discharger was adjusted to generate a corona discharge current of 17 µA. The electrophotographic photoreceptors prepared in Application Examples 11 through 40 and Comparative Examples 2 through 4 were positively charged by the corona discharge in a dark environment and each photoreceptor was measured for the charged electric potential. The photoreceptors were then exposed to white light, and the exposure E/50 (lux·sec) at which the surface potential of each electrophotographic photoreceptor decreased by half, from 700V down to 350V, was measured. This half decay exposure reflects the sensitivity of the electrophotographic photoreceptor: the smaller the half decay exposure, the higher the sensitivity.

Results

The results of the measurement for Application Examples 11 through 20 and Comparative Example 2 are as shown in Table H below.

The results for Application Examples 11 through 20 and Comparative Example 2 were obtained for positively charged, single-layered photoreceptors for use in photocopiers. The comparisons between each Application Example and Comparative Example suggest that through the use of the electron-transfer materials of the chemical formulae (7) through (16), a photoreceptor can be obtained that has a higher sensitivity than the photoreceptor using the compound of the formula (24). Also, the chargeability of the photoreceptor is enhanced.

The results of the measurement for Application Examples 21 through 30 and Comparative Example 3 are as shown in Table I.

The results for Application Examples 21 through 30 and Comparative Example 3 were obtained for positively charged, multi-layered photoreceptors for use in printers. The comparisons between each Application Example and Comparative Example suggest that through the use of the electron-transfer materials of the chemical formulae (7) through (16), a photoreceptor can be obtained that has a higher sensitivity than the photoreceptor using the compound of the formula (24).

The results of the measurement for Application Examples 31 through 40 and Comparative Example 4 are as shown in Table J.

The results for Application Examples 31 through 40 and Comparative Example 4 were obtained for positively charged, single-layered photoreceptors for use in printers. The comparisons between each Application Example and Comparative Example suggest that through the use of the electron-transfer materials of the chemical formulae (7) through (16), a photoreceptor can be obtained that has a higher sensitivity than the photoreceptor using the compound of the formula (24).

Next, a corona discharger was adjusted to generate a corona discharge current of 17 µA. The electrophotographic photoreceptors prepared in Application Examples 41 through 50 and Comparative Example 5 were negatively charged by the corona discharge in a dark environment and each photoreceptor was measured for the charged electric potential. The photoreceptors were then exposed to white light, and the exposure E/50 (lux·sec) at which the absolute value of the surface potential of each electrophotographic photoreceptor decreased by half, from −700V up to −350V, was measured. The results are shown in Table K. The half decay exposure reflects the sensitivity of the electrophotographic photoreceptor: the smaller the half decay exposure, the higher the sensitivity.

The results for Application Examples 41 through 50 and Comparative Example 5 were obtained for negatively charged, single-layered photoreceptors for use in printers. The comparisons between each Application Example and Comparative Example suggest that through the use of the electron-transfer materials of the chemical formulae (7) through (16), a photoreceptor can be obtained that has a higher sensitivity than the photoreceptor using the compound of the formula (24).

While a description has been given of examples of electrophotographic photoreceptors in which the organic film is used as the photosensitive layer, these examples are illustrative rather than restrictive and do not limit the scope of the invention in any way. For example, the present invention also encompasses within its scope an electrophotographic photoreceptor in which the above-described organic film is used as a foundation layer disposed between the photosensitive layer and the electroconductive substrate. Although organic film for use as the foundation layer needs to have a proper conductivity, the organic film containing the compound represented by the general formula (1) has a high electron mobility and is thus suitable for this purpose so that a highly sensitive electrophotographic photoreceptor can be obtained through the use of such organic film.

Alternatively, the organic film may be used as a protection layer formed over the photosensitive layer. To summarize, the present invention encompasses within its scope any electrophotographic photoreceptor incorporating organic film that contains the compound represented by the general formula (1).

While cases have been described in which a benzoquinone compound is reacted with a compound incorporating an active methylene in the presence of a base catalyst alone, the present invention also encompasses other cases. According to the present invention, the yield of the desired product can be increased by carrying out the reaction using, along with the base catalyst, a solvent that can hardly dissolve the desired product. As used herein, the term "desired product" refers to any of the compounds represented by the general formulae (1) through (6) and (44).

When the reaction is carried out by using the base catalyst alone, a side reaction takes place by which the compound having an active methylene further adds to the desired product that has resulted from the reaction of the benzoquinone compound with the compound having an active methylene. As a result, by-products are produced.

When the benzoquinone compound reacts with the active methylene using a solvent that can hardly dissolve the desired product (inert solvent), along with the base catalyst, the resulting desired product is removed from the reaction system by crystallizing it with the help of the solvent that can hardly dissolve the desired product.

As a result, the further addition of the compound having an active methylene to the desired product can be prevented.

It is believed that by allowing the reaction to proceed in the solvent that can hardly dissolve the desired product, the side reaction can be suppressed so that the yield of the desired product is increased.

Preferably, the solvent is an alcohol solvent, such as methanol, ethanol and butanol, a saturated aliphatic hydrocarbon, such as heptane and hexane, or water. These solvents may be used independently or as a mixture of two or more solvents. Of these, water, methanol, ethanol, and butanol are particularly preferred because of their cost performance and low solubility against the desired product.

The solvent for use with the base catalyst (inert solvent) is not limited to alcohols, saturated aliphatic hydrocarbons or water. The solvent may be any solvent that requires 50 ml or more to dissolve 1 g of the desired product and may be used independently or as a mixture of two or more solvents.

Other examples of the production process of the compound of the present invention will now be described in detail.

PRODUCTION EXAMPLE 16

A mixture of 0.44 g (2 mmols) of 2,6-di-tert-butylbenzoquinone, which served as a benzoquinone compound, 0.35 g (2 mmols) of methylphenylpyrazolone, which served as a compound having an active methylene, 0.5 mL pyridine, which served as a base catalyst, and 4 mL water was allowed to undergo reaction for 5 hours at 45° C. while being stirred. Subsequently, the reaction mixture was added to 4 mL water and the mixture was filtrated. The resulting crystals were washed with 8 mL methanol and were then recrystallized with a mixture of chloroform and methanol. As a result, 0.63 g of 2,6-di-tert-butyl-4-(3-methyl-1-phenyl-5-oxo-4-pyrazolidene)-2,5-cyclohexadiene-1-one was obtained. The yield of the product was 84%.

PRODUCTION EXAMPLE 17

The process was carried out in the same manner as in Production Example 16, except that 1 ml pyridine and 2 ml water were used. The product was obtained at a yield of 65%.

PRODUCTION EXAMPLE 18

The process was carried out in the same manner as in Production Example 16, except that 1 ml pyridine and 4 ml water were used. The product was obtained at a yield of 75%.

PRODUCTION EXAMPLE 19

The process was carried out in the same manner as in Production Example 16, except that methanol was used in place of water. The product was produced at a yield of 62%.

PRODUCTION EXAMPLE 20

The process was carried out in the same manner as in Production Example 16, except that hexane was used in place of water. The product was produced at a yield of 51%.

PRODUCTION EXAMPLE 21

The process was carried out in the same manner as in Production Example 16, except that 2 ml chloroform was used in place of water. The product was produced at a yield of 34%.

PRODUCTION EXAMPLE 22

The process was carried out in the same manner as in Production Example 16, except that 2 ml toluene was used in place of water. The product was produced at a yield of 35%.

The comparisons between each of Production Examples 16 through 20 and Production Example 7 indicate that while each process can produce the same compound represented by the formula (8), higher yields of 84%, 65%, 75%, 62%, and 51% were achieved in Production Examples 16, 17, 18, 19, and 20, respectively, as compared to the 32% yield in Production Example 7. In comparison, the yields obtained in Production Examples 21 and 22 with the use of chloroform and toluene were comparable to that of Production Example 7, with no apparent increase in the yield.

PRODUCTION EXAMPLES 23 THROUGH 37

Different compounds were used as a compound having an active methylene group. The reaction temperature, reaction time, and yield are shown in Tables L(1) and L(2) for each compound. The structure formula and the name of the compound are shown in Tables M(1) through. M(3) for each of the compounds of the formulae (29) through (43) obtained in respective Production Examples.

The melting point and the results of the elemental analysis are shown in Table N for each of the compounds of the formulae (29) through (43) obtained in Production Examples 23 through 37.

The IR and NMR charts are shown in FIGS. 24 through 53 for each of the compounds of the formulae (29) through (43) obtained in Production Examples 23 through 37.

Next, the examples of measuring the electron mobility of the electron transfer agent of the present invention are described in conjunction with comparative examples.

EXAMPLES 11 THROUGH 25

The electron mobility was measured in the same manner as in Example 1 above, except that the compound represented by the formula (7) was replaced by the compound represented by the formulae (29) through (43).

Results

The electron mobilities measured at an electric field of $3.0 \times 10^5$ V/cm are shown in Table O.

As can be seen from Table O, the electron mobility was $1 \times 10^{-8}$ (cm$^2$/V·sec) or higher in each of Examples 11 through 25 and was in each case higher than the electron mobility obtained in Comparative Example 1 ($1 \times 10^{-9}$ (cm$^2$/V·sec)).

Examples of Electrophotographic Photoreceptors for Use in Printers

APPLICATION EXAMPLES 51 THROUGH 65

In each Application Example, an organic electroluminescence element was obtained by replacing the compound of the chemical formula (7) of Application Example 1 with each of the compounds of the chemical formulae (29) through (43). The amount of luminescence that each of the organic electroluminescence elements obtained, in Application Examples 51 through 65 emitted when applied a direct current at 5V, is shown in Table P.

As can be seen from Table P, the amount of luminescence was 60 (cd/m$^2$) or larger and was sufficiently high in each of Application Examples 51 through 65.

Examples of Electrophotographic Photoreceptors for Use in Photocopiers

APPLICATION EXAMPLES 66 THROUGH 80

In each Application Example, an electrophotographic photoreceptor was obtained by replacing the compound of the chemical formula (7) of Application Example 11 with each of the compounds of the chemical formulae (29) through (43).

Examples of Electrophotographic Photoreceptors for Use in Printers

APPLICATION EXAMPLES 81 THROUGH 95

In each Application Example, an electrophotographic photoreceptor was obtained by replacing the compound of the chemical formula (7) of Application Example 21 with each of the compounds of the chemical formulae (29) through (43).

APPLICATION EXAMPLES 96 THROUGH 110

In each Application Example, an electrophotographic photoreceptor was obtained by replacing the compound of the chemical formula (7) of Application Example 31 with each of the compounds of the chemical formulae (29) through (43).

APPLICATION EXAMPLES 111 THROUGH 125

In each Application Example, an electrophotographic photoreceptor was obtained by replacing the compound of the chemical formula (7) of Application Example 41 with each of the compounds of the formulae (29) through (43).

Conditions for Measurement

A corona discharger was adjusted to generate a corona discharge current of 17 µA. The electrophotographic photoreceptors prepared in Application Examples 66 through 110 were positively charged by the corona discharge in a dark environment and each photoreceptor was measured for the charged electric potential. The photoreceptors were then exposed to white light, and the exposure E/50 (lux·sec) at which the surface potential of each electrophotographic photoreceptor decreased by half, from 700V down to 350V, was measured. This half decay exposure reflects the sensitivity of the electrophotographic photoreceptor.

Results

The results of the measurement for Application Examples 66 through 80 are shown in Table Q below together with the results of Comparative Example 2.

The results for Application Examples 66 through 80 and Comparative Example 2 were obtained for positively charged, single-layered photoreceptors for use in photocopiers. The comparisons between each Application Example and Comparative Example suggest that through the use of the electron-transfer materials of the chemical formulae (29) through (43), a photoreceptor can be obtained that has a higher sensitivity than the photoreceptor using the compound of the formula (24). Also, the chargeability of the photoreceptor is enhanced.

The results of the measurement for Application Examples 81 through 95 are shown in Table R below together with the results of Comparative Example 3.

The results for Application Examples 81 through 95 and Comparative Example 3 were obtained for positively charged, multi-layered photoreceptors for use in printers. The comparisons between each Application Example and Comparative Example suggest that through the use of the electron-transfer materials of the chemical formulae (29) through (43), a photoreceptor can be obtained that has a higher sensitivity than the photoreceptor using the compound of the formula (24).

The results of the measurement for Application Examples 96 through 110 are shown in Table S below together with the results of Comparative Example 4.

The results for Application Examples 96 through 110 and Comparative Example 4 were obtained for positively charged, single-layered photoreceptors for use in printers. The comparisons between each Application Example and Comparative Example suggest that through the use of the electron-transfer materials of the chemical formulae (29) through (43), a photoreceptor can be obtained that has a higher sensitivity than the photoreceptor using the compound of the formula (24).

Next, a corona discharger was adjusted to generate a corona discharge current of 17 µA. The electrophotographic photoreceptors prepared in Application Examples 111 through 125 were negatively charged by the corona discharge in a dark environment and each photoreceptor was measured for the charged electric potential. The photoreceptors were then exposed to white light, and the exposure E/50 (lux·sec) at which the absolute value of the surface potential of each electrophotographic photoreceptor decreased by half, from −700V up to −350V, was measured. The results are shown in Table T. The half decay exposure reflects the sensitivity of the electrophotographic photoreceptor.

The results for Application Examples 111 through 125 and Comparative Example 5 were obtained for negatively charged, single-layered photoreceptors for use in printers. The comparisons between each Application Example and Comparative Example suggest that through the use of the electron-transfer materials of the chemical formulae (29)

through (43), a photoreceptor can be obtained that has a higher sensitivity than the photoreceptor using the compound of the formula (24).

Other examples of the production process of the compound of the present invention will now be described in detail.

PRODUCTION EXAMPLE 38

A mixture of 0.88 g (4 mmols) of 2,6-di-tert-butylbenzoquinone, which served as a benzoquinone compound, 0.75 g (4 mmols) of 3-methyl-1-p-tolyl-5-pyrazolone, which served as a cyclic compound having an active methylene, and 4 mL pyridine, which served as a base catalyst, was allowed to undergo reaction for 20 hours at 25° C. while being stirred. Subsequently, the reaction mixture was concentrated and was purified through column chromatography (hexane:ethyl acetate=10:1). As a result, 0.83 g of the compound shown by the chemical formula (45) is obtained as the desired product (yield=53%).

PRODUCTION EXAMPLES 39 THROUGH 53

Different compounds were used as a compound having an active methylene group. The reaction temperature, reaction time, and yield are shown in Tables U(1) and U(2) for each compound. The structure formula and the name of the compound are shown in Tables V(1) through V(3) for each of the compounds of the formulae (45) through (60) obtained in respective Production Examples.

The melting point and the results of the elemental analysis are shown in Table W for each of the compounds of the formulae (45) through (60) obtained in Production Examples 38 through 53.

The IR and NMR spectra are shown in FIGS. 54 through 85 for each of the compounds of the formulae (45) through (60) obtained in Production Examples 38 through 53.

EXAMPLES 26 THROUGH 41

The electron mobility was measured in the same manner as in Example 1 above, except that the compound represented by the formula (7) was replaced by the compound represented by the formulae (45) through (60).

Results

The electron mobilities measured at an electric field of $3.0 \times 10^5$ V/cm are shown in Table X.

As can be seen from Table X, the electron mobility was $1 \times 10^{-8}$ (cm$^2$/V·sec) or higher in each of Examples 26 through 41 and was in each case higher than the electron mobility obtained in Comparative Example 1.

Production Examples of Organic Electroluminescence Elements

APPLICATION EXAMPLES 126 THROUGH 141

Each of the organic electroluminescence elements of Application Examples 126 through 141 was obtained by replacing the compound of the chemical formula (7) of Application Example 1 with each of the compounds of the chemical formulae (45) through (60). The amount of luminescence that each of the organic electroluminescence elements obtained, in Application Examples 126 through 141 emitted when applied a direct current at 5V, is shown in Table Y As can be seen from Table Y, the amount of luminescence was 60 (cd/m$^2$) or higher and was sufficiently high in each of Application Examples 126 through 141.

Production Examples of Electrophotographic Photoreceptors for Use in Photocopiers

APPLICATION EXAMPLES 142 THROUGH 157

In each Application Example, an electrophotographic photoreceptor was obtained by replacing the compound of the chemical formula (7) with each of the compounds of the chemical formulae (45) through (60).

Production Examples of Electrophotographic Photoreceptors for Use in Printers

APPLICATION EXAMPLES 158 THROUGH 173

In each Application Example, an electrophotographic photoreceptor was obtained by replacing the compound of the chemical formula (7) of Application Example 21 with Each of the Compounds of the Chemical Formulae (45) Through (60).

APPLICATION EXAMPLES 174 THROUGH 189

In each Application Example, an electrophotographic photoreceptor was obtained by replacing the compound of the chemical formula (7) of Application Example 31 with each of the compounds of the chemical formulae (45) through (60). Application Examples 190 through 205

In each Application Example, an electrophotographic photoreceptor was obtained by replacing the compound of the chemical formula (7) of Application Example 41 with each of the compounds of the formulae (45) through (60).

Conditions for Measurement

A corona discharger was adjusted to generate a corona discharge current of 17 µA. The electrophotographic photoreceptors prepared in Application Examples 142 through 157, 158 through 173, and 174 through 189 were each positively charged by the corona discharge in a dark environment and each photoreceptor was measured for the charged electric potential. The photoreceptors were then exposed to white light, and the exposure E/50 (lux·sec) at which the surface potential of each electrophotographic photoreceptor decreased by half, from 700V down to 350V, was measured. This half decay exposure reflects the sensitivity of the electrophotographic photoreceptor.

Results

The results of the measurement for Application Examples 142 through 157 and the results for Comparative Example 2 are as shown in Table Z.

The results for Application Examples 142 through 157 and Comparative Example 2 were obtained for positively charged, single-layered photoreceptors for use in photocopiers. The comparisons between each of Application Examples 142 through 157 and Comparative Example 2 suggest that through the use of the electron-transfer materials of the chemical formulae (45) through (60), a photoreceptor can be obtained that has a higher sensitivity than the photoreceptor using the compound of the formula (24). Also, the chargeability of the photoreceptor is enhanced.

The results of the measurement for Application Examples 158 through 173 and Application Example 3 are as shown in Table AA below.

The results for Application Examples 158 through 173 and Comparative Example 3 were obtained for positively charged, multi-layered photoreceptors for use in printers. The comparisons between each of Application Examples 158 through 173 and Comparative Example 3 suggest that through the use of the electron-transfer materials of the chemical formulae (45) through (60), a photoreceptor can be obtained that has a higher sensitivity than the photoreceptor using the compound of the formula (24).

The results of the measurement for Application Examples 174 through 189 and Comparative Example 4 are as shown in Table AB below.

The results for Application Examples 174 through 189 and Comparative Example 4 were obtained for positively charged, single-layered photoreceptors for use in printers. The comparisons between each of Application Examples 174 through 189 and Comparative Example 4 suggest that through the use of the electron-transfer materials of the chemical formulae (45) through (60), a photoreceptor can be obtained that has a higher sensitivity than the photoreceptor using the compound of the formula (24).

Next, a corona discharger was adjusted to generate a corona discharge current of 17 μA. The electrophotographic photoreceptors prepared in Application Examples 190 through 205 were each negatively charged by the corona discharge in a dark environment and each photoreceptor was measured for the charged electric potential. The photoreceptors were then exposed to white light, and the exposure E/50 (lux·sec) at which the absolute value of the surface potential of each electrophotographic photoreceptor decreased by half, from −700V up to −350V, was measured. The results are shown in Table AC. The half decay exposure reflects the sensitivity of the electrophotographic photoreceptor.

The results for Application Examples 190 through 205 and Comparative Example 5 were obtained for negatively charged, single-layered photoreceptors for use in printers. The comparisons between each of Application Examples 190 through 205 and Comparative Example 5 suggest that through the use of the electron-transfer materials of the chemical formulae (45) through (60), a photoreceptor can be obtained that has a higher sensitivity than the photoreceptor using the compound of the formula (24).

As set forth, the electron-transfer compounds of the present invention have a structure in which two ring structures, a quinone ring and a ring structure incorporating an active methylene group, are connected with each other via a double bond and therefore have a large molecular skeleton that permits a large distance for electron movement within the molecule. Accordingly, the compounds of the present invention show a high electron mobility to allow electrons to move freely within the molecule and thus are capable of coloring only faintly, which helps reduce the light absorption. Asymmetrical molecular structure of the compounds of the present invention contributes to their high compatibility with resins.

The present invention also provides a simple process for producing the electron-transfer compounds that makes use of a base catalyst. Also, an efficient electron-transfer agent can be obtained by mixing the electron-transfer compound with a proper resin. Further, a highly sensitive photosensitive layer can be obtained by using the electron-transfer compound in electrophotographic photoreceptors.

The high compatibility of the electron-transfer compound with binder resins makes it possible to disperse the compound in the photosensitive layer uniformly and abundantly. In this regard, the incident light is not prevented from passing through to the charge-generation material because of the ability of the electron-transfer compound to color only faintly. As a result, a highly sensitive electrophotographic photoreceptor is obtained. Such an electrophotographic photoreceptor can be used to serve both as the positive charge type and as the negative charge type.

Moreover, the electron-transfer compounds of the present invention can be used as an electron-transfer material for use in organic electroluminescence elements. The present invention permits selection of substituents that can provide the characteristics required of the electron-transfer compound for serving as a particular high-performance material and permits designing a desired molecular structure for the electron-transfer compound.

TABLE A1

A list of general formulas (substituents $R_1$–$R_6$)

| No. | General formula |
|-----|-----------------|
| 101 | Quinone ring (O=, =O) fused with pyrazolone ring bearing $R_1$, $R_2$, $R_3$, $R_4$, $R_5$, $R_6$; carbonyl O, N-$R_6$, N= |
| 102 | As 101 but with S= replacing one O= on quinone; C=O on pyrazolone |
| 103 | As 101 but with S= on quinone and C=S on pyrazolone |
| 104 | O= on quinone and C=S on pyrazolone |
| 105 | Dicyanomethylene (NC)(NC)C= replacing one quinone O; C=O on pyrazolone; substituents $R_1$–$R_6$ |
| 106 | Dicyanomethylene (NC)(NC)C= replacing one quinone O; C=S on pyrazolone; substituents $R_1$–$R_6$ |

TABLE A1-continued

A list of general formulas (substituents R₁~R₆)

| No. | General formula |
|---|---|
| 107 | (structure) |
| 108 | (structure) |
| 109 | (structure) |
| 110 | (structure) |
| 111 | (structure) |
| 112 | (structure) |
| 113 | (structure) |
| 114 | (structure) |

TABLE A2

A list of general formulas (substituents R₁~R₆)

| No. | General formula |
|---|---|
| 115 | (structure) |
| 116 | (structure) |
| 117 | (structure) |
| 118 | (structure) |
| 119 | (structure) |
| 120 | (structure) |
| 121 | (structure) |
| 122 | (structure) |

TABLE A2-continued
A list of general formulas (substituents $R_1$–$R_6$)
| No. | General formula |
|---|---|
| 123 | 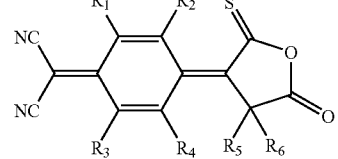 |
| 124 | 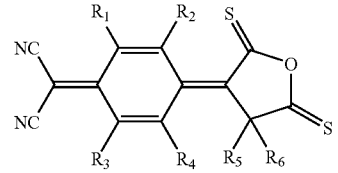 |
| 125 | 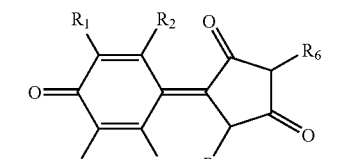 |
| 126 | 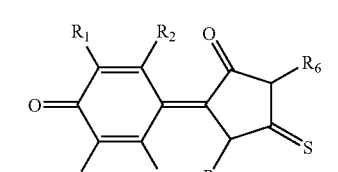 |
| 127 | 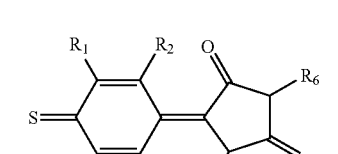 |
| 128 | 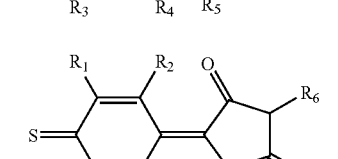 |
TABLE A3
A list of general formulas (substituents $R_1$–$R_6$)
| No. | General formula |
|---|---|
| 129 | 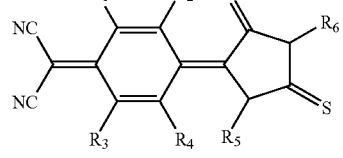 |
| 130 | 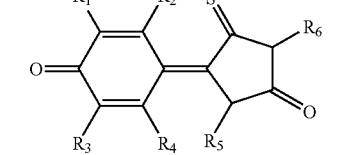 |
| 131 | 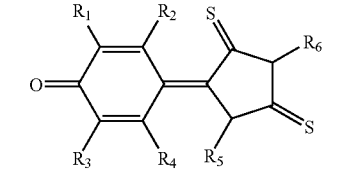 |
| 132 | 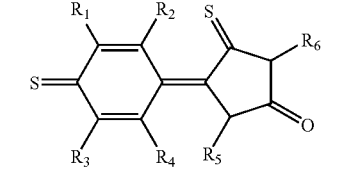 |
| 133 | 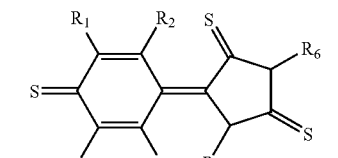 |
| 134 | 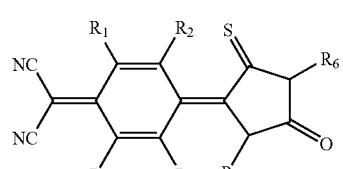 |
| 135 | 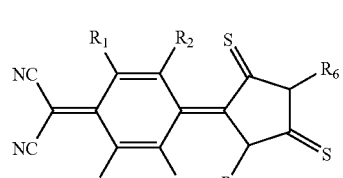 |
| 136 | 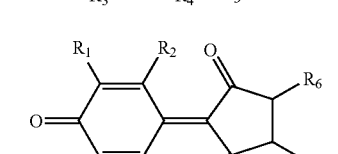 |
| 137 | 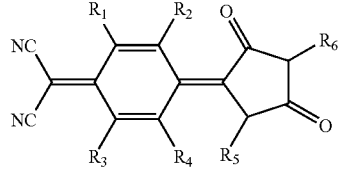 |

TABLE A3-continued

A list of general formulas (substituents R$_1$~R$_6$)

| No. | General formula |
|---|---|
| 138 | (structure) |
| 139 | (structure) |
| 140 | (structure) |
| 141 | (structure) |
| 142 | (structure) |

TABLE A4

A list of general formulas (substituents R$_1$~R$_6$)

| No. | General formula |
|---|---|
| 143 | (structure) |
| 144 | (structure) |
| 145 | (structure) |
| 146 | (structure) |
| 147 | (structure) |
| 148 | (structure) |
| 149 | (structure) |
| 150 | (structure) |
| 151 | (structure) |
| 152 | (structure) |

TABLE A4-continued
A list of general formulas (substituents $R_1$~$R_6$)
| No. | General formula |
|---|---|
| 153 | 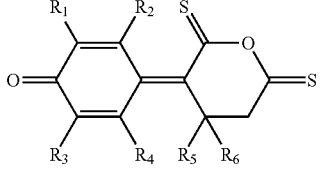 |
| 154 | 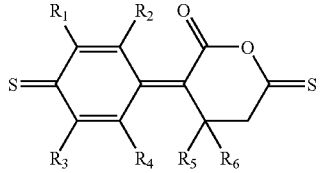 |
| 155 | 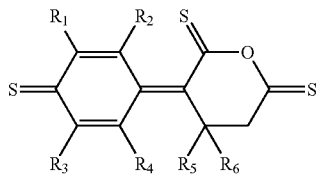 |
| 156 | 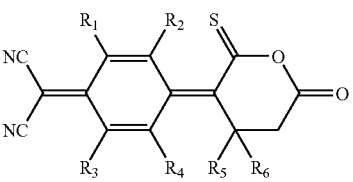 |
TABLE A5
A list of general formulas (substituents $R_1$~$R_6$)
| No. | General formula |
|---|---|
| 157 | 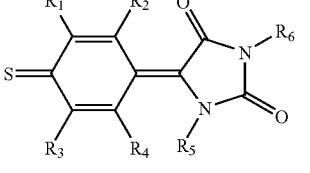 |
| 158 | 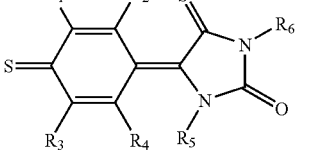 |
| 159 | 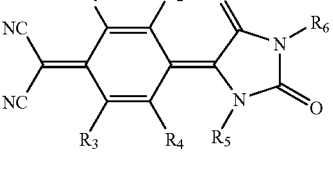 |
TABLE A5-continued
A list of general formulas (substituents $R_1$~$R_6$)
| No. | General formula |
|---|---|
| 160 | 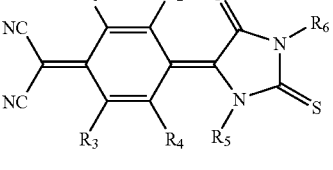 |
| 161 | 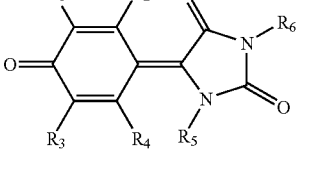 |
| 162 | 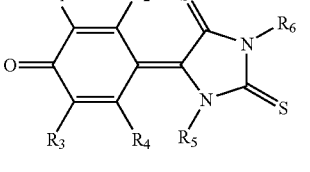 |
| 163 | 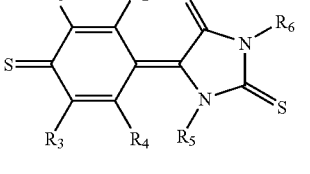 |
| 164 | 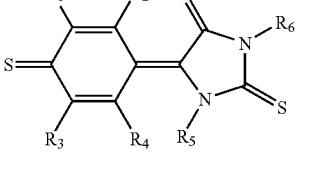 |
| 165 | 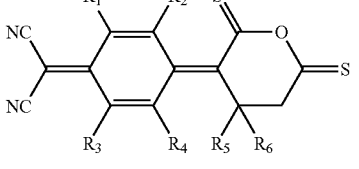 |
| 166 | 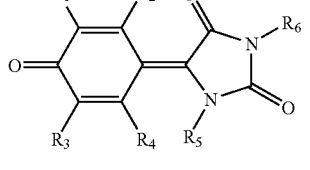 |
| 167 | 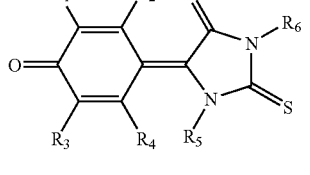 |

TABLE A5-continued

A list of general formulas (substituents R₁~R₆)

| No. | General formula |
|---|---|
| 168 | (structure) |
| 169 | (structure) |
| 170 | (structure) |

TABLE A6

A list of general formulas (substituents R₁~R₆)

| No. | General formula |
|---|---|
| 171 | (structure) |
| 172 | (structure) |
| 173 | (structure) |
| 174 | (structure) |

TABLE A6-continued

A list of general formulas (substituents R₁~R₆)

| No. | General formula |
|---|---|
| 175 | (structure) |
| 176 | (structure) |
| 177 | (structure) |
| 178 | (structure) |
| 179 | (structure) |
| 180 | (structure) |
| 181 | (structure) |
| 182 | (structure) |

TABLE A6-continued
A list of general formulas (substituents R₁~R₆)
| No. | General formula |
|---|---|
| 183 | 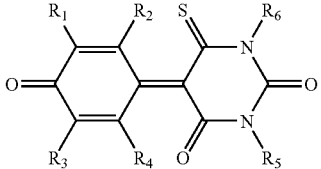 |
| 184 | 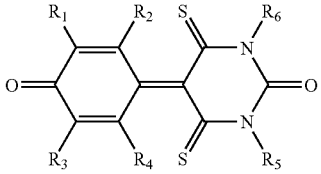 |
TABLE A7
A list of general formulas (substituents R₁~R₆)
| No. | General formula |
|---|---|
| 185 | 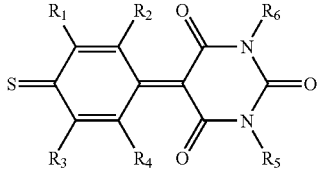 |
| 186 | 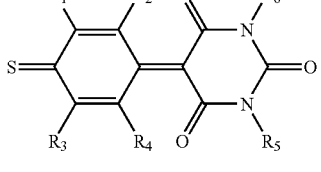 |
| 187 | 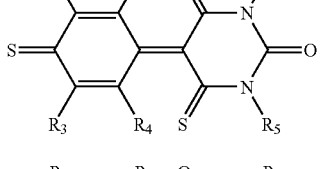 |
| 188 | 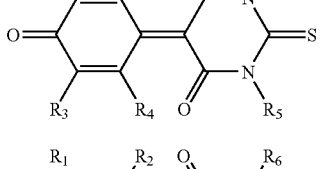 |
| 189 | 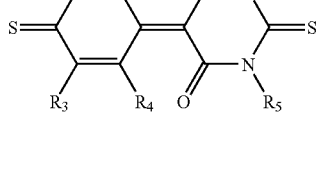 |
TABLE A7-continued
A list of general formulas (substituents R₁~R₆)
| No. | General formula |
|---|---|
| 190 | 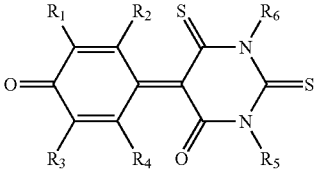 |
| 191 | 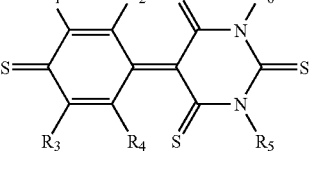 |
| 192 | 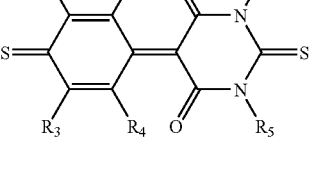 |
| 193 | 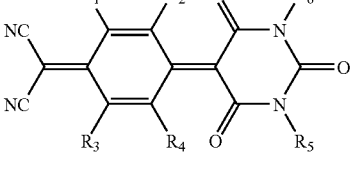 |
| 194 | 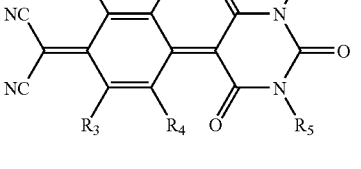 |
| 195 | 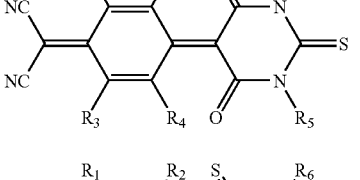 |
| 196 | 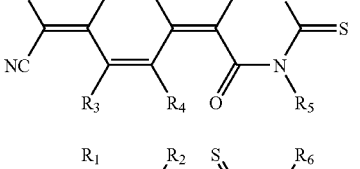 |
| 197 | 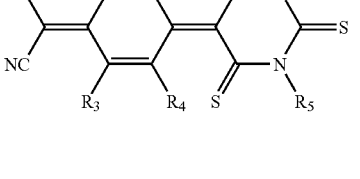 |

TABLE A7-continued
A list of general formulas (substituents R1~R6)
| No. | General formula |
|---|---|
| 198 | 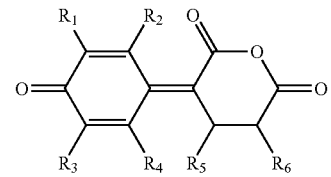 |
TABLE A8
A list of general formulas (substituents R1~R6)
| No. | General formula |
|---|---|
| 199 | |
| 200 | |
| 201 | |
| 202 | |
| 203 | |
| 204 | |
TABLE A8-continued
A list of general formulas (substituents R1~R6)
| No. | General formula |
|---|---|
| 205 | |
| 206 | |
| 207 | |
| 208 | |
| 209 | |
| 210 | |
| 211 | |
| 212 | |

TABLE A9

A list of general formulas (substituents $R_1$~$R_6$)

| No. | General formula |
|---|---|
| 213 | (structure with $R_1, R_2, R_3, R_4, R_5, R_6$, O, S, S) |
| 214 | (structure with $R_1, R_2, R_3, R_4, R_5, R_6$, S, O, O) |
| 215 | (structure with $R_1, R_2, R_3, R_4, R_5, R_6$, S, O, S) |
| 216 | (structure with $R_1, R_2, R_3, R_4, R_5, R_6$, S, S, S) |
| 217 | (structure with $R_1, R_2, R_3, R_4, R_5, R_6$, S, S, S) |
| 218 | (structure with NC, NC, $R_1, R_2, R_3, R_4, R_5, R_6$, O, O) |
| 219 | (structure with NC, NC, $R_1, R_2, R_3, R_4, R_5, R_6$, S, O) |
| 220 | (structure with NC, NC, $R_1, R_2, R_3, R_4, R_5, R_6$, O, S) |

TABLE A9-continued

A list of general formulas (substituents $R_1$~$R_6$)

| No. | General formula |
|---|---|
| 221 | (structure with NC, NC, $R_1, R_2, R_3, R_4, R_5, R_6$, S, S) |
| 222 | (structure with $R_1, R_2, R_3, R_4, R_5, R_6$, O, O, O, O) |
| 223 | (structure with $R_1, R_2, R_3, R_4, R_5, R_6$, S, O, O) |
| 224 | (structure with $R_1, R_2, R_3, R_4, R_5, R_6$, S, O, O) |
| 225 | (structure with $R_1, R_2, R_3, R_4, R_5, R_6$, S, O, S) |
| 226 | (structure with $R_1, R_2, R_3, R_4, R_5, R_6$, S, S, O) |

TABLE A10

A list of general formulas (substituents $R_1$~$R_6$)

| No. | General formula |
|---|---|
| 227 | (structure with $R_1, R_2, R_3, R_4, R_5, R_6$, S, S, S) |

TABLE A10-continued
A list of general formulas (substituents R₁~R₆)
| No. | General formula |
|---|---|
| 228 | 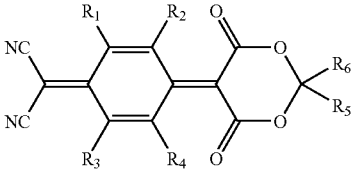 |
| 229 | 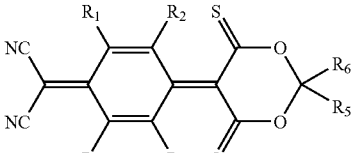 |
| 230 | 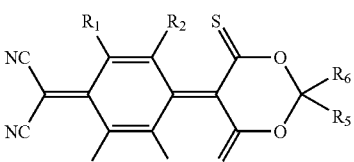 |
| 231 | 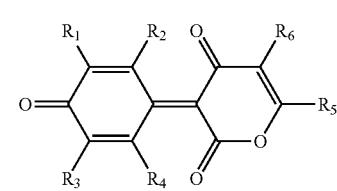 |
| 232 | 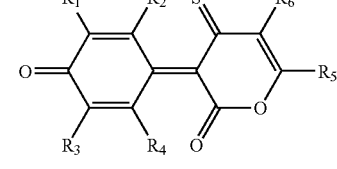 |
| 233 | 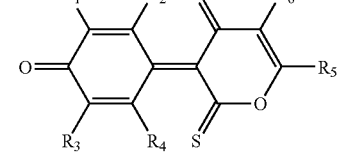 |
| 234 | 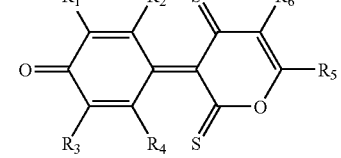 |
| 235 | 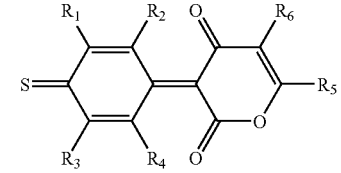 |
TABLE A10-continued
A list of general formulas (substituents R₁~R₆)
| No. | General formula |
|---|---|
| 236 | 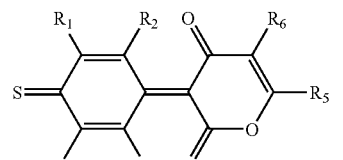 |
| 237 | 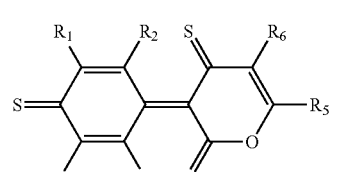 |
| 238 | 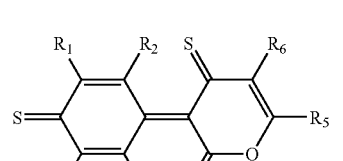 |
| 239 | 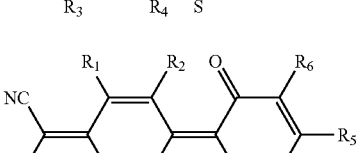 |
| 240 | 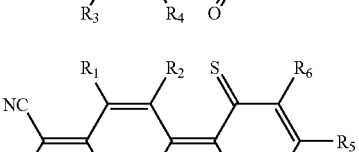 |
TABLE A11
A list of general formulas (substituents R₁~R₆)
| No. | General formula |
|---|---|
| 241 | 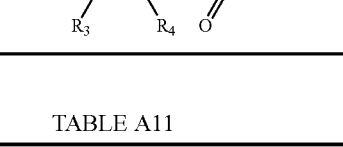 |
| 242 | 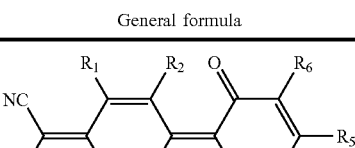 |

TABLE A11-continued

A list of general formulas (substituents $R_1$~$R_6$)

| No. | General formula |
|---|---|
| 243 | (structure with $R_1$, $R_2$, $R_3$, $R_4$, $R_5$, $R_6$) |
| 244 | (structure with $R_1$, $R_2$, $R_3$, $R_4$, $R_5$, $R_6$) |
| 245 | (structure with $R_1$, $R_2$, $R_3$, $R_4$, $R_5$, $R_6$) |
| 246 | (structure with $R_1$, $R_2$, $R_3$, $R_4$, $R_5$, $R_6$) |
| 247 | (structure with $R_1$, $R_2$, $R_3$, $R_4$, $R_5$, $R_6$) |
| 248 | (structure with $R_1$, $R_2$, $R_3$, $R_4$, $R_5$, $R_6$) |
| 249 | (structure with $R_1$, $R_2$, $R_3$, $R_4$, $R_5$, $R_6$) |

TABLE A11-continued

A list of general formulas (substituents $R_1$~$R_6$)

| No. | General formula |
|---|---|
| 250 | (structure with $R_1$, $R_2$, $R_3$, $R_4$, $R_5$, $R_6$) |
| 251 | (structure with $R_1$, $R_2$, $R_3$, $R_4$, $R_5$, $R_6$) |
| 252 | (structure with $R_1$, $R_2$, $R_3$, $R_4$, $R_5$, $R_6$) |
| 253 | (structure with $R_1$, $R_2$, $R_3$, $R_4$, $R_5$, $R_6$) |
| 254 | (structure with $R_1$, $R_2$, $R_3$, $R_4$, $R_5$, $R_6$) |

TABLE A12

A list of general formulas (substituents $R_1$~$R_6$)

| No. | General formula |
|---|---|
| 255 | (structure with NC, $R_1$, $R_2$, $R_3$, $R_4$, $R_5$, $R_6$) |
| 256 | (structure with NC, $R_1$, $R_2$, $R_3$, $R_4$, $R_5$, $R_6$) |

TABLE A12-continued

A list of general formulas (substituents $R_1$~$R_6$)

| No. | General formula |
|---|---|
| 257 | [structure with $R_1$, $R_2$, $R_3$, $R_4$, NC, NC, O, S, $R_5$, $R_6$] |
| 258 | [structure with $R_1$, $R_2$, $R_3$, $R_4$, NC, NC, S, S, $R_5$, $R_6$] |
| 259 | [structure with $R_1$, $R_2$, $R_3$, $R_4$, O, O, O, Me, $R_5$, $R_6$] |
| 260 | [structure with $R_1$, $R_2$, $R_3$, $R_4$, O, S, O, Me, $R_5$, $R_6$] |
| 261 | [structure with $R_1$, $R_2$, $R_3$, $R_4$, O, O, S, Me, $R_5$, $R_6$] |
| 262 | [structure with $R_1$, $R_2$, $R_3$, $R_4$, O, S, S, Me, $R_5$, $R_6$] |
| 263 | [structure with $R_1$, $R_2$, $R_3$, $R_4$, S, O, O, Me, $R_5$, $R_6$] |
| 264 | [structure with $R_1$, $R_2$, $R_3$, $R_4$, S, O, S, Me, $R_5$, $R_6$] |

TABLE A12-continued

A list of general formulas (substituents $R_1$~$R_6$)

| No. | General formula |
|---|---|
| 265 | [structure with $R_1$, $R_2$, $R_3$, $R_4$, S, S, O, Me, $R_5$, $R_6$] |
| 266 | [structure with $R_1$, $R_2$, $R_3$, $R_4$, S, S, S, Me, $R_5$, $R_6$] |
| 267 | [structure with $R_1$, $R_2$, $R_3$, $R_4$, NC, NC, O, O, Me, $R_5$, $R_6$] |
| 268 | [structure with $R_1$, $R_2$, $R_3$, $R_4$, NC, NC, S, O, Me, $R_5$, $R_6$] |

TABLE A13

A list of general formulas (substituents $R_1$~$R_6$)

| No. | General formula |
|---|---|
| 269 | [structure with $R_1$, $R_2$, $R_3$, $R_4$, NC, NC, O, S, Me, $R_5$, $R_6$] |
| 270 | [structure with $R_1$, $R_2$, $R_3$, $R_4$, NC, NC, S, S, Me, $R_5$, $R_6$] |
| 271 | [structure with $R_1$, $R_2$, $R_3$, $R_4$, O, O, benzofuran, $R_5$, $R_6$] |

TABLE A13-continued
A list of general formulas (substituents $R_1$~$R_6$)
| No. | General formula |
|---|---|
| 272 | 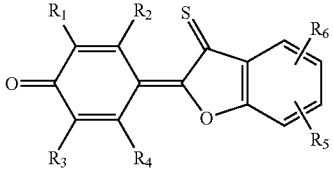 |
| 273 | 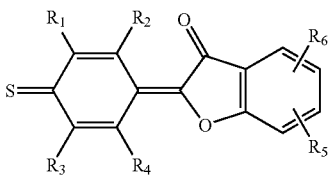 |
| 274 | 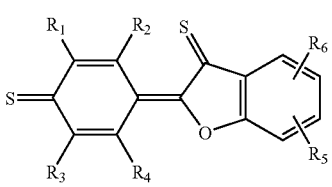 |
| 275 | 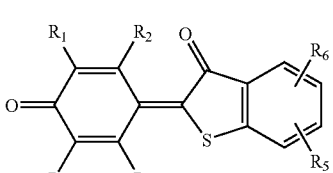 |
| 276 | 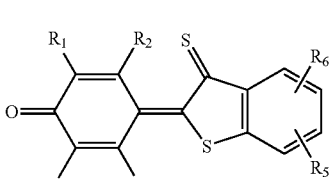 |
| 277 | 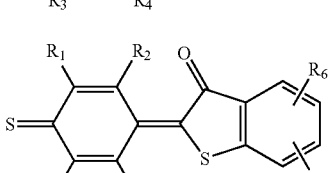 |
| 278 | 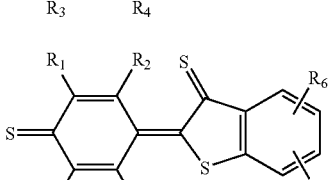 |
| 279 | 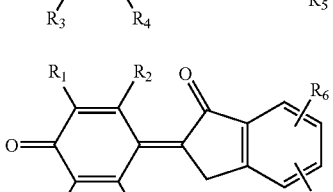 |
TABLE A13-continued
A list of general formulas (substituents $R_1$~$R_6$)
| No. | General formula |
|---|---|
| 280 | 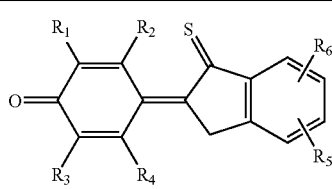 |
| 281 | 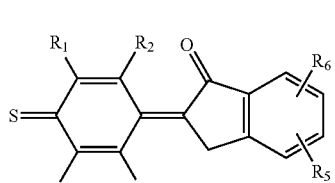 |
| 282 | 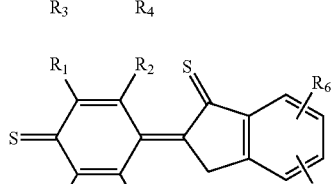 |
TABLE A14
A list of general formulas (substituents $R_1$~$R_6$)
| No. | General formula |
|---|---|
| 283 | 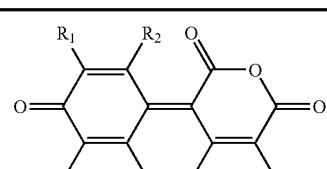 |
| 284 | 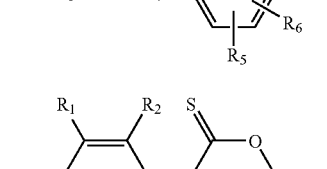 |
| 285 | 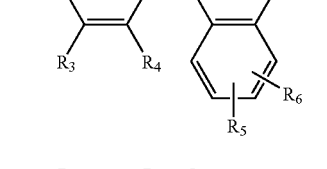 |

TABLE A14-continued

A list of general formulas (substituents R$_1$~R$_6$)

| No. | General formula |
|---|---|
| 286 | |
| 287 | |
| 288 | |
| 289 | |
| 290 | |
| 291 | |
| 292 | |
| 293 | |
| 294 | |

TABLE A15

A list of general formulas (substituents R$_1$~R$_6$)

| No. | General formula |
|---|---|
| 295 | |
| 296 | |
| 297 | |

TABLE A15-continued

A list of general formulas (substituents R$_1$~R$_6$)

| No. | General formula |
|---|---|
| 298 | (structure) |
| 299 | (structure) |
| 300 | (structure) |

TABLE A16

A list of general formulas (substituents R$_1$~R$_6$)

| No. | General formula |
|---|---|
| 301 | (structure) |
| 302 | (structure) |
| 303 | (structure) |
| 304 | (structure) |
| 305 | (structure) |
| 306 | (structure) |

TABLE A17

A list of general formulas (substituents R$_1$~R$_6$)

| No. | General formula |
|---|---|
| 307 | (structure) |
| 308 | (structure) |

TABLE A17-continued

A list of general formulas (substituents R1~R6)

| No. | General formula |
|---|---|
| 309 | [structure] |
| 310 | [structure] |
| 311 | [structure] |
| 312 | [structure] |

TABLE A18

A list of general formulas (substituents R1~R6)

| No. | General formula |
|---|---|
| 313 | [structure] |
| 314 | [structure] |

TABLE A19

A list of general formulas (substituents R1~R5)

| No. | General formula |
|---|---|
| 315 | [structure] |
| 316 | [structure] |
| 317 | [structure] |
| 318 | [structure] |
| 319 | [structure] |
| 320 | [structure] |

TABLE A19-continued

A list of general formulas (substituents R₁~R₅)

| No. | General formula |
|---|---|
| 321 | (structure) |
| 322 | (structure) |
| 323 | (structure) |
| 324 | (structure) |
| 325 | (structure) |
| 326 | (structure) |
| 327 | (structure) |
| 328 | (structure) |

TABLE A20

A list of general formulas (substituents R₁~R₅)

| No. | General formula |
|---|---|
| 329 | (structure) |
| 330 | (structure) |
| 331 | (structure) |
| 332 | (structure) |
| 333 | (structure) |
| 334 | (structure) |
| 335 | (structure) |
| 336 | (structure) |

TABLE A20-continued

A list of general formulas (substituents R₁~R₅)

| No. | General formula |
|---|---|
| 337 | (structure) |
| 338 | (structure) |
| 339 | (structure) |
| 340 | (structure) |
| 341 | (structure) |
| 342 | (structure) |

TABLE A21

A list of general formulas (substituents R₁~R₅)

| No. | General formula |
|---|---|
| 343 | (structure) |
| 344 | (structure) |
| 345 | (structure) |
| 346 | (structure) |
| 347 | (structure) |
| 348 | (structure) |
| 349 | (structure) |
| 350 | (structure) |
| 351 | (structure) |

TABLE A21-continued
A list of general formulas (substituents R₁~R₅)
| No. | General formula |
|---|---|
| 352 | 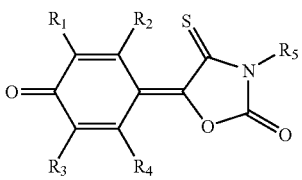 |
| 353 | 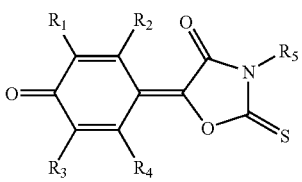 |
| 354 | 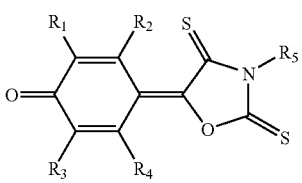 |
| 355 | 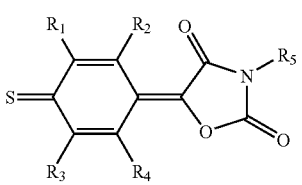 |
| 356 | 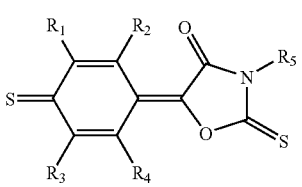 |
TABLE A22
A list of general formulas (substituents R₁~R₅)
| No. | General formula |
|---|---|
| 357 | 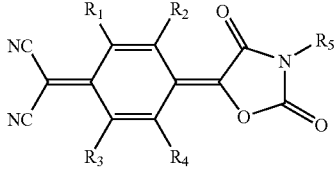 |
| 358 | 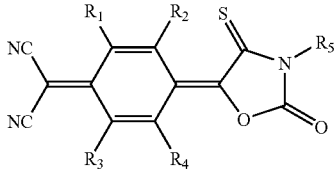 |
TABLE A22-continued
A list of general formulas (substituents R₁~R₅)
| No. | General formula |
|---|---|
| 359 | 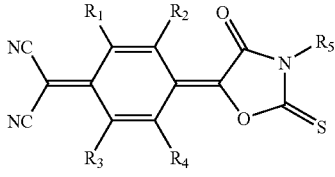 |
| 360 | 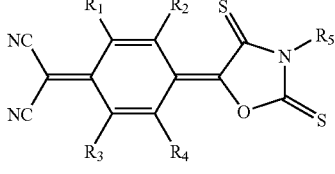 |
| 361 | 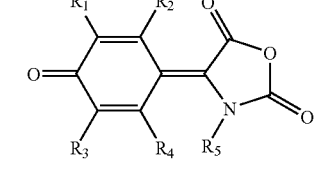 |
| 362 | 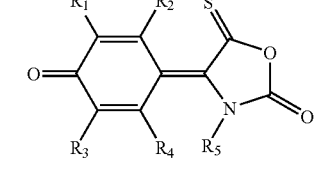 |
| 363 | 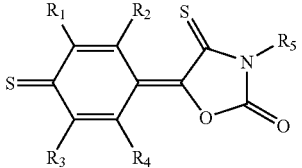 |
| 364 | 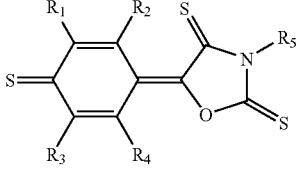 |
| 365 | |
| 366 | |

TABLE A22-continued

A list of general formulas (substituents R₁~R₅)

| No. | General formula |
|---|---|
| 367 | (structure with R₁, R₂, R₃, R₄, R₅) |
| 368 | (structure with R₁, R₂, R₃, R₄, R₅) |
| 369 | (structure with R₁, R₂, R₃, R₄, R₅) |
| 370 | (structure with R₁, R₂, R₃, R₄, R₅) |

TABLE A23

A list of general formulas (substituents R₁~R₅)

| No. | General formula |
|---|---|
| 371 | (structure with R₁, R₂, R₃, R₄, R₅) |
| 372 | (structure with R₁, R₂, R₃, R₄, R₅) |
| 373 | (structure with R₁, R₂, R₃, R₄, R₅) |

TABLE A23-continued

A list of general formulas (substituents R₁~R₅)

| No. | General formula |
|---|---|
| 374 | (structure with R₁, R₂, R₃, R₄, R₅) |
| 375 | (structure with R₁, R₂, R₃, R₄, R₅) |
| 376 | (structure with R₁, R₂, R₃, R₄, R₅) |
| 378 | (structure with R₁, R₂, R₃, R₄, R₅) |
| 379 | (structure with R₁, R₂, R₃, R₄, R₅) |
| 380 | (structure with R₁, R₂, R₃, R₄, R₅) |
| 381 | (structure with R₁, R₂, R₃, R₄, R₅) |
| 382 | (structure with R₁, R₂, R₃, R₄, R₅) |

TABLE A23-continued

A list of general formulas (substituents R₁~R₅)

| No. | General formula |
|-----|----------------|
| 383 | (structure) |
| 384 | (structure) |
| 385 | (structure) |

TABLE A24

A list of general formulas (substituents R₁~R₅)

| No. | General formula |
|-----|----------------|
| 386 | (structure) |
| 387 | (structure) |
| 388 | (structure) |
| 389 | (structure) |
| 390 | (structure) |
| 391 | (structure) |
| 392 | (structure) |
| 393 | (structure) |
| 394 | (structure) |
| 395 | (structure) |
| 396 | (structure) |
| 397 | (structure) |

TABLE A24-continued
A list of general formulas (substituents R_1~R_5)
| No. | General formula |
|---|---|
| 398 | 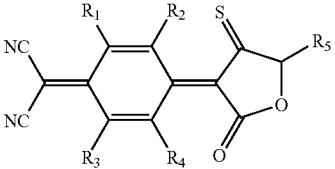 |
| 399 | 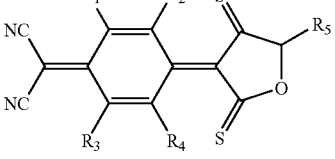 |
TABLE A25
A list of general formulas (substituents R_1~R_5)
| No. | General formula |
|---|---|
| 400 | 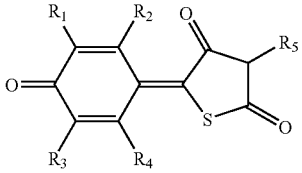 |
| 401 | 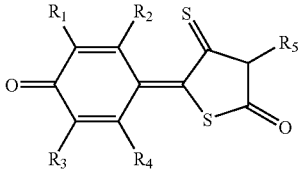 |
| 402 | 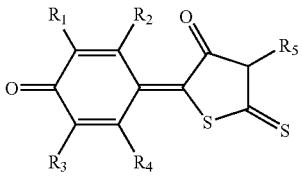 |
| 403 | 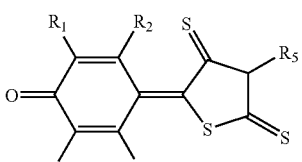 |
| 404 | 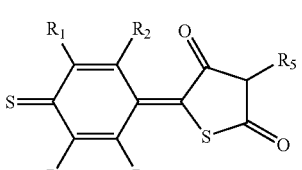 |
TABLE A25-continued
A list of general formulas (substituents R_1~R_5)
| No. | General formula |
|---|---|
| 405 | 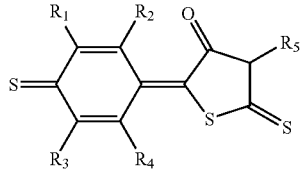 |
| 406 | 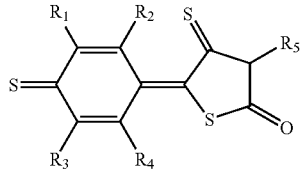 |
| 407 | 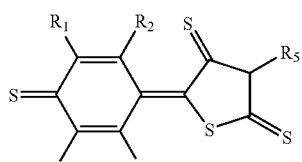 |
| 408 | 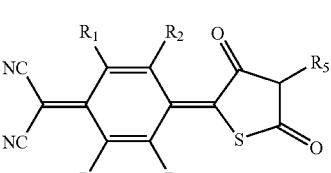 |
| 409 | 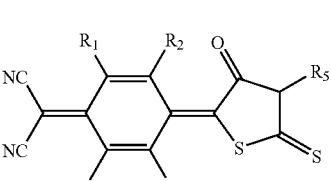 |
| 410 | 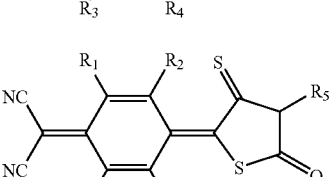 |
| 411 | 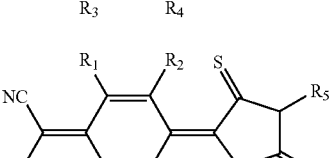 |
| 412 | 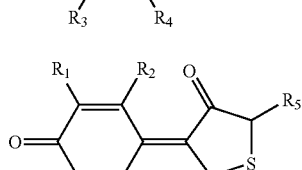 |

TABLE A25-continued

A list of general formulas (substituents $R_1$~$R_5$)

| No. | General formula |
|---|---|
| 413 | (structure) |

TABLE A26

A list of general formulas (substituents $R_1$~$R_5$)

| No. | General formula |
|---|---|
| 414 | (structure) |
| 415 | (structure) |
| 416 | (structure) |
| 417 | (structure) |
| 418 | (structure) |
| 419 | (structure) |

TABLE A26-continued

A list of general formulas (substituents $R_1$~$R_5$)

| No. | General formula |
|---|---|
| 420 | (structure) |
| 421 | (structure) |
| 422 | (structure) |
| 423 | (structure) |

TABLE B

A list of substituents

| Substituent's No | substituent |
|---|---|
| S1 | —H |
| S2 | —$CH_3$ |
| S3 | -t-Bu |
| S4 | —$OCH_3$ |
| S5 | —$CF_3$ |
| S6 | —$NO_2$ |
| S7 | —$CO_2CH_3$ |
| S8 | —CH=CH—CH=$CH_2$ |
| S9 | —$C_2H_5$ |
| S10 | —Cl |
| S11 | (phenyl) |
| S12 | (thienyl) |
| S13 | (furyl) |
| S14 | (4-t-Bu-phenyl) |

TABLE B-continued

A list of substituents

| Substituent's No | substituent |
|---|---|
| S15 | 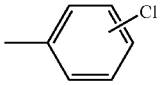 -Cl (para-chlorophenyl) |
| S16 | 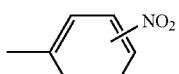 -NO2 (para-nitrophenyl) |
| S17 | 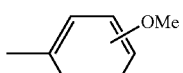 -OMe (para-methoxyphenyl) |
| S18 | naphthyl |
| S19 | biphenyl |
| S20 | cyclohexyl-H |
| S21 | cyclohexadienyl |
| S22 | t-Bu-phenyl |
| S23 | cyclohexyl-H |

TABLE C1

A list of compounds (substituents R1~R6)

| $R_1$ | $R_2$ | $R_3$ | $R_4$ | $R_5$ | $R_6$ |
|---|---|---|---|---|---|
| S3 | S1 | S3 | S1 | S11 | S11 |
| S3 | S2 | S3 | S1 | S11 | S11 |
| S3 | S2 | S3 | S2 | S11 | S11 |
| S3 | S1 | S12 | S1 | S11 | S11 |
| S3 | S2 | S12 | S1 | S11 | S11 |
| S3 | S2 | S12 | S2 | S11 | S11 |
| S3 | S1 | S13 | S1 | S11 | S11 |
| S3 | S2 | S13 | S1 | S11 | S11 |
| S3 | S2 | S13 | S2 | S11 | S11 |
| S3 | S11 | S3 | S2 | S11 | S11 |
| S3 | S1 | S3 | S1 | S11 | S13 |
| S3 | S1 | S3 | S1 | S11 | S12 |
| S3 | S2 | S3 | S1 | S11 | S13 |
| S3 | S2 | S3 | S1 | S11 | S12 |
| S3 | S1 | S12 | S1 | S11 | S13 |
| S3 | S1 | S13 | S1 | S11 | S12 |
| S3 | S2 | S12 | S1 | S11 | S13 |
| S3 | S2 | S13 | S1 | S11 | S12 |
| S3 | S1 | S3 | S1 | S12 | S13 |

TABLE C1-continued

A list of compounds (substituents R1~R6)

| $R_1$ | $R_2$ | $R_3$ | $R_4$ | $R_5$ | $R_6$ |
|---|---|---|---|---|---|
| S3 | S1 | S3 | S1 | S13 | S12 |
| S3 | S2 | S3 | S1 | S12 | S13 |
| S3 | S2 | S3 | S1 | S13 | S12 |
| S3 | S1 | S13 | S1 | S12 | S13 |
| S3 | S1 | S12 | S1 | S13 | S13 |
| S3 | S2 | S12 | S1 | S12 | S13 |
| S3 | S2 | S13 | S1 | S13 | S12 |
| S3 | S1 | S3 | S1 | S3 | S18 |
| S3 | S1 | S3 | S1 | S14 | S15 |
| S3 | S1 | S3 | S1 | S15 | S14 |
| S3 | S1 | S3 | S1 | S17 | S13 |
| S3 | S1 | S3 | S1 | S16 | S12 |
| S3 | S1 | S3 | S1 | S12 | S11 |
| S3 | S1 | S3 | S1 | S12 | S13 |
| S3 | S1 | S3 | S1 | S13 | S11 |
| S3 | S1 | S3 | S1 | S13 | S12 |
| S3 | S2 | S3 | S1 | S12 | S11 |
| S3 | S2 | S3 | S1 | S13 | S11 |
| S3 | S1 | S4 | S2 | S11 | S13 |
| S3 | S6 | S7 | S4 | S2 | S12 |
| S3 | S10 | S11 | S6 | S19 | S16 |
| S3 | S2 | S20 | S10 | S7 | S11 |

TABLE C2

A list of compounds (substituents R1~R6)

| $R_1$ | $R_2$ | $R_3$ | $R_4$ | $R_5$ | $R_6$ |
|---|---|---|---|---|---|
| S3 | S3 | S3 | S3 | S3 | S18 |
| S3 | S20 | S2 | S11 | S16 | S3 |
| S3 | S11 | S10 | S7 | S5 | S13 |
| S3 | S7 | S6 | S1 | S20 | S15 |
| S3 | S4 | S1 | S20 | S18 | S20 |
| S12 | S1 | S3 | S1 | S11 | S13 |
| S12 | S1 | S3 | S1 | S3 | S18 |
| S12 | S2 | S3 | S1 | S11 | S13 |
| S12 | S1 | S3 | S1 | S14 | S15 |
| S12 | S1 | S3 | S1 | S15 | S14 |
| S12 | S1 | S3 | S1 | S17 | S13 |
| S12 | S1 | S3 | S1 | S16 | S12 |
| S12 | S1 | S3 | S1 | S12 | S11 |
| S12 | S1 | S3 | S1 | S12 | S13 |
| S12 | S1 | S3 | S1 | S13 | S11 |
| S12 | S1 | S3 | S1 | S13 | S12 |
| S12 | S1 | S12 | S1 | S12 | S11 |
| S12 | S1 | S12 | S1 | S13 | S12 |
| S12 | S1 | S13 | S1 | S12 | S13 |
| S12 | S1 | S13 | S1 | S13 | S11 |
| S12 | S1 | S12 | S1 | S13 | S12 |
| S12 | S1 | S4 | S2 | S11 | S13 |
| S12 | S6 | S7 | S4 | S2 | S12 |
| S12 | S10 | S11 | S6 | S19 | S16 |
| S12 | S2 | S20 | S10 | S7 | S11 |
| S12 | S3 | S3 | S3 | S3 | S18 |
| S12 | S20 | S2 | S11 | S16 | S3 |
| S12 | S11 | S10 | S7 | S5 | S13 |
| S12 | S7 | S6 | S1 | S20 | S15 |
| S12 | S4 | S1 | S20 | S18 | S20 |
| S13 | S1 | S3 | S1 | S11 | S13 |
| S13 | S1 | S3 | S1 | S3 | S18 |
| S13 | S2 | S3 | S1 | S11 | S13 |
| S13 | S1 | S3 | S1 | S14 | S15 |
| S13 | S1 | S3 | S1 | S15 | S14 |
| S13 | S1 | S3 | S1 | S17 | S13 |
| S13 | S1 | S3 | S1 | S16 | S12 |
| S13 | S1 | S3 | S1 | S12 | S11 |
| S13 | S1 | S3 | S1 | S12 | S13 |
| S13 | S1 | S3 | S1 | S13 | S11 |
| S13 | S1 | S3 | S1 | S13 | S12 |
| S13 | S2 | S13 | S1 | S12 | S11 |

TABLE C3

A list of compounds (substituents R1~R6)

| $R_1$ | $R_2$ | $R_3$ | $R_4$ | $R_5$ | $R_6$ |
|---|---|---|---|---|---|
| S13 | S1 | S12 | S1 | S12 | S13 |
| S13 | S2 | S12 | S1 | S13 | S11 |
| S13 | S1 | S13 | S1 | S13 | S12 |
| S13 | S1 | S4 | S2 | S11 | S13 |
| S13 | S6 | S7 | S4 | S2 | S12 |
| S13 | S10 | S11 | S6 | S19 | S16 |
| S13 | S2 | S20 | S10 | S7 | S11 |
| S13 | S3 | S3 | S3 | S3 | S18 |
| S13 | S20 | S2 | S11 | S16 | S3 |
| S13 | S11 | S10 | S7 | S5 | S13 |
| S13 | S7 | S6 | S1 | S20 | S15 |
| S13 | S4 | S1 | S20 | S18 | S20 |
| S11 | S1 | S2 | S20 | S7 | S11 |
| S11 | S6 | S20 | S7 | S3 | S18 |
| S11 | S1 | S12 | S2 | S11 | S13 |
| S11 | S10 | S3 | S1 | S16 | S3 |
| S11 | S2 | S1 | S6 | S5 | S13 |
| S11 | S3 | S10 | S2 | S20 | S15 |
| S11 | S20 | S6 | S4 | S18 | S20 |
| S11 | S11 | S11 | S11 | S11 | S13 |
| S11 | S7 | S4 | S10 | S2 | S12 |
| S11 | S4 | S7 | S3 | S19 | S16 |
| S11 | S1 | S11 | S1 | S11 | S13 |
| S11 | S2 | S11 | S1 | S11 | S13 |
| S11 | S1 | S11 | S1 | S11 | S12 |
| S11 | S2 | S11 | S1 | S11 | S12 |
| S11 | S1 | S12 | S1 | S11 | S13 |
| S11 | S2 | S12 | S1 | S11 | S13 |
| S11 | S1 | S12 | S1 | S11 | S12 |
| S11 | S2 | S12 | S1 | S11 | S12 |
| S11 | S1 | S13 | S1 | S11 | S13 |
| S11 | S2 | S13 | S1 | S11 | S13 |
| S11 | S1 | S13 | S1 | S11 | S12 |
| S11 | S2 | S13 | S1 | S11 | S12 |
| S11 | S1 | S11 | S1 | S14 | S15 |
| S11 | S1 | S11 | S1 | S12 | S11 |
| S11 | S1 | S11 | S1 | S13 | S11 |
| S11 | S2 | S11 | S1 | S12 | S11 |
| S11 | S2 | S11 | S1 | S13 | S11 |
| S11 | S1 | S11 | S1 | S13 | S13 |
| S11 | S1 | S11 | S1 | S13 | S12 |

TABLE C4

A list of compounds (substituents R1~R6)

| $R_1$ | $R_2$ | $R_3$ | $R_4$ | $R_5$ | $R_6$ |
|---|---|---|---|---|---|
| S11 | S1 | S11 | S1 | S12 | S13 |
| S11 | S1 | S11 | S1 | S13 | S13 |
| S11 | S1 | S12 | S1 | S12 | S11 |
| S11 | S1 | S12 | S1 | S13 | S11 |
| S11 | S2 | S12 | S1 | S12 | S11 |
| S11 | S2 | S12 | S1 | S13 | S11 |
| S11 | S1 | S12 | S1 | S12 | S12 |
| S11 | S1 | S12 | S1 | S13 | S12 |
| S11 | S1 | S12 | S1 | S12 | S13 |
| S11 | S1 | S12 | S1 | S13 | S13 |
| S11 | S1 | S13 | S1 | S12 | S11 |
| S11 | S1 | S13 | S1 | S13 | S11 |
| S11 | S2 | S13 | S1 | S12 | S11 |
| S11 | S2 | S13 | S1 | S13 | S11 |
| S11 | S1 | S13 | S1 | S12 | S12 |
| S11 | S1 | S13 | S1 | S13 | S12 |
| S11 | S1 | S13 | S1 | S12 | S13 |
| S11 | S1 | S13 | S1 | S13 | S13 |
| S11 | S11 | S11 | S1 | S11 | S13 |
| S11 | S1 | S7 | S1 | S11 | S13 |
| S15 | S1 | S15 | S1 | S11 | S13 |
| S17 | S1 | S11 | S1 | S11 | S13 |
| S11 | S1 | S11 | S1 | S12 | S11 |
| S11 | S1 | S11 | S1 | S11 | S11 |

TABLE C4-continued

A list of compounds (substituents R1~R6)

| $R_1$ | $R_2$ | $R_3$ | $R_4$ | $R_5$ | $R_6$ |
|---|---|---|---|---|---|
| S13 | S1 | S13 | S1 | S11 | S13 |
| S8 | S1 | S2 | S1 | S11 | S13 |
|  | S21 | S8 | S1 | S11 | S13 |
|  | S21 | S8 | S1 | S12 | S11 |
|  | S21 | S3 | S1 | S11 | S13 |
|  | S21 |  | S21 | S11 | S13 |
|  | S22 |  | S21 | S11 | S12 |
|  | S23 | S9 | S1 | S11 | S13 |
| S2 | S2 | S2 | S1 | S14 | S15 |
| S2 | S2 | S2 | S1 | S11 | S13 |
| S2 | S1 | S11 | S7 | S20 | S15 |
| S2 | S1 | S11 | S7 | S12 | S11 |
| S2 | S6 | S4 | S1 | S18 | S20 |
| S2 | S10 | S7 | S20 | S5 | S13 |
| S2 | S2 | S2 | S2 | S2 | S12 |
| S2 | S3 | S20 | S4 | S19 | S16 |
| S2 | S3 | S20 | S4 | S13 | S11 |

TABLE C5

A list of compounds (substituents R1~R6)

| $R_1$ | $R_2$ | $R_3$ | $R_4$ | $R_5$ | $R_6$ |
|---|---|---|---|---|---|
| S2 | S3 | S13 | S4 | S13 | S11 |
| S2 | S20 | S3 | S6 | S11 | S13 |
| S2 | S11 | S1 | S10 | S3 | S18 |
| S2 | S7 | S10 | S3 | S16 | S3 |
| S2 | S4 | S6 | S11 | S7 | S11 |
| S20 | S1 | S7 | S10 | S16 | S3 |
| S20 | S6 | S22 | S3 | S7 | S22 |
| S20 | S10 | S4 | S22 | S3 | S18 |
| S20 | S2 | S3 | S7 | S18 | S20 |
| S20 | S3 | S2 | S1 | S5 | S13 |
| S20 | S20 | S20 | S20 | S20 | S15 |
| S20 | S20 | S20 | S20 | S12 | S11 |
| S20 | S11 | S6 | S2 | S19 | S16 |
| S20 | S11 | S6 | S2 | S13 | S11 |
| S20 | S7 | S1 | S4 | S11 | S13 |
| S20 | S4 | S10 | S6 | S2 | S12 |
| S1 | S1 | S1 | S1 | S19 | S16 |
| S1 | S1 | S1 | S1 | S13 | S11 |
| S1 | S6 | S10 | S20 | S11 | S13 |
| S1 | S10 | S6 | S7 | S2 | S12 |
| S1 | S2 | S11 | S4 | S16 | S3 |
| S1 | S3 | S4 | S6 | S7 | S11 |
| S1 | S20 | S7 | S2 | S3 | S18 |
| S1 | S11 | S2 | S3 | S18 | S20 |
| S1 | S7 | S20 | S11 | S5 | S13 |
| S1 | S4 | S3 | S10 | S20 | S15 |
| S1 | S4 | S3 | S10 | S12 | S11 |
| S6 | S1 | S10 | S4 | S3 | S18 |
| S6 | S6 | S6 | S6 | S16 | S3 |
| S6 | S10 | S1 | S2 | S7 | S11 |
| S6 | S2 | S4 | S3 | S20 | S15 |
| S6 | S2 | S4 | S3 | S12 | S11 |
| S6 | S3 | S7 | S11 | S18 | S20 |
| S6 | S20 | S11 | S10 | S5 | S13 |
| S6 | S11 | S20 | S1 | S2 | S12 |
| S6 | S7 | S3 | S20 | S19 | S16 |
| S6 | S7 | S3 | S20 | S13 | S11 |
| S6 | S4 | S2 | S7 | S11 | S13 |
| S10 | S1 | S6 | S3 | S5 | S13 |
| S10 | S6 | S1 | S11 | S20 | S15 |
| S10 | S6 | S1 | S11 | S12 | S11 |

TABLE C6

A list of compounds (substituents R1~R6)

| R₁ | R₂ | R₃ | R₄ | R₅ | R₆ |
|---|---|---|---|---|---|
| S10 | S10 | S10 | S10 | S18 | S20 |
| S10 | S2 | S7 | S1 | S11 | S13 |
| S10 | S3 | S11 | S20 | S2 | S12 |
| S10 | S20 | S4 | S7 | S19 | S16 |
| S10 | S20 | S4 | S7 | S13 | S11 |
| S10 | S11 | S3 | S4 | S7 | S11 |
| S10 | S7 | S2 | S6 | S3 | S18 |
| S10 | S4 | S20 | S2 | S16 | S3 |
| S7 | S1 | S20 | S6 | S18 | S20 |
| S7 | S6 | S3 | S2 | S5 | S13 |
| S7 | S10 | S2 | S4 | S20 | S15 |
| S7 | S10 | S2 | S4 | S12 | S11 |
| S7 | S2 | S10 | S11 | S19 | S16 |
| S7 | S2 | S10 | S11 | S13 | S11 |
| S7 | S3 | S6 | S10 | S11 | S13 |
| S7 | S20 | S1 | S3 | S2 | S12 |
| S7 | S11 | S4 | S20 | S16 | S3 |
| S7 | S7 | S7 | S7 | S7 | S11 |
| S7 | S4 | S11 | S1 | S3 | S18 |
| S4 | S1 | S3 | S11 | S2 | S12 |
| S4 | S6 | S2 | S10 | S19 | S16 |
| S4 | S6 | S2 | S10 | S13 | S11 |
| S4 | S10 | S20 | S3 | S11 | S13 |
| S4 | S2 | S6 | S20 | S3 | S18 |
| S4 | S3 | S1 | S7 | S16 | S3 |
| S4 | S20 | S10 | S1 | S7 | S11 |
| S4 | S11 | S7 | S6 | S20 | S15 |
| S4 | S11 | S7 | S6 | S12 | S11 |
| S4 | S7 | S11 | S2 | S18 | S20 |
| S4 | S4 | S4 | S4 | S5 | S13 |

TABLE C7

A list of compounds (substituents R1~R6)

| R₁ | R₂ | R₃ | R₄ | R₅ |
|---|---|---|---|---|
| S3 | S1 | S3 | S1 | S11 |
| S3 | S1 | S12 | S1 | S11 |
| S3 | S1 | S13 | S1 | S11 |
| S3 | S1 | S3 | S1 | S3 |
| S3 | S2 | S3 | S1 | S11 |
| S3 | S2 | S12 | S1 | S11 |
| S3 | S2 | S13 | S1 | S11 |
| S3 | S1 | S3 | S1 | S14 |
| S3 | S1 | S3 | S1 | S15 |
| S3 | S1 | S3 | S1 | S17 |
| S3 | S1 | S3 | S1 | S16 |
| S3 | S1 | S3 | S1 | S12 |
| S3 | S1 | S3 | S1 | S13 |
| S3 | S2 | S3 | S1 | S12 |
| S3 | S2 | S3 | S1 | S13 |
| S3 | S1 | S4 | S2 | S11 |
| S3 | S6 | S7 | S4 | S2 |
| S3 | S10 | S11 | S6 | S19 |
| S3 | S2 | S20 | S10 | S7 |
| S3 | S3 | S3 | S3 | S3 |
| S3 | S20 | S2 | S11 | S16 |
| S3 | S11 | S10 | S7 | S4 |
| S3 | S7 | S6 | S1 | S20 |
| S3 | S4 | S1 | S20 | S15 |
| S12 | S1 | S3 | S1 | S11 |
| S12 | S1 | S3 | S1 | S3 |
| S12 | S2 | S3 | S1 | S11 |
| S12 | S1 | S12 | S1 | S11 |
| S12 | S1 | S13 | S1 | S11 |
| S12 | S1 | S12 | S1 | S3 |
| S12 | S1 | S13 | S1 | S3 |
| S12 | S2 | S12 | S1 | S11 |
| S12 | S2 | S13 | S1 | S11 |
| S12 | S1 | S3 | S1 | S14 |
| S12 | S1 | S3 | S1 | S15 |

TABLE C7-continued

A list of compounds (substituents R1~R6)

| R₁ | R₂ | R₃ | R₄ | R₅ |
|---|---|---|---|---|
| S12 | S1 | S3 | S1 | S17 |
| S12 | S1 | S3 | S1 | S16 |
| S12 | S1 | S3 | S1 | S12 |
| S12 | S1 | S3 | S1 | S13 |
| S12 | S1 | S12 | S1 | S12 |
| S12 | S1 | S13 | S1 | S13 |

TABLE C8

A list of compounds (substituents R₁~R₅)

| R₁ | R₂ | R₃ | R₄ | R₅ |
|---|---|---|---|---|
| S12 | S1 | S12 | S1 | S13 |
| S12 | S1 | S13 | S1 | S12 |
| S12 | S1 | S4 | S2 | S11 |
| S12 | S6 | S7 | S4 | S2 |
| S12 | S10 | S11 | S6 | S19 |
| S12 | S2 | S20 | S10 | S7 |
| S12 | S3 | S3 | S3 | S3 |
| S12 | S20 | S2 | S11 | S16 |
| S12 | S11 | S10 | S7 | S4 |
| S12 | S7 | S6 | S1 | S20 |
| S12 | S4 | S1 | S20 | S15 |
| S13 | S1 | S3 | S1 | S11 |
| S13 | S1 | S3 | S1 | S3 |
| S13 | S2 | S3 | S1 | S11 |
| S13 | S1 | S12 | S1 | S11 |
| S13 | S1 | S12 | S1 | S3 |
| S13 | S1 | S13 | S1 | S11 |
| S13 | S1 | S13 | S1 | S3 |
| S13 | S2 | S13 | S1 | S11 |
| S13 | S1 | S3 | S1 | S14 |
| S13 | S1 | S3 | S1 | S15 |
| S13 | S1 | S3 | S1 | S17 |
| S13 | S1 | S3 | S1 | S16 |
| S13 | S1 | S3 | S1 | S12 |
| S13 | S1 | S3 | S1 | S13 |
| S13 | S1 | S12 | S1 | S12 |
| S13 | S1 | S12 | S1 | S13 |
| S13 | S1 | S13 | S1 | S12 |
| S13 | S1 | S13 | S1 | S13 |
| S13 | S1 | S4 | S2 | S11 |
| S13 | S6 | S7 | S4 | S2 |
| S13 | S10 | S11 | S6 | S19 |
| S13 | S2 | S20 | S10 | S7 |
| S13 | S3 | S3 | S3 | S3 |
| S13 | S20 | S2 | S11 | S16 |
| S13 | S11 | S10 | S7 | S4 |
| S13 | S7 | S6 | S1 | S20 |
| S13 | S4 | S1 | S20 | S15 |
| S11 | S1 | S2 | S20 | S7 |
| S11 | S6 | S20 | S7 | S3 |

TABLE C9

A list of compounds (substituents R₁~R₅)

| R₁ | R₂ | R₃ | R₄ | R₅ |
|---|---|---|---|---|
| S11 | S1 | S12 | S2 | S11 |
| S11 | S10 | S3 | S1 | S16 |
| S11 | S2 | S1 | S6 | S4 |
| S11 | S3 | S10 | S2 | S20 |
| S11 | S20 | S6 | S4 | S15 |
| S11 | S11 | S11 | S11 | S11 |
| S11 | S7 | S4 | S10 | S2 |
| S11 | S4 | S7 | S3 | S19 |
| S11 | S1 | S11 | S1 | S11 |

TABLE C9-continued

A list of compounds (substituents R₁~R₅)

| R₁ | R₂ | R₃ | R₄ | R₅ |
|---|---|---|---|---|
| S11 | S2 | S11 | S1 | S11 |
| S11 | S1 | S11 | S1 | S14 |
| S11 | S1 | S11 | S1 | S12 |
| S11 | S1 | S11 | S1 | S13 |
| S11 | S1 | S12 | S1 | S11 |
| S11 | S2 | S12 | S1 | S11 |
| S11 | S1 | S12 | S1 | S14 |
| S11 | S1 | S12 | S1 | S12 |
| S11 | S1 | S12 | S1 | S13 |
| S11 | S1 | S13 | S1 | S11 |
| S11 | S2 | S13 | S1 | S11 |
| S11 | S1 | S13 | S1 | S14 |
| S11 | S1 | S13 | S1 | S12 |
| S11 | S1 | S13 | S1 | S13 |
| S11 | S11 | S11 | S1 | S11 |
| S11 | S1 | S7 | S1 | S11 |
| S15 | S1 | S15 | S1 | S11 |
| S17 | S1 | S11 | S1 | S11 |
| S11 | S1 | S11 | S1 | S12 |
| S11 | S1 | S11 | S1 | S13 |
| S13 | S1 | S13 | S1 | S11 |
| S8 | S1 | S2 | S1 | S11 |
|  | S21 | S8 | S1 | S11 |
|  | S21 | S8 | S1 | S12 |
|  | S21 | S3 | S1 | S11 |
|  | S21 |  | S21 | S11 |
|  | S22 |  | S21 | S11 |
|  | S23 | S9 | S1 | S11 |
| S2 | S2 | S2 | S1 | S14 |
| S2 | S2 | S2 | S1 | S11 |
| S2 | S1 | S11 | S7 | S20 |
| S2 | S1 | S11 | S7 | S12 |

TABLE C10

A list of compounds (substituents R₁~R₅)

| R₁ | R₂ | R₃ | R₄ | R₅ |
|---|---|---|---|---|
| S2 | S6 | S4 | S1 | S15 |
| S2 | S10 | S7 | S20 | S4 |
| S2 | S2 | S2 | S2 | S2 |
| S2 | S3 | S20 | S4 | S19 |
| S2 | S3 | S20 | S4 | S13 |
| S2 | S3 | S13 | S4 | S13 |
| S2 | S20 | S3 | S6 | S11 |
| S2 | S11 | S1 | S10 | S3 |
| S2 | S7 | S10 | S3 | S16 |
| S2 | S4 | S6 | S11 | S7 |
| S20 | S1 | S7 | S10 | S16 |
| S20 | S6 | S11 | S3 | S7 |
| S20 | S10 | S4 | S11 | S3 |
| S20 | S2 | S3 | S7 | S15 |
| S20 | S3 | S2 | S1 | S4 |
| S20 | S20 | S20 | S20 | S20 |
| S20 | S20 | S20 | S20 | S12 |
| S20 | S11 | S6 | S2 | S19 |
| S20 | S11 | S6 | S2 | S13 |
| S20 | S7 | S1 | S4 | S11 |
| S20 | S4 | S10 | S6 | S2 |
| S1 | S1 | S1 | S1 | S19 |
| S1 | S1 | S1 | S1 | S13 |
| S1 | S6 | S10 | S20 | S11 |
| S1 | S10 | S6 | S7 | S2 |
| S1 | S2 | S11 | S4 | S16 |
| S1 | S3 | S4 | S6 | S7 |
| S1 | S20 | S7 | S2 | S3 |
| S1 | S11 | S2 | S3 | S15 |
| S1 | S7 | S20 | S11 | S4 |
| S1 | S4 | S3 | S10 | S20 |
| S1 | S4 | S3 | S10 | S12 |

TABLE C10-continued

A list of compounds (substituents R₁~R₅)

| R₁ | R₂ | R₃ | R₄ | R₅ |
|---|---|---|---|---|
| S6 | S1 | S10 | S4 | S3 |
| S6 | S6 | S6 | S6 | S16 |
| S6 | S10 | S1 | S2 | S7 |
| S6 | S2 | S4 | S3 | S20 |
| S6 | S2 | S4 | S3 | S12 |
| S6 | S3 | S7 | S11 | S15 |
| S6 | S20 | S11 | S10 | S4 |
| S6 | S11 | S20 | S1 | S2 |
| S6 | S7 | S3 | S20 | S19 |

TABLE C11

A list of compounds (substituents R₁~R₅)

| R₁ | R₂ | R₃ | R₄ | R₅ |
|---|---|---|---|---|
| S6 | S7 | S3 | S20 | S13 |
| S6 | S4 | S2 | S7 | S11 |
| S10 | S1 | S6 | S3 | S4 |
| S10 | S6 | S1 | S11 | S20 |
| S10 | S6 | S1 | S11 | S12 |
| S10 | S10 | S10 | S10 | S15 |
| S10 | S2 | S7 | S1 | S11 |
| S10 | S3 | S11 | S20 | S2 |
| S10 | S20 | S4 | S7 | S19 |
| S10 | S20 | S4 | S7 | S13 |
| S10 | S11 | S3 | S4 | S7 |
| S10 | S7 | S2 | S6 | S3 |
| S10 | S4 | S20 | S2 | S16 |
| S7 | S1 | S20 | S6 | S15 |
| S7 | S6 | S3 | S2 | S4 |
| S7 | S10 | S2 | S4 | S20 |
| S7 | S10 | S2 | S4 | S12 |
| S7 | S2 | S10 | S11 | S19 |
| S7 | S2 | S10 | S11 | S13 |
| S7 | S3 | S6 | S10 | S11 |
| S7 | S20 | S1 | S3 | S2 |
| S7 | S11 | S4 | S20 | S16 |
| S7 | S7 | S7 | S7 | S7 |
| S7 | S4 | S11 | S1 | S3 |
| S4 | S1 | S3 | S11 | S2 |
| S4 | S6 | S2 | S10 | S19 |
| S4 | S6 | S2 | S10 | S13 |
| S4 | S10 | S20 | S3 | S11 |
| S4 | S2 | S6 | S20 | S3 |
| S4 | S3 | S1 | S7 | S16 |
| S4 | S20 | S10 | S1 | S7 |
| S4 | S11 | S7 | S6 | S20 |
| S4 | S11 | S7 | S6 | S12 |
| S4 | S7 | S11 | S2 | S15 |
| S4 | S4 | S4 | S4 | S4 |

TABLE D1

Synthesis examples obtained in production examples 7~15

| Production Example | A compound having an active methylene | Reaction Temperature Reaction Time Yield (%) |
|---|---|---|
| 7 | 3-methyl-1-phenyl-1H-pyrazol-5(4H)-one | 20° C.<br>20 hours<br>32 |
| 8 | 1-(4-chlorophenyl)-3-methyl-1H-pyrazol-5(4H)-one | 20° C.<br>20 hours<br>67 |
| 9 | 1-(4-bromophenyl)-3-methyl-1H-pyrazol-5(4H)-one | 20° C.<br>20 hours<br>63 |
| 10 | 1-phenyl-3-(trifluoromethyl)-1H-pyrazol-5(4H)-one | 45° C.<br>3.5 hours<br>41 |
| 11 | 3-(furan-2-yl)-1-phenyl-1H-pyrazol-5(4H)-one | 20° C.<br>20 hours<br>37 |
| 12 | 1-phenyl-3-(thiophen-2-yl)-1H-pyrazol-5(4H)-one | 20° C.<br>20 hours<br>37 |
| 13 | 1,4-bis(5-oxo-1-phenyl-4,5-dihydro-1H-pyrazol-3-yl)benzene | 45° C.<br>8 hours<br>30 |
| 14 | 2,2-dimethyl-1,3-dioxane-4,6-dione | 20° C.<br>20 hours<br>55 |
| 15 | 1,3-diethyl-2-thioxodihydropyrimidine-4,6(1H,5H)-dione | 20° C.<br>30 minute<br>10 |

TABLE D2

Compounds obtained in production examples 7–15

| Production Example | Compound | Name of compound |
|---|---|---|
| 7 | Formula(8) | 2,6-Di-tert-butyl-4-(3-methyl-1-phenyl-5-oxo-4-pyrazolilidene)-2,5-cyclohexadiene-1-one |
| 8 | Formula(9) | 2,6-Di-tert-butyl-4-[3-methyl-1-(4-chlorophenyl)-5-oxo-4-pyrazolilidene]-2,5-cyclohexadiene-1-one |
| 9 | Formula(10) | 2,6-Di-tert-butyt-4-[3-methyl-1-(4-bromophenyl)-5-oxo-4-pyrazolilidene]-2,5-cyclohexadiene-1-one |
| 10 | Formula(11) | 2,6-Di-tert-butyl-4-(3-trifluoromethyl-1-phenyl-5-oxo-4-pyrazolilidene]-2,5-cyclohexadiene-1-one |
| 11 | Formula(12) | 2,6-Di-tert-butyt-4-[3-(2-furanyl)-1-phenyl-5-oxo-4-pyrazolilidene]-2,5-cyclohexadiene-1-one |

TABLE D3

Compounds obtained in Production Examples

| Production Example | Compound | Name of compound |
|---|---|---|
| 12 | Formula(13) | 2,6-Di-tert-butyl-4-[3-(2-thienyl)-1-phenyl-5-oxo-4-pyrazolilidene]-2,5-cyclohexadiene-1-one |
| 13 | Formula(14) | 1,3-Bis-3-(2,6-di-tert-butyl-1-oxo-2,5-cyclohexadiene-4-ylidene)-1-phenyl-5-oxo-4-pyrazolylbenzene |
| 14 | Formula(15) | 2,6-Di-tert-butyl-4-(2,2-dimethyl-1,3-dioxane-4,6-dione-5-ylidene)-2,5-cyclohexadiene-1-one |
| 15 | Formula(16) | 2,6-Di-tert-butyl-4-(1,3-diethyl-2-thioxo-4,6-dioxo-5-pyrimidinylidene)-2,5-cyclohexadiene-1-one |

TABLE E

The melting point and the results of the element analysis for each compounds of the formulae (7)~(16)

| | | Results of the element analysis | |
|---|---|---|---|
| Compound | Melting Point(° C.) | Calculated Value(%) | Observed Valve(%) |
| (7) | 135.6~136.4 | C: 72.58, H: 8.33, N: 8.91 | C: 72.32, H: 8.45, N: 8.71 |
| (8) | 165.7~166.0 | C: 76.56, H: 7.50, N: 7.44 | C: 76.66, H: 7.67, N: 7.70 |
| (9) | 214.4~215.1 | C: 70.15, H: 6.62, N: 6.82 | C: 70.35, H: 6.48, N: 6.61 |
| (10) | 212.6~213.3 | C: 63.30, H: 5.98, N: 6.15 | C: 63.41, H: 5.88, N: 6.03 |
| (11) | 159.0~159.5 | C: 66.96, H: 5.85, N: 6.51 | C: 67.11, H: 5.78, N: 6.34 |

TABLE E-continued

The melting point and the results of the element analysis for each compounds of the formulae (7)~(16)

| | | Results of the element analysis | |
|---|---|---|---|
| Compound | Melting Point(° C.) | Calculated Value(%) | Observed Valve(%) |
| (12) | 200.5~201.0 | C: 75.68, H: 6.59, N: 6.54 | C: 75.47, H: 6.79, N: 6.83 |
| (13) | 227.5~228.1 | C: 72.94, H: 6.35, N: 6.30 | C: 72.82, H: 6.21, N: 6.45 |
| (14) | 316.9~317.5 (Decomposition) | C: 78.17, H: 6.81, N: 7.01 | C: 78.23, H: 6.63, N: 6.88 |
| (15) | 153.8~154.5 | C: 69.34, H: 7.56 | C: 69.27, H: 7.66 |
| (16) | 127.3~128.2 | C: 65.64, H: 7.51, N: 6.96 | C: 65.71, H: 7.39, N: 6.81 |

TABLE F

Measurement results of Electron Mobilites for Example and Comparative Example

| Example | Electron Mobilites(cm$^2$/V · sec) |
|---|---|
| Example 1 | $2 \times 10^{-8}$ |
| Example 2 | $6 \times 10^{-8}$ |
| Example 3 | $1 \times 10^{-8}$ |
| Example 4 | $1 \times 10^{-8}$ |
| Example 5 | $6 \times 10^{-8}$ |
| Example 6 | $3 \times 10^{-8}$ |
| Example 7 | $6 \times 10^{-8}$ |
| Example 8 | $1 \times 10^{-8}$ |
| Example 9 | $1 \times 10^{-8}$ |
| Example 10 | $4 \times 10^{-8}$ |
| Comparative Example 1 | $1 \times 10^{-9}$ |

TABLE G

The amount of luminescence of the organic electro luminescence Elements obtained in Application Examples 1~10

| Example | The amount of luminescence (cd/m$^2$) |
|---|---|
| Application Example 1 | 100 |
| Application Example 2 | 120 |
| Application Example 3 | 60 |
| Application Example 4 | 60 |
| Application Example 5 | 110 |
| Application Example 6 | 90 |
| Application Example 7 | 100 |
| Application Example 8 | 80 |
| Application Example 9 | 80 |
| Application Example 10 | 100 |

TABLE H

Electrical Potential and Half-decay exposure for Application Examples 11~20 and Comparative Example 2

| Example | Electrical Potential (V) | Half-decay exposure (Lux · sec) |
|---|---|---|
| Application Example 11 | 640 | 3.4 |
| Application Example 12 | 670 | 2.9 |
| Application Example 13 | 620 | 4.8 |
| Application Example 14 | 630 | 4.7 |
| Application Example 15 | 660 | 3.3 |
| Application Example 16 | 650 | 4.0 |
| Application Example 17 | 650 | 3.6 |
| Application Example 18 | 630 | 4.2 |
| Application Example 19 | 620 | 4.3 |
| Application Example 20 | 640 | 3.9 |
| Comparative Example 2 | 580 | 6.1 |

TABLE I

Electrical Potential and Half-decay exposure for Application Examples 21~30 and Comparative Example 3

| Example | Electrical Potential (V) | Half-decay exposure (Lux · sec) |
|---|---|---|
| Application Example 21 | 580 | 1.8 |
| Application Example 22 | 590 | 1.4 |
| Application Example 23 | 540 | 2.3 |
| Application Example 24 | 560 | 2.0 |
| Application Example 25 | 570 | 1.5 |
| Application Example 26 | 550 | 1.9 |
| Application Example 27 | 570 | 1.6 |
| Application Example 28 | 550 | 1.9 |
| Application Example 29 | 580 | 2.1 |
| Application Example 30 | 560 | 1.7 |
| Comparative Example 3 | 550 | 2.8 |

TABLE J

Electrical Potential and Half-decay exposure for Application Examples 31~40 and Comparative Example 4

| Example | Electrical Potential (V) | Half-decay exposure (Lux · sec) |
|---|---|---|
| Application Example 31 | 530 | 2.0 |
| Application Example 32 | 550 | 1.8 |
| Application Example 33 | 520 | 2.3 |
| Application Example 34 | 550 | 2.2 |
| Application Example 35 | 570 | 1.7 |
| Application Example 36 | 540 | 1.8 |
| Application Example 37 | 530 | 1.9 |
| Application Example 38 | 540 | 2.2 |
| Application Example 39 | 550 | 2.1 |
| Application Example 40 | 560 | 2.0 |
| Comparative Example 4 | 540 | 3.0 |

TABLE K

Electrical Potential and Half-decay exposure for Application Example 41~50 and Comparative Example 5

| Example | Electrical Potential (V) | Half-decay exposure (Lux · sec) |
|---|---|---|
| Application Example 41 | −600 | 1.5 |
| Application Example 42 | −590 | 1.2 |
| Application Example 43 | −610 | 2.0 |
| Application Example 44 | −600 | 2.1 |
| Application Example 45 | −580 | 1.3 |
| Application Example 46 | −600 | 1.6 |
| Application Example 47 | −590 | 1.2 |
| Application Example 48 | −610 | 1.9 |
| Application Example 49 | −600 | 2.0 |

TABLE K-continued

Electrical Potential and Half-decay exposure for Application Example 41~50 and Comparative Example 5

| Example | Electrical Potential (V) | Half-decay exposure (Lux · sec) |
| --- | --- | --- |
| Application Example 50 | −570 | 1.8 |
| Comparative Example 5 | −620 | 3.5 |

TABLE L1

Synthesis examples obtained in production examples 23~31

| Production Example | A compound having an active methylene | Reaction Temperature Reaction Time Yield (%) |
| --- | --- | --- |
| 23 | [structure: 1-phenyl-3-(4-trifluoromethylphenyl)-pyrazol-5-one] | 25<br>20 hours<br>49 |
| 24 | [structure: 1-(1-naphthyl)-3-(2-furyl)-pyrazol-5-one] | 25<br>16 hours<br>20 |
| 25 | [structure: 1-(benzothiazol-2-yl)-3-methyl-pyrazol-5-one] | 20<br>20 hours<br>64 |
| 26 | [structure: 1-phenyl-3-n-propyl-pyrazol-5-one] | 25<br>20 hours<br>50 |
| 27 | [structure: 1-t-Bu-3-(2-thienyl)-pyrazol-5-one] | 50<br>6 hours<br>5 |
| 28 | [structure: 1-t-Bu-3-(2-furyl)-pyrazol-5-one] | 50<br>6 hours<br>2 |
| 29 | [structure: 1-t-Bu-4-trifluoromethyl-pyrazol-5-one] | 70<br>3 hours<br>9 |

TABLE L1-continued

Synthesis examples obtained in production examples 23~31

| Production Example | A compound having an active methylene | Reaction Temperature Reaction Time Yield (%) |
|---|---|---|
| 30 | (pyrazolone with i-Pr and N-phenyl) | 25 / 20 hours / 44 |
| 31 | (pyrazolone with n-Bu and N-phenyl) | 25 / 20 hours / 39 |

TABLE L2

Synthesis examples obtained in production examples 32~37

| Production Example | A compound having an active methylene | Reaction Temperature Reaction Time Yield (%) |
|---|---|---|
| 32 | (pyrazolone with H₃C and N-(4-Me-phenyl)) | 25 / 20 hours / 30 |
| 33 | (pyrazolone with n-Pr and N-(4-Me-phenyl)) | 25 / 20 hours / 49 |
| 34 | (pyrazolone with 2-thienyl and N-(4-Me-phenyl)) | 25 / 20 hours / 28 |
| 35 | (pyrazolone with 2-furyl and N-(4-Me-phenyl)) | 25 / 20 hours / 38 |
| 36 | (pyrazolone with 2-furyl and N-(4-i-Pr-phenyl)) | 25 / 20 hours / 41 |
| 37 | (pyrazolone with n-Pr and N-(4-i-Pr-phenyl)) | 25 / 20 hours / 36 |

TABLE M1

Compounds obtained in production examples 23~27

| Production Example | Compound | | Name of compound |
|---|---|---|---|
| 23 | Formula (29) | 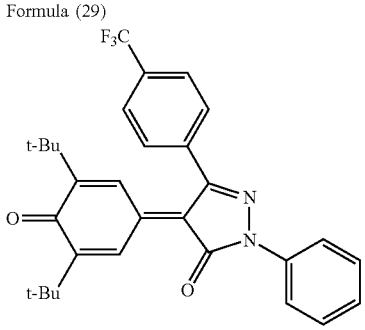 | 2,6-Di-tert-butyl-4-[1-phenyl-3-(4-trifluoro methylphenyl)-5-oxo-4-pyrazolilidene]-2,5-cyclohexadiene-1-one |
| 24 | Formula (30) | 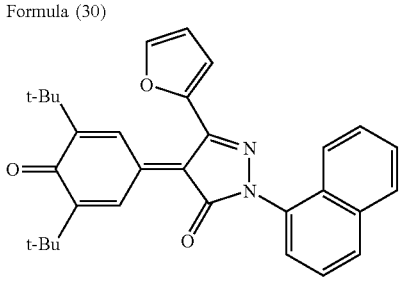 | 2,6-Di-tert-butyl-4-[3-(2-furanyl)-1-(1-naphthyl)-5-oxo-4-pyrazolilidene]-2,5-cyclohexadiene-1-one |
| 25 | Formula (31) | 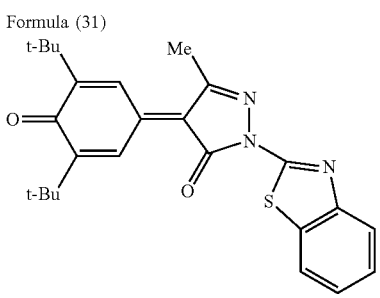 | 2,6-Di-tert-butyl-4-[1-(2-benzothiazolyl)-3-methyl-5-oxo-4-pyrazolilidene]-2,5-cyclohexadiene-1-one |
| 26 | Formula (32) | 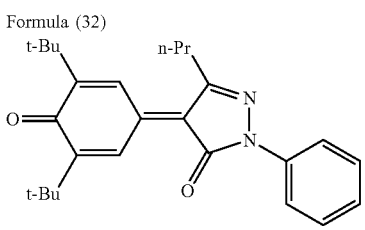 | 2,6-Di-tert-butyl-4-(1-phenyl-3-propyl-5-oxo-4-pyrazolilidene)-2,5-cyclohexadiene-1-one |
| 27 | Formula (33) | 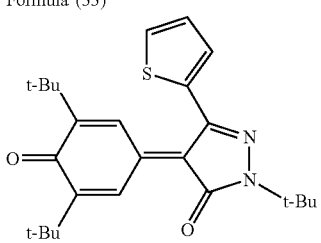 | 2,6-Di-tert-butyl-4-[1-tert-butyl-3-(2-thienyl)-5-oxo-4-pyrazolilidene]-2,5-cyclohexadiene-1-one |

TABLE M2

Compounds obtained in production examples 28~33

| Production Example | Compound | | Name of compound |
|---|---|---|---|
| 28 | Formula (34) | 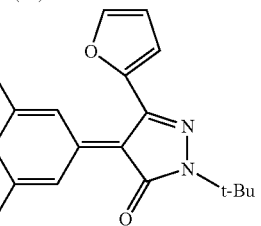 | 2,6-Di-tert-butyl-4-[1-tert-butyl-3-(2-furanyl)-5-oxo-4-pyrazolilidene]-2,5-cyclohexadiene-1-one |
| 29 | Formula (35) | 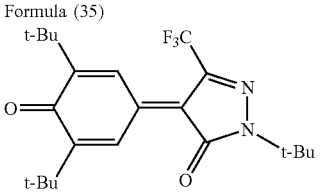 | 2,6-Di-tert-butyl-4-(1-tert-butyl-3-trifluoromethyl-5-oxo-4-pyrazolilidene)-2,5-cyclohexadiene-1-one |
| 30 | Formula (36) | 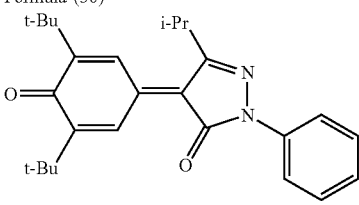 | 2,6-Di-tert-butyl-4-(3-iso-propyl-1-phenyl-5-oxo-4-pyrazolilidene)-2,5-cyclohexadiene-1-one |
| 31 | Formula (37) | 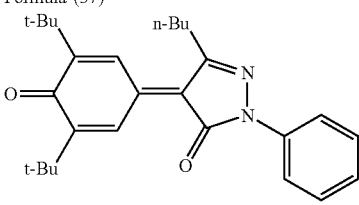 | 2,6-Di-tert-butyl-4-(3-butyl-1-phenyl-5-oxo-4-pyrazolilidene)-2,5-cyclohexadiene-1-one |
| 32 | Formula (38) | 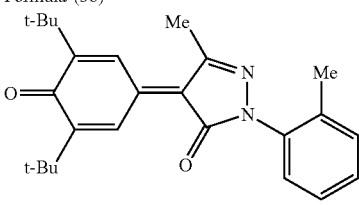 | 2,6-Di-tert-butyl-4-[3-methyl-1-(2-methylphenyl)-5-oxo-4-pyrazolilidene]-2,5-cyclohexadiene-1-one |
| 33 | Formula (39) | 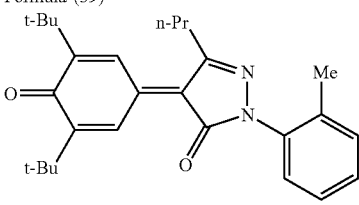 | 2,6-Di-tert-butyl-4-[1-(2-methylphenyl)-3-propyl-5-oxo-4-pyrazolilidene]-2,5-cyclohexadiene-1-one |

TABLE M3

Compounds obtained in production examples 34~37

| Production Example | Compound | Name of compound |
|---|---|---|
| 34 | Formula (40) | 2,6-Di-tert-butyl-4-[1-(2-methylphenyl)-3-(2-thienyl)-5-oxo-4-pyrazolilidene]-2,5-cyclohexadiene-1-one |
| 35 | Formula (41) | 2,6-Di-tert-butyl-4-[3-(2-furanyl)-1-(2-methylphenyl)-5-oxo-4-pyrazolilidene]-2,5-cyclohexadiene-1-one |
| 36 | Formula (42) | 2,6-Di-tert-butyl-4-[3-(2-furanyl)-1-(4-iso-propylphenyl)-5-oxo-4-pyrazolilidene]-2,5-cyclohexadiene-1-one |
| 37 | Formula (43) | 2,6-Di-tert-butyl-4-[3-propyl-1-(4-iso-propylphenyl)-5-oxo-4-pyrazolilidene]-2,5-cyclohexadiene-1-one |

TABLE N

The melting point and the results of the element analysis for each compounds of the formulae (29)~(43)

| Compound | Melting Point (° C.) | Calculated Value (%) | Observed Value (%) |
|---|---|---|---|
| (29) | 261.0~262.9 | C: 71.13, H: 5.77, N: 5.53 | C: 71.34, H: 5.42, N: 5.32 |
| (30) | 175.0~175.5 | C: 77.80, H: 6.32, N: 5.85 | C: 77.67, H: 6.12, N: 5.65 |
| (31) | 260.9~261.7 | C: 69.26, H: 6.28, N: 9.69 | C: 69.07, H: 6.48, N: 9.71 |
| (32) | 155.4~156.1 | C: 77.19, H: 7.97, N: 6.92 | C: 77.23, H: 7.82, N: 6.67 |
| (33) | 179.9~180.6 | C: 70.72, H: 7.60, N: 6.60 | C: 70.58, H: 7.48, N: 6.55 |
| (34) | 153.7~154.4 | C: 73.50, H: 7.90, N: 6.86 | C: 73.24, H: 7.95, N: 6.77 |
| (35) | 130.7~131.4 | C: 64.37, H: 7.12, N: 6.82 | C: 64.49, H: 7.02, N: 6.93 |
| (36) | 166.4~167.1 | C: 77.19, H: 7.97, N: 6.92 | C: 77.35, H: 7.86, N: 6.83 |

TABLE N-continued

The melting point and the results of the element analysis for each compounds of the formulae (29)~(43)

| Compound | Melting Point (° C.) | Results of the element analysis | |
|---|---|---|---|
| | | Calculated Value (%) | Observed Value (%) |
| (37) | 149.6~150.2 | C: 77.48, H: 8.19, N: 6.69 | C: 77.63, H: 8.35, N: 6.65 |
| (38) | 68.0~70.0 | C: 76.89, H: 7.74, N: 7.17 | C: 76.65, H: 7.57, N: 7.01 |
| (39) | 87.1~87.9 | C: 77.48, H: 8.19, N: 6.69 | C: 77.62, H: 8.34, N: 6.82 |
| (40) | 170.0~170.7 | C: 73.33, H: 6.59, N: 6.11 | C: 73.37, H: 6.67, N: 6.34 |
| (41) | 154.0~154.5 | C: 75.99, H: 6.83, N: 6.33 | C: 75.82, H: 6.97, N: 6.51 |
| (42) | 157.8~158.5 | C: 76.57, H: 7.28, N: 5.95 | C: 76.77, H: 7.12, N: 6.01 |
| (43) | 75.0~78.0 | C: 77.99, H: 8.58, N: 6.27 | C: 78.12, H: 8.45, N: 6.34 |

TABLE O

Measurement results of Electron mobilities for example 11~25 and Comparative example

| Example | Electron mobilities(cm$^2$/V · sec) |
|---|---|
| Example 11 | $1 \times 10^{-8}$ |
| Example 12 | $3 \times 10^{-8}$ |
| Example 13 | $3 \times 10^{-8}$ |
| Example 14 | $1 \times 10^{-7}$ |
| Example 15 | $5 \times 10^{-8}$ |
| Example 16 | $2 \times 10^{-7}$ |
| Example 17 | $1 \times 10^{-8}$ |
| Example 18 | $1 \times 10^{-7}$ |
| Example 19 | $1 \times 10^{-7}$ |
| Example 20 | $8 \times 10^{-8}$ |
| Example 21 | $6 \times 10^{-8}$ |
| Example 22 | $2 \times 10^{-7}$ |
| Example 23 | $2 \times 10^{-7}$ |
| Example 24 | $4 \times 10^{-8}$ |
| Example 25 | $2 \times 10^{-7}$ |
| Comparative Example 1 | $1 \times 10^{-9}$ |

TABLE P

The amount of luminescence of the organic electro luminescence elements obtained in Application Examples 51~65

| Example | The amount of luminescence (cd/m$^2$) |
|---|---|
| Application example 51 | 60 |
| Application example 52 | 100 |
| Application example 53 | 90 |
| Application example 54 | 140 |
| Application example 55 | 110 |
| Application example 56 | 150 |
| Application example 57 | 80 |
| Application example 58 | 130 |
| Application example 59 | 150 |
| Application example 60 | 130 |
| Application example 61 | 120 |
| Application example 62 | 130 |
| Application example 63 | 120 |
| Application example 64 | 70 |
| Application example 65 | 130 |

TABLE Q

Electrical Potential and half-decay exposure for Application Examples 66~80 and Comparative Examples 2

| Example | Electrical Potential (V) | Half-decay exposure (Lux · sec) |
|---|---|---|
| Application example 66 | 670 | 4.5 |
| Application example 67 | 640 | 4.6 |
| Application example 68 | 630 | 4.3 |
| Application example 69 | 650 | 2.4 |
| Application example 70 | 640 | 3.8 |
| Application example 71 | 620 | 2.3 |
| Application example 72 | 660 | 4.7 |
| Application example 73 | 650 | 2.7 |
| Application example 74 | 670 | 2.6 |
| Application example 75 | 680 | 2.9 |
| Application example 76 | 630 | 3.9 |
| Application example 77 | 640 | 3.7 |
| Application example 78 | 670 | 3.5 |
| Application example 79 | 660 | 3.9 |
| Application example 80 | 640 | 2.8 |
| Comparative Example 2 | 580 | 6.1 |

TABLE R

Electrical Potential and half-decay exposure for Application Examples 81~95 and Comparative Examples 3

| Example | Electrical Potential (V) | Half-decay exposure (Lux · sec) |
|---|---|---|
| Application Example 81 | 600 | 2.4 |
| Application Example 82 | 570 | 2.3 |
| Application Example 83 | 560 | 2.2 |
| Application Example 84 | 570 | 1.3 |
| Application Example 85 | 560 | 1.6 |
| Application Example 86 | 590 | 1.2 |
| Application Example 87 | 570 | 2.1 |
| Application Example 88 | 580 | 1.4 |
| Application Example 89 | 570 | 1.3 |
| Application Example 90 | 590 | 1.5 |
| Application Example 91 | 600 | 1.9 |
| Application Example 92 | 560 | 1.7 |
| Application Example 93 | 580 | 1.9 |
| Application Example 94 | 580 | 2.3 |
| Application Example 95 | 570 | 1.6 |
| Comparative Example 3 | 550 | 2.8 |

TABLE S

Electrical Potential and Half-decay exposure for Application Example 96~110 and Comparative Example 4

| Example | Electrical Potential (V) | Half-decay exposure (Lux · sec) |
|---|---|---|
| Application Example 96 | 560 | 2.2 |
| Application Example 97 | 540 | 2.1 |
| Application Example 98 | 530 | 2.2 |
| Application Example 99 | 550 | 1.6 |
| Application Example 100 | 530 | 2.2 |
| Application Example 101 | 540 | 1.5 |
| Application Example 102 | 520 | 2.3 |
| Application Example 103 | 550 | 1.7 |
| Application Example 104 | 530 | 1.6 |
| Application Example 105 | 570 | 1.8 |
| Application Example 106 | 560 | 2.0 |
| Application Example 107 | 530 | 1.9 |
| Application Example 108 | 570 | 1.9 |
| Application Example 109 | 560 | 2.2 |
| Application Example 110 | 540 | 1.6 |
| Comparative Example 4 | 540 | 3.0 |

TABLE T

Electrical Potential and Half-decay exposure for Application Example 111~125 and Comparative Example 5

| Example | Electrical Potential (V) | Half-decay exposure (Lux · sec) |
|---|---|---|
| Application Example 111 | −610 | 2.1 |
| Application Example 112 | −580 | 1.9 |
| Application Example 113 | −580 | 1.7 |
| Application Example 114 | −590 | 1.1 |
| Application Example 115 | −570 | 1.6 |
| Application Example 116 | −580 | 1.0 |
| Application Example 117 | −560 | 2.2 |
| Application Example 118 | −600 | 1.2 |
| Application Example 119 | −580 | 1.1 |
| Application Example 120 | −620 | 1.3 |
| Application Example 121 | −610 | 1.7 |
| Application Example 122 | −580 | 1.5 |
| Application Example 123 | −600 | 1.4 |
| Application Example 124 | −590 | 1.9 |
| Application Example 125 | −570 | 1.3 |
| Comparative Example 5 | −620 | 3.5 |

TABLE U1

Synthesis examples obtained in production 38~46

| Production Example | A compound having an active methylene | Reaction Temperature Reaction Time Yield (%) |
|---|---|---|
| 38 | 3-methyl-1-(4-methylphenyl)-pyrazolin-5-one | 25° C. 20 hours 53 |
| 39 | 1-(4-methylphenyl)-3-n-propyl-pyrazolin-5-one | 25° C. 20 hours 34 |
| 40 | 1-(2-chlorophenyl)-3-methyl-pyrazolin-5-one | 25° C. 20 hours 31 |
| 41 | 1-(2-chlorophenyl)-3-n-propyl-pyrazolin-5-one | 25° C. 20 hours 36 |
| 42 | 1-(2-chlorophenyl)-3-(2-thienyl)-pyrazolin-5-one | 25° C. 20 hours 29 |
| 43 | 1-(2-chlorophenyl)-3-(2-furyl)-pyrazolin-5-one | 25° C. 20 hours 32 |
| 44 | 3-methyl-1-(2-pyridyl)-pyrazolin-5-one | 25° C. 20 hours 21 |
| 45 | 3-n-propyl-1-(2-pyridyl)-pyrazolin-5-one | 25° C. 20 hours 25 |
| 46 | 3-(2-furyl)-1-(2-pyridyl)-pyrazolin-5-one | 25° C. 20 hours 31 |

TABLE U2

Synthesis examples obtained in production 47~53

| Production Example | A compound having an active methylene | Reaction Temperature Reaction Time Yield (%) |
|---|---|---|
| 47 | 1-(3-chlorophenyl)-3-methyl-pyrazolin-5-one | 20° C. 3 hours 41 |

TABLE U2-continued

Synthesis examples obtained in production 47~53

| Production Example | A compound having an active methylene | Reaction Temperature Reaction Time Yield (%) |
|---|---|---|
| 48 | (pyrazolone with n-Pr and 3-chlorophenyl) | 20° C. 1.5 hours 53 |
| 49 | (pyrazolone with thienyl and 3-chlorophenyl) | 20° C. 20 hours 30 |
| 50 | (pyrazolone with n-Pr and 2,5-dichlorophenyl) | 20° C. 20 hours 32 |
| 51 | (pyrazolone with thienyl and 2,5-dichlorophenyl) | 20° C. 20 hours 18 |
| 52 | (1,2-diphenylpyrazolidine-3,5-dione) | 20° C. 20 hours 57 |
| 53 | (1,2-dimethylpyrazolidine-3,5-dione) | 20° C. 20 hours 36 |

TABLE V1

Compounds obtained in production 38~43

| Production Example | Compound | Name of compound |
|---|---|---|
| 38 | Formula (45) | 2,6-Di-tert-butyl-4-[1-(4-methylphenyl)-3-methyl-5-oxo-4-pyrazolilidene]-2,5-cyclohexadien-1-one |
| 39 | Formula (46) | 2,6-Di-tert-butyl-4-[3-(4-methylphenyl)-1-propyl-5-oxo-4-pyrazolilidene]-2,5-cyclohexadien-1-one |
| 40 | Formula (47) | 2,6-Di-tert-butyl-4-[1-(2-chlorophenyl)-3-methyl-5-oxo-4-pyrazolilidene]-2,5-cyclohexadien-1-one |

TABLE V1-continued

Compounds obtained in production 38~43

| Production Example | Compound | Name of compound |
|---|---|---|
| 41 | Formula (48) 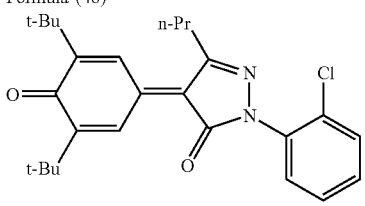 | 2,6-Di-tert-butyl-4-[1-(2-chlorophenyl)-3-propyl-5-oxo-4-pyrazolilidene]-2,5-cyclohexadiene-1-one |
| 42 | Formula (49) 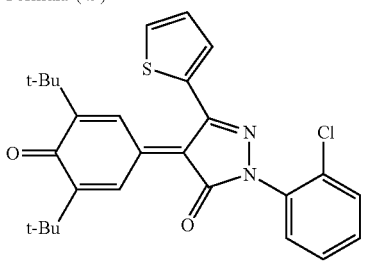 | 2,6-Di-tert-butyl-4-[1-(2-chlorophenyl)-3-(2-thienyl)-5-oxo-4-pyrazolilidene]-2,5-cyclohexadiene-1-one |
| 43 | Formula (50) 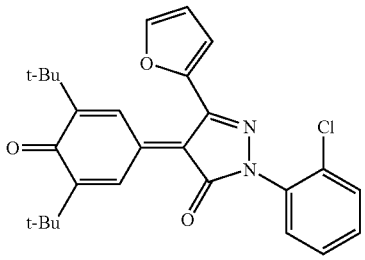 | 2,6-Di-tert-butyl-4-[1-(2-chlorophenyl)-3-(2-furanyl)-5-oxo-4-pyrazolilidene]-2,5-cyclohexadiene-1-one |

TABLE V2

Compounds obtained in production 44~49

| Production Example | Compound | Name of compound |
|---|---|---|
| 44 | Formula (51) 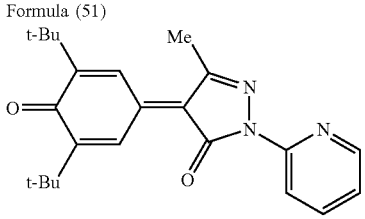 | 2,6-Di-tert-butyl-4-[3-methyl-1-(2-pyridinyl)-5-oxo-4-pyrazolilidene]-2,5-cyclohexadiene-1-one |
| 45 | Formula (52) 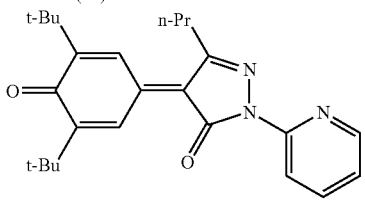 | 2,6-Di-tert-butyl-4-[3-propyl-1-(2-pyridinyl)-5-oxo-4-pyrazolilidene]-2,5-cyclohexadiene-1-one |

TABLE V2-continued

Compounds obtained in production 44~49

| Production Example | Compound | Name of compound |
|---|---|---|
| 46 | Formula (53) | 2,6-Di-tert-butyl-4-[3-(2-furanyl)-1-(2-pyridinyl)-5-oxo-4-pyrazolilidene]-2,5-cyclohexadiene-1-one |
| 47 | Formula (54) | 2,6-Di-tert-butyl-4-[1-(3-chlorophenyl)-3-methyl-5-oxo-4-pyrazolilidene]-2,5-cyclohexadiene-1-one |
| 48 | Formula (55) | 2,6-Di-tert-butyl-4-[1-(3-chlorophenyl)-3-propyl-5-oxo-4-pyrazolilidene]-2,5-cyclohexadiene-1-one |
| 49 | Formula (56) | 2,6-Di-tert-butyl-4-[1-(3-chlorophenyl)-3-(2-thienyl)-5-oxo-4-pyrazolilidene]-2,5-cyclohexadiene-1-one |

TABLE V3

Compounds obtained in production 50~53

| Production Example | Compound | Name of compound |
|---|---|---|
| 50 | Formula (57) | 2,6-Di-tert-butyl-4-[1-(2,5-dichlorophenyl)-3-propyl-5-oxo-4-pyrazolilidene]-2,5-cyclohexadiene-1-one |

TABLE V3-continued

Compounds obtained in production 50~53

| Production Example | Compound | | Name of compound |
|---|---|---|---|
| 51 | Formula (58) | 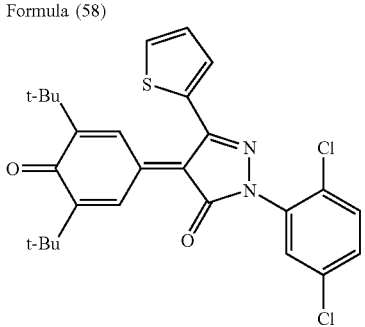 | 2,6-Di-tert-butyl-4-[1-(2,5-dichlorophenyl)-3-(2-thienyl)-5-oxo-4-pyrazolilidene]-2,5-cyclohexadiene-1-one |
| 52 | Formula (59) | 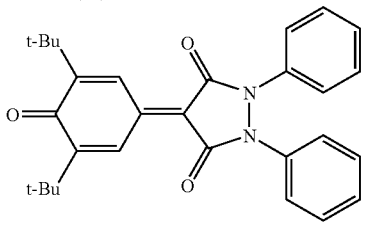 | 2,6-Di-tert-butyl-4-(1,2-diphenyl-3,5-dioxo-4-pyrazolilidene)-2,5-cyclohexadiene-1-one |
| 53 | Formula (60) | 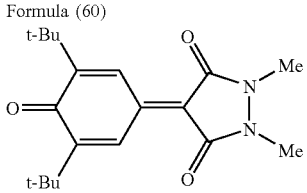 | 2,6-Di-tert-butyl-4-(1,2-dimethyl-3,5-dioxo-4-pyrazolilidene)-2,5-cyclohexadiene-1-one |

TABLE W

The melting point and the results of the element analysis for each compounds of the formulae(45)~(60)

| Compound | Melting Point (° C.) | Results of the element analysis | |
|---|---|---|---|
| | | Calculated Value (%) | Observed Value (%) |
| (45) | 188.6~189.2 | C: 76.89, H: 7.74, N: 7.17 | C: 76.68, H: 7.45, N: 7.22 |
| (46) | 154.6~155.0 | C: 77.48, H: 8.19, N: 6.69 | C: 77.67, H: 8.01, N: 6.59 |
| (47) | 71.7~72.4 | C: 70.15, H: 6.62, N: 6.82 | C: 70.22, H: 6.72, N: 6.70 |
| (48) | 116.8~117.5 | C: 71.14, H: 7.12, N: 6.38 | C: 71.18, H: 7.34, N: 6.48 |
| (49) | 179.0~179.3 | C: 67.70, H: 5.68, N: 5.85 | C: 67.56, H: 5.60, N: 5.92 |
| (50) | 178.8~179.3 | C: 70.05, H: 5.88, N: 6.05 | C: 70.20, H: 5.81, N: 6.00 |
| (51) | 193.2~193.8 | C: 73.18, H: 7.21, N: 11.13 | C: 73.30, H: 7.24, N: 11.24 |
| (52) | 138.4~139.1 | C: 74.04, H: 7.70, N: 10.36 | C: 74.24, H: 7.81, N: 10.26 |
| (53) | 222.5~222.9 | C: 72.71, H: 6.34, N: 9.78 | C: 72.62, H: 6.15, N: 9.82 |
| (54) | 162.9~163.5 | C: 70.15, H: 6.62, N: 6.82 | C: 70.31, H: 6.32, N: 6.68 |
| (55) | 165.8~166.3 | C: 71.14, H: 7.12, N: 6.38 | C: 71.26, H: 7.03, N: 6.42 |
| (56) | 179.7~181.2 | C: 67.70, H: 5.68, N: 5.85 | C: 67.81, H: 5.61, N: 5.78 |
| (57) | 131.5~132.1 | C: 65.96, H: 6.39, N: 5.92 | C: 65.83, H: 6.49, N: 5.81 |
| (58) | 137.6~138.9 | C: 63.16, H: 5.10, N: 5.46 | C: 63.33, H: 5.21, N: 5.34 |
| (59) | 174.8~175.8 | C: 76.63, H: 6.65, N: 6.16 | C: 76.68, H: 6.56, N: 6.19 |
| (60) | 162.8~164.0 | C: 69.06, H: 7.93, N: 8.48 | C: 69.15, H: 7.82, N: 8.28 |

TABLE X

Measurement results of electron mobilities for example 26~41 and Comparative examples

| Example | Electron Mobilities (cm$^2$/V · sec) |
|---|---|
| Example 26 | $1 \times 10^{-7}$ |
| Example 27 | $1 \times 10^{-7}$ |
| Example 28 | $4 \times 10^{-8}$ |
| Example 29 | $7 \times 10^{-7}$ |
| Example 30 | $1 \times 10^{-7}$ |
| Example 31 | $2 \times 10^{-7}$ |
| Example 32 | $2 \times 10^{-7}$ |
| Example 33 | $1 \times 10^{-7}$ |
| Example 34 | $8 \times 10^{-8}$ |
| Example 35 | $2 \times 10^{-8}$ |
| Example 36 | $4 \times 10^{-8}$ |
| Example 37 | $4 \times 10^{-8}$ |
| Example 38 | $2 \times 10^{-8}$ |
| Example 39 | $1 \times 10^{-7}$ |
| Example 40 | $7 \times 10^{-8}$ |
| Example 41 | $6 \times 10^{-8}$ |
| Comparative examples 1 | $1 \times 10^{-9}$ |

TABLE Y

The amount of luminescence of the organic electro luminescence elements obtained in Application Examples 126~141

| Example | The amount of luminescence (cd/m$^2$) |
|---|---|
| Application Example 126 | 100 |
| Application Example 127 | 110 |
| Application Example 128 | 70 |
| Application Example 129 | 150 |
| Application Example 130 | 120 |
| Application Example 131 | 120 |
| Application Example 132 | 90 |
| Application Example 133 | 120 |
| Application Example 134 | 80 |
| Application Example 135 | 70 |
| Application Example 136 | 90 |
| Application Example 137 | 80 |
| Application Example 138 | 60 |
| Application Example 139 | 120 |
| Application Example 140 | 90 |
| Application Example 141 | 100 |

TABLE Z

Electrical potential and half-decay exposure for Application Examples 142~157 and Comparative example 2

| Example | Electrical potential (V) | Half-decay exposure (Lux · sec) |
|---|---|---|
| Application Example 142 | 650 | 3.5 |
| Application Example 143 | 630 | 3.2 |
| Application Example 144 | 620 | 4.5 |
| Application Example 145 | 690 | 2.2 |
| Application Example 146 | 640 | 3.4 |
| Application Example 147 | 670 | 3.0 |
| Application Example 148 | 650 | 3.0 |
| Application Example 149 | 660 | 3.2 |
| Application Example 150 | 680 | 4.3 |
| Application Example 151 | 670 | 4.5 |
| Application Example 152 | 680 | 4.2 |
| Application Example 153 | 620 | 4.0 |
| Application Example 154 | 650 | 4.6 |
| Application Example 155 | 630 | 3.3 |
| Application Example 156 | 650 | 4.4 |
| Application Example 157 | 680 | 4.5 |
| Comparative example 2 | 580 | 6.1 |

TABLE AA

Electrical potential and half-decay exposure for Application Example 158~173 and Comparative example 3

| Example | Electrical Potential (V) | Half-decay exposure (Lux · sec) |
|---|---|---|
| Application Example 158 | 600 | 1.6 |
| Application Example 159 | 540 | 1.3 |
| Application Example 160 | 570 | 2.5 |
| Application Example 161 | 600 | 1.1 |
| Application Example 162 | 580 | 1.6 |
| Application Example 163 | 610 | 1.3 |
| Application Example 164 | 590 | 1.2 |
| Application Example 165 | 580 | 1.3 |
| Application Example 166 | 600 | 2.3 |
| Application Example 167 | 570 | 2.4 |
| Application Example 168 | 580 | 2.2 |
| Application Example 169 | 560 | 2.1 |
| Application Example 170 | 570 | 2.3 |
| Application Example 171 | 590 | 1.4 |
| Application Example 172 | 560 | 2.4 |
| Application Example 173 | 580 | 2.5 |
| Comparative example 3 | 550 | 2.8 |

TABLE AB

Electrical potential and half-decay exposure for Application Example 174~189 and Comparative example 4

| Example | Electrical Potential (V) | Half-decay exposure (Lux · sec) |
|---|---|---|
| Application Example 174 | 550 | 2.2 |
| Application Example 175 | 530 | 1.9 |
| Application Example 176 | 540 | 2.4 |
| Application Example 177 | 580 | 1.5 |
| Application Example 178 | 530 | 1.8 |
| Application Example 179 | 560 | 1.6 |
| Application Example 180 | 550 | 1.6 |
| Application Example 181 | 570 | 1.8 |
| Application Example 182 | 540 | 2.6 |
| Application Example 183 | 580 | 2.4 |
| Application Example 184 | 570 | 2.0 |
| Application Example 185 | 520 | 1.9 |
| Application Example 186 | 560 | 2.1 |
| Application Example 187 | 550 | 1.7 |
| Application Example 188 | 590 | 2.3 |
| Application Example 189 | 580 | 2.5 |
| Comparative example 4 | 540 | 3.0 |

TABLE AC

Electrical potential and half-decay exposure for Application Example 190~205 and Comparative example 5

| Example | Electrical Potential (V) | Half-decay exposure (Lux · sec) |
|---|---|---|
| Application Example 190 | −590 | 1.9 |
| Application Example 191 | −570 | 1.8 |
| Application Example 192 | −560 | 2.3 |
| Application Example 193 | −600 | 1.1 |
| Application Example 194 | −570 | 1.6 |
| Application Example 195 | −590 | 1.5 |
| Application Example 196 | −550 | 1.7 |
| Application Example 197 | −590 | 1.6 |
| Application Example 198 | −580 | 1.9 |
| Application Example 199 | −590 | 2.1 |
| Application Example 200 | −570 | 1.9 |
| Application Example 201 | −560 | 2.0 |
| Application Example 202 | −580 | 2.3 |
| Application Example 203 | −570 | 1.7 |
| Application Example 204 | −620 | 2.0 |

TABLE AC-continued

Electrical potential and half-decay exposure for Application Example 190~205 and Comparative example 5

| Example | Electrical Potential (V) | Half-decay exposure (Lux · sec) |
|---|---|---|
| Application Example 205 | −610 | 2.1 |
| Comparative Example 5 | −620 | 3.5 |

The invention claimed is:

1. An electrophotographic photoreceptor comprising an electroconductive substrate having at least a photosensitive layer disposed thereon, wherein the photosensitive layer contains as a charge-transfer material a compound represented by the following general formula (4):

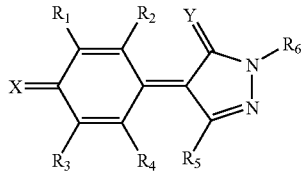

General formula (4)

wherein X and Y are oxygen, R1 and R3 are tert-butyl, R2 and R4 are hydrogen, R5 is alkyl or aryl, R6 is aryl.

2. An electrophotographic photoreceptor comprising an electroconductive substrate having at least a photosensitive layer disposed thereon, wherein the photosensitive layer contains as a charge-transfer material a compound represented by the following general formula (4):

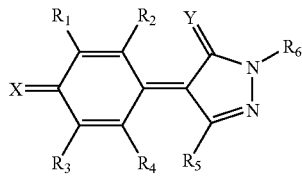

General formula (4)

wherein X and Y are oxygen, R1 and R3 are tert-butyl, R2 and R4 are hydrogen, R5 is methyl, and R6 is selected from a group consisting of methyl, phenyl, para-chlorophenyl, para-bromophenyl, ortho-methylphenyl, para-methylphenyl, ortho-chlorophenyl, meta-chlorophenyl.

3. An electrophotographic photoreceptor comprising an electroconductive substrate having at least a photosensitive layer disposed thereon, wherein the photosensitive layer contains as a charge-transfer material a compound represented by the following general formula (4):

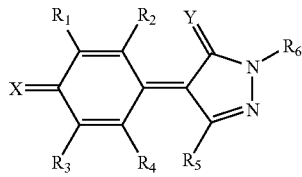

General formula (4)

wherein X and Y are oxygen, R1 and R3 are tert-butyl, R2 and R4 are hydrogen, R5 is n-propyl, and R6 is selected from a group consisting of phenyl, ortho-methylphenyl, para-isopropylphenyl, para-methylphenyl, ortho-chlorophenyl, meta-chlorophenyl, and 2,5-dichlorophenyl.

* * * * *